United States Patent
Faure et al.

(10) Patent No.: US 10,889,840 B2
(45) Date of Patent: Jan. 12, 2021

(54) CONVERSION OF METHYLGLYOXAL INTO HYDROXYACETONE USING NOVEL ENZYMES AND APPLICATIONS THEREOF

(71) Applicant: METABOLIC EXPLORER, Saint Beauzire (FR)

(72) Inventors: Laetitia Faure, Les Martres de Veyre (FR); Gwenaëlle Corre, Saint Beauzire (FR); Céline Raynaud, Saint Beauzire (FR); Laurence Dumon-Seignovert, Pont du Chateau (FR)

(73) Assignee: METABOLIC EXPLORER, Saint Beauzire (FR)

( * ) Notice: Subject to any disclaimer, the term of this patent is extended or adjusted under 35 U.S.C. 154(b) by 0 days.

(21) Appl. No.: 16/465,560

(22) PCT Filed: Dec. 29, 2017

(86) PCT No.: PCT/EP2017/084841
§ 371 (c)(1),
(2) Date: May 30, 2019

(87) PCT Pub. No.: WO2018/122388
PCT Pub. Date: Jul. 5, 2018

(65) Prior Publication Data
US 2020/0181652 A1  Jun. 11, 2020

(30) Foreign Application Priority Data
Dec. 29, 2016  (EP) ..................................... 16306848

(51) Int. Cl.
| *C12N 15/70* | (2006.01) |
| *C12P 7/18* | (2006.01) |
| *C12N 9/04* | (2006.01) |
| *C12N 9/02* | (2006.01) |
| *C12N 9/88* | (2006.01) |
| *C12P 7/28* | (2006.01) |

(52) U.S. Cl.
CPC .............. *C12P 7/18* (2013.01); *C12N 9/0006* (2013.01); *C12N 9/0008* (2013.01); *C12N 9/0036* (2013.01); *C12N 9/88* (2013.01); *C12P 7/28* (2013.01); *C12Y 101/01072* (2013.01); *C12Y 101/01283* (2013.01); *C12Y 102/01013* (2013.01); *C12Y 402/01136* (2015.07); *C12Y 402/03003* (2013.01); *C12Y 404/01005* (2013.01)

(58) Field of Classification Search
CPC .............. C12N 9/0004; C12N 15/70

USPC ......................................................... 435/148
See application file for complete search history.

(56) References Cited

U.S. PATENT DOCUMENTS

| 8,969,053 B2 * | 3/2015 | Voelker ................ C12N 9/0006 |
| | | 435/148 |
| 2014/0132690 A1 | 5/2014 | Yan et al. |

FOREIGN PATENT DOCUMENTS

| EP | 2532751 A1 | 12/2012 |
| EP | 3196312 A1 | 7/2017 |
| WO | WO 98/37204 A1 | 8/1998 |
| WO | WO 2005/047498 A1 | 5/2005 |
| WO | WO 2005/073364 A2 | 8/2005 |
| WO | WO 2008/116848 A1 | 10/2008 |
| WO | WO 2008/116852 A1 | 10/2008 |
| WO | WO 2008/116853 A1 | 10/2008 |
| WO | WO 2011/012693 A1 | 2/2011 |
| WO | WO 2011/012697 A2 | 2/2011 |
| WO | WO 2011/012702 A1 | 2/2011 |
| WO | WO 2012/055798 A1 | 5/2012 |
| WO | WO 2015/173247 A1 | 11/2015 |

OTHER PUBLICATIONS

Altaras et al., "Enhanced Production of (R)-1,2-Propanediol by Metabolically Engineered *Escherichia coli*," Biotechnol. Prog., vol. 16, 2000, pp. 940-946(7 pages).
Altaras et al., Metabolic Engineering of a 1,2-Propanediol Pathway in *Escherichia coli*, Applied and Environmental Microbiology, vol. 65, No. 3, Mar. 1999, pp. 1180-1185 (6 pages).
Altschul et al., "Basic Local Alignment Search Tool", J. Mol. Biol. vol. 215, 1990, pp. 403-410 (8 pages).
Badía et al, "Fermentation Mechanism of Fucose and Rhamnose in *Salmonella typhimurium* and Klebsiella pneumoniae", Journal of Bacteriology, vol. 161, No. 1, Jan. 1985, pp. 435-437 (3 pages).
Bennett et al., "Microbial formation, biotechnological production and applications of 1,2-propanediol", Appl Microbiol Biotechnol, vol. 55, 2001, pp. 1-9 ( 9 pages).
Berríos-Rivera et al, "The effect of carbon sources and lactate dehydrogenase deletion of 1,2-propanediol production in *Escherichia coli*", J. Ind Microbiol Biotechnol, vol. 30, 2003, pp. 34-40 (7 pages).

(Continued)

*Primary Examiner* — Tekchand Saidha
(74) *Attorney, Agent, or Firm* — Birch, Stewart, Kolasch & Birch, LLP

(57) ABSTRACT

The present invention relates to new methylglyoxal reductase (MGR) enzymes which are useful for efficiently converting methylglyoxal into hydroxyacetone. The invention more particularly relates to a method for efficiently converting methylglyoxal into hydroxyacetone using said enzymes, to a method for producing 1,2-propanediol using a microorganism overexpressing said enzymes, and to said microorganism.

19 Claims, 1 Drawing Sheet
Specification includes a Sequence Listing.

(56) References Cited

OTHER PUBLICATIONS

Bertani et al., "The Mode of Phage Liberation by Lysogenic *Escherichia coli*", Studies of Lysogenesis, vol. 62, May 14, 1951, pp. 293-300 (8 pages).

Bocanegra et al., "Creation of an NADP-Dependent Pyruvate Dehydrogenase Multienzyme Complex by Protein Engineering", Biochemistry, vol. 32, No. 22, Mar. 23, 1993, pp. 2737-2740 (4 pages).

Cameron et al., "Metabolic Engineering of Propanediol Pathways", Biotechnol. Prog. vol. 14, 1998, pp. 116-125 (10 pages).

Carrier et al., "Library of Synthetic 5' Secondary Structures to Manipulate mRNA Stability in *Escherichia coli*", Biotechnol. Prog., vol. 15, 1999, pp. 58-64 (7 pages).

Chandrangsu et al., "Methylglyoxal resistance in Bacillus subtilis: contributions of bacillithiol-dependent and independent pathways", Molecular Microbiology, vol. 91, No. 4, 2014, pp. 706-715 (10 pages).

Datsenko et al., "One-step inactivation of chromosomal genes in *Escherichia coli* K-12 using PCR products", PNAS, vol. 97, No. 12, Jun. 6, 2000, pp. 6640-6645 (6 pages).

Davis et al.,"Characterizing the Native Codon Usages of a Genome: An Axis Projection Approach", Mol. Biol. Evol., vol. 28, No. 1, 2011, pp. 211-221 (11 pages).

Demerec et al., "A Proposal for a Uniform Nomenclature in Bacterial Genetics", Genetics, vol. 54, Jul. 1966, pp. 61-76 (16 pages).

Deml et al., "Multiple Effects of Codon Usage Optimization on Expression and Immunogenicity of DNA Candidate Vaccines Encoding the Human Immunodeficiency Virus Type 1 Gag Protein", Journal of Virology, vol. 75, No. 22, Nov. 2001, pp. 10991-11001 (11 pages).

Graf et al, "Concerted Action of Multiple cis-Acting Sequences is Required for Rev Dependence of Late Human Immunodefiency Virus Type 1 Gene Expression" , Journal of Virology, vol. 74, No. 22, Nov. 2000, pp. 108220-10826 ( 5 pages).

Huang et al., "Characterization of Methylglyoxal Synthase from Clostridium acetobutylicum ATCC 824 and Its Use in the Formation of 1,2-Propanediol", Applied and Environmental Microbiology, vol. 65, No. 7, Jul. 1999, pp. 3244-3247 ( 4 pages).

Katzberg et al., "Engineering Cofactor Preference of Ketone Reducing Biocatalysts: A Mutagenesis Study on a γ-Diketone Reductase from the Yeast *Saccharomyces cerevisiae* Serving as an Example", Int. J. Mol. Sci., vol. 11, 2010, pp. 1735-1758 (24 pages).

Ko et al., "Conversion of Methylglyoxal to Acetol by *Escherichia coli* Aldo-Keto Reductases", Journal of Bacteriology, vol. 187, No. 16, Aug. 2005, pp. 5782-5789 (8 pages).

Lee et al., "Control of Substrate Access to the Active Site in Methane Monooxygenase" Nature. Author Manuscript, vol. 494, No. 7437, Feb. 21, 2013, 12 pages total.

Lim et al., "Amplification of the NADPH-Related Genes zwf and gnd for the Oddball Biosynthesis of PHB in an *E. coli* Transformant Harboring a Cloned phbCAB Operon", Journal of Bioscience and Bioengineering, vol. 93, No. 6, 2002, pp. 543-549 (7 pages).

Marbaix et al., "Extremely Conserved ATP- or ADP-dependent Enzymatic System for Nicotinamide Nucleotide Repair", The Journal of Biological Chemistry, vol. 286, No. 48, Dec. 2, 2011, pp. 41246-41252 (8 pages).

Needleman et al., A General Method Applicable to the Search for Similarities in the Amino Acid Sequence of Two Proteins, J. Mol. Biol. No. 48, 1970, pp. 443-453 (11 pages).

Salis, "The Ribosome Binding Site Calculator", Methods in Enzymology, vol. 498, Dec. 2011, pp. 19-42 (25 pages).

Segel, "Enzyme kinetics" John Wiley & Sons, 1993, pp. 44-54, 100-112 (13 pages).

Subedi et al., "Role of GldA in dihydroxyacetone and methylglyoxal metabolism of *Escherichia coli* K12", FEMS Microbiol Lett., vol. 279, 2008, pp. 180-187 (8 pages).

\* cited by examiner

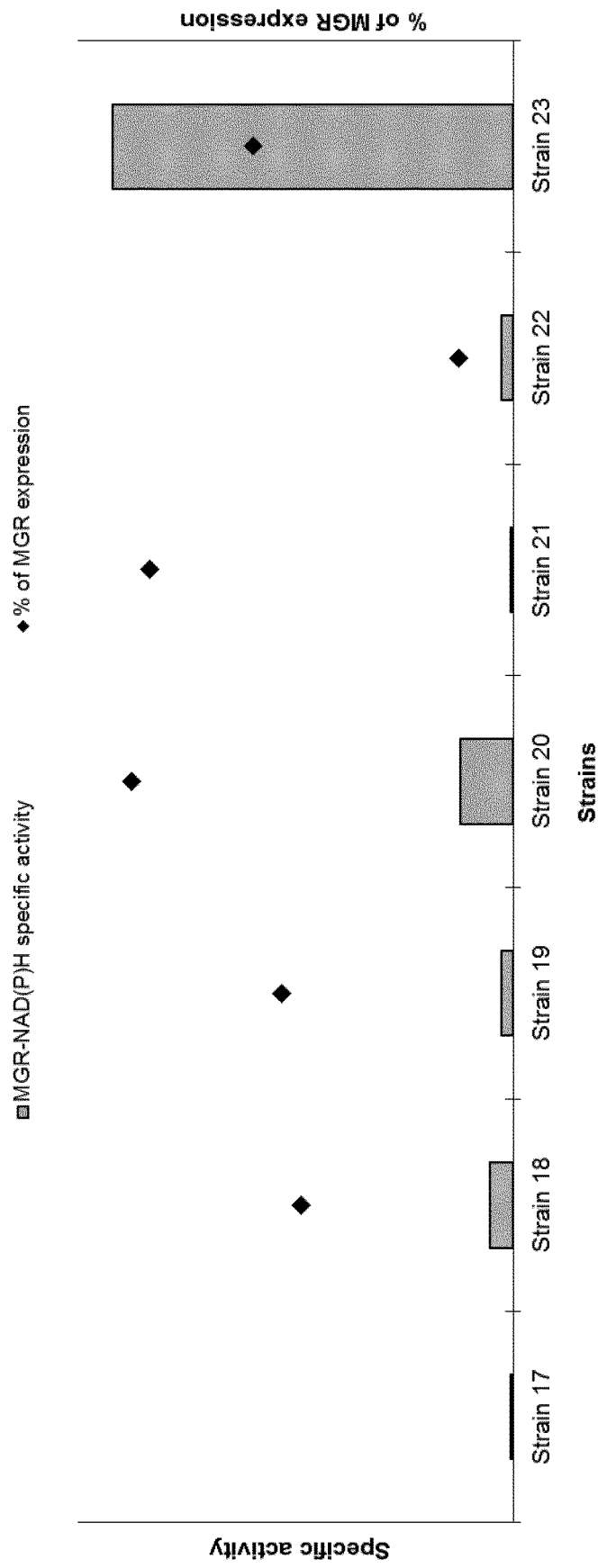
*Specific Methylglyoxal reductase (MGR) activity of strains harbouring different MGR enzymes and percentages of expression of the related MGR enzymes in the related strains.*

CONVERSION OF METHYLGLYOXAL INTO HYDROXYACETONE USING NOVEL ENZYMES AND APPLICATIONS THEREOF

INTRODUCTION

The present invention relates to new methylglyoxal reductase (MGR) enzymes which are useful for efficiently converting methylglyoxal into hydroxyacetone. The invention more particularly relates to a method for efficiently converting methylglyoxal into hydroxyacetone using said enzymes, to a method for producing 1,2-propanediol using a microorganism overexpressing said enzymes, and to said microorganism.

1,2-propanediol or propylene glycol, a C3 di-alcohol with formula $C_3H_8O_2$ or HO—CH2—CHOH—CH3, is a widely-used chemical, well-known under its CAS number 57-55-6, that has found numerous industrial applications, such as in pharmaceuticals, cosmetics, aeronautics, food industry, tobacco and textile, to name a few. It is a colorless, nearly odorless, clear, viscous liquid with a faintly sweet taste, hygroscopic and miscible with water, acetone and chloroform, that is primarily used as a component of unsaturated polyester resins, but also of liquid detergents, coolants, anti-freeze and de-icing fluids for aircraft. It can further be used as a humectant (E1520), solvent and preservative in food and for tobacco products. Propylene glycol has been increasingly used since 1993-1994 as a replacement for ethylene derivatives, which are recognised as being more toxic than propylene derivatives.

1,2-propanediol is currently mainly produced by chemical means using a propylene oxide hydration process that consumes large amounts of water, employs highly toxic substances and generates by-products such as tert-butanol and 1-phenyl ethanol. Such chemical processes further typically lead to the production of a mixture of (R)-1,2-propanediol and (S)-1,2-propanediol.

Natural or synthetic metabolic pathway(s) for 1,2-propanediol production in microorganisms represents an attractive alternative as it alleviates many of the above-mentioned problems.

To date, two natural biological pathways have been characterized for the fermentative production of 1,2-propanediol from sugars in microorganisms.

In the first pathway, which is functional in *E. coli* under anaerobic conditions, 6-deoxy sugars (e.g. L-rhamnose or L-fucose) are cleaved into dihydroxyacetone phosphate and (S)-lactaldehyde, which can be further reduced into (S)-1,2-propanediol by a 1,2-propanediol oxidoreductase, also called lactaldehyde reductase (LAR) and encoded by the fucO gene (Badia et al., 1985). However, fermentation processes relying on this pathway are not economically viable due to the elevated costs of the deoxyhexoses substrates.

The second natural pathway involves the metabolism of common sugars (e.g. glucose or xylose), including more specifically the glycolysis pathway followed by the methylglyoxal pathway. It converts dihydroxyacetone phosphate into methylglyoxal, which can then be reduced either into (R)-lactaldehyde or hydroxyacetone (i.e. acetol), depending upon the nature of the reductase. These two compounds are then transformed into (R)-1,2-propanediol. This pathway is typically observed in microorganisms naturally producing (R)-1,2-propanediol, such as *Clostridium sphenoides* and *Thermoanaerobacter thermosaccharolyticum*. However, the production performances exhibited by these organisms are highly limited.

Given that the methylglyoxal pathway is functional in Enterobacteriaceae, several investigations have been conducted to engineer a synthetic pathway for improving the production of 1,2-propanediol using simple carbon sources in said microorganisms, more particularly in *E. coli* (WO 98/37204; Cameron et al., 1998; Altaras and Cameron, 1999; Huang et al., 1999; Altaras and Cameron, 2000; Berrios-Rivera et al., 2003).

In recombinantly engineered *E. coli* strains producing 1,2-propanediol, 1,2-propanediol can be derived from central metabolism in three steps. Methylglyoxal synthase converting dihydroxyacetone phosphate into methylglyoxal is the mandatory first step, which is followed by the second step of conversion of methylglyoxal into (R)-lactaldehyde or hydroxyacetone by methylglyoxal reductases (Cameron et al., 1998; Bennet et al., 2001; Ko et al., 2005). The NADPH-dependent aldehyde reductase YqhD has been shown to more particularly convert methylglyoxal into hydroxyacetone (WO 2008/116853), while the glycerol dehydrogenase GldA has been shown to convert methylglyoxal into (R)-lactaldehyde (Subedi et al., 2008). In the last step, hydroxyacetone or lactaldehyde are converted into 1,2-propanediol by distinct enzymatic activities, in particular glycerol dehydrogenase (encoded by the gldA gene) or 1,2-propanediol oxidoreductase (encoded by the fucO gene) (Altaras and Cameron, 2000).

In order to further improve the production of 1,2-propanediol in said *E. coli* strains, the native YqhD enzyme has been replaced with new mutant YqhD enzymes exhibiting a greater catalytic efficiency (i.e. increased $k_{cat}$/Km) and affinity toward methylglyoxal and NADPH, notably with the mutant enzyme YqhD* (G149E) (YqhD: $k_{cat}$/Km=0.4 $mM^{-1} \cdot s^{-1}$ and Km=2.09 mM, versus YqhD* (G149E): $k_{cat}$/Km=0.8 $mM^{-1}s^{-1}$ and Km=2.92 mM) (WO 2011/012697).

However, the inventors have observed that YqhD* (G149E) must be highly expressed in the microorganism so as to allow the production of 1,2-propanediol, which results in a metabolic burden, and therefore generates a stress to the microorganism due to deprivation of carbon and energy.

There is thus a need in the art to provide alternative methylglyoxal reductases (MGR), which can reduce the methylglyoxal metabolic with a higher catalytic efficiency at a lower expression level, so as to efficiently produce (R)-1, 2-propanediol.

The present invention addresses the above discussed needs in the art.

The inventors have indeed surprisingly discovered that enzymes known so far as reductases using various substrates such as hexanaldehyde, glyceraldehyde or butyraldehyde are also capable of using methylglyoxal as a substrate, and thereby of converting said substrate into hydroxyacetone. Unexpectedly, said enzymes exhibit a catalytic efficiency toward methylglyoxal and NADPH that is at least seven times higher than the one of YqhD* (G149E). Based on this discovery, the inventors have modified existing *E. coli* strains producing 1,2-propanediol, and observed that said strains could produce more 1,2-propanediol in grams per biomass, while maintaining a lower expression level of these new methylglyoxal reductases than for YqhD* (G149E).

The present invention therefore provides herein an improved method for efficiently converting in a microorganism methylglyoxal into hydroxyacetone by using said enzymes, a method for producing 1,2-propanediol in a microorganism, and a microorganism producing 1,2-propanediol overexpressing said enzymes.

DETAILED DESCRIPTION OF THE INVENTION

It shall be understood that the following detailed description is not limitative and that various modifications, substitutions, omissions, and changes may be made without departing from the scope of the invention. It shall also be understood that the terminology used herein is for the purpose of describing particular embodiments of the invention, and is not intended to be limiting.

All publications, patents and patent applications cited herein, whether supra or infra, are hereby incorporated by reference in their entirety.

Furthermore, unless otherwise stated, all technical and scientific terms used herein have the same meanings as commonly understood by one of ordinary skill in the art. Conventional microbiological and molecular biological techniques are also those well-known and commonly used in the art. Such techniques are well known to the skilled person in the art and are fully explained in the literature.

The singular forms "a," "an," and "the" include plural reference unless the context clearly dictates otherwise.

The terms "comprise," "contain," "involve," or "include" or variations such as "comprises," "comprising," "containing," "involved," "includes," "including," are used herein in an inclusive sense, i.e. to specify the presence of the stated features but not to preclude the presence or addition of further features in various embodiments of the invention.

The term "activity," "catalytic activity," or "function" of an enzyme designates, in the context of the invention, the reaction that is catalyzed by said enzyme for converting its corresponding substrate(s) into another molecule(s) (product(s)). As well-known in the art, the activity of an enzyme can be assessed by measuring its catalytic efficiency and/or Michaelis constant.

The "catalytic efficiency" or "specificity constant" of an enzyme provides a direct measure of its performance, or in other words, of how efficiently an enzyme converts its substrate(s) into a product(s). Indeed, the higher the catalytic efficiency, the lesser enzyme needed to convert a given amount of substrate(s) into a product(s). A comparison of specificity constants can also be used as a measure of the preference of an enzyme for different substrates (i.e., substrate specificity). The following equation, known as the Michaelis-Menten model, can be used to describe the kinetics of enzymes:

$$E + S \underset{k_r}{\overset{k_f}{\rightleftharpoons}} ES \xrightarrow{k_{cat}} E + P$$

where E, S, ES, and P represent enzyme, substrate, enzyme-substrate complex, and product respectively. The symbols $k_f$, $k_r$, and $k_{cat}$ denote the rate constants for the "forward" binding and "reverse" unbinding of substrate, and for the "catalytic" conversion of substrate(s) into product(s) respectively. The catalytic efficiency is equal to the ratio $k_{cat}$/Km.

The "catalytic constant" ($k_{cat}$) is the rate of product formation when the enzyme is saturated with substrate and is expressed in $M^{-1}s^{-1}$. In other words, it designates the number of substrate molecules the enzyme converts into product per unit of time.

The "Michaelis constant" (Km) in turn is a measure of the affinity of an enzyme for its substrate (the lower the Km, the higher the affinity), and is expressed in M. It is more particularly defined as follows:

$$K_M = \frac{k_r + k_{cat}}{k_f}$$

and is equal to the substrate concentration at which the enzyme converts substrate(s) into product(s) at half its maximal rate. The lower the Km, the higher the affinity.

It is within the skill of the person in the art to measure the above-mentioned parameters of an enzyme (Segel, 1993).

The terms "methylglyoxal reductase" or "MGR" refer to an enzyme of which the activity is to reduce a carbonyl function, such as an aldehyde or a ketone function, into a hydroxyl function, that is herein of converting methylglyoxal into either hydroxyacetone or lactaldehyde. Said activity may be NADPH dependent or NADH dependent (i.e. cofactor dependent), and can occur in aerobic and/or anaerobic conditions. In the context of the present invention, preferred methylglyoxal reductases are methylglyoxal reductases that convert methylglyoxal into hydroxyacetone.

The term "microorganism," as used herein, refers to a living microscopic organism, which may be a single cell or a multicellular organism and which can generally be found in nature. In the context of the present invention, the microorganism is preferably a bacterium, yeast or fungus. More preferably, the microorganism of the invention belongs to the family of the bacteria Enterobacteriaceae, Clostridiaceae, Bacillaceae, Streptomycetaceae, and Corynebacteriaceae or to the family of yeasts Saccharomycetaceae. Even more preferably, the microorganism according to the invention is the Enterobacteriaceae bacterium *Escherichia coli* or *Klebsiella pneumoniae*, the Clostridiaceae bacterium *Clostridium sphenoides* or *Thermoanaerobacterium thermosaccharolyticum*, the Corynebacteriaceae bacterium *Corynebacterium glutamicum*, or the Saccharomycetaceae yeast *Saccharomyces cerevisiae*. Most preferably, the microorganism of the invention is *Escherichia coli*.

The terms "genetically modified microorganism" and "recombinant microorganism" are interchangeable and refer to a microorganism as defined above that is not found in nature and therefore genetically differs from its natural counterpart. In other words, it refers to a microorganism that is modified by introduction and/or by deletion and/or by modification of its genetic elements. Such modification can be performed for example by genetic engineering, or by forcing the development and evolution of new metabolic pathways by combining directed mutagenesis and evolution under specific selection pressure (see, for example, WO2005/073364 or WO2008/116852, incorporated herein by reference).

A microorganism can be genetically modified by modulating the expression level of one or more endogenous genes. By "modulating," it is meant herein that the expression level of said gene can be up-regulated (i.e. overexpressed), down-regulated (i.e. underexpressed or attenuated), or even completely abolished by comparison to its natural expression level (i.e. deleted). By "up-regulating," or "overexpressing" a gene of interest, it is meant herein increasing the expression level of said gene in a microorganism, as compared to the unmodified microorganism. By contrast, "down-regulating," "underexpressing," or "attenuating" a gene of interest means decreasing the expression level of said gene in a microorganism, as compared to the unmodified microorganism. The expression of a gene of interest can also be completely abolished, meaning that the expression level of said gene is null. The above-described modulation can therefore result in an enhancement of activity of the gene product, or alternatively, in a lower or null activity of the gene product.

By "gene," it is meant herein a nucleotide sequence which comprises at least a region coding for a protein of interest. Said region may further be flanked on each 5' and/or 3' end by untranslated regions (UTRs, named 5'UTR and/or 3'UTR), which may contain regulatory elements that control protein synthesis. In order to facilitate the understanding of the invention, the genes described in the present application are named according to their standard nomenclature (Demerec et al., 1966); these denominations must not however be construed as being limitative, notably regarding the species of origin of said gene, considering that the amino acid sequence of the protein encoded by each gene is provided herein.

The term "endogenous gene" refers herein to a gene as defined above that is naturally present in a microorganism.

An endogenous gene can notably be overexpressed by introducing heterologous sequences which favour upregulation in addition to endogenous regulatory elements, or by substituting those endogenous regulatory elements with such heterologous sequences, or by introducing one or more supplementary copies of the endogenous gene chromosomally (i.e. into the chromosome) or extra-chromosomally (e.g. into a plasmid or vector) within the microorganism. In this regard, several copies of a gene can be introduced on a chromosome by methods well-known in the art such as by genetic recombination. By contrast, when a gene is expressed extra-chromosomally, it can be carried by different types of plasmid that may differ in respect to their origin of replication depending on the microorganism in which they can replicate, and by their copy number in the cell. For example, a microorganism transformed by a plasmid can contain 1 to 5 copies of the plasmid, or about 20 copies of it, or even up to 500 copies of it, depending on the nature of the selected plasmid. A variety of plasmids, which differ in respect of their origin of replication and of their copy number in a cell, are well known in the art and can be easily selected by the skilled practitioner for such purposes. Examples of low copy number plasmids which can replicate in *E. coli* include, without limitation, the pSC101 plasmid (tight replication), the RK2 plasmid (tight replication), as well as the pACYC and pRSF1010 plasmids, while an example of high copy number plasmid which can replicate in *E. coli* is pSK bluescript II.

Another way to modulate the expression of an endogenous gene is to exchange its promoter (i.e. wild-type promoter) with a stronger or weaker promoter to up or down-regulate its expression level. Promoters suitable for such purpose can be homologous (originating from the same species) or heterologous (originating from a different species) or artificial (designed and synthetized de novo), and are well-known in the art. It is within the skill of the person in the art to select appropriate promoters for modulating the expression of an endogenous gene. Promoters that are the most convenient for increasing gene expression level are well-known to the skilled person in the art: these include, among others, promoters Ptrc, Ptac, Plac, and the lambda promoter $P_R$ and $P_L$. These promoters can be "inducible" by a particular compound or by specific external conditions such as temperature or light, and/or may be homologous or heterologous.

Endogenous gene expression level can also be increased or decreased by introducing mutations into their coding sequence. Mutations can be introduced by site-directed mutagenesis using for example Polymerase Chain Reaction (PCR), by random mutagenesis techniques for example via mutagenic agents (Ultra-Violet rays or chemical agents like nitrosoguanidine (NTG) or ethylmethanesulfonate (EMS)) or DNA shuffling or error-prone PCR. A deletion of all or a part of an endogenous gene can alternatively be performed to totally inhibit its expression within the microorganism.

In addition, or alternatively, a microorganism can be genetically modified to overexpress one or more exogenous genes, provided that said genes are introduced into the microorganism with all the regulatory elements necessary for their expression in the host microorganism. The genetic modification or transformation of microorganisms with exogenous DNA is a routine task for those skilled in the art.

By "exogenous gene," it is meant herein a gene that is not naturally occurring in a microorganism. In order to express (i.e. overexpress) an exogenous gene in a microorganism, such gene can be directly integrated into the microorganism chromosome, or be expressed extra-chromosomally within the microorganism, as explained above. Exogenous genes according to the invention are advantageously homologous genes.

In the context of the invention, the term "homologous gene" or "homolog" not only refers to a gene inherited by two species (i.e. microorganism species) by a theoretical common genetic ancestor, but also includes genes which may be genetically unrelated that have, nonetheless, evolved to encode proteins which perform similar functions and/or have similar structure (i.e. functional homolog). Therefore, the term "functional homolog" refers herein to a gene that encodes a functionally homologous protein.

Using the information available in databases such as UniProt (for proteins), GenBank (for genes), or NCBI (for proteins or genes), the skilled practitioner can easily determine the sequence of a specific protein and/or gene of a microorganism, and identify based on this sequence the one of equivalent proteins or genes, or homologs thereof, in another microorganism. This routine work can be performed for example by alignment of a specific gene (or protein) sequence of a microorganism with gene (or protein) sequences or the genome (or proteome) of other microorganisms, which can be found in the above-mentioned databases. Such sequence alignment can advantageously be performed using the BLAST algorithm developed by Altschul et al. (1990). Once a sequence homology has been established between those sequences, a consensus sequence can be derived and used to design degenerate probes in order to clone the corresponding homolog gene (and hence homolog protein) of the related microorganism. These routine methods of molecular biology are well known to those skilled in the art.

It shall be further understood that, in the context of the present invention, should an exogenous gene encoding a protein of interest be expressed in a specific microorganism, a synthetic version of this gene is preferably constructed by replacing non-preferred codons or less preferred codons with preferred codons of said microorganism which encode the same amino acid. It is indeed well-known in the art that codon usage varies between microorganism species, which may impact the recombinant expression level of the protein of interest. To overcome this issue, codon optimization methods have been developed, and are extensively described by Graf et al. (2000), Deml et al. (2001) and Davis & Olsen (2011). Several software programs have notably been developed for codon optimization determination such as the GeneOptimizer® software (Lifetechnologies) or the OptimumGene™ software of (GenScript). In other words, the exogenous gene encoding a protein of interest is preferably codon-optimized for expression in a specific microorganism.

A microorganism can also be genetically modified to increase or decrease the activity of one or more proteins which are naturally or not naturally expressed in the microorganism.

Increasing such activity can be achieved by improving the protein catalytic efficiency (if the protein is an enzyme), and/or decreasing protein turnover.

Improving the protein catalytic efficiency means increasing the $k_{cat}$ and/or decreasing the Km for a given substrate and/or a given cofactor, and/or increasing the Ki for a given inhibitor. Ki is also a Michaelis-Menten constant that the man skilled in the art is able to determine (Segel, 1993). Decreasing protein turnover means stabilizing the protein. Methods to improve protein catalytic efficiency and/or decrease protein turnover are well known from the man skilled in the art. Those include rational engineering with sequence and/or structural analysis and directed mutagenesis, as well as random mutagenesis and screening. Stabilizing the protein can also be achieved by adding a "tag" peptide sequence either at the N-terminus or the C-terminus of the protein. Such tags are well known in the art, and include, among others, the Glutathione-S-Transferase (GST).

As used herein, the term "mutant" refers to a functional protein or a functional gene, the sequence of which is modified on at least one position (i.e., at least one amino acid of said protein or at least one nucleotide of said gene is modified, respectively). It is to be understood that this at least one sequence modification results in a functional protein mutant or in a functional gene mutant, having advantageously an improved biological activity compared to the wild-type or parent protein or the wild-type or parent gene.

Increasing a protein activity can also be achieved by improving the protein expression, through, for example, a decrease in protein turnover, a decrease in messenger RNA (mRNA) turnover, an increase in the transcription of the gene encoding said protein, or an increase in mRNA translation.

Decreasing mRNA turnover can be achieved by modifying the gene sequence of the 5'-untranslated region (5'-UTR) and/or the coding region, and/or the 3'-UTR (Carrier and Keasling, 1999).

Increasing the transcription of a gene, whether endogenous or exogenous, can be achieved by increasing the number of its copies within the microorganism and/or by placing said gene under the control of a stronger promoter, according to the methods described above.

Increasing translation of the mRNA can be achieved by modifying the Ribosome Binding Site (RBS). A RBS is a sequence on mRNA that is bound by the ribosome when initiating protein translation. It can be either the 5' cap of a mRNA in eukaryotes, a region 6-7 nucleotides upstream of the start codon AUG in prokaryotes (called the Shine-Dalgarno sequence), or an internal ribosome entry site (IRES) in viruses. By modifying this sequence, it is possible to change the protein translation initiation rate, to proportionally alter its production rate, and control its activity inside the cell. It is also possible to optimize the strength of a RBS sequence to achieve a targeted translation initiation rate by using the software RBS CALCULATOR (Salis, 2011). It is within the skill of the person in the art to select the RBS sequence based on the nature of the mRNA.

By contrast, decreasing the activity of a protein can mean either decreasing its specific catalytic activity by mutating the gene encoding said protein, or decreasing its expression by deleting the coding region of said gene.

The terms "fermentative process", "fermentation" or "culture" are used herein interchangeably to denote the growth of a microorganism.

The term "fermentation conditions" refers to the experimental conditions allowing the growth of a given microorganism. The growth of a microorganism is generally performed in fermenters with an appropriate growth medium adapted to the microorganism being used, and which can be easily determined by the skilled person in the art.

In the context of the present invention, by "fermentative conversion", it is meant that the conversion of methylglyoxal into hydroxyacetone occurs when the microorganism is cultured under appropriate fermentation conditions.

A "culture medium" means herein a medium (e.g., a sterile, liquid media) comprising nutrients essential or beneficial to the maintenance and/or growth of the microorganism such as carbon sources or carbon substrates; nitrogen sources, for example peptone, yeast extracts, meat extracts, malt extracts, urea, ammonium sulfate, ammonium chloride, ammonium nitrate and ammonium phosphate; phosphorus sources, for example monopotassium phosphate or dipotassium phosphate; trace elements (e.g., metal salts) for example magnesium salts, cobalt salts and/or manganese salts; as well as growth factors such as amino acids and vitamins.

The term "source of carbon," "carbon source" or "carbon substrate" according to the present invention refers to any molecule that a microorganism is capable to metabolize and which contains at least one carbon atom. Examples of preferred carbon sources according to the invention include, without limitation, carbohydrates.

The term "carbohydrate" is a carbon source as defined above and which further comprises two atoms of hydrogen and one atom of oxygen. $CO_2$ is not a carbohydrate because it does not contain hydrogen. Examples of carbohydrates include, without limitation, monosaccharides such as glucose, fructose, mannose, xylose, arabinose, galactose and the like, disaccharides such as sucrose, cellobiose, maltose, lactose, and the like, oligosaccharides such as raffinose, stachyose, maltodextrins and the like, polysaccharides such as cellulose, hemicellulose, starch and the like, methanol, formaldehyde and glycerol. Particularly preferred carbohydrates according to the invention are arabinose, fructose, galactose, glucose, lactose, maltose, sucrose, xylose and any mixture thereof. More preferably, the carbohydrate is chosen among glucose, xylose, sucrose or mixtures thereof. Even more preferably, the preferred carbohydrate is a mixture of glucose and xylose.

In a preferred embodiment of the invention, the carbon source is derived from renewable feed-stock. Renewable feed-stock is defined as raw material required for certain industrial processes that can be regenerated within a brief delay and in sufficient amount to permit its transformation into the desired product. Vegetal biomass pre-treated or not, is a particularly preferred renewable carbon source.

Additional definitions are provided throughout the specification.

The present invention may be understood more readily by reference to the following detailed description, including preferred embodiments of the invention, and examples included herein.

In a first aspect, the present invention is directed to a method for the fermentative conversion of methylglyoxal into hydroxyacetone, comprising the step of expressing, in a microorganism, at least one methylglyoxal reductase having a catalytic efficiency $k_{cat}$/Km equal or superior to 5 mM$^{-1}$s$^{-1}$ and a Michaelis constant Km superior to 0 mM and equal or inferior to 11 mM. In particular, the present invention is directed to a method for the efficient fermentative conversion of methylglyoxal into hydroxyacetone, comprising the step of expressing, in a microorganism, at least one methylglyoxal reductase having a catalytic efficiency $k_{cat}$/Km equal or superior to 5 mM$^{-1}$s$^{-1}$ and a Michaelis constant Km superior to 0 mM and equal or inferior to 11 mM. Accordingly, the invention relates to the use of at least one enzyme having the above listed properties, to efficiently convert, by microbial fermentation, methylglyoxal into hydroxyacetone. An efficient fermentative conversion as understood in the context of the present invention is therefore achieved when methylglyoxal is converted into hydroxyacetone by at least one methylglyoxal reductase having a catalytic efficiency $k_{cat}$/Km equal or superior to 5 mM$^{-1}$s$^{-1}$ and a Michaelis constant Km superior to 0 mM and equal or inferior to 11 mM. The inventors have indeed discovered that enzymes displaying the above activities greatly improve the rate of conversion of methylglyoxal into hydroxyacetone, as compared to conventional methylglyoxal reductases, in particular to those encoded by the YqhD or YqhD* genes, of which the Km and $k_{cat}$/kM are 2.09 mM, 0.40 mM$^{-1}$s$^{-1}$ and 2.92 mM, 0.80 mM$^{-1}$s$^{-1}$, respectively. The enzymes according to the invention therefore greatly reduce the metabolic burden for performing said conversion, and hence can facilitate the growth of the microorganism.

The inventors have more particularly identified specific enzymes that have the capacity to perform the above conversion.

According to a preferred embodiment, said methylglyoxal reductase is selected from the group consisting of the YjgB enzyme of sequence SEQ ID NO: 1 and its mutants, the YahK enzyme of sequence SEQ ID NO: 3 and its mutants, the YhdN enzyme of sequence SEQ ID NO: 5 and its mutant, the Gld enzyme of sequence SEQ ID NO: 7 and its mutants, and combinations thereof. Examples of preferred YjgB mutants are YjgB* (N240Y) of sequence SEQ ID NO: 9, YjgB*(I165V) of SEQ ID NO: 125 and YjgB*(Q39R/I165V/A296V) of sequence SEQ ID NO: 127.

Most preferably, said methylglyoxal reductase is the YjgB enzyme of sequence SEQ ID NO: 1.

Even more preferably, YjgB enzyme of sequence SEQ ID NO: 1 is expressed in combination with the YahK enzyme of sequence SEQ ID NO: 3, the YhdN enzyme of sequence SEQ ID NO: 5, the Gld enzyme of sequence SEQ ID NO: 7, the YafB enzyme of sequence SEQ ID NO: 11 or the YqhD enzyme of sequence SEQ ID NO: 13 or its mutant YqhD* (G149E) of sequence SEQ ID NO: 15.

Information about the corresponding amino-acid and nucleotide sequences, and catalytic properties of said enzymes are provided in Table 1 below. It notably indicates that said enzymes are not known to exhibit a methylglyoxal reductase activity.

In a preferred embodiment of the invention, the microorganism overexpresses methylglyoxal reductase either alone or in combination with another methylglyoxal reductase as described above. More precisely, in a preferred embodiment, the above method involves the step of culturing, under fermentative conditions, a microorganism overexpressing at least one gene coding for said enzyme, in a culture medium comprising a carbohydrate as a source of carbon, and efficiently converting methylglyoxal into hydroxyacetone. To do so, the source of carbon is accordingly preferably reduced into the intermediate metabolite dihydroxyacetone phosphate (DHAP) by said microorganism by way of central carbon metabolism, using appropriate pathways and enzymes described for example in Neidhardt et al. (1996), incorporated herein by reference. DHAP is then transformed into methylglyoxal (MG) by the action of methylglyoxal synthase (EC 4.2.3.3).

As described above, it is within the skill of the person in the art to overexpress a gene coding for said enzyme in a microorganism. Preferably, this overexpression can be achieved by overexpressing a nucleotide sequence, such as a known gene or a variant thereof, encoding each enzyme. Said nucleotide sequence can be already present in the microorganism of interest, in which case it is said to be an endogenous gene and can be overexpressed according to any of the method described above. By contrast, when a microorganism does not naturally comprise genes coding for such enzymes, said microorganism can be advantageously transformed with one or more exogenous nucleotide sequences, such as genes from other microorganisms or variants thereof, which encode said enzyme(s) according to any of the method described above: said exogenous nucleotide sequences are also said to be overexpressed. A gene encoding a specific protein can be easily retrieved by the skilled practitioner by loading for example the amino-acid sequence of said protein into the UniProt or NCBI database, and by searching for the corresponding encoding nucleotide sequence which can be expressed in a particular microorganism. Moreover, it is possible and well known to the man skilled in the art how to deduce an artificial nucleotide sequence from a given amino acid sequence in order to synthetize an artificial gene encoding a specific protein of interest.

The person skilled in the art can easily determine the culture conditions necessary for growing the microorganisms according to the invention. In particular, it is well known that bacteria can be fermented at a temperature comprised between 20° C. and 55° C., preferentially between 25° C. and 40° C. *E. coli* can more particularly be cultured at a temperature comprised between about 30° C. and about 37° C.

This culturing process can be performed either in a batch process, in a fed-batch process or in a continuous process, and under aerobic, micro-aerobic or anaerobic conditions.

A fermentation "under aerobic conditions" means that oxygen is provided to the culture by dissolving gas into the liquid phase of the culture. This can be achieved by (1) sparging oxygen containing gas (e.g. air) into the liquid phase, or (2) shaking the vessel containing the culture medium in order to transfer the oxygen contained in the head space into the liquid phase. The main advantage of fermentation under aerobic conditions is that the presence of oxygen as an electron acceptor improves the capacity of the strain to produce more energy under the form of ATP for cellular processes, thereby improving the general metabolism of the strain.

Micro-aerobic conditions can be used herein and are defined as culture conditions wherein low percentages of oxygen (e.g. using a mixture of gas containing between 0.1 and 10% of oxygen, completed to 100% with nitrogen) are dissolved into the liquid phase.

By contrast, "anaerobic conditions" are defined as culture conditions wherein no oxygen is provided into the culture medium. Strict anaerobic conditions can be achieved by sparging an inert gas such as nitrogen into the culture medium to remove traces of other gas. Nitrate can be used as an electron acceptor to improve ATP production by the strain and improve its metabolism.

The above method is more particularly useful when applied to a microbial fermentation process, which is directed to the production of 1,2-propanediol, in particular to the production of (R)-1,2-propanediol. The inventors have indeed discovered that the substitution of the YqhD enzyme (native or mutated) in E. coli strains capable of producing 1,2-propanediol, with methylglyoxal reductases according to the invention greatly enhances the production of 1,2-propanediol, at a very low expression level.

Thus, in another aspect, the invention relates to a microorganism genetically modified for the production of 1,2-propanediol, wherein said microorganism overexpresses at least one gene coding for a methylglyoxal reductase according to the invention. Preferred embodiments regarding said methylglyoxal reductase are as described above.

Accordingly, since the methylglyoxal reductase according to the invention is directly used to convert methylglyoxal into hydroxyacetone, the microorganism further preferably comprises the deletion of the yqhD or yqhD* gene coding for the methylglyoxal reductase of sequence SEQ ID NO: 13 or SEQ ID NO: 15.

The substitution or deletion of the yqhD or yqhD* gene encoding the native or mutated YqhD enzyme, respectively, with one or more the methylglyoxal reductases according to the invention is particularly advantageous, as this relieves the metabolic burden associated with the expression of yqhD or yqhD* by the microorganism. Indeed, as the native or mutated YqhD enzyme enzymes have a lower catalytic efficiency than the methylglyoxal reductases according to the invention, they must be overexpressed, and may represent up to 40% of the total protein in a microorganism, imposing a significant level of stress on the cellular machinery.

The term "microorganism genetically modified for the production of 1,2-propanediol" refers herein to microorganisms modified either through the introduction or deletion of genetic elements, or through an evolution step as described in patent application WO 2005/073364. In particular, it designates a genetically modified microorganism presenting an improved 1,2-propanediol production in comparison to unmodified microorganisms, (i.e. without genetic modifications). Such microorganisms are well-known in the art, and have notably been extensively described e.g. in patents applications WO 2008/116848, WO 2008/116853, WO 2011/012693, WO 2011/012697, WO 2011/012702 or EP2532751, which are all herein incorporated by reference.

Preferred genetic modifications for the production of 1,2-propanediol, more particularly for the production of (R)1,2-propanediol, are the following:

overexpression of at least one gene selected among the mgsA gene encoding methylglyoxal synthase of sequence SEQ ID NO: 17 or a mutant thereof such as MgsA* (H21Q) of SEQ ID NO: 19, the gldA gene encoding a glycerol dehydrogenase of sequence SEQ ID NO: 21 or mutant thereof such as GldA* (A160T) (this mutant is also NADH dependent) of sequence SEQ ID NO: 23 and the fucO gene encoding lactaldehyde reductase of sequence SEQ ID NO: 25;

deletion of either the edd gene encoding phosphogluconate dehydratase of sequence SEQ ID NO: 27 and/or the eda gene encoding 2-keto-3-deoxygluconate 6-phosphate aldolase of sequence SEQ ID NO: 29;

attenuation of the synthesis of unwanted by-products by deletion of at least one of the genes coding for enzymes involved in synthesis of lactate from methylglyoxal (such as the gloA gene encoding glyoxalase I of sequence SEQ ID NO: 31, aldA gene encoding aldehyde dehydrogenase A of sequence SEQ ID NO: 33, aldB gene encoding acetaldehyde dehydrogenase B of sequence SEQ ID NO: 35), lactate from pyruvate (ldhA gene encoding lactate dehydrogenase of sequence SEQ ID NO: 37), formate (pflA gene encoding pyruvate formate lyase of sequence SEQ ID NO: 39, pflB gene encoding pyruvate formate lyase of sequence SEQ ID NO: 41), ethanol (adhE gene encoding aldehyde-alcohol dehydrogenase of sequence SEQ ID NO: 43) and acetate (ackA gene encoding acetate kinase of sequence SEQ ID NO: 45, pta gene encoding phosphate acetyltransferase of sequence SEQ ID NO: 47, poxB gene encoding pyruvate oxidase of sequence SEQ ID NO: 49);

elimination of the pathways consuming phosphoenolpyruvate (PEP) such as pyruvate kinases of sequence SEQ ID NO: 51 and SEQ ID NO: 53 (encoded by the pykA and pykF genes) and/or by promoting the synthesis of PEP e.g. by overexpressing the ppsA gene coding for PEP synthase of sequence SEQ ID NO: 55;

specific mutation in the lpd gene encoding lipoamide dehydrogenase of sequence SEQ ID NO: 57;

the arcA gene encoding the ArcA transcriptional dual regulator of sequence SEQ ID NO: 59 and the ndh gene encoding NADH:ubiquinone oxidoreductase II of sequence SEQ ID NO: 61 can be deleted;

the gapA gene encoding glyceraldehyde 3-phosphate dehydrogenase of sequence SEQ ID NO: 63 can be under the control of temperature inducible promoter;

overexpression of genes involved in the importation and metabolism of sucrose (cscB gene encoding sucrose permease of sequence SEQ ID NO: 65, cscA gene encoding sucrose hydrolase of sequence SEQ ID NO: 67, cscK gene encoding fructokinase of sequence SEQ ID NO: 69, scrA gene encoding Enzyme II of the phosphoenolpyruvate-dependent phosphotransferase system of sequence SEQ ID NO: 71, scrKgene encoding ATP-dependent fructokinase of sequence SEQ ID NO: 73, scrB gene encoding sucrose 6-phosphate hydrolase (invertase) of sequence SEQ ID NO: 75, scrY gene encoding sucrose porine of sequence SEQ ID NO: 77); and combinations thereof.

A most preferred genetic modification for the production of 1,2-propanediol, more particularly for the production of (R)1,2-propanediol, is the overexpression of the mgsA gene.

It shall be understood that these preferred genetic modifications, in particular the overexpression of the mgsA gene, can preferably be combined with the embodiments described below.

More precisely, in order to convert hydroxyacetone into 1,2-propanediol, the microorganism according to the invention preferably further overexpresses the gldA gene coding for the NADH dependent glycerol dehydrogenase of sequence SEQ ID NO: 21, or a mutant thereof coding for the NADH dependent glycerol dehydrogenase of sequence SEQ ID NO: 23. The latter is particularly advantageous over the wild-type gldA gene, since it encodes a glycerol dehydrogenase that is less inhibited by the substrate (hydroxyacetone) and products (NAD+ and 1,2-propanediol) of the reaction.

Nevertheless, the reduction of hydroxyacetone into 1,2-propanediol is not total with the enzymes of sequence SEQ ID NO: 21 and 23, notably due to the internal redox state of the cell under anaerobic conditions. In this context, it can therefore be particularly preferred to increase NADPH dependent acetol reductase activity as well as NAPDH supply.

Accordingly, in a preferred embodiment of the present invention, in order to enhance the conversion of hydroxyacetone into 1,2-propanediol, the microorganism according to the invention preferably further overexpresses at least one gene coding for a NADPH dependent acetol reductase, said NADPH dependent acetol reductase having at least 60% amino acid identity with any of the sequences SEQ ID NO: 79, SEQ ID NO: 81, SEQ ID NO: 83, SEQ ID NO: 85, SEQ ID NO: 87, and SEQ ID NO: 5.

Preferably, said NADPH dependent acetol reductase has at least 70%, 75%, 80%, 85%, 90%, 95% sequence identity to the above sequences, and more preferably has at least 96%, 97%, 98%, 99%, or 99,999% sequence identity to said sequences, provided that the activity of the enzyme is retained, albeit possibly with a different efficacy. In some cases, said NADPH dependent acetol reductase may correspond to any one of the above sequences (i.e. have 100% sequence identity).

Sequence identity between amino acid sequences can be determined by methods well-known in the art, such as by optimal alignment with the global homology alignment algorithm of Needleman and Wunsch (1970), by computerized implementations of this algorithm (such as CLUSTAL W) or by visual inspection.

Even more preferably, the NADPH dependent acetol reductase according to the invention is of sequence SEQ ID NO: 79.

NADPH dependent acetol reductase activity can further be enhanced by decreasing NADH dependent HAR activity.

Accordingly, in another preferred embodiment, in order to enhance the conversion of hydroxyacetone into 1,2-propanediol, the microorganism according to the invention can further comprise the deletion of the gldA or gldA* gene coding for the NADH dependent glycerol dehydrogenase of sequence SEQ ID NO: 21 or SEQ ID NO: 23, and/or overexpress a mutant thereof coding for a NADPH dependent glycerol dehydrogenase. It shall be understood that said embodiment can preferably be combined with the one described above, wherein NADPH dependent acetol reductase activity is increased.

As indicated above, said functional mutant has a different cofactor specificity than the wild-type GldA enzyme, since it is NADPH dependent. This can be easily achieved by the skilled practitioner by cofactor engineering (Katzberg et al., 2010).

More precisely, the change in GldA cofactor specificity can be mediated by at least one mutation at position D37. Thus, in a preferred embodiment, the amino acid residue at position D37 can be replaced by a glycine (D37G), an alanine (D37A) or a valine (D37V). In a most preferred embodiment, the amino acid residue at position D37 is replaced by a glycine (D37G).

In a preferred embodiment, the change in GldA cofactor specificity can be improved by combining a mutation at position D37 with at least one mutation at position P161. Preferably, the amino acid residue at position P161 can be replaced by a serine (P161S) or a threonine (P161T). More preferably, the amino acid residue at position P161 is replaced by a serine (P161S).

In a most preferred embodiment, the change in GldA cofactor specificity can be improved by combining mutations at positions D37 and P161 with at least one mutation at position L164. Preferably, the amino acid residue at position L164 can be replaced by an alanine (L164A), a glycine (L164G) or a valine (L164V). More preferably, the amino acid residue at position L164 is replaced by an alanine (L164A).

In a particularly preferred embodiment, the microorganism of the invention overexpresses a mutant gldA* gene encoding a NADPH dependent glycerol dehydrogenase comprising at least the following mutations: D37G, P161S and L164A, such as the enzyme of sequence SEQ ID NO: 87.

The production of 1,2-propanediol can further be improved by combining an increase in NADPH dependent acetol reductase activity as described above with an increase in NADPH availability in the cell. Strategies for increasing NADPH availability in the cell are well-known to the skilled practitioner (Lee et al., 2013).

Accordingly, in a further preferred embodiment, in order to increase NADPH availability, the microorganism of the invention can further comprise at least one of the following genetic modifications:

the overexpression of the pntAB gene operon coding for the nicotinamide nucleotide transhydrogenase of sequences SEQ ID NO: 89 and SEQ ID NO: 91, as described by WO 2012/055798A1 (incorporated herein by reference);

the attenuation of the pgi gene coding for the phosphoglucose isomerase of sequence SEQ ID NO: 93;

the attenuation of the pfkA gene coding for the phosphofructokinase of sequence SEQ ID NO: 95, as described by WO 2005/047498 (incorporated herein by reference);

the overexpression of the zwf gene coding for the glucose-6-phosphate dehydrogenase of sequence SEQ ID NO: 97, as described by Lim et al., 2002 (incorporated herein by reference);

the overexpression of the yjeF gene coding for the ADP-dependent dehydratase of sequence SEQ ID NO: 99, as described by Marbaix et al., 2011 (incorporated herein by reference);

the overexpression of the gapN gene coding for the NADP-dependent glyceraldehyde-3-phosphate dehydrogenase of sequence SEQ ID NO: 101;

the overexpression of a mutant lpd* gene coding for the NADP-dependent lipoamide dehydrogenase of sequence SEQ ID NO: 103, as described by Bocanegra et al., 1993 (incorporated herein by reference); and combinations thereof.

The microorganism of the invention can further be genetically engineered so as to exclusively convert the carbon source into hydroxyacetone, thereby attenuating or abolishing the synthesis of unwanted by-products, in particular lactate. Thus, it is a preferred embodiment of the invention to provide a microorganism as described above which further comprises the deletion of the gloA gene coding for the glyoxalase I of sequence SEQ ID NO: 31.

According to a particularly preferred embodiment, the microorganism of the invention comprises at least:

the overexpression of the mgsA or mgsA* gene coding for the methylglyoxal synthase of SEQ ID NO: 17 or 19, and a gene coding for an enzyme selected from the NADH dependent glycerol dehydrogenase of SEQ ID NO: 21 or 23 and enzymes of SEQ ID NO: 79, 81, 83, 85, 87 and 5, and the deletion of the genes gloA coding for the glyoxalase I of SEQ ID NO:31, pflAB coding for the pyruvate formate lyases of SEQ ID NO:39 and 41, adhE coding for the aldehyde alcohol dehydrogenase of SEQ ID NO: 43, ldhA coding for the lactate dehydrogenase of SEQ ID NO: 37, aldA and aldB coding for the lactaldehyde dehydrogenases of SEQ ID NO: 33 and 35, edd coding for the phosphogluconate dehydratase of SEQ ID NO: 27, arcA coding for the transcriptional dual regulator of SEQ ID NO: 59, and ndh coding for the NADH dehydrogenase of SEQ ID NO: 61.

According to an even more preferred embodiment, the microorganism of the invention comprises at least:
  the overexpression of the mgsA or mgsA* gene of SEQ ID NO: 18 or 20 and a gene chosen among the genes of SEQ ID NO: 22 or 24, and SEQ ID NO: 80, 82, 84, 86, 88 and 6, and
  the deletion of the genes gloA of SEQ ID NO: 32, pflAB of SEQ ID NO: 40 and 42, adhE of SEQ ID NO: 44, IdhA of SEQ ID NO: 37, aldA and aldB of SEQ ID NO: 34 and 36, edd of SEQ ID NO: 28, arcA of SEQ ID NO: 60, and ndh of SEQ ID NO: 62.

Preferred embodiments regarding the family, genus and/or species of said microorganism are as described above.

TABLE 1

Enzymes and genes according to the invention (n/a: not available)

| Name | Microorganism of origin | Enzyme Uniprot name | Enzyme Uniprot reference | Enzyme SEQ ID NO: | Gene RefSeq or Gen Bank reference | Gene SEQ ID NO: | Enzyme co-factor |
|---|---|---|---|---|---|---|---|
| YjgB | Escherichia coli | aldehyde reductase | P27250 | 1 | NP_418690.4 | 2 | NADPH |
| YahK | Escherichia coli | aldehyde reductase | P75691 | 3 | NP_414859.1 | 4 | NADPH |
| YhdN | Bacillus subtilis | general stress protein 69 | P80874 | 5 | NP_388834.1 | 6 | NADPH |
| Gld | Gluconobacter oxydans | putative oxido-reductase | Q5FQJ0 | 7 | WP_011253139.1 | 8 | NADPH |
| YjgB* (N240Y) | n/a | n/a | n/a | 9 | n/a | 10 | NADPH |
| YafB | Escherichia coli | 2,5-diketo-D-gluconic acid reductase B | P30863 | 11 | NP_414743.1 | 12 | NADPH |
| YqhD | Escherichia coli | alcohol dehydrogenase | Q46856 | 13 | NP_417484.1 | 14 | NADPH |
| YqhD* (G149E) | n/a | n/a | n/a | 15 | n/a | 16 | NADPH |
| MgsA | Escherichia coli | methylglyoxal synthase | P0A731 | 17 | NP_415483.2 | 18 | n/a |
| MgsA* (H21Q) | n/a | n/a | n/a | 19 | n/a | 20 | n/a |
| GldA | Escherichia coli | glycerol dehydrogenase | P0A9S5 | 21 | NP_418380.4 | 22 | NADH |
| GldA* (A160T) | n/a | n/a | n/a | 23 | n/a | 24 | NADH |
| FucO | Escherichia coli | lactaldehyde reductase | P0A9S1 | 25 | NP_417279.2 | 26 | NADH |
| Edd | Escherichia coli | phosphogluconate dehydratase | P0ADF6 | 27 | NP_416365.1 | 28 | n/a |
| Eda | Escherichia coli | 2-keto-3-deoxygluconate 6-phosphate aldolase | P0A955 | 29 | NP_416364.1 | 30 | n/a |
| GloA | Escherichia coli | lactoyl glutathione lyase | P0AC81 | 31 | NP_416168.1 | 32 | n/a |
| AldA | Escherichia coli | lactaldehyde dehydrogenase A | P25553 | 33 | NP_415933.1 | 34 | n/a |
| AldB | Escherichia coli | aldehyde dehydrogenase B | P37685 | 35 | NP_418045.4 | 36 | n/a |
| LdhA | Escherichia coli | D-lactate dehydrogenase | P52643 | 37 | NP_415898.1 | 38 | NADH |
| PflA | Escherichia coli | pyruvate formate lyase activating enzyme | P0A9N4 | 39 | NP_415422.1 | 40 | n/a |
| PflB | Escherichia coli | pyruvate formate lyase | P09373 | 41 | NP_415423.1 | 42 | n/a |
| AdhE | Escherichia coli | aldehyde-alcohol dehydrogenase | P0A9Q7 | 43 | NP_415757.1 | 44 | NADH |
| AckA | Escherichia coli | acetate kinase | P0A6A3 | 45 | NP_416799.1 | 46 | n/a |
| Pta | Escherichia coli | phosphate acetyltransferase | P0A9M8 | 47 | NP_416800.1 | 48 | n/a |

TABLE 1-continued

Enzymes and genes according to the invention (n/a: not available)

| Name | Micro-organism of origin | Enzyme Uniprot name | Enzyme Uniprot reference | Enzyme SEQ ID NO: | Gene RefSeq or Gen Bank reference | Gene SEQ ID NO: | Enzyme co-factor |
|---|---|---|---|---|---|---|---|
| PoxB | Escherichia coli | pyruvate oxidase | P07003 | 49 | NP_415392.1 | 50 | n/a |
| PykA | Escherichia coli | pyruvate kinase II | P21599 | 51 | NP_416368.1 | 52 | n/a |
| PykF | Escherichia coli | pyruvate kinase I | P0AD61 | 53 | NP_416191.1 | 54 | n/a |
| PpsA | Escherichia coli | phosphoenol pyruvate synthase | P23538 | 55 | NP_416217.1 | 56 | n/a |
| Lpd | Escherichia coli | lipoamide dehydrogenase | P0A9P0 | 57 | NP_414658.1 | 58 | n/a |
| ArcA | Escherichia coli | transcriptional dual regulator | P0A9Q1 | 59 | NP_418818.1 | 60 | n/a |
| Ndh | Escherichia coli | NADH dehydrogenase | P00393 | 61 | NP_415627.1 | 62 | n/a |
| GapA | Escherichia coli | glyceraldehyde 3-phosphate dehydrogenase | P0A9B2 | 63 | NP_416293.1 | 64 | n/a |
| CscB | Escherichia coli | sucrose permease | E0IXR1 | 65 | WP_001197025.1 | 66 | n/a |
| CscA | Escherichia coli | sucrose hydrolase | E0IXQ9 | 67 | WP_000194515.1 | 68 | n/a |
| CscK | Escherichia coli | Fructokinase | E0IXR0 | 69 | WP_001274885.1 | 70 | n/a |
| ScrA | Escherichia coli | Enzyme II of the phosphoenol pyruvate-dependent phosphotransferase system | P08470 | 71 | NG_034574.1 | 72 | n/a |
| ScrK | Escherichia coli | ATP-dependent fructokinase | P26984 | 73 | NG_034460.1 | 74 | n/a |
| ScrB | Escherichia coli | sucrose 6-phosphate hydrolase | P37075 | 75 | NG_034574.1 | 76 | n/a |
| ScrY | Escherichia coli | sucrose porine | P22340 | 77 | NG_034472.1 | 78 | n/a |
| Adh | Clostridium beijerinckii | NADP-dependent isopropanol dehydrogenase | P25984 | 79 | GenBank: AF157307.2 | 80 | NADPH |
| Adh | Thermoanae robacter-brockii | NADP-dependent isopropanol dehydrogenase | P14941 | 81 | GenBank: X64841.1 | 82 | NADPH |
| Adh1 | Entamoeba histolytica | NADP-dependent isopropanol dehydrogenase | P35630 | 83 | GenBank: M88600.1 | 84 | NADPH |
| Gld2 | Hypocrea jecorina | Glycerol 2-dehydrogenase (NADP(+)) | Q0GYU4 | 85 | GenBank: DQ422038.1 | 86 | NADPH |
| GldA* (D37G, P161S, L164A) | n/a | n/a | n/a | 87 | n/a | 88 | NADPH |
| PntA | Escherichia coli | nicotinamide nucleotide trans-hydrogenase alpha subunit | P07001 | 89 | NP_416120.1 | 90 | n/a |
| PntB | Escherichia coli | nicotinamide nucleotide trans-hydrogenase beta subunit | P0AB67 | 91 | NP_416119.1 | 92 | n/a |
| Pgi | Escherichia coli | phosphoglucose isomerase | P0A6T1 | 93 | NP_418449.1 | 94 | n/a |
| PfkA | Escherichia coli | phosphor-fructokinase | P0A796 | 95 | NP_418351.1 | 96 | n/a |
| Zwf | Escherichia coli | glucose-6-phosphate dehydrogenase | P0AC53 | 97 | NP_416366.1 | 98 | n/a |
| YjeF | Escherichia coli | ADP-dependent dehydratase | P31806 | 99 | NP_418588.1 | 100 | n/a |

TABLE 1-continued

Enzymes and genes according to the invention (n/a: not available)

| Name | Micro-organism of origin | Enzyme Uniprot name | Enzyme Uniprot reference | Enzyme SEQ ID NO: | Gene RefSeq or Gen Bank reference | Gene SEQ ID NO: | Enzyme co-factor |
|---|---|---|---|---|---|---|---|
| GapN | Streptococcus mutans | NADP-dependent glyceraldehyde-3-phosphate dehydrogenase | Q59931 | 101 | NP_721104.1 | 102 | n/a |
| Lpd* | n/a | NADP-dependent lipoamide dehydrogenase | n/a | 103 | n/a | 104 | n/a |
| YdjG* (D232E) | n/a | n/a | n/a | 105 | n/a | 106 | NADPH |
| Adh3.2 | Dickeya zeae | Group III alcohol dehydrogenase | R4Z7U3 | 107 | GenBank: HF546062.1 | 108 | NADPH |
| YdhF | Escherichia coli | Oxidoreductase YdhF | P76187 | 109 | WP_000250656.1 | 110 | NADPH |
| YeaE | Escherichia coli | Uncharacterized protein YeaE | P76234 | 111 | NP_416295.1 | 112 | NADPH |
| Gld2 | Hypocrea jecorina | Glycerol 2-dehydrogenase (NADP(+)) | Q0GYU4 | 113 | GenBank: DQ422038.1 | 114 | NADPH |
| YiaY | Escherichia coli | Probable alcohol dehydrogenase | P37686 | 115 | WP_000741518.1 | 116 | NADH |
| BudC | Klebsiella pneumoniae | Diacetyl reductase [(S)-acetoin forming] | Q48436 | 117 | WP_004151179.1 | 118 | NADH |
| YjgB* (I165V) | n/a | n/a | n/a | 125 | n/a | 126 | NADPH |
| YjgB* (Q39R/ I165V/ A296V) | n/a | n/a | n/a | 127 | n/a | 128 | NADPH |

As indicated above, the microorganism of the invention is useful for producing 1,2 propanediol, in particular (R)-1,2-propanediol.

Accordingly, in a further aspect, the present invention relates to a method for the fermentative production of 1,2-propanediol, comprising the steps of:

a) culturing, under fermentative conditions, a microorganism genetically modified for the production of 1,2-propanediol, in a culture medium comprising a carbohydrate as a source of carbon; and b) recovering 1,2-propanediol from said culture medium, wherein said microorganism overexpresses at least one gene coding for a methylglyoxal reductase as described above and efficiently converts methylglyoxal into hydroxyacetone.

The source of carbon can be preferably reduced by the microorganism so as to provide the intermediate metabolite methylglyoxal.

Preferred embodiments for the microorganism and carbon source described above apply herein mutatis mutandis.

According to a preferred embodiment, the above method further comprises the step c) of purifying the 1,2-propanediol recovered from step b). It is within the skill of the practitioner to purify the desired product from the culture medium, using conventional methods in the art, such as the ones described in patent applications WO 2011/076690 and WO 2012/130316, both incorporated herein by reference.

DRAWINGS

FIG. 1. Methylglyoxal reductase (MGR) specific activity of strains harbouring different MGR enzymes and percentages of expression of the related MGR enzymes in the related strains.

EXAMPLES

In currently available 1,2-propanediol production E. coli strains, methylglyoxal is transformed into hydroxyacetone by the methylglyoxal reductase (MGR) enzyme YqhD* (G149E). However, YqhD*(G149E) exhibits a low catalytic efficiency and must be highly expressed so as to allow the production of 1,2-propanediol (it represents up to 40% of the total proteins expressed in the strain). This high level of expression results in a metabolic burden for the microorganism, and therefore generates a stress to the cell due to deprivation of carbon and energy.

Furthermore, even if the expression level of YqhD* (G149E) was pushed at a higher expression level, its catalytic efficiency would not be sufficient to reach a maximal 1,2-propanediol production performance. Thus, in order to increase 1,2-propanediol production, it is necessary to use a methylglyoxal reductase enzyme with a higher catalytic efficiency than YqhD*(G149E). To do so, several candidate enzymes, not known for reducing methylglyoxal, were evaluated by measuring their catalytic efficiencies in vitro. The best performing enzymes were then screened for their capacity to detoxify methylglyoxal (MG) in vivo. The enzymes exhibiting the highest resistance to methylglyoxal were then introduced into a 1,2-propanediol production E. coli strain.

Material and Methods:

In the examples given below, methods well-known in the art were used to construct E. coli strains containing replicating vectors and/or various chromosomal deletions, and substitutions using homologous recombination well described by Datsenko & Wanner, (2000) for *Escherichia coli*. In the same manner, the use of plasmids or vectors to express or overexpress one or several genes in a recombinant microorganism are well-known by the man skilled in the art. Examples of suitable *E. coli* expression vectors include pTrc, pACYC184, pBR322, pUC18, pUC19, pKC30, pRep4, pHS1, pHS2, pPLc236, etc. . . . (Studier et al., 1990; and Pouwels et al., 1985)

Several protocols have been used in the following examples. Protocol 1 (chromosomal modifications by homologous recombination, selection of recombinants), protocol 2 (transduction of phage P1) and protocol 3 (antibiotic cassette excision, the resistance genes were removed when necessary) used in this invention have been fully described in patent application EP 2532751, incorporated herein by reference. Chromosomal modifications were verified by a PCR analysis with appropriate oligonucleotides that the person skilled in the art is able to design.

Protocol 4: Construction of Recombinant Plasmids

Recombinant DNA technology is described in Molecular Cloning: Sambrook and Russell (2001). Briefly, the DNA fragments were PCR amplified using oligonucleotides and appropriate genomic DNA as matrix (that the person skilled in the art will be able to define). The DNA fragments and chosen plasmid were digested with compatible restriction enzymes, then ligated and transformed into competent cells. Transformants were analysed and recombinant plasmids of interest were verified by DNA sequencing.

Example 1: Identification of New Methylglyoxal Reductase (MGR) Enzymes 1.1 Determination of the Methylglyoxal Reductase Activity of Various Candidate Enzymes 1.1.1. Construction of Strains 1 to 16

To determine the kinetic parameters of various aldehyde reductase enzymes candidates, the following strains were constructed:

TABLE 2 strains constructed and used for the determination of the kinetic parameters of 16 aldehyde reductase enzyme candidates

| Strain | | Methylglyoxal reductase enzyme | | |
|---|---|---|---|---|
| Number | Name | Uniprot Ref | Microorganism of origin | gene sequence |
| 1 | YqhD | Q46856 | E. coli | SEQ ID No14 |
| 2 | YqhD*(G149E) | — | E. coli | SEQ ID No16 |
| 3 | YafB | P30863 | E. coli | SEQ ID No12 |
| 4 | YhdN | P80874 | Bacillus subtilis | SEQ ID No6 |
| 5 | YahK | P75691 | E. coli | SEQ ID No4 |
| 6 | Gld | Q5FQJ0 | Gluconobacter oxydans | SEQ ID No8 |
| 7 | YdjG*(D232E) | — | E. coli | SEQ ID No106 |
| 8 | Adh3.2 | R4Z7U3 | Dickeya zeae | SEQ ID No108 |
| 9 | YdhF | P76187 | E. coli | SEQ ID No110 |
| 10 | YeaE | P76234 | E. coli | SEQ ID No112 |
| 11 | Gld2 | Q0GYU74 | Hypocrea jecorina | SEQ ID No114 |
| 12 | YiaY | P37686 | E. coli | SEQ ID No116 |
| 13 | BudC | Q48436 | Klebsiella pneumoniae | SEQ ID No118 |
| 14 | GldA*(A160T) | — | E. coli | SEQ ID No24 |
| 15 | YjgB | P27250 | E. coli | SEQ ID No2 |
| 16 | YjgB*(N240Y) | — | E. coli | SEQ ID No10 |
| 17 | YjgB*(I165V) | | E. coli | SEQ ID No126 |
| 18 | YjgB* (Q39R/I165V/A296V) | | E. coli | SEQ ID No128 |

The genes coding for the different putative methylglyoxal reductase enzymes were cloned into the expression plasmid pPAL7 (Biorad®) and the plasmids obtained were transformed into strain BL21(DE3)star, except for strains 2 and 7.

For strain 2, the plasmid was cloned into a BL21(DE3)star strain deleted for yqhD obtained as following. The yqhD gene was inactivated in strain MG1655 using the homologous recombination strategy (according to Protocol 1). Oligonucleotides for DyqhD: SEQ ID No 119 and 120, were used to PCR amplify the resistance cassette. The strain retained was designated MG1655 DyqhD::Cm. Finally, the DyqhD::Cm deletion was transferred by P1 phage transduction (according to Protocol 2) into the strain BL21(DE3)star and the pPAL7-yqhD*(G149E) plasmid was introduced resulting in strain 2.

For strain 7, the plasmid was cloned into a BL21(DE3)star strain deleted for ydjG obtained as following. The ydjG gene was inactivated in strain MG1655 using the homologous recombination strategy (according to Protocol 1). Oligonucleotides for DydjG: SEQ ID No 121 and 122, were used to PCR amplify the resistance cassette. The strain retained was designated MG1655 DydjG::Km. Finally, the DydjG::Km deletion was transferred by P1 phage transduction (according to Protocol 2) into the strain BL21 (DE3)star and the pPAL7-ydjG*(D232E) plasmid was introduced resulting in strain 7.

Strain 14, bearing the GldA*(A160T) enzyme, was the same as strain number 20 described in patent application EP14305691, incorporated herein by reference.

1.1.2. Overproduction of Proteins

Cultures for the overproduction of proteins were realized in a 2 L Erlenmeyer flask, using LB broth (Bertani, 1951) that was supplemented with 2.5 g/l glucose and 100 mg/L of ampicillin. An overnight preculture was used to inoculate a 500 mL culture to an $OD_{600nm}$ of about 0.15. This preculture was carried out in a 500 mL Erlenmeyer flask filled with 50 mL of LB broth that was supplemented with 2.5 g/L glucose and 100 mg/L of ampicillin. The culture was first kept on a shaker at 37° C. and 200 rpm until $OD_{600\,nm}$ was about 0.5 and then the culture was moved on a second shaker at 25° C. and 200 rpm until $OD_{600\,nm}$ was 0.6-0.8 (about one hour), before induction with 500 μM IPTG. The culture was kept at 25° C. and 200 rpm until $OD_{600\,nm}$ was around 4, and then it was stopped. Cells were centrifuged at 7000 rpm, 5 minutes at 4° C., and then stored at −20° C.

1.1.3. Protein Purification

Step 1: Preparation of Cell-Free Extracts.

About 400 mg of *E. coli* biomass was suspended in 60 ml of 100 mM potassium phosphate pH 7.6, and a protease inhibitor cocktail. The cell suspension (15 ml per conical tube) was sonicated on ice (*Bandelin sonoplus*, 70 W) in a 50 ml conical tube during 8 cycles of 30 sec with 30 sec intervals. After sonication, cells were incubated for 30 min at room temperature with 5 mM MgCl2 and 1 UI/ml of DNaseI. Cells debris were removed by centrifugation at 12000 g for 30 min at 4° C.

Step 2: Affinity Purification

Except for the strain 14, the proteins were purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated 30 min with 100 mM potassium phosphate pH 7.6, 100 mM fluoride at room temperature. The protein was eluted from the column with 2 column volumes of 100 mM potassium phosphate pH 7.6. The tag remained tightly bound to the resin and the purified protein was released. The fractions containing the protein were pooled, concentrated and loaded on a gel filtration column (Superdex 200 10/300 GL column, GE Healthcare) equilibrated with different storage buffers (Table 3). Protein concentration was measured using the Bradford protein assay.

For strain 14, the purification protocol was previously described in patent application WO 2015/173247, incorporated herein by reference.

TABLE 3

Protein storage buffer

| Enzyme | Storage buffer |
|---|---|
| YqhD | 50 mM Hepes pH 7.5 |
| YqhD*(G149E) | 50 mM Hepes pH 7.5 |
| YafB | 1M Tris-HCl pH 7 150 mM NaCl |
| YeaE | 50 mM Hepes pH 7.5 |
| YdhF | 50 mM Hepes pH 7.5 |
| YhdN | 100 mM Potassium Phosphate pH 7.6 |
| Gld2 | 100 mM MES pH 6.5 |
| YahK | 100 mM Potassium Phosphate pH 7.6 150 mM NaCl |
| Gld | 50 mM Hepes pH 7.5 |
| YdjG*(D232E) | 100 mM Potassium Phosphate pH 7.6 |
| Adh3.2 | 100 mM Potassium Phosphate pH 7.6 150 mM NaCl |
| YiaY | 100 mM Potassium Phosphate pH 7.6 150 mM NaCl |
| BudC | 100 mM Potassium Phosphate pH 7.6 150 mM NaCl |
| GldA*(A160T) | 100 mM MES pH 6.5 |
| YjgB | 100 mM Potassium Phosphate pH 7.6 150 mM NaCl |
| YjgB*(N240Y) | 100 mM Potassium Phosphate pH 7.6 150 mM NaCl |
| YjgB*(I165V) | 100 mM Potassium Phosphate pH 7.6 150 mM NaCl |
| YjgB* (Q39R/I165V/A296V) | 100 mM Potassium Phosphate pH 7.6 150 mM NaCl |

1.1.4. Determination of Kinetic Parameters of Purified Putative Methylalyoxal Reductase Enzymes Methylglyoxal reductase activity (MGR) was determined by measuring the consumption of NAD(P)H at 340 nm on a spectrophotometer at 30° C. ($\Delta_{340}$=6290 $M^{-1}$ $cm^{-1}$). The reaction mixture (1 mL) containing assay buffer and purified enzyme was incubated for 5 min at 30° C. Then, 0.1-40 mM methylglyoxal was added to start the reaction. One unit of enzyme activity was defined as the amount of enzyme catalyzing the decrease of 1 μmol of NAD(P)H per min. Kinetic parameters were determined with Sigmaplot. The kinetic parameters of the purified enzymes are provided in Table 4.

1.1.5. Determination of Reaction Product

The reaction product by the different putative enzymes from methylglyoxal (MG) was measured by GC-MS (Agilent Technologies) for the Hydroxyacetone (HA) and by UHPLC-MS/MS for the Lactaldehyde (LA) after reaction with methylbenzothiazolinone-2-hydrazone (MBTH) and $FeCl_3$. The reaction mixture (1 mL) containing assay buffer, 10 mM methylglyoxal, 5 mM NADPH and 5-10 μg of purified enzyme was incubated for 30 min at 30° C. 1 μl of the reaction product was injected. A reaction mixture without MG was prepared as a control. The reaction product of the purified enzymes is provided in Table 4.

TABLE 4

Kinetic parameters and reaction product of purified enzymes

| Enzyme | Assay buffer | Cofactor | Km mM | kcat/Km $mM^{-1}s^{-1}$ | Reaction product |
|---|---|---|---|---|---|
| YqhD | 20 mM Hepes (pH 7.5) 0.1 mM ZnSO4 | NADPH | 2.09 | 0.40 | HA |
| YqhD* (G149E) | 20 mM Hepes (pH 7.5) 0.1 mM ZnSO4 | NADPH | 2.92 | 0.80 | HA |
| YafB | 20 mM Hepes (pH 7.5) | NADPH | 8.20 | 2.06 | HA |
| YeaE | 20 mM Hepes (pH 7.5) | NADPH | 1.59 | 0.91 | ND |
| YdhF | 20 mM Hepes (pH 7.5) | NADPH | 21.8 | 0.35 | HA |
| YhdN | 20 mM Hepes (pH 7.5) 0.1 mM ZnSO4 | NADPH | 0.64 | 5.92 | HA |
| Gld2 | 10 mM sodium phosphate (pH 7) | NADPH | 7.7 | 11.1 | LA |

TABLE 4-continued

Kinetic parameters and reaction product of purified enzymes

| Enzyme | Assay buffer | Cofactor | Km mM | kcat/Km mM$^{-1}$s$^{-1}$ | Reaction product |
|---|---|---|---|---|---|
| YahK | 20 mM Hepes (pH 7.5) | NADPH | 1.41 | 8.3 | HA |
| Gld | 20 mM Hepes (pH 7.5) | NADPH | 1.10 | 8.74 | HA |
| YdjG* (D232E) | 20 mM Hepes (pH 7.5) | NADPH | 3.25 | 0.01 | HA |
| Adh3.2 | 20 mM Hepes (pH 7.5) | NADPH | 6.7 | 0.17 | HA |
| YiaY | 20 mM Hepes (pH 7.5) 0.1 mM FeSO4 | NADH | 2.84 | 0.34 | HA |
| BudC | 50 mM Imidazole (pH 7) | NADH | 74.8 | 4.2 | ND |
| GldA* (A160T) | 100 mM MES-KOH (pH 6.5) 0.1 mM FeSO4 30 mM ammonium sulfate | NADH | 3.17 | 7.8 | LA |
| YjgB | 40 mM Hepes (pH 7.5) | NADPH | 10.6 | 51.6 | HA |
| YjgB* (N240Y) | 40 mM Hepes (pH 7.5) | NADPH | 1.6 | 40.4 | ND |
| YjgB*(I165V) | 40 mM Hepes (pH 7.5) | NADPH | 5.5 | 57.02 | ND |
| YjgB* (Q39R/I165V/A296V) | 40 mM Hepes (pH 7.5) | NADPH | 0.88 | 39.9 | ND |

HA: Hydroxyacetone,
LA: Lactaldehyde,
ND: Not determined

Five enzymes producing Hydroxyacetone and having a catalytic efficiency at least two times higher than that of YqhD*(G149E) (mutated enzyme which itself has a catalytic efficiency two times higher than the native YqhD enzyme) were selected for further characterization and screening: Gld, YhdN, YafB, YahK and YjgB.

1.2. Selection of the Best Methylglyoxal Reductase Enzymes

1.2.1. Construction of Strains 17 to 23

The selected MGR enzymes were subsequently screened by cloning the corresponding genes into the modified *E. coli* strain 15: MG1655 DgloA Dedd DpflAB DldhA DadhE DgldA DyqhD constructed as following. To inactivate the glyoxalase I encoded by gloA, the phosphogluconate dehydratase encoded by edd, the pyruvate formate lyase activating enzyme and the pyruvate formate lyase encoded by pflA and pflB respectively, the lactate dehydrogenase encoded by ldhA and the alcohol dehydrogenase encoded by adhE, the DgloA, Dedd, DpflAB, DldhA and DadhE deletions described in patent application WO 2008/116852 (incorporated herein by reference) were transferred by P1 phage (according to Protocol 2) into strain MG1655 and the resistance genes were removed according to protocol 3. To inactivate the glycerol dehydrogenase encoded by gldA, the DgldA deletion described in patent application patent application WO 2015/173247 (incorporated herein by reference) was transferred by P1 phage (according to Protocol 2) into the previous strain. Finally, to inactivate the aldehyde reductase encoded by yqhD, the DyqhD::Cm deletion described above was transferred by P1 phage transduction (according to Protocol 2) into the previous strain, resulting in strain 17.

Then, the genes described in Table 5 below were expressed under defined RBS on pME101VB06 plasmid described in patent application EP 2532751 (incorporated herein by reference), and each plasmid was introduced into strain 17 resulting in strains 18 to 23.

TABLE 5 description of the methylglyoxal reductase strains 18 to 23

| Strain | Enzyme |
|---|---|
| 18 | Gld |
| 19 | YhdN |
| 20 | YafB |
| 21 | YqhD*(G149E) |
| 22 | YahK |
| 23 | YjgB |

1.2.2. Methylalyoxal Reductase Assay on Crude Extract

Methylglyoxal reductase activity (MGR) was determined by measuring the consumption of NAD(P)H at 340 nm on a spectrophotometer at 30° C. ($\lambda_{340}$=6290 M$^{-1}$ cm$^{-1}$). The reaction mixture (1 mL) containing assay buffer and crude extract was incubated for 5 min at 30° C. Then, 10 mM methylglyoxal was added to start the reaction. One unit of enzyme activity was defined as the amount of enzyme catalyzing the decrease of 1 µmol of NAD(P)H per min. Specific enzyme activity was expressed as units of enzyme activity per mg of protein. The activity value determined without substrate in the assay was subtracted.

1.2.3. Determination of Expression Level of the Methylalyoxal Reductase Enzymes In parallel to the specific activity in all strains, the expression level of the different MGR was quantified by SDS-PAGE analysis. A same quantity of crude extract was loaded on SDS-PAGE and the expression level was determined as the ratio of the band volume of the MGR relative to the total lane volume, using BioRad Image Lab™ Software.

The specific activities of these different enzymes were very different and not directed related to the expression level. For example, strain 21 shows a high expression with a low specific activity while strain 22 shows a 5 times lower expression level but a 4 times higher specific activity (FIG. 1).

1.2.4. Screening on Methylglyoxal (MG)

Since in vitro activity may not reflect real in vivo activity, strains 17 to 23 were screened for their resistance to MG on LB agar plates. Strains were cultivated at 37° C. in LB rich medium supplemented with 50 µg/mL spectinomycin, up to an OD600 nm of about 1. Then 100 µL of 0, 10$^{-1}$ or 10$^{-2}$ dilutions were plated on LB agar plates supplemented with 50 μg/mL spectinomycin, and 0, 2, 3 or 4 mM MG. Plates were incubated at 37° C. for 48 h.

Table 6 below indicates the least dilution and the highest MG concentration at which some clones grew, which gave an indication of the resistance level of the strain (the higher the MG concentration and the lower dilution for a given concentration, the higher resistance).

TABLE 6 screening on methylglyoxal of strains 17 to 23

| Strain | 17 | 18 | 19 | 20 | 21 | 22 | 23 |
|---|---|---|---|---|---|---|---|
| MGR | x | Gld | YhdN | YafB | YqhD* | YahK | YjgB |
| mM MG | 0 | 2 | 2 | 3 | 2 | 3 | 3 |
| Dilution | $10^{-2}$ | $10^{-2}$ | $10^{-2}$ | $10^{-1}$ | $10^{-2}$ | $10^{-2}$ | $10^{-2}$ |
| Resistance level | − | + | + | ++ | + | +++ | +++ |

−: no resistance;
+: medium resistance;
++: high resistance;
+++: very high resistance The YahK and YjgB enzymes allowing the better MG resistance, these candidate MGR enzymes were retained to replace YqhD*(G149E) in the MPG producing strains. The skilled practitioner would nevertheless readily understand that the enzymes Gld, YafB and YhdN, would also be suitable to replace YqhD*(G149E) in said MPG producing strains.

Example 2: Production of 1.2-Propanediol with the New Methylglyoxal Reductase (MGR) Enzymes According to the Invention 2.1. Construction of Strains 24 to 26

To inactivate the ptsG gene, the homologous recombination strategy was used (according to Protocol 1). Oligonucleotides for DptsG: SEQ ID No 123 and 124, were used to PCR amplify the resistance cassette. The strain retained was designated MG1655 DptsG::Km. The DptsG::Km deletion was transferred by P1 phage transduction (according to Protocol 2) into E. coli MPG production strain 5 described in patent application WO 2015/173247 (incorporated herein by reference), giving rise to strain 24. Thereafter, yahK and yjgB were chromosomally overexpressed under the Ptrc promoter and under defined RBS and either construction was transferred by P1 phage (according to Protocol 2) into strain 24 further modified by deleting yqhD as described in Example 1, giving rise to strain 25 for YahK and strain 26 for YjgB.

2.2. Evaluation of MPG Production Strains 1,2-propanediol production strains were cultivated in shake flasks (as described in patent application EP 2532751, incorporated herein by reference, except that glucose and xylose were used as carbon sole and 40 g·L-1 of MOPS were added in the media in order to maintain a pH above 6.0 throughout fermentation course) and in 2 L fermenters as follows:

Inocula were obtained after 24 hour precultures realised in baffled flasks containing 50 mL of minimal media (M1) completed with 10% of LB media (w:w) at 37° C.

Subsequently, 2.5 L fermentors (Pierre Guerin) were filled with 700 mL of minimal medium (M2) and were inoculated to a biomass concentration of 0.2 g·L$^{-1}$ with a preculture volume ranging between 55 to 80 mL. For the strain 26, zinc was added in the batch medium at a final concentration of 4 mg·L$^{-1}$.

The culture temperature was maintained constant at 37° C. and pH was maintained to the working value (6.8) by automatic addition of NH$_4$OH solution (10%) The initial agitation rate was set at 200 RPM and the initial airflow rate was set at 40 NL·h$^{-1}$. The dissolved oxygen concentration was maintained at values between 20 and 40%, preferentially 30% saturation by increasing the agitation and then if necessary by increasing the aeration. When it was needed, antibiotics were added at a concentration of 50 mg·L$^{-1}$ for spectinomycin.

Fedbatch media was composed of sugars (glucose/xylose; ratio 2:1) and alimentation rate was adjusted automatically to maintained a sugar concentration of 30 g·L$^{-1}$ in the fermentation broth by measuring $CO_2$ production.

Cultures were stopped after 54 hours.

TABLE 7

Composition of M1 and M2 media

| Component | M1 Concentration (g/L) | M2 Concentration (g/L) |
|---|---|---|
| Glucose | 20.00 | 21.0 |
| Xylose | 0.00 | 9.0 |
| (NH$_4$)$_2$SO$_4$ | 4.88 | 4.88 |
| Citric acid•H$_2$O | 1.70 | 0.00 |
| KH$_2$PO$_4$ | 1.65 | 6.76 |
| MgSO$_4$•7H$_2$O | 1.00 | 1.80 |
| K$_2$HPO$_4$•3H$_2$O | 0.92 | 0.00 |
| (NH$_4$)$_2$HPO$_4$ | 0.40 | 0.00 |
| Fe(III) citrate•H$_2$O | 0.1064 | 0.0000 |
| FeSO$_4$•7H$_2$O | 0.0000 | 0.1000 |
| CaCl$_2$•2H$_2$O | 0.08 | 0.08 |
| MnCl$_2$•4H$_2$O | 0.0150 | 0.0000 |
| Zn(CH$_3$COO)$_2$•2H$_2$O | 0.0130 | 0.0000 |
| Thiamine•HCl | 0.0100 | 0.0140 |
| EDTA, 2Na•2H$_2$O | 0.0084 | 0.0000 |
| H$_3$BO$_3$ | 0.0030 | 0.0000 |
| CoCl$_2$•6H$_2$O | 0.0025 | 0.0036 |
| Na$_2$MoO$_4$•2H$_2$O | 0.0025 | 0.0000 |
| CuCl$_2$•2H$_2$O | 0.0015 | 0.0000 |

1.2-propanediol (PG) and its precursor hydroxyacetone (HA) were quantified by HPLC-RID with Biorad HPX-87H column.

In shake flasks, production strains with yahKor yjgB overexpression produced more PG+HA in gram by gram of biomass than the strain with yqhD*(G149E) overexpression. In 2 L fermenters, only the strain with yjgB overexpression was better.

TABLE 8

PG + HA Yield for PG producing strains in gram PG + HA per gram of biomass.

| | Strain 24 | Strain 25 | Strain 26 |
|---|---|---|---|
| Shake flasks | 1.88 | 2.15 | 2.14 |
| 2 L fermenters | 3.25 | 3.63 | 5.42 |

The behaviour of strain 25 in 2 L fermenters was attributed to inhibition of YahK by HA.

REFERENCES

Altaras N E and Cameron D C (1999), Appl. Environ. Microbiol., 65: 1180-1185

Altaras N E and Cameron D C (2000), Biotechnol. Prog., 16: 940-946

Altschul S, Gish W, Miller W, Myers E, Lipman D J (1990). J. Mol. Biol; 215 (3): 403-410

Badia J, Ros J, Aguilar J (1985), J. Bacteriol. 161: 435-437
Bennett G N and San K Y (2001), Appl. Microbiol. Biotechnol. 55: 1-9
Berrios-Rivera S J, San K Y, Bennett G N (2003), J. Ind. Microbiol. Biotechnol., 30: 34-40
Bertani et al., 1951. J Bacteriol. 62: 293-300,
Bocanegra J, Scrutton N, Perham R (1993) Biochemistry, 32 (11): 2737-2740
Cameron DC, Altaras N E, Hoffman M L, Shaw A J (1998), Biotechnol. Prog., 14: 116-125
Carrier T & Keasling J (1999), Biotechnol Prog., 15 (1): 58-64
Datsenko K A & Wanner B L, (2000), *Proc Natl Acad Sci USA.*, 97: 6640-6645
Davis J J & Olsen G J. (2011). Mol. Biol. Evol.; 28(1):211-221
Demerec M, Adelberg E A, Clark A J, Hartmen P E (1966), Genetics, 54:61-76
Deml L, Bojak A, Steck S, Graf M, Wild J, Schirmbeck R, Wolf H, Wagner R. (2011)
Graf M, Bojak A, Deml L, Bieler K, Wolf H, Wagner R. (2000). J. Virol.; 74(22): 10/22-10826
Huang K, Rudolph F B, Bennett G N (1999), Appl. Environ. Microbiol., 65: 3244-3247
Katzberg M, Skorupa-Parachin N, Gorwa-Grauslund M, Bertau M (2010), Int. J. Mol. Sci., 11(4): 1735-1758
Ko J, Kim I, Yoo S, Min B, Kim K, Park C (2005), J. Bact., 187(16):5782-5789
Lee S, McCormick M, Lippard S, Cho U (2013), Nature, 494: 380-384
Lim S, Jung Y, Shin H, Lee Y (2002), J Biosci Bioeng., 93 (6):543-549
Marbaix A, Noel G, Detroux A, Vertommen D, Schaftingen E, Linster C (2011), J Biol Chem., 286 (48), 41246-41252
Needleman and Wunsch (1970), J. Mol. Biol., 48(3), 443-453
Neidhardt (1996) ed., *Escherichia coli* and *Salmonella*: cellular and molecular biology, 2nd ed., vol 2
Pouwels et al. Eds. (1985). Cloning Vectors. Elsevier: New York
Salis H (2011), Methods Enzymol., 498:19-42
Sambrook and Russell, (2001), Molecular Cloning: $3^{rd}$ edition, Cold Spring Harbor Laboratory Press, N Y, Vol 1, 2, 3
Segel I (1993), Enzyme kinetics, John Wiley & Sons, pp. 44-54 and 100-112
Studier et al. (1990). Gene Expression Technology: Methods in Enzymology; 185, Academic Press, San Diego, Calif.
Subedi KP, Kim I, Kim J, Min B, Park C (2008), FEMS Microbiol. Letters, 279(2):180-187

The invention claimed is:

1. A method for the fermentative conversion of methylglyoxal into hydroxyacetone, comprising the step of expressing, in a microorganism, at least one methylglyoxal reductase having a catalytic efficiency $k_{cat}$/Km equal or superior to 5 mM$^{-1}$s$^{-1}$ wherein said methylglyoxal reductase is selected from the group consisting of YjgB having the sequence of SEQ ID NO: 1, YjgB* (N240Y) having the sequence of SEQ ID NO: 9, YigB*(I165V) having the sequence of SEQ ID NO: 125 and YigB*(Q39R/I165V/A296V) having the sequence of SEQ ID NO: 127.

2. The method according to claim 1, wherein said methylglyoxal reductase is the YjgB enzyme of sequence SEQ ID NO: 1.

3. The method according to claim 2, wherein the YjgB enzyme is expressed in combination with the YahK enzyme of sequence SEQ ID NO: 3, the YhdN enzyme of sequence SEQ ID NO: 5, the Gld enzyme of sequence SEQ ID NO: 7, the YafB enzyme of sequence SEQ ID NO: 11 or the YqhD enzyme of sequence SEQ ID NO: 13.

4. A method for the fermentative production of 1,2-propanediol, comprising the steps of:
a) culturing, under fermentative conditions, a microorganism genetically modified for the production of 1,2-propanediol, in a culture medium comprising a carbohydrate as a source of carbon; and
b) recovering 1,2-propanediol from said culture medium, wherein said microorganism overexpresses at least one gene coding for a methylglyoxal reductase as defined in claim 1 and converts methylglyoxal into hydroxyacetone.

5. The method according to claim 4, further comprising the step c) of purifying the 1,2-propanediol recovered from step b).

6. The method according to claim 4, wherein said microorganism further comprises the deletion of the *yqhD* or *yqhD\** gene coding for the methylglyoxal reductase of sequence SEQ ID NO: 13 or SEQ ID NO: 15.

7. The method according to claim 4, wherein said microorganism further overexpresses the *gldA* gene coding for the NADH dependent glycerol dehydrogenase of sequence SEQ ID NO: 21, or a mutant thereof coding for a NADH dependent glycerol dehydrogenase of sequence SEQ ID NO: 23.

8. The method according to claim 4, wherein said microorganism further overexpresses at least one gene coding for a NADPH dependent acetol reductase, said NADPH dependent acetol reductase retaining enzymatic activity and having at least 90% amino acid identity with a sequence selected from the group consisting of SEQ ID NO: 79, SEQ ID NO: 81, SEQ ID NO: 83, SEQ ID NO: 85, SEQ ID NO: 87, and SEQ ID NO: 5.

9. The method according to claim 8, wherein said microorganism further comprises the deletion of the *gldA* or *gldA\** gene coding for the NADH dependent glycerol dehydrogenase of sequence SEQ ID NO: 21 or SEQ ID NO: 23, and/or overexpresses a mutant thereof coding for a NADPH dependent glycerol dehydrogenase.

10. The method according to claim 4, wherein said microorganism further comprises at least one of the following genetic modifications:
the overexpression of the *pntAB* gene operon coding for the nicotinamide nucleotide transhydrogenase of sequences SEQ ID NO: 89 and SEQ ID NO: 91,
the attenuation of the *pgi* gene coding for the phosphoglucose isomerase of sequence SEQ ID NO: 93,
the attenuation of the *pfIcA* gene coding for the phosphofructokinase of sequence SEQ ID NO: 95,
the overexpression of the *zwf* gene coding for the glucose-6-phosphate dehydrogenase of sequence SEQ ID NO: 97,
the overexpression of the *yjeF* gene coding for the ADP-dependent dehydratase of sequence SEQ ID NO: 99,
the overexpression of the *gapN* gene coding for the NADP-dependent glyceraldehyde-3-phosphate dehydrogenase of sequence SEQ ID NO: 101,
the overexpression of a mutant *lpd\** gene coding for the NADP-dependent lipoamide dehydrogenase of sequence SEQ ID NO: 103, and
combinations thereof.

11. The method according to claim 4, wherein said microorganism further comprises the deletion of the *gloA* gene coding for the glyoxalase I of sequence SEQ ID NO: 31.

12. The method according to claim 4, wherein said microorganism is selected from the group consisting of Enterobacteriaceae, Clostridiaceae, Bacillaceae, Streptomycetaceae, Corynebacteriaceae, and Saccharomycetaceae.

13. The method of claim 12, wherein said microorganism is selected from the group consisting of *Escherichia coli, Klebsiella pneumoniae, Thermoanaerobacterium thermosaccharolyticum, Clostridium sphenoides, Corynebacterium glutamicum* and *Saccharomyces cerevisiae*.

14. The method according to claim 13, wherein the microorganism is *Escherichia coli*.

15. A microorganism genetically modified for the production of 1,2-propanediol, wherein said microorganism is as defined in claim 4.

16. The method according to claim 4, wherein said microorganism further overexpresses the *mgsA* gene coding for the methylglyoxal synthase of sequence SEQ ID NO: 17 or of sequence SEQ ID NO: 19.

17. The method according to claim 4, wherein said microorganism overexpresses a mutant *gldA* gene coding for a NADPH dependent glycerol dehydrogenase comprising at least a replacement of the aspartic acid amino acid residue at position 37 of SEQ ID NO: 21 or 23 with a glycine, an alanine, or a valine.

18. The method according to claim 4, wherein said microorganism overexpresses a mutant *gldA* gene coding for a NADPH dependent glycerol dehydrogenase of sequence SEQ ID NO: 87.

19. The method according to claim 4, wherein said carbohydrate is selected from the group consisting of arabinose, fructose, galactose, glucose, lactose, maltose, sucrose, and xylose, and any mixture thereof.

\* \* \* \* \*

```
                        SEQUENCE LISTING

<160> NUMBER OF SEQ ID NOS: 128

<210> SEQ ID NO 1
<211> LENGTH: 339
<212> TYPE: PRT
<213> ORGANISM: Escherichia coli (strain K12)

<400> SEQUENCE: 1

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
```

```
                195                 200                 205
Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
290                 295                 300

Val Ala Pro Thr Thr Glu Leu Phe Pro Met Ser Lys Ile Asn Asp Ala
305                 310                 315                 320

Ile Gln His Val Arg Asp Gly Lys Ala Arg Tyr Arg Val Val Leu Lys
                325                 330                 335

Ala Asp Phe
```

<210> SEQ ID NO 2
<211> LENGTH: 1020
<212> TYPE: DNA
<213> ORGANISM: Escherichia coli (strain K12)

<400> SEQUENCE: 2

```
atgtcgatga taaaaagcta tgccgcaaaa gaagcgggcg cgaactggaa agtttatgag    60
tacgatcccg gtgagctgag gccacaagat gttgaagtgc aggtggatta ctgcgggatc   120
tgccattccg atctgtcgat gatcgataac gaatggggat tttcacaata tccgctggtt   180
gccgggcatg aggtgattgg gcgcgtggtg gcactcggga gcgccgcgca ggataaaggt   240
ttgcaggtcg gtcagcgtgt cgggattggc tggacggcgc gtagctgtgg tcactgcgac   300
gcctgtatta gcggtaatca gatcaactgc gagcaaggtg cggtgccgac gattatgaat   360
cgcggtggct tgccgagaag ttgcgtgcgc gactggcaat gggtgattcc actgccagaa   420
aatattgata tcgagtccgc cgggccgctg ttgtgcggcg tatcacggt ctttaaacca   480
ctgttgatgc accatatcac tgctaccagc cgcgttgggg taattggtat tggcgggctg   540
gggcatatcg ctataaaact tctgcacgca atgggatgcg aggtgacagc ctttagttct   600
aatccggcga agagcagga agtgctggcg atgggtgccg ataaagtggt gaatagccgc   660
gatccgcagg cactgaaagc actggcgggg cagtttgatc tcattatcaa caccgtcaac   720
gtcagcctcg actggcagcc ctatttgag gcgctgacct atggcggtaa tttccatacg   780
gtcggtgcgg ttctcacgcc gctgtctgtt ccggccttta cgttaattgc gggcgatcgc   840
agcgtctctg gttctgctac cggcacgcct tatgagctgc gtaagctgat gcgttttgcc   900
gcccgcagca aggttgcgcc gaccaccgaa ctgttcccga tgtcgaaaat taacgacgcc   960
atccagcatg tgcgcgacgg taaggcgcgt taccgcgtgg tgttgaaagc cgatttttga  1020
```

<210> SEQ ID NO 3
<211> LENGTH: 349
<212> TYPE: PRT
<213> ORGANISM: Escherichia coli (strain K12)

<400> SEQUENCE: 3

Met Lys Ile Lys Ala Val Gly Ala Tyr Ser Ala Lys Gln Pro Leu Glu

```
  1               5                   10                  15
Pro Met Asp Ile Thr Arg Arg Glu Pro Gly Pro Asn Asp Val Lys Ile
                    20                  25                  30
Glu Ile Ala Tyr Cys Gly Val Cys His Ser Asp Leu His Gln Val Arg
                35                  40                  45
Ser Glu Trp Ala Gly Thr Val Tyr Pro Cys Val Pro Gly His Glu Ile
    50                  55                  60
Val Gly Arg Val Val Ala Val Gly Asp Gln Val Glu Lys Tyr Ala Pro
65                  70                  75                  80
Gly Asp Leu Val Gly Val Gly Cys Ile Val Asp Ser Cys Lys His Cys
                85                  90                  95
Glu Glu Cys Glu Asp Gly Leu Glu Asn Tyr Cys Asp His Met Thr Gly
                100                 105                 110
Thr Tyr Asn Ser Pro Thr Pro Asp Glu Pro Gly His Thr Leu Gly Gly
                115                 120                 125
Tyr Ser Gln Gln Ile Val Val His Glu Arg Tyr Val Leu Arg Ile Arg
            130                 135                 140
His Pro Gln Glu Gln Leu Ala Ala Val Ala Pro Leu Leu Cys Ala Gly
145                 150                 155                 160
Ile Thr Thr Tyr Ser Pro Leu Arg His Trp Gln Ala Gly Pro Gly Lys
                    165                 170                 175
Lys Val Gly Val Val Gly Ile Gly Gly Leu Gly His Met Gly Ile Lys
                180                 185                 190
Leu Ala His Ala Met Gly Ala His Val Val Ala Phe Thr Thr Ser Glu
                195                 200                 205
Ala Lys Arg Glu Ala Ala Lys Ala Leu Gly Ala Asp Glu Val Val Asn
    210                 215                 220
Ser Arg Asn Ala Asp Glu Met Ala Ala His Leu Lys Ser Phe Asp Phe
225                 230                 235                 240
Ile Leu Asn Thr Val Ala Ala Pro His Asn Leu Asp Asp Phe Thr Thr
                    245                 250                 255
Leu Leu Lys Arg Asp Gly Thr Met Thr Leu Val Gly Ala Pro Ala Thr
                260                 265                 270
Pro His Lys Ser Pro Glu Val Phe Asn Leu Ile Met Lys Arg Arg Ala
            275                 280                 285
Ile Ala Gly Ser Met Ile Gly Gly Ile Pro Glu Thr Gln Glu Met Leu
        290                 295                 300
Asp Phe Cys Ala Glu His Gly Ile Val Ala Asp Ile Glu Met Ile Arg
305                 310                 315                 320
Ala Asp Gln Ile Asn Glu Ala Tyr Glu Arg Met Leu Arg Gly Asp Val
                325                 330                 335
Lys Tyr Arg Phe Val Ile Asp Asn Arg Thr Leu Thr Asp
                340                 345
```

<210> SEQ ID NO 4
<211> LENGTH: 1050
<212> TYPE: DNA
<213> ORGANISM: Escherichia coli (strain K12)

<400> SEQUENCE: 4

| | | |
|---|---|---|
| atgaagatca aagctgttgg tgcatattcc gctaaacaac cacttgaacc gatggatatc | | 60 |
| acccggcgtg aaccgggacc gaatgatgtc aaaatcgaaa tcgcttactg tggcgtttgc | | 120 |
| cattccgatc tccaccaggt ccgttccgag tgggcgggga cggtttaccc ctgcgtgccg | | 180 |

```
ggtcatgaaa ttgtggggcg tgtggtagcc gttggtgatc aggtagaaaa atatgcgccg       240
ggcgatctgg tcggtgtcgg ctgcattgtc gacagttgta acattgcga agagtgtgaa       300 gacgggttgg aaaactactg tgatcacatg accggcacct ataactcgcc gacgccggac      360
gaaccgggcc atactctggg cggctactca acagatcg tcgttcatga gcgatatgtt        420
ctgcgtattc gtcacccgca agagcagctg gcggcggtgg ctcctttgtt gtgtgcaggg      480
atcaccacgt attcgccgct acgtcactgg caggccgggc cgggtaaaaa agtgggcgtg      540
gtcggcatcg gcggtctggg acatatgggg attaagctgg cccacgcgat gggggcacat      600
gtggtggcat ttaccacttc tgaggcaaaa cgcgaagcgg caaaagcccct ggggccgat      660 gaagttgtta actcacgcaa tgccgatgag atggcggctc atctgaagag tttcgatttc      720
attttgaata cagtagctgc gccacataat ctcgacgatt ttaccacctt gctgaagcgt      780
gatggcacca tgacgctggt tggtgcgcct gcgacaccgc ataaatcgcc ggaagttttc      840
aacctgatca tgaaacgccg tgcgatagcc ggttctatga ttggcggcat tccagaaact      900
caggagatgc tcgattttg cgccgaacat ggcatcgtgg ctgatataga gatgattcgg       960
gccgatcaaa ttaatgaagc ctatgagcga atgctgcgcg tgatgtgaa atatcgttt      1020 gttatcgata atcgcacact aacagactga                                      1050

<210> SEQ ID NO 5
<211> LENGTH: 331
<212> TYPE: PRT
<213> ORGANISM: Bacillus subtilis (strain 168)

<400> SEQUENCE: 5

Met Glu Tyr Thr Ser Ile Ala Asp Thr Gly Ile Glu Ala Ser Arg Ile
1               5                   10                  15

Gly Leu Gly Thr Trp Ala Ile Gly Gly Thr Met Trp Gly Gly Thr Asp
            20                  25                  30

Glu Lys Thr Ser Ile Glu Thr Ile Arg Ala Ala Leu Asp Gln Gly Ile
        35                  40                  45

Thr Leu Ile Asp Thr Ala Pro Ala Tyr Gly Phe Gly Gln Ser Glu Glu
    50                  55                  60

Ile Val Gly Lys Ala Ile Lys Glu Tyr Gly Lys Arg Asp Gln Val Ile
65                  70                  75                  80

Leu Ala Thr Lys Thr Ala Leu Asp Trp Lys Asn Asn Gln Leu Phe Arg
                85                  90                  95

His Ala Asn Arg Ala Arg Ile Val Glu Glu Val Glu Asn Ser Leu Lys
            100                 105                 110

Arg Leu Gln Thr Asp Tyr Ile Asp Leu Tyr Gln Val His Trp Pro Asp
        115                 120                 125

Pro Leu Val Pro Ile Glu Glu Thr Ala Glu Val Met Lys Glu Leu Tyr
    130                 135                 140

Asp Ala Gly Lys Ile Arg Ala Ile Gly Val Ser Asn Phe Ser Ile Glu
145                 150                 155                 160

Gln Met Asp Thr Phe Arg Ala Val Ala Pro Leu His Thr Ile Gln Pro
                165                 170                 175

Pro Tyr Asn Leu Phe Glu Arg Glu Met Glu Glu Ser Val Leu Pro Tyr
            180                 185                 190

Ala Lys Asp Asn Lys Ile Thr Thr Leu Leu Tyr Gly Ser Leu Cys Arg
        195                 200                 205

Gly Leu Leu Thr Gly Lys Met Thr Glu Glu Tyr Thr Phe Glu Gly Asp
    210                 215                 220
```

Asp Leu Arg Asn His Asp Pro Lys Phe Gln Lys Pro Arg Phe Lys Glu
225                 230                 235                 240

Tyr Leu Ser Ala Val Asn Gln Leu Asp Lys Leu Ala Lys Thr Arg Tyr
                245                 250                 255

Gly Lys Ser Val Ile His Leu Ala Val Arg Trp Ile Leu Asp Gln Pro
            260                 265                 270

Gly Ala Asp Ile Ala Leu Trp Gly Ala Arg Lys Pro Gly Gln Leu Glu
        275                 280                 285

Ala Leu Ser Glu Ile Thr Gly Trp Thr Leu Asn Ser Glu Asp Gln Lys
    290                 295                 300

Asp Ile Asn Thr Ile Leu Glu Asn Thr Ile Ser Asp Pro Val Gly Pro
305                 310                 315                 320

Glu Phe Met Ala Pro Pro Thr Arg Glu Glu Ile
                325                 330

<210> SEQ ID NO 6
<211> LENGTH: 996
<212> TYPE: DNA
<213> ORGANISM: Bacillus subtilis (strain 168)

<400> SEQUENCE: 6
atggaatata ccagtatagc agatacagga atagaagcct ccagaatcgg cctcggcaca      60
tgggccattg gcggaacgat gtggggaggc actgacgaaa aaacatcgat tgaaacaatc     120
cgcgccgctc ttgatcaggg gattacactg attgacaccg caccggctta cggcttcggg     180
cagtccgagg aaattgtcgg aaaggcaatc aaagagtacg caaaagaga ccaggtgatt      240
ctcgcaacga aacggctct ggactggaag aacaaccagc tgttccgcca tgcgaacaga      300
gcgagaattg tagaggaagt tgagaattct ttgaagcggc ttcaaacaga ctatattgat     360
ctttatcagg tgcattggcc cgatccgctt gtgccaattg aagaaacggc tgaagtcatg     420
aaggaattat atgatgcggg aaaaatccgg gcgattggcg tcagcaattt ttcaattgag     480
caaatggata catttcgcgc cgtcgcacct ctccatacga ttcagcctcc atataatctg     540
tttgaaagag agatggaaga gagtgtcctt cctttatgcga aagataacaa gataacaaca     600
ttattatacg gcagtttatg cagagggctg ttaacaggca aatgactga agaatataca     660
tttgagggcg atgatctgcg taatcacgat ccaaaattcc agaagccccg ctttaaagag     720
tatctttctg ctgtgaatca attggataag ctggcgaaga cacgttatgg aaaatcagtg     780
attcacttgg ctgtcagatg gatcttagat cagccgggag cggatatcgc tctttgggga     840
gcaagaaagc ctgggcagct tgaggcccta tctgagatta caggctggac gctgaacagt     900
gaagatcaga agatatcaa tactatattg gaaaatacga tatcagaccc tgtcggaccg     960
gagtttatgg ccccgccgac cagagaggaa atataa                              996

<210> SEQ ID NO 7
<211> LENGTH: 332
<212> TYPE: PRT
<213> ORGANISM: Gluconobacter oxydans (strain 621H)

<400> SEQUENCE: 7

Met Ala Ser Asp Thr Ile Arg Ile Pro Gly Ile Asp Thr Pro Leu Ser
1               5                  10                  15

Arg Val Ala Leu Gly Thr Trp Ala Ile Gly Gly Trp Met Trp Gly Gly
            20                  25                  30

Pro Asp Asp Asp Asn Gly Val Arg Thr Ile His Ala Ala Leu Asp Glu

```
            35                  40                  45
Gly Ile Asn Leu Ile Asp Thr Ala Pro Val Tyr Gly Phe Gly His Ser
 50                  55                  60
Glu Glu Ile Val Gly Arg Ala Leu Ala Glu Lys Pro Asn Lys Ala His
 65                  70                  75                  80
Val Ala Thr Lys Leu Gly Leu His Trp Val Gly Glu Asp Glu Lys Asn
                 85                  90                  95
Met Lys Val Phe Arg Asp Ser Arg Pro Ala Arg Ile Arg Lys Glu Val
            100                 105                 110
Glu Asp Ser Leu Arg Arg Leu Arg Val Glu Thr Ile Asp Leu Glu Gln
        115                 120                 125
Ile His Trp Pro Asp Asp Lys Thr Pro Ile Asp Glu Ser Ala Arg Glu
130                 135                 140
Leu Gln Lys Leu His Gln Asp Gly Lys Ile Arg Ala Leu Gly Val Ser
145                 150                 155                 160
Asn Phe Ser Pro Glu Gln Met Asp Ile Phe Arg Glu Val Ala Pro Leu
                165                 170                 175
Ala Thr Ile Gln Pro Pro Leu Asn Leu Phe Glu Arg Thr Ile Glu Lys
            180                 185                 190
Asp Ile Leu Pro Tyr Ala Glu Lys His Asn Ala Val Val Leu Ala Tyr
        195                 200                 205
Gly Ala Leu Cys Arg Gly Leu Leu Thr Gly Lys Met Asn Arg Asp Thr
210                 215                 220
Thr Phe Pro Lys Asp Asp Leu Arg Ser Asn Asp Pro Lys Phe Gln Lys
225                 230                 235                 240
Pro Asn Phe Glu Lys Tyr Leu Ala Ala Met Asp Glu Phe Glu Lys Leu
                245                 250                 255
Ala Glu Lys Arg Gly Lys Ser Val Met Ala Phe Ala Val Arg Trp Val
            260                 265                 270
Leu Asp Gln Gly Pro Val Ile Ala Leu Trp Gly Ala Arg Lys Pro Gly
        275                 280                 285
Gln Val Ser Gly Val Lys Asp Val Phe Gly Trp Ser Leu Thr Asp Glu
290                 295                 300
Glu Lys Lys Ala Val Asp Asp Ile Leu Ala Arg His Val Pro Asn Pro
305                 310                 315                 320
Ile Asp Pro Thr Phe Met Ala Pro Pro Ala Arg Asp
                325                 330

<210> SEQ ID NO 8
<211> LENGTH: 999
<212> TYPE: DNA
<213> ORGANISM: artificial
<220> FEATURE:
<223> OTHER INFORMATION: codon optimized gene gld

<400> SEQUENCE: 8
atggcaagcg ataccattcg tattccgggt attgatacac cgctgagccg tgttgcactg      60
ggcacctggg caattggtgg ttggatgtgg ggtggtccgg atgatgataa tggtgttcgt     120
accattcatg cagcactgga tgaaggtatt aatctgattg ataccgctcc ggtttatggt     180
tttggtcata gcgaagaaat tgttggtcgt gcactggcag aaaaaccgaa taaagcacat     240
gttgcaacca aactgggtct gcattgggtt ggtgaagatg agaaaaacat gaaagtgttt     300
cgtgatagcc gtccggcacg tattcgtaaa gaagttgaag atagcctgcg tcgtctgcgt     360
gttgaaacca ttgatctgga acaaattcat tggcctgatg ataaaacccc gattgatgaa     420
```

```
agcgcacgtg aactgcagaa actgcatcag gatggtaaaa ttcgtgccct gggtgttagc    480
aattttagtc cggaacaaat ggatatcttt cgtgaagttg caccgctggc aaccattcag    540
cctccgctga acctgtttga acgtaccatt gaaaaagata ttctgccgta tgccgaaaaa    600
cataatgcag ttgttctggc atatggtgca ctgtgtcgtg tctgctgac cggcaaaatg     660 aatcgtgata ccacctttcc gaaagatgat ctgcgtagca atgatccgaa atttcagaaa    720
ccgaacttcg agaaatatct ggctgcaatg gatgagtttg aaaaactggc cgagaaacgt    780
ggtaaaagcg ttatggcatt tgcagttcgt tgggttctgg atcagggtcc ggttattgca    840
ctgtggggtg cacgtaaacc gggtcaggtt agcggtgtta agatgtttt tggttggagc     900 ctgaccgacg aagaaaaaaa agcagttgat gatattctgg cacgtcatgt tccgaatccg    960
attgatccga cctttatggc accgcctgca cgtgattaa                            999
```

<210> SEQ ID NO 9
<211> LENGTH: 339
<212> TYPE: PRT
<213> ORGANISM: artificial
<220> FEATURE:
<223> OTHER INFORMATION: YjgB*(N240Y)

<400> SEQUENCE: 9

```
Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
    130                 135                 140

Glu Ser Ala Gly Pro Leu Leu Cys Gly Gly Ile Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
    210                 215                 220

Leu Lys Ala Leu Ala Gly Gln Phe Asp Leu Ile Ile Asn Thr Val Tyr
225                 230                 235                 240

Val Ser Leu Asp Trp Gln Pro Tyr Phe Glu Ala Leu Thr Tyr Gly Gly
                245                 250                 255
```

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Ala Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala
305                 310                 315                 320

Ile Gln His Val Arg Asp Gly Lys Ala Arg Tyr Arg Val Val Leu Lys
                325                 330                 335

Ala Asp Phe

<210> SEQ ID NO 10
<211> LENGTH: 1020
<212> TYPE: DNA
<213> ORGANISM: artificial
<220> FEATURE:
<223> OTHER INFORMATION: yjgB*(N240Y)

<400> SEQUENCE: 10

```
atgtcgatga taaaaagcta tgccgcaaaa gaagcgggcg cgaactggaa agtttatgag      60
tacgatcccg gtgagctgag gccacaagat gttgaagtgc aggtggatta ctgcgggatc     120
tgccattccg atctgtcgat gatcgataac gaatggggat tttcacaata tccgctggtt     180
gccgggcatg aggtgattgg gcgcgtggtg gcactcggga gcgccgcgca ggataaaggt     240
ttgcaggtcg gtcagcgtgt cgggattggc tggacggcgc gtagctgtgg tcactgcgac     300
gcctgtatta gcggtaatca gatcaactgc gagcaaggtg cggtgccgac gattatgaat     360
cgcggtggct tgccgagaaa gttgcgtgcg gactggcaat gggtgattcc actgccagaa     420
aatattgata tcgagtccgc cgggccgctg ttgtgcggcg gtatcacggt ctttaaacca     480
ctgttgatgc accatatcac tgctaccagc cgcgttgggg taattggtat tggcgggctg     540
gggcatatcg ctataaaact tctgcacgca atgggatgcg aggtgacagc ctttagttct     600
aatccggcga agagcagga agtgctggcg atgggtgccg ataaagtggt gaatagccgc     660
gatccgcagg cactgaaagc actggcgggg cagtttgatc tcattatcaa caccgtctac     720
gtcagcctcg actggcagcc ctattttgag gcgctgacct atggcggtaa tttccatacg     780
gtcggtgcgg ttctcacgcc gctgtctgtt ccggccttta cgttaattgc gggcgatcgc     840
agcgtctctg gttctgctac cggcacgcct tatgagctgc gtaagctgat gcgttttgcc     900
gcccgcagca aggttgcgcc gaccaccgaa ctgttcccga tgtcgaaaat taacgacgcc     960
atccagcatg tgcgcgacgg taaggcgcgt taccgcgtgg tgttgaaagc cgattttga     1020
```

<210> SEQ ID NO 11
<211> LENGTH: 267
<212> TYPE: PRT
<213> ORGANISM: Escherichia coli (strain K12)

<400> SEQUENCE: 11

Met Ala Ile Pro Ala Phe Gly Leu Gly Thr Phe Arg Leu Lys Asp Asp
1               5                   10                  15

Val Val Ile Ser Ser Val Ile Thr Ala Leu Glu Leu Gly Tyr Arg Ala
            20                  25                  30

Ile Asp Thr Ala Gln Ile Tyr Asp Asn Glu Ala Ala Val Gly Gln Ala
        35                  40                  45

Ile Ala Glu Ser Gly Val Pro Arg His Glu Leu Tyr Ile Thr Thr Lys

```
                50                  55                  60
Ile Trp Ile Glu Asn Leu Ser Lys Asp Lys Leu Ile Pro Ser Leu Lys
 65                  70                  75                  80

Glu Ser Leu Gln Lys Leu Arg Thr Asp Tyr Val Asp Leu Thr Leu Ile
                 85                  90                  95

His Trp Pro Ser Pro Asn Asp Glu Val Ser Val Glu Glu Phe Met Gln
            100                 105                 110

Ala Leu Leu Glu Ala Lys Lys Gln Gly Leu Thr Arg Glu Ile Gly Ile
        115                 120                 125

Ser Asn Phe Thr Ile Pro Leu Met Glu Lys Ala Ile Ala Ala Val Gly
    130                 135                 140

Ala Glu Asn Ile Ala Thr Asn Gln Ile Glu Leu Ser Pro Tyr Leu Gln
145                 150                 155                 160

Asn Arg Lys Val Val Ala Trp Ala Lys Gln His Gly Ile His Ile Thr
                165                 170                 175

Ser Tyr Met Thr Leu Ala Tyr Gly Lys Ala Leu Lys Asp Glu Val Ile
            180                 185                 190

Ala Arg Ile Ala Ala Lys His Asn Ala Thr Pro Ala Gln Val Ile Leu
        195                 200                 205

Ala Trp Ala Met Gly Glu Gly Tyr Ser Val Ile Pro Ser Ser Thr Lys
    210                 215                 220

Arg Lys Asn Leu Glu Ser Asn Leu Lys Ala Gln Asn Leu Gln Leu Asp
225                 230                 235                 240

Ala Glu Asp Lys Lys Ala Ile Ala Ala Leu Asp Cys Asn Asp Arg Leu
                245                 250                 255

Val Ser Pro Glu Gly Leu Ala Pro Glu Trp Asp
            260                 265
```

<210> SEQ ID NO 12
<211> LENGTH: 804
<212> TYPE: DNA
<213> ORGANISM: Escherichia coli (strain K12)

<400> SEQUENCE: 12

```
atggctatcc ctgcatttgg tttaggtact ttccgtctga agacgacgt tgttatttca    60
tctgtgataa cggcgcttga acttggttat cgcgcaattg ataccgcaca aatctatgat   120
aacgaagccg cagtaggtca ggcgattgca gaaagtggcg tgccacgtca tgaactctac   180
atcaccacta aaatctggat tgaaaatctc agcaaagaca aattgatccc aagtctgaaa   240
gagagcctgc aaaaattgcg taccgattat gttgatctga cgctaatcca ctggccgtca   300
ccaaacgatg aagtctctgt tgaagagttt atgcaggcgc tgctggaagc caaaaaacaa   360
gggctgacgc gtgagatcgg tatttccaac ttcacgatcc cgttgatgga aaaagcgatt   420
gctgctgttg gtgctgaaaa catcgctact aaccagattg aactctctcc ttatctgcaa   480
aaccgtaaag tggttgcctg ggctaaacag cacggcatcc atattacttc ctatatgacg   540
ctggcgtatg gtaaggccct gaaagatgag gttattgctc gtatcgcagc taaacacaat   600
gcgactccgg cacaagtgat tctggcgtgg gctatggggg aaggttactc agtaattcct   660
tcttctacta acgtaaaaaa cctggaaagt aatcttaagg cacaaaattt acagcttgat   720
gccgaagata aaaagcgat cgccgcactg gattgcaacg accgcctggt tagcccggaa   780
ggtctggctc ctgaatggga ttaa                                          804
```

<210> SEQ ID NO 13

<211> LENGTH: 387
<212> TYPE: PRT
<213> ORGANISM: Escherichia coli (strain K12)

<400> SEQUENCE: 13

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
            100                 105                 110

Asn Ile Asp Pro Trp His Ile Leu Gln Thr Gly Gly Lys Glu Ile Lys
        115                 120                 125

Ser Ala Ile Pro Met Gly Cys Val Leu Thr Leu Pro Ala Thr Gly Ser
    130                 135                 140

Glu Ser Asn Ala Gly Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
```

385

<210> SEQ ID NO 14
<211> LENGTH: 1164
<212> TYPE: DNA
<213> ORGANISM: Escherichia coli (strain K12)

<400> SEQUENCE: 14

```
atgaacaact ttaatctgca caccccaacc cgcattctgt ttggtaaagg cgcaatcgct    60
ggtttacgcg aacaaattcc tcacgatgct cgcgtattga ttacctacgg cggcggcagc   120
gtgaaaaaaa ccggcgttct cgatcaagtt ctggatgccc tgaaaggcat ggacgtgctg   180
gaatttggcg gtattgagcc aaacccggct tatgaaacgc tgatgaacgc cgtgaaactg   240
gttcgcgaac agaaagtgac tttcctgctg gcggttggcg gcggttctgt actggacggc   300
accaaattta tcgccgcagc ggctaactat ccggaaaata tcgatccgtg gcacattctg   360
caaacgggcg taaagagat aaaagcgcc atcccgatgg ctgtgtgct gacgctgcca   420
gcaaccggtt cagaatccaa cgcaggcgcg gtgatctccc gtaaaaccac aggcgacaag   480
caggcgttcc attctgccca tgttcagccg gtatttgccg tgctcgatcc ggtttatacc   540
tacaccctgc cgccgcgtca ggtggctaac ggcgtagtgg acgcctttgt acacaccgtg   600
gaacagtatg ttaccaaacc ggttgatgcc aaaattcagg accgtttcgc agaaggcatt   660
ttgctgacgc taatcgaaga tggtccgaaa gccctgaaag agccagaaaa ctacgatgtg   720
cgcgccaacg tcatgtgggc ggcgactcag gcgctgaacg gtttgattgg cgctggcgta   780
ccgcaggact gggcaacgca tatgctgggc acgaactga ctgcgatgca cggtctggat   840
cacgcgcaaa cactggctat cgtcctgcct gcactgtgga tgaaaaacg cgataccaag   900
cgcgctaagc tgctgcaata tgctgaacgc gtctggaaca tcactgaagg ttccgatgat   960
gagcgtattg acgccgcgat tgccgcaacc cgcaatttct ttgagcaatt aggcgtgccg  1020
acccacctct ccgactacgg tctgacggc agctccatcc cggctttgct gaaaaaactg  1080
gaagagcacg gcatgaccca actgggcgaa atcatgaca ttacgttgga tgtcagccgc  1140
cgtatatacg aagccgcccg ctaa                                        1164
```

<210> SEQ ID NO 15
<211> LENGTH: 387
<212> TYPE: PRT
<213> ORGANISM: artificial
<220> FEATURE:
<223> OTHER INFORMATION: YqhD*(G149E)

<400> SEQUENCE: 15

```
Met Asn Asn Phe Asn Leu His Thr Pro Thr Arg Ile Leu Phe Gly Lys
1               5                   10                  15

Gly Ala Ile Ala Gly Leu Arg Glu Gln Ile Pro His Asp Ala Arg Val
            20                  25                  30

Leu Ile Thr Tyr Gly Gly Gly Ser Val Lys Lys Thr Gly Val Leu Asp
        35                  40                  45

Gln Val Leu Asp Ala Leu Lys Gly Met Asp Val Leu Glu Phe Gly Gly
    50                  55                  60

Ile Glu Pro Asn Pro Ala Tyr Glu Thr Leu Met Asn Ala Val Lys Leu
65                  70                  75                  80

Val Arg Glu Gln Lys Val Thr Phe Leu Leu Ala Val Gly Gly Gly Ser
                85                  90                  95

Val Leu Asp Gly Thr Lys Phe Ile Ala Ala Ala Ala Asn Tyr Pro Glu
```

```
               100                 105                 110
Asn Ile Asp Pro Trp His Ile Leu Gln Thr Gly Gly Lys Glu Ile Lys
            115                 120                 125

Ser Ala Ile Pro Met Gly Cys Val Leu Thr Leu Pro Ala Thr Gly Ser
        130                 135                 140

Glu Ser Asn Ala Glu Ala Val Ile Ser Arg Lys Thr Thr Gly Asp Lys
145                 150                 155                 160

Gln Ala Phe His Ser Ala His Val Gln Pro Val Phe Ala Val Leu Asp
                165                 170                 175

Pro Val Tyr Thr Tyr Thr Leu Pro Pro Arg Gln Val Ala Asn Gly Val
            180                 185                 190

Val Asp Ala Phe Val His Thr Val Glu Gln Tyr Val Thr Lys Pro Val
        195                 200                 205

Asp Ala Lys Ile Gln Asp Arg Phe Ala Glu Gly Ile Leu Leu Thr Leu
    210                 215                 220

Ile Glu Asp Gly Pro Lys Ala Leu Lys Glu Pro Glu Asn Tyr Asp Val
225                 230                 235                 240

Arg Ala Asn Val Met Trp Ala Ala Thr Gln Ala Leu Asn Gly Leu Ile
                245                 250                 255

Gly Ala Gly Val Pro Gln Asp Trp Ala Thr His Met Leu Gly His Glu
            260                 265                 270

Leu Thr Ala Met His Gly Leu Asp His Ala Gln Thr Leu Ala Ile Val
        275                 280                 285

Leu Pro Ala Leu Trp Asn Glu Lys Arg Asp Thr Lys Arg Ala Lys Leu
    290                 295                 300

Leu Gln Tyr Ala Glu Arg Val Trp Asn Ile Thr Glu Gly Ser Asp Asp
305                 310                 315                 320

Glu Arg Ile Asp Ala Ala Ile Ala Ala Thr Arg Asn Phe Phe Glu Gln
                325                 330                 335

Leu Gly Val Pro Thr His Leu Ser Asp Tyr Gly Leu Asp Gly Ser Ser
            340                 345                 350

Ile Pro Ala Leu Leu Lys Lys Leu Glu Glu His Gly Met Thr Gln Leu
        355                 360                 365

Gly Glu Asn His Asp Ile Thr Leu Asp Val Ser Arg Arg Ile Tyr Glu
    370                 375                 380

Ala Ala Arg
385

<210> SEQ ID NO 16
<211> LENGTH: 1164
<212> TYPE: DNA
<213> ORGANISM: artificial
<220> FEATURE:
<223> OTHER INFORMATION: YqhD*(G149E)

<400> SEQUENCE: 16
atgaacaact ttaatctgca caccccaacc cgcattctgt ttggtaaagg cgcaatcgct     60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
gttcgcgaac agaaagtgac tttcctgctg gcggttggcg gcggttctgt actggacggc    300
accaaattta tcgccgcagc ggctaactat ccggaaaata tcgatccgtg gcacattctg    360
caaacgggcg gtaaagagat taaaagcgcc atcccgatgg gctgtgtgct gacgctgcca    420
```

```
gcaaccggtt cagaatccaa cgcagaagcg gtgatatccc gtaaaaccac aggcgacaag    480
caggcgttcc attctgccca tgttcagccg gtatttgccg tgctcgatcc ggtttatacc    540
tacaccctgc cgccgcgtca ggtggctaac ggcgtagtgg acgcctttgt acacaccgtg    600
gaacagtatg ttaccaaacc ggttgatgcc aaaattcagg accgtttcgc agaaggcatt    660
ttgctgacgc taatcgaaga tggtccgaaa gccctgaaag agccagaaaa ctacgatgtg    720
cgcgccaacg tcatgtgggc ggcgactcag gcgctgaacg gtttgattgg cgctggcgta    780
ccacaggact gggcaacgca tatgctgggc acgaactga ctgcgatgca cggtctggat    840
cacgcgcaaa cactggctat cgtcctgcct gcactgtgga atgaaaaacg cgataccaag    900
cgcgctaagc tgctgcaata tgctgaacgc gtctggaaca tcactgaagg ttccgatgat    960
gagcgtattg acgccgcgat tgccgcaacc cgcaatttct ttgagcaatt aggcgtgccg   1020
acccacctct ccgactacgg tctggacggc agctccatcc cggctttgct gaaaaaactg   1080
gaagagcacg gcatgaccca actgggcgaa aatcacgaca ttacgttgga tgtcagccgc   1140
cgtatatacg aagccgcccg ctaa                                          1164
```

<210> SEQ ID NO 17
<211> LENGTH: 152
<212> TYPE: PRT
<213> ORGANISM: Escherichia coli (strain K12)

<400> SEQUENCE: 17

```
Met Glu Leu Thr Thr Arg Thr Leu Pro Ala Arg Lys His Ile Ala Leu
1               5                   10                  15

Val Ala His Asp His Cys Lys Gln Met Leu Met Ser Trp Val Glu Arg
                20                  25                  30

His Gln Pro Leu Leu Glu Gln His Val Leu Tyr Ala Thr Gly Thr Thr
            35                  40                  45

Gly Asn Leu Ile Ser Arg Ala Thr Gly Met Asn Val Asn Ala Met Leu
        50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150
```

<210> SEQ ID NO 18
<211> LENGTH: 459
<212> TYPE: DNA
<213> ORGANISM: Escherichia coli (strain K12)

<400> SEQUENCE: 18

```
atggaactga cgactcgcac tttacctgcg cggaaacata ttgcgctggt ggcacacgat     60
cactgcaaac aaatgctgat gagctgggtg gaacggcatc aaccgttact ggaacaacac    120
gtactgtatg caacaggcac taccggtaac ttaatttccc gcgcgaccgg catgaacgtc    180
```

```
aacgcgatgt tgagtggccc aatgggggt gaccagcagg ttggcgcatt gatctcagaa    240
gggaaaattg atgtattgat tttcttctgg gatccactaa atgccgtgcc gcacgatcct    300
gacgtgaaag ccttgctgcg tctggcgacg gtatggaaca ttccggtcgc caccaacgtg    360
gcaacggcag acttcataat ccagtcgccg catttcaacg acgcggtcga tattctgatc    420
cccgattatc agcgttatct cgcggaccgt ctgaagtaa                          459
```

<210> SEQ ID NO 19
<211> LENGTH: 152
<212> TYPE: PRT
<213> ORGANISM: artificial
<220> FEATURE:
<223> OTHER INFORMATION: MgsA* (H21Q)

<400> SEQUENCE: 19

```
Met Glu Leu Thr Thr Arg Thr Leu Pro Ala Arg Lys His Ile Ala Leu
1               5                   10                  15

Val Ala His Asp Gln Cys Lys Gln Met Leu Met Ser Trp Val Glu Arg
            20                  25                  30

His Gln Pro Leu Leu Glu Gln His Val Leu Tyr Ala Thr Gly Thr Thr
        35                  40                  45

Gly Asn Leu Ile Ser Arg Ala Thr Gly Met Asn Val Asn Ala Met Leu
    50                  55                  60

Ser Gly Pro Met Gly Gly Asp Gln Gln Val Gly Ala Leu Ile Ser Glu
65                  70                  75                  80

Gly Lys Ile Asp Val Leu Ile Phe Phe Trp Asp Pro Leu Asn Ala Val
                85                  90                  95

Pro His Asp Pro Asp Val Lys Ala Leu Leu Arg Leu Ala Thr Val Trp
            100                 105                 110

Asn Ile Pro Val Ala Thr Asn Val Ala Thr Ala Asp Phe Ile Ile Gln
        115                 120                 125

Ser Pro His Phe Asn Asp Ala Val Asp Ile Leu Ile Pro Asp Tyr Gln
    130                 135                 140

Arg Tyr Leu Ala Asp Arg Leu Lys
145                 150
```

<210> SEQ ID NO 20
<211> LENGTH: 459
<212> TYPE: DNA
<213> ORGANISM: artificial
<220> FEATURE:
<223> OTHER INFORMATION: MgsA* (H21Q)

<400> SEQUENCE: 20

```
atggaactga cgactcgcac tttacctgcg cggaaacata ttgcgctggt ggcacacgat    60
caatgcaaac agatgctgat gagctgggtg aacggcatc aaccgttact ggaacaacac    120
gtactgtatg caacaggcac taccggtaac ttaatttccc gcgcgaccgg catgaacgtc    180
aacgcgatgt tgagtggccc aatgggggt gaccagcagg ttggcgcatt gatctcagaa    240
gggaaaattg atgtattgat tttcttctgg gatccactaa atgccgtgcc gcacgatcct    300
gacgtgaaag ccttgctgcg tctggcgacg gtatggaaca ttccggtcgc caccaacgtg    360
gcaacggcag acttcataat ccagtcgccg catttcaacg acgcggtcga tattctgatc    420
cccgattatc agcgttatct cgcggaccgt ctgaagtaa                          459
```

<210> SEQ ID NO 21
<211> LENGTH: 367

<212> TYPE: PRT
<213> ORGANISM: Escherichia coli (strain K12)

<400> SEQUENCE: 21

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
130                 135                 140

Asn Asn Pro Asn Met Val Ile Val Asp Thr Lys Ile Val Ala Gly Ala
145                 150                 155                 160

Pro Ala Arg Leu Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
        210                 215                 220

Val Val Thr Pro Ala Leu Glu Arg Val Ile Glu Ala Asn Thr Tyr Leu
225                 230                 235                 240

Ser Gly Val Gly Phe Glu Ser Gly Gly Leu Ala Ala Ala His Ala Val
                245                 250                 255

His Asn Gly Leu Thr Ala Ile Pro Asp Ala His His Tyr Tyr His Gly
            260                 265                 270

Glu Lys Val Ala Phe Gly Thr Leu Thr Gln Leu Val Leu Glu Asn Ala
        275                 280                 285

Pro Val Glu Glu Ile Glu Thr Val Ala Ala Leu Ser His Ala Val Gly
290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
            340                 345                 350

Leu Val Ala Asp Gln Tyr Gly Gln Arg Phe Leu Gln Glu Trp Glu
        355                 360                 365

<210> SEQ ID NO 22
<211> LENGTH: 1104
<212> TYPE: DNA
<213> ORGANISM: Escherichia coli (strain K12)

<400> SEQUENCE: 22

```
atggaccgca ttattcaatc accgggtaaa tacatccagg gcgctgatgt gattaatcgt    60
ctgggcgaat acctgaagcc gctggcagaa cgctggttag tggtgggtga caaatttgtt   120
ttaggttttg ctcaatccac tgtcgagaaa agctttaaag atgctggact ggtagtagaa   180
attgcgccgt ttggcggtga atgttcgcaa atgagatcg accgtctgcg tggcatcgcg    240
gagactgcgc agtgtggcgc aattctcggt atcggtggcg aaaaaccct cgatactgcc    300
aaagcactgg cacatttcat gggtgttccg gtagcgatcg caccgactat cgcctctacc   360
gatgcaccgt gcagcgcatt gtctgttatc tacaccgatg agggtgagtt tgaccgctat   420
ctgctgttgc caaataaccc gaatatggtc attgtcgaca ccaaaatcgt cgctggcgca   480
cctgcacgtc tgttagcggc gggtatcggc gatgcgctgg caacctggtt tgaagcgcgt   540
gcctgctctc gtagcggcgc gaccaccatg gcgggcggca agtgcaccca ggctgcgctg   600
gcactggctg aactgtgcta acaccctg ctggaagaag cgaaaaagc gatgcttgct     660
gccgaacagc atgtagtgac tccggcgctg agcgcgtga ttgaagcgaa cacctatttg    720
agcggtgttg gttttgaaag tggtggtctg gctgcggcgc acgcagtgca taacggcctg   780
accgctatcc cggacgcgca tcactattat cacggtgaaa agtggcatt cggtacgctg    840
acgcagctgg ttctggaaaa tgcgccggtg gaggaaatcg aaaccgtagc tgcccttagc   900
catgcggtag gtttgccaat aactctcgct caactggata ttaaagaaga tgtcccggcg   960
aaaatgcgaa ttgtggcaga agcggcatgt gcagaaggtg aaaccattca acacatgcct  1020
ggcggcgcga cgccagatca ggtttacgcc gctctgctgg tagccgacca gtacggtcag  1080
cgtttcctgc aagagtggga ataa                                          1104
```

<210> SEQ ID NO 23
<211> LENGTH: 367
<212> TYPE: PRT
<213> ORGANISM: artificial
<220> FEATURE:
<223> OTHER INFORMATION: GldA*(A160T)

<400> SEQUENCE: 23

```
Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
            20                  25                  30

Leu Val Val Gly Asp Lys Phe Val Leu Gly Phe Ala Gln Ser Thr Val
        35                  40                  45

Glu Lys Ser Phe Lys Asp Ala Gly Leu Val Val Glu Ile Ala Pro Phe
    50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
            100                 105                 110

Ile Ala Pro Thr Ile Ala Ser Thr Asp Ala Pro Cys Ser Ala Leu Ser
        115                 120                 125

Val Ile Tyr Thr Asp Glu Gly Glu Phe Asp Arg Tyr Leu Leu Leu Pro
    130                 135                 140

Asn Asn Pro Asn Met Val Ile Val Asp Thr Lys Ile Val Ala Gly Thr
```

```
                145                 150                 155                 160
Pro Ala Arg Leu Leu Ala Ala Gly Ile Gly Asp Ala Leu Ala Thr Trp
                    165                 170                 175
Phe Glu Ala Arg Ala Cys Ser Arg Ser Gly Ala Thr Thr Met Ala Gly
                    180                 185                 190
Gly Lys Cys Thr Gln Ala Ala Leu Ala Leu Ala Glu Leu Cys Tyr Asn
                    195                 200                 205
Thr Leu Leu Glu Glu Gly Glu Lys Ala Met Leu Ala Ala Glu Gln His
        210                 215                 220
Val Val Thr Pro Ala Leu Glu Arg Val Ile Glu Ala Asn Thr Tyr Leu
225                 230                 235                 240
Ser Gly Val Gly Phe Glu Ser Gly Leu Ala Ala His Ala Val
                        245                 250                 255
His Asn Gly Leu Thr Ala Ile Pro Asp Ala His His Tyr Tyr His Gly
                260                 265                 270
Glu Lys Val Ala Phe Gly Thr Leu Thr Gln Leu Val Leu Glu Asn Ala
            275                 280                 285
Pro Val Glu Glu Ile Glu Thr Val Ala Ala Leu Ser His Ala Val Gly
        290                 295                 300
Leu Pro Ile Thr Leu Ala Gln Leu Asp Ile Lys Glu Asp Val Pro Ala
305                 310                 315                 320
Lys Met Arg Ile Val Ala Glu Ala Ala Cys Ala Glu Gly Glu Thr Ile
                    325                 330                 335
His Asn Met Pro Gly Gly Ala Thr Pro Asp Gln Val Tyr Ala Ala Leu
                    340                 345                 350
Leu Val Ala Asp Gln Tyr Gly Gln Arg Phe Leu Gln Glu Trp Glu
            355                 360                 365

<210> SEQ ID NO 24
<211> LENGTH: 1104
<212> TYPE: DNA
<213> ORGANISM: artificial
<220> FEATURE:
<223> OTHER INFORMATION: GldA*(A160T)

<400> SEQUENCE: 24
atggaccgca ttattcaatc accgggtaaa tacatccagg gcgctgatgt gattaatcgt      60
ctgggcgaat acctgaagcc gctggcagaa cgctggttag tggtgggtga caaatttgtt     120
ttaggttttg ctcaatccac tgtcgagaaa agctttaaag atgctggact ggtagtagaa     180
attgcgccgt ttggcggtga atgttcgcaa atgagatcg accgtctgcg tggcatcgcg     240
gagactgcgc agtgtggcgc aattctcggt atcggtggcg aaaaaccct cgatactgcc     300
aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc aaataacccc gaatatggtc attgtcgaca ccaaaatcgt cgctggcaca     480
cctgcacgtc tgctagcggc gggtatcggc gatgcgctgg caacctggtt tgaagcgcgt     540
gcctgctctc gtagcggcgc gaccaccatg gcgggcggca gtgcaccca ggctgcgctg     600
gcactggctg aactgtgcta caacaccctg ctggaagaag cgaaaaagc gatgcttgct     660
gccgaacagc atgtagtgac tccggcgctg agcgcgtga ttgaagcgaa cacctatttg     720
agcggtgttg gttttgaaag tggtggtctg gctcgcgcgc acgcagtgca taacggcctg     780
accgctatcc cggacgcgca tcactattat cacggtgaaa aagtggcatt cggtacgctg     840
```

-continued

```
acgcagctgg ttctggaaaa tgcgccggtg gaggaaatcg aaaccgtagc tgcccttagc    900
catgcggtag gtttgccaat aactctcgct caactggata ttaaagaaga tgtcccggcg    960
aaaatgcgaa ttgtggcaga agcggcatgt gcagaaggtg aaaccattca caacatgcct   1020
ggcggcgcga cgccagatca ggtttacgcc gctctgctgg tagccgacca gtacggtcag   1080
cgtttcctgc aagagtggga ataa                                          1104
```

<210> SEQ ID NO 25
<211> LENGTH: 382
<212> TYPE: PRT
<213> ORGANISM: Escherichia coli (strain K12)

<400> SEQUENCE: 25

```
Met Ala Asn Arg Met Ile Leu Asn Glu Thr Ala Trp Phe Gly Arg Gly
1               5                   10                  15

Ala Val Gly Ala Leu Thr Asp Glu Val Lys Arg Gly Tyr Gln Lys
            20                  25                  30

Ala Leu Ile Val Thr Asp Lys Thr Leu Val Gln Cys Gly Val Val Ala
        35                  40                  45

Lys Val Thr Asp Lys Met Asp Ala Ala Gly Leu Ala Trp Ala Ile Tyr
    50                  55                  60

Asp Gly Val Val Pro Asn Pro Thr Ile Thr Val Val Lys Glu Gly Leu
65                  70                  75                  80

Gly Val Phe Gln Asn Ser Gly Ala Asp Tyr Leu Ile Ala Ile Gly Gly
                85                  90                  95

Gly Ser Pro Gln Asp Thr Cys Lys Ala Ile Gly Ile Ile Ser Asn Asn
            100                 105                 110

Pro Glu Phe Ala Asp Val Arg Ser Leu Glu Gly Leu Ser Pro Thr Asn
        115                 120                 125

Lys Pro Ser Val Pro Ile Leu Ala Ile Pro Thr Thr Ala Gly Thr Ala
130                 135                 140

Ala Glu Val Thr Ile Asn Tyr Val Ile Thr Asp Glu Glu Lys Arg Arg
145                 150                 155                 160

Lys Phe Val Cys Val Asp Pro His Asp Ile Pro Gln Val Ala Phe Ile
                165                 170                 175

Asp Ala Asp Met Met Asp Gly Met Pro Pro Ala Leu Lys Ala Ala Thr
            180                 185                 190

Gly Val Asp Ala Leu Thr His Ala Ile Glu Gly Tyr Ile Thr Arg Gly
        195                 200                 205

Ala Trp Ala Leu Thr Asp Ala Leu His Ile Lys Ala Ile Glu Ile Ile
    210                 215                 220

Ala Gly Ala Leu Arg Gly Ser Val Ala Gly Asp Lys Asp Ala Gly Glu
225                 230                 235                 240

Glu Met Ala Leu Gly Gln Tyr Val Ala Gly Met Gly Phe Ser Asn Val
                245                 250                 255

Gly Leu Gly Leu Val His Gly Met Ala His Pro Leu Gly Ala Phe Tyr
            260                 265                 270

Asn Thr Pro His Gly Val Ala Asn Ala Ile Leu Leu Pro His Val Met
        275                 280                 285

Arg Tyr Asn Ala Asp Phe Thr Gly Glu Lys Tyr Arg Asp Ile Ala Arg
    290                 295                 300

Val Met Gly Val Lys Val Glu Gly Met Ser Leu Glu Glu Ala Arg Asn
305                 310                 315                 320

Ala Ala Val Glu Ala Val Phe Ala Leu Asn Arg Asp Val Gly Ile Pro
```

```
                325                 330                 335
Pro His Leu Arg Asp Val Gly Val Arg Lys Glu Asp Ile Pro Ala Leu
        340                 345                 350

Ala Gln Ala Ala Leu Asp Asp Val Cys Thr Gly Gly Asn Pro Arg Glu
    355                 360                 365

Ala Thr Leu Glu Asp Ile Val Glu Leu Tyr His Thr Ala Trp
370                 375                 380

<210> SEQ ID NO 26
<211> LENGTH: 1149
<212> TYPE: DNA
<213> ORGANISM: Escherichia coli (strain K12)

<400> SEQUENCE: 26
atggctaaca gaatgattct gaacgaaacg gcatggtttg gtcggggtgc tgttggggct        60
ttaaccgatg aggtgaaacg ccgtggttat cagaaggcgc tgatcgtcac cgataaaacg       120
ctggtgcaat gcggcgtggt ggcgaaagtg accgataaga tggatgctgc agggctggca       180
tgggcgattt acgacggcgt agtgcccaac ccaacaatta ctgtcgtcaa agaagggctc       240
ggtgtattcc agaatagcgg cgcggattac ctgatcgcta ttggtggtgg ttctccacag       300
gatacttgta aagcgattgg cattatcagc aacaacccgg agtttgccga tgtgcgtagc       360
ctggaagggc tttccccgac caataaaccc agtgtaccga ttctggcaat tcctaccaca       420
gcaggtactg cggcagaagt gaccattaac tacgtgatca ctgacgaaga gaaacggcgc       480
aagtttgttt gcgttgatcc gcatgatatc ccgcaggtgg cgtttattga cgctgacatg       540
atggatggta tgcctccagc gctgaaagct gcgacgggtg tcgatgcgct cactcatgct       600
attgaggggt atattacccg tggcgcgtgg gcgctaaccg atgcactgca cattaaagcg       660
attgaaatca ttgctggggc gctgcgagga tcggttgctg gtgataagga tgccggagaa       720
gaaatggcgc tcgggcagta tgttgcgggt atgggcttct cgaatgttgg gttagggttg       780
gtgcatggta tggcgcatcc actgggcgcg ttttataaca ctccacacgg tgttgcgaac       840
gccatcctgt taccgcatgt catgcgttat aacgctgact ttaccggtga agtaccgc         900 gatatcgcgc gcgttatggg cgtgaaagtg aaggtatga gcctggaaga ggcgcgtaat       960
gccgctgttg aagcggtgtt tgctctcaac cgtgatgtcg gtattccgcc acatttgcgt      1020
gatgttggtg tacgcaagga agacattccg gcactggcgc aggcggcact ggatgatgtt      1080
tgtaccggtg gcaacccgcg tgaagcaacg cttgaggata ttgtagagct ttaccatacc      1140
gcctggtaa                                                             1149

<210> SEQ ID NO 27
<211> LENGTH: 603
<212> TYPE: PRT
<213> ORGANISM: Escherichia coli (strain K12)

<400> SEQUENCE: 27

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60
```

Arg Asn Asn Ile Ala Ile Ile Thr Ser Tyr Asn Asp Met Leu Ser Ala
 65                  70                  75                  80

His Gln Pro Tyr Glu His Tyr Pro Glu Ile Ile Arg Lys Ala Leu His
                 85                  90                  95

Glu Ala Asn Ala Val Gly Gln Val Ala Gly Gly Val Pro Ala Met Cys
            100                 105                 110

Asp Gly Val Thr Gln Gly Gln Asp Gly Met Glu Leu Ser Leu Leu Ser
        115                 120                 125

Arg Glu Val Ile Ala Met Ser Ala Ala Val Gly Leu Ser His Asn Met
130                 135                 140

Phe Asp Gly Ala Leu Phe Leu Gly Val Cys Asp Lys Ile Val Pro Gly
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190

Ile Arg Gln Leu Tyr Ala Glu Gly Lys Val Asp Arg Met Ala Leu Leu
        195                 200                 205

Glu Ser Glu Ala Ala Ser Tyr His Ala Pro Gly Thr Cys Thr Phe Tyr
210                 215                 220

Gly Thr Ala Asn Thr Asn Gln Met Val Val Glu Phe Met Gly Met Gln
225                 230                 235                 240

Leu Pro Gly Ser Ser Phe Val His Pro Asp Ser Pro Leu Arg Asp Ala
                245                 250                 255

Leu Thr Ala Ala Ala Arg Gln Val Thr Arg Met Thr Gly Asn Gly
            260                 265                 270

Asn Glu Trp Met Pro Ile Gly Lys Met Ile Asp Glu Lys Val Val Val
        275                 280                 285

Asn Gly Ile Val Ala Leu Leu Ala Thr Gly Gly Ser Thr Asn His Thr
290                 295                 300

Met His Leu Val Ala Met Ala Arg Ala Ala Gly Ile Gln Ile Asn Trp
305                 310                 315                 320

Asp Asp Phe Ser Asp Leu Ser Asp Val Val Pro Leu Met Ala Arg Leu
                325                 330                 335

Tyr Pro Asn Gly Pro Ala Asp Ile Asn His Phe Gln Ala Ala Gly Gly
            340                 345                 350

Val Pro Val Leu Val Arg Glu Leu Leu Lys Ala Gly Leu Leu His Glu
        355                 360                 365

Asp Val Asn Thr Val Ala Gly Phe Gly Leu Ser Arg Tyr Thr Leu Glu
370                 375                 380

Pro Trp Leu Asn Asn Gly Glu Leu Asp Trp Arg Glu Gly Ala Glu Lys
385                 390                 395                 400

Ser Leu Asp Ser Asn Val Ile Ala Ser Phe Glu Gln Pro Phe Ser His
                405                 410                 415

His Gly Gly Thr Lys Val Leu Ser Gly Asn Leu Gly Arg Ala Val Met
            420                 425                 430

Lys Thr Ser Ala Val Pro Val Glu Asn Gln Val Ile Glu Ala Pro Ala
        435                 440                 445

Val Val Phe Glu Ser Gln His Asp Val Met Pro Ala Phe Glu Ala Gly
450                 455                 460

Leu Leu Asp Arg Asp Cys Val Val Val Arg His Gln Gly Pro Lys
465                 470                 475                 480

Ala Asn Gly Met Pro Glu Leu His Lys Leu Met Pro Pro Leu Gly Val

```
                    485                 490                 495
Leu Leu Asp Arg Cys Phe Lys Ile Ala Leu Val Thr Asp Gly Arg Leu
                500                 505                 510

Ser Gly Ala Ser Gly Lys Val Pro Ser Ala Ile His Val Thr Pro Glu
            515                 520                 525

Ala Tyr Asp Gly Gly Leu Leu Ala Lys Val Arg Asp Gly Asp Ile Ile
        530                 535                 540

Arg Val Asn Gly Gln Thr Gly Glu Leu Thr Leu Leu Val Asp Glu Ala
545                 550                 555                 560

Glu Leu Ala Ala Arg Glu Pro His Ile Pro Asp Leu Ser Ala Ser Arg
                565                 570                 575

Val Gly Thr Gly Arg Glu Leu Phe Ser Ala Leu Arg Glu Lys Leu Ser
            580                 585                 590

Gly Ala Glu Gln Gly Ala Thr Cys Ile Thr Phe
        595                 600

<210> SEQ ID NO 28
<211> LENGTH: 1812
<212> TYPE: DNA
<213> ORGANISM: Escherichia coli (strain K12)

<400> SEQUENCE: 28
atgaatccac aattgttacg cgtaacaaat cgaatcattg aacgttcgcg cgagactcgc    60
tctgcttatc tcgcccggat agaacaagcg aaaacttcga ccgttcatcg ttcgcagttg   120
gcatgcggta acctggcaca cggtttcgct gcctgccagc cagaagacaa agcctctttg   180
aaaagcatgt tgcgtaacaa tatcgccatc atcacctcct ataacgacat gctctccgcg   240
caccagcctt atgaacacta tccagaaatc attcgtaaag ccctgcatga agcgaatgcg   300
gttggtcagg ttgcgggcgg tgttccggcg atgtgtgatg tgtcaccca ggggcaggat    360 ggaatggaat gtcgctgct aagccgcgaa gtgatagcga tgtctgcggc ggtggggctg   420
tcccataaca tgtttgatgg tgctctgttc ctcggtgtgt gcgacaagat tgtcccgggt   480
ctgacgatgg cagccctgtc gtttggtcat ttgcctgcgg tgtttgtgcc gtctggaccg   540
atggcaagcg gtttgccaaa taagaaaaaa gtgcgtattc gccagcttta tgccgaaggt   600
aaagtggacc gcatggcctt actggagtca gaagccgcgt cttaccatgc gccgggaaca   660
tgtactttct acggtactgc caacaccaac cagatggtgg tggagtttat ggggatgcag   720
ttgccaggct cttcttttgt tcatccggat tctccgctgc gcgatgcttt gaccgccgca   780
gctgcgcgtc aggttacacg catgaccggt aatggtaatg aatggatgcc gatcggtaag   840
atgatcgatg agaaagtggt ggtgaacggt atcgttgcac tgctggcgac cggtggttcc   900
actaaccaca ccatgcacct ggtggcgatg gcgcgcgcgg ccggtattca gattaactgg   960
gatgacttct ctgacctttc tgatgttgta ccgctgatgg cacgtctcta cccgaacggt  1020
ccggccgata ttaaccactt ccaggcggca ggtggcgtac cggttctggt gcgtgaactg  1080
ctcaaagcag gcctgctgca tgaagatgtc aatacggtgg caggtttttgg tctgtctcgt  1140 tatacccttg aaccatggct gaataatggt gaactggact ggcgggaagg ggcggaaaaa  1200
tcactcgaca gcaatgtgat cgcttccttc gaacaacctt tctctcatca tggtgggaca  1260
aaagtgttaa gcggtaacct gggccgtgcg ttatgaaaaa cctctgccgt gccggttgag  1320
aaccaggtga ttgaagcgcc agcggttgtt tttgaaagcc agcatgacgt tatgccggcc  1380
tttgaagcgg gtttgctgga ccgcgattgt gtcgttgttg tccgtcatca ggggccaaaa  1440
```

```
gcgaacggaa tgccagaatt acataaactc atgccgccac ttggtgtatt attggaccgg    1500
tgtttcaaaa ttgcgttagt taccgatgga cgactctccg gcgcttcagg taaagtgccg    1560
tcagctatcc acgtaacacc agaagcctac gatggcgggc tgctggcaaa agtgcgcgac    1620
ggggacatca ttcgtgtgaa tggacagaca ggcgaactga cgctgctggt agacgaagcg    1680
gaactggctg ctcgcgaacc gcacattcct gacctgagcg cgtcacgcgt gggaacagga    1740
cgtgaattat tcagcgcctt gcgtgaaaaa ctgtccggtg ccgaacaggg cgcaacctgt    1800 atcactttt aa                                                        1812
```

<210> SEQ ID NO 29
<211> LENGTH: 213
<212> TYPE: PRT
<213> ORGANISM: Escherichia coli (strain K12)

<400> SEQUENCE: 29

```
Met Lys Asn Trp Lys Thr Ser Ala Glu Ser Ile Leu Thr Thr Gly Pro
 1               5                  10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
                85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
    130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Ala Asp Ala Leu
            180                 185                 190

Glu Ala Gly Asp Tyr Asp Arg Ile Thr Lys Leu Ala Arg Glu Ala Val
        195                 200                 205

Glu Gly Ala Lys Leu
    210
```

<210> SEQ ID NO 30
<211> LENGTH: 642
<212> TYPE: DNA
<213> ORGANISM: Escherichia coli (strain K12)

<400> SEQUENCE: 30

```
atgaaaaact ggaaaacaag tgcagaatca atcctgacca ccggcccggt tgtaccggtt      60
atcgtggtaa aaaaactgga acacgcggtg ccgatggcaa agcgttggt tgctggtggg     120 gtgcgcgttc tggaagtgac tctgcgtacc gagtgtgcag ttgacgctat ccgtgctatc     180
gccaaagaag tgcctgaagc gattgtgggt gccggtacgg tgctgaatcc acagcagctg     240
```

```
gcagaagtca ctgaagcggg tgcacagttc gcaattagcc cgggtctgac cgagccgctg    300
ctgaaagctg ctaccgaagg gactattcct ctgattccgg ggatcagcac tgtttccgaa    360
ctgatgctgg gtatggacta cggtttgaaa gagttcaaat tcttcccggc tgaagctaac    420
ggcggcgtga aagccctgca ggcgatcgcg ggtccgttct cccaggtccg tttctgcccg    480
acgggtggta tttctccggc taactaccgt gactacctgg cgctgaaaag cgtgctgtgc    540
atcggtggtt cctggctggt tccggcagat gcgctggaag cgggcgatta cgaccgcatt    600
actaagctgg cgcgtgaagc tgtagaaggc gctaagctgt aa                      642
```

<210> SEQ ID NO 31
<211> LENGTH: 135
<212> TYPE: PRT
<213> ORGANISM: Escherichia coli (strain K12)

<400> SEQUENCE: 31

```
Met Arg Leu Leu His Thr Met Leu Arg Val Gly Asp Leu Gln Arg Ser
1               5                   10                  15

Ile Asp Phe Tyr Thr Lys Val Leu Gly Met Lys Leu Leu Arg Thr Ser
            20                  25                  30

Glu Asn Pro Glu Tyr Lys Tyr Ser Leu Ala Phe Val Gly Tyr Gly Pro
        35                  40                  45

Glu Thr Glu Glu Ala Val Ile Glu Leu Thr Tyr Asn Trp Gly Val Asp
    50                  55                  60

Lys Tyr Glu Leu Gly Thr Ala Tyr Gly His Ile Ala Leu Ser Val Asp
65                  70                  75                  80

Asn Ala Ala Glu Ala Cys Glu Lys Ile Arg Gln Asn Gly Gly Asn Val
                85                  90                  95

Thr Arg Glu Ala Gly Pro Val Lys Gly Gly Thr Thr Val Ile Ala Phe
            100                 105                 110

Val Glu Asp Pro Asp Gly Tyr Lys Ile Glu Leu Ile Glu Glu Lys Asp
        115                 120                 125

Ala Gly Arg Gly Leu Gly Asn
    130                 135
```

<210> SEQ ID NO 32
<211> LENGTH: 408
<212> TYPE: DNA
<213> ORGANISM: Escherichia coli (strain K12)

<400> SEQUENCE: 32

```
atgcgtcttc ttcataccat gctgcgcgtt ggcgatttgc aacgctccat cgatttttat     60
accaaagtgc tgggcatgaa actgctgcgt accagcgaaa acccggaata caaatactca    120
ctggcgtttg ttggctacgg cccggaaacc gaagaagcgg tgattgaact gacctacaac    180
tggggcgtgg ataaatacga actcggcact gcttatggtc acatcgcgct agcgtagat     240 aacgccgctg aagcgtgcga aaaaatccgt caaaacgggg gtaacgtgac ccgtgaagcg    300
ggtccggtaa aaggcggtac tacggttatc gcgtttgtgg aagatccgga cggttacaaa    360
attgagttaa tcgaagagaa agacgccggt cgcggtctgg caactaa                  408
```

<210> SEQ ID NO 33
<211> LENGTH: 479
<212> TYPE: PRT
<213> ORGANISM: Escherichia coli (strain K12)

<400> SEQUENCE: 33

```
Met Ser Val Pro Val Gln His Pro Met Tyr Ile Asp Gly Gln Phe Val
1               5                   10                  15

Thr Trp Arg Gly Asp Ala Trp Ile Asp Val Val Asn Pro Ala Thr Glu
            20                  25                  30

Ala Val Ile Ser Arg Ile Pro Asp Gly Gln Ala Glu Asp Ala Arg Lys
        35                  40                  45

Ala Ile Asp Ala Ala Glu Arg Ala Gln Pro Glu Trp Glu Ala Leu Pro
50                  55                  60

Ala Ile Glu Arg Ala Ser Trp Leu Arg Lys Ile Ser Ala Gly Ile Arg
65                  70                  75                  80

Glu Arg Ala Ser Glu Ile Ser Ala Leu Ile Val Glu Glu Gly Gly Lys
                85                  90                  95

Ile Gln Gln Leu Ala Glu Val Glu Val Ala Phe Thr Ala Asp Tyr Ile
            100                 105                 110

Asp Tyr Met Ala Glu Trp Ala Arg Arg Tyr Glu Gly Glu Ile Ile Gln
        115                 120                 125

Ser Asp Arg Pro Gly Glu Asn Ile Leu Leu Phe Lys Arg Ala Leu Gly
130                 135                 140

Val Thr Thr Gly Ile Leu Pro Trp Asn Phe Pro Phe Leu Ile Ala
145                 150                 155                 160

Arg Lys Met Ala Pro Ala Leu Leu Thr Gly Asn Thr Ile Val Ile Lys
                165                 170                 175

Pro Ser Glu Phe Thr Pro Asn Asn Ala Ile Ala Phe Ala Lys Ile Val
            180                 185                 190

Asp Glu Ile Gly Leu Pro Arg Gly Val Phe Asn Leu Val Leu Gly Arg
        195                 200                 205

Gly Glu Thr Val Gly Gln Glu Leu Ala Gly Asn Pro Lys Val Ala Met
210                 215                 220

Val Ser Met Thr Gly Ser Val Ser Ala Gly Glu Lys Ile Met Ala Thr
225                 230                 235                 240

Ala Ala Lys Asn Ile Thr Lys Val Cys Leu Glu Leu Gly Gly Lys Ala
                245                 250                 255

Pro Ala Ile Val Met Asp Asp Ala Asp Leu Glu Leu Ala Val Lys Ala
            260                 265                 270

Ile Val Asp Ser Arg Val Ile Asn Ser Gly Gln Val Cys Asn Cys Ala
        275                 280                 285

Glu Arg Val Tyr Val Gln Lys Gly Ile Tyr Asp Gln Phe Val Asn Arg
290                 295                 300

Leu Gly Glu Ala Met Gln Ala Val Gln Phe Gly Asn Pro Ala Glu Arg
305                 310                 315                 320

Asn Asp Ile Ala Met Gly Pro Leu Ile Asn Ala Ala Leu Glu Arg
                325                 330                 335

Val Glu Gln Lys Val Ala Arg Val Glu Glu Gly Ala Arg Val Ala
            340                 345                 350

Phe Gly Gly Lys Ala Val Glu Gly Lys Gly Tyr Tyr Pro Pro Thr
        355                 360                 365

Leu Leu Leu Asp Val Arg Gln Glu Met Ser Ile Met His Glu Glu Thr
370                 375                 380

Phe Gly Pro Val Leu Pro Val Val Ala Phe Asp Thr Leu Glu Asp Ala
385                 390                 395                 400

Ile Ser Met Ala Asn Asp Ser Asp Tyr Gly Leu Thr Ser Ser Ile Tyr
                405                 410                 415
```

Thr Gln Asn Leu Asn Val Ala Met Lys Ala Ile Lys Gly Leu Lys Phe
            420                 425                 430

Gly Glu Thr Tyr Ile Asn Arg Glu Asn Phe Glu Ala Met Gln Gly Phe
            435                 440                 445

His Ala Gly Trp Arg Lys Ser Gly Ile Gly Gly Ala Asp Gly Lys His
            450                 455                 460

Gly Leu His Glu Tyr Leu Gln Thr Gln Val Val Tyr Leu Gln Ser
465                 470                 475

<210> SEQ ID NO 34
<211> LENGTH: 1440
<212> TYPE: DNA
<213> ORGANISM: Escherichia coli (strain K12)

<400> SEQUENCE: 34

| | | | | | |
|---|---|---|---|---|---|
| atgtcagtac | ccgttcaaca | tcctatgtat | atcgatggac | agtttgttac | ctggcgtgga | 60 |
| gacgcatgga | ttgatgtggt | aaaccctgct | acagaggctg | tcatttcccg | catacccgat | 120 |
| ggtcaggccg | aggatgcccg | taaggcaatc | gatgcagcga | acgtgcaca | accagaatgg | 180 |
| gaagcgttgc | ctgctattga | cgcgccagt | tggttgcgca | aaatctccgc | cgggatccgc | 240 |
| gaacgcgcca | gtgaaatcag | tgcgctgatt | gttgaagaag | ggggcaagat | ccagcagctg | 300 |
| gctgaagtcg | aagtggcttt | tactgccgac | tatatcgatt | acatggcgga | gtgggcacgg | 360 |
| cgttacgagg | cgagattat | tcaaagcgat | cgtccaggaa | aaatattct | tttgtttaaa | 420 |
| cgtgcgcttg | gtgtgactac | cggcattctg | ccgtggaact | tcccgttctt | cctcattgcc | 480 |
| cgcaaaatgg | ctcccgctct | tttgaccggt | aataccatcg | tcattaaacc | tagtgaattt | 540 |
| acgccaaaca | atgcgattgc | attcgccaaa | atcgtcgatg | aaataggcct | tccgcgcggc | 600 |
| gtgtttaacc | ttgtactggg | cgtggtgaa | accgttgggc | aagaactggc | gggtaaccca | 660 |
| aaggtcgcaa | tggtcagtat | gacaggcagc | gtctctgcag | gtgagaagat | catggcgact | 720 |
| gcggcgaaaa | acatcaccaa | agtgtgtctg | gaattgggg | gtaaagcacc | agctatcgta | 780 |
| atggacgatg | ccgatcttga | actggcagtc | aaagccatcg | ttgattcacg | cgtcattaat | 840 |
| agtgggcaag | tgtgtaactg | tgcagaacgt | gtttatgtac | agaaaggcat | ttatgatcag | 900 |
| ttcgtcaatc | ggctgggtga | agcgatgcag | gcggttcaat | ttggtaaccc | cgctgaacgc | 960 |
| aacgacattg | cgatggggcc | gttgattaac | gccgcggcgc | tggaaagggt | cgagcaaaaa | 1020 |
| gtggcgcgcg | cagtagaaga | aggggcgaga | gtggcgttcg | gtggcaaagc | ggtagagggg | 1080 |
| aaaggatatt | attatccgcc | gacattgctg | ctggatgttc | gccaggaaat | gtcgattatg | 1140 |
| catgaggaaa | cctttggccc | ggtgctgcca | gttgtcgcat | ttgacacgct | ggaagatgct | 1200 |
| atctcaatgg | ctaatgacag | tgattacggc | ctgacctcat | caatctatac | ccaaaatctg | 1260 |
| aacgtcgcga | tgaaagccat | taaagggctg | aagtttggtg | aaacttacat | caaccgtgaa | 1320 |
| aacttcgaag | ctatgcaagg | cttccacgcc | ggatggcgta | aatccggtat | tggcggcgca | 1380 |
| gatggtaaac | atggcttgca | tgaatatctg | cagacccagg | tggtttattt | acagtcttaa | 1440 |

<210> SEQ ID NO 35
<211> LENGTH: 512
<212> TYPE: PRT
<213> ORGANISM: Escherichia coli (strain K12)

<400> SEQUENCE: 35

Met Thr Asn Asn Pro Pro Ser Ala Gln Ile Lys Pro Gly Glu Tyr Gly
1               5                   10                  15

-continued

```
Phe Pro Leu Lys Leu Lys Ala Arg Tyr Asp Asn Phe Ile Gly Gly Glu
             20                  25                  30

Trp Val Ala Pro Ala Asp Gly Glu Tyr Tyr Gln Asn Leu Thr Pro Val
         35                  40                  45

Thr Gly Gln Leu Leu Cys Glu Val Ala Ser Ser Gly Lys Arg Asp Ile
     50                  55                  60

Asp Leu Ala Leu Asp Ala Ala His Lys Val Lys Asp Lys Trp Ala His
 65                  70                  75                  80

Thr Ser Val Gln Asp Arg Ala Ala Ile Leu Phe Lys Ile Ala Asp Arg
                 85                  90                  95

Met Glu Gln Asn Leu Glu Leu Leu Ala Thr Ala Glu Thr Trp Asp Asn
             100                 105                 110

Gly Lys Pro Ile Arg Glu Thr Ser Ala Ala Asp Val Pro Leu Ala Ile
         115                 120                 125

Asp His Phe Arg Tyr Phe Ala Ser Cys Ile Arg Ala Gln Glu Gly Gly
     130                 135                 140

Ile Ser Glu Val Asp Ser Glu Thr Val Ala Tyr His Phe His Glu Pro
145                 150                 155                 160

Leu Gly Val Val Gly Gln Ile Ile Pro Trp Asn Phe Pro Leu Leu Met
                 165                 170                 175

Ala Ser Trp Lys Met Ala Pro Ala Leu Ala Ala Gly Asn Cys Val Val
             180                 185                 190

Leu Lys Pro Ala Arg Leu Thr Pro Leu Ser Val Leu Leu Leu Met Glu
         195                 200                 205

Ile Val Gly Asp Leu Leu Pro Pro Gly Val Val Asn Val Val Asn Gly
     210                 215                 220

Ala Gly Gly Val Ile Gly Glu Tyr Leu Ala Thr Ser Lys Arg Ile Ala
225                 230                 235                 240

Lys Val Ala Phe Thr Gly Ser Thr Glu Val Gly Gln Gln Ile Met Gln
                 245                 250                 255

Tyr Ala Thr Gln Asn Ile Ile Pro Val Thr Leu Glu Leu Gly Gly Lys
             260                 265                 270

Ser Pro Asn Ile Phe Phe Ala Asp Val Met Asp Glu Glu Asp Ala Phe
         275                 280                 285

Phe Asp Lys Ala Leu Glu Gly Phe Ala Leu Phe Ala Phe Asn Gln Gly
     290                 295                 300

Glu Val Cys Thr Cys Pro Ser Arg Ala Leu Val Gln Glu Ser Ile Tyr
305                 310                 315                 320

Glu Arg Phe Met Glu Arg Ala Ile Arg Arg Val Glu Ser Ile Arg Ser
                 325                 330                 335

Gly Asn Pro Leu Asp Ser Val Thr Gln Met Gly Ala Gln Val Ser His
             340                 345                 350

Gly Gln Leu Glu Thr Ile Leu Asn Tyr Ile Asp Ile Gly Lys Lys Glu
         355                 360                 365

Gly Ala Asp Val Leu Thr Gly Gly Arg Arg Lys Leu Leu Glu Gly Glu
     370                 375                 380

Leu Lys Asp Gly Tyr Tyr Leu Glu Pro Thr Ile Leu Phe Gly Gln Asn
385                 390                 395                 400

Asn Met Arg Val Phe Gln Glu Glu Ile Phe Gly Pro Val Leu Ala Val
                 405                 410                 415

Thr Thr Phe Lys Thr Met Glu Glu Ala Leu Glu Leu Ala Asn Asp Thr
             420                 425                 430

Gln Tyr Gly Leu Gly Ala Gly Val Trp Ser Arg Asn Gly Asn Leu Ala
```

```
              435                 440                 445
Tyr Lys Met Gly Arg Gly Ile Gln Ala Gly Arg Val Trp Thr Asn Cys
        450                 455                 460

Tyr His Ala Tyr Pro Ala His Ala Ala Phe Gly Gly Tyr Lys Gln Ser
465                 470                 475                 480

Gly Ile Gly Arg Glu Thr His Lys Met Met Leu Glu His Tyr Gln Gln
                485                 490                 495

Thr Lys Cys Leu Leu Val Ser Tyr Ser Asp Lys Pro Leu Gly Leu Phe
        500                 505                 510
```

<210> SEQ ID NO 36
<211> LENGTH: 1539
<212> TYPE: DNA
<213> ORGANISM: Escherichia coli (strain K12)

<400> SEQUENCE: 36

| | | | | | |
|---|---|---|---|---|---|
| atgaccaata | atccccttc | agcacagatt | aagcccggcg | agtatggttt | ccccctcaag | 60 |
| ttaaaagccc | gctatgacaa | ctttattggc | ggcgaatggg | tagcccctgc | cgacggcgag | 120 |
| tattaccaga | atctgacgcc | ggtgaccggg | cagctgctgt | gcgaagtggc | gtcttcgggc | 180 |
| aaacgagaca | tcgatctggc | gctggatgct | gcgcacaaag | tgaaagataa | atgggcgcac | 240 |
| acctcggtgc | aggatcgtgc | ggcgattctg | tttaagattg | ccgatcgaat | ggaacaaaac | 300 |
| ctcgagctgt | tagcgacagc | tgaaacctgg | ataacggca | aacccattcg | cgaaaccagt | 360 |
| gctgcggatg | taccgctggc | gattgaccat | tccgctatt | cgcctcgtg | tattcgggcg | 420 |
| caggaaggtg | ggatcagtga | agttgatagc | gaaaccgtgg | cctatcattt | ccatgaaccg | 480 |
| ttaggcgtgg | tggggcagat | tatcccgtgg | aacttcccgc | tgctgatggc | gagctggaaa | 540 |
| atggctcccg | cgctggcggc | gggcaactgt | gtggtgctga | acccgcacg | tcttaccccg | 600 |
| cttttctgtac | tgctgctaat | ggaaattgtc | ggtgatttac | tgccgccggg | cgtggtgaac | 660 |
| gtggtcaatg | cgcaggtgg | ggtaattggc | gaatatctgg | cgacctcgaa | acgcatcgcc | 720 |
| aaagtggcgt | ttaccggctc | aacggaagtg | ggccaacaaa | ttatgcaata | cgcaacgcaa | 780 |
| aacattattc | cggtgacgct | ggagttgggc | ggtaagtcgc | caaatatctt | ctttgctgat | 840 |
| gtgatggatg | aagaagatgc | cttttcgat | aaagcgctgg | aaggctttgc | actgtttgcc | 900 |
| tttaaccagg | cgaagtttg | cacctgtccg | agtcgtgctt | tagtgcagga | atctatctac | 960 |
| gaacgcttta | tggaacgcgc | catccgccgt | gtcgaaagca | ttcgtagcgg | taacccgctc | 1020 |
| gacagcgtga | cgcaaatggg | cgcgcaggtt | tctcacgggc | aactggaaac | catcctcaac | 1080 |
| tacattgata | tcggtaaaaa | agagggcgct | gacgtgctca | caggcgggcg | cgcaagctg | 1140 |
| ctggaaggtg | aactgaaaga | cggctactac | ctcgaaccga | cgattctgtt | tggtcagaac | 1200 |
| aatatgcggg | tgttccagga | ggagattttt | ggcccggtgc | tggcggtgac | caccttcaaa | 1260 |
| acgatggaag | aagcgctgga | gctggcgaac | gatacgcaat | atggcctggg | cgcgggcgtc | 1320 |
| tggagccgca | acggtaatct | ggcctataag | atggggcgcg | gcatacaggc | tgggcgcgtg | 1380 |
| tggaccaact | gttatcacgc | ttacccggca | catgcggcgt | ttggtggcta | caaacaatca | 1440 |
| ggtatcggtc | gcgaaaccca | caagatgatg | ctggagcatt | accagcaaac | caagtgcctg | 1500 |
| ctggtgagct | actcggataa | accgttgggg | ctgttctga | | | 1539 |

<210> SEQ ID NO 37
<211> LENGTH: 329
<212> TYPE: PRT
<213> ORGANISM: Escherichia coli (strain K12)

<400> SEQUENCE: 37

| | | | | | | | | | | | | | | |
|---|---|---|---|---|---|---|---|---|---|---|---|---|---|---|
| Met | Lys | Leu | Ala | Val | Tyr | Ser | Thr | Lys | Gln | Tyr | Asp | Lys | Lys | Tyr | Leu |
| 1 | | | | 5 | | | | | 10 | | | | | 15 | |

Gln Gln Val Asn Glu Ser Phe Gly Phe Glu Leu Glu Phe Phe Asp Phe
            20             25             30

Leu Leu Thr Glu Lys Thr Ala Lys Thr Ala Asn Gly Cys Glu Ala Val
        35             40            45

Cys Ile Phe Val Asn Asp Asp Gly Ser Arg Pro Val Leu Glu Glu Leu
    50             55            60

Lys Lys His Gly Val Lys Tyr Ile Ala Leu Arg Cys Ala Gly Phe Asn
65             70            75            80

Asn Val Asp Leu Asp Ala Ala Lys Glu Leu Gly Leu Lys Val Val Arg
        85             90            95

Val Pro Ala Tyr Asp Pro Glu Ala Val Ala Glu His Ala Ile Gly Met
        100           105          110

Met Met Thr Leu Asn Arg Arg Ile His Arg Ala Tyr Gln Arg Thr Arg
        115           120          125

Asp Ala Asn Phe Ser Leu Glu Gly Leu Thr Gly Phe Thr Met Tyr Gly
    130             135            140

Lys Thr Ala Gly Val Ile Gly Thr Gly Lys Ile Gly Val Ala Met Leu
145             150           155          160

Arg Ile Leu Lys Gly Phe Gly Met Arg Leu Leu Ala Phe Asp Pro Tyr
        165           170          175

Pro Ser Ala Ala Ala Leu Glu Leu Gly Val Glu Tyr Val Asp Leu Pro
        180           185          190

Thr Leu Phe Ser Glu Ser Asp Val Ile Ser Leu His Cys Pro Leu Thr
        195           200          205

Pro Glu Asn Tyr His Leu Leu Asn Glu Ala Ala Phe Glu Gln Met Lys
    210             215            220

Asn Gly Val Met Ile Val Asn Thr Ser Arg Gly Ala Leu Ile Asp Ser
225             230           235          240

Gln Ala Ala Ile Glu Ala Leu Lys Asn Gln Lys Ile Gly Ser Leu Gly
        245           250          255

Met Asp Val Tyr Glu Asn Glu Arg Asp Leu Phe Phe Glu Asp Lys Ser
        260           265          270

Asn Asp Val Ile Gln Asp Asp Val Phe Arg Arg Leu Ser Ala Cys His
    275             280            285

Asn Val Leu Phe Thr Gly His Gln Ala Phe Leu Thr Ala Glu Ala Leu
        290           295          300

Thr Ser Ile Ser Gln Thr Thr Leu Gln Asn Leu Ser Asn Leu Glu Lys
305             310           315          320

Gly Glu Thr Cys Pro Asn Glu Leu Val
        325

<210> SEQ ID NO 38
<211> LENGTH: 990
<212> TYPE: DNA
<213> ORGANISM: Escherichia coli (strain K12)

<400> SEQUENCE: 38
atgaaactcg ccgtttatag cacaaaacag tacgacaaga agtacctgca acaggtgaac    60
gagtcctttg gctttgagct ggaattttt gactttctgc tgacggaaaa aaccgctaaa   120
actgccaatg gctgcgaagc ggtatgtatt ttcgtaaacg atgacggcag ccgcccggtg   180

```
ctggaagagc tgaaaaagca cggcgttaaa tatatcgccc tgcgctgtgc cggtttcaat    240
aacgtcgacc ttgacgcggc aaaagaactg gggctgaaag tagtccgtgt tccagcctat    300
gatccagagg ccgttgctga acacgccatc ggtatgatga tgacgctgaa ccgccgtatt    360
caccgcgcgt atcagcgtac ccgtgatgct aacttctctc tggaaggtct gaccggcttt    420
actatgtatg caaaacggc aggcgttatc ggtaccggta aaatcggtgt ggcgatgctg     480
cgcattctga aaggttttgg tatgcgtctg ctggcgttcg atccgtatcc aagtgcagcg    540
gcgctggaac tcggtgtgga gtatgtcgat ctgccaaccc tgttctctga atcagacgtt    600
atctctctgc actgcccgct gacaccggaa actatcatc tgttgaacga agccgccttc     660
gaacagatga aaatggcgt gatgatcgtc aataccagtc gcggtgcatt gattgattct     720
caggcagcaa ttgaagcgct gaaaaatcag aaaattggtt cgttgggtat ggacgtgtat    780
gagaacgaac gcgatctatt ctttgaagat aaatccaacg acgtgatcca ggatgacgta    840
ttccgtcgcc tgtctgcctg ccacaacgtg ctgtttaccg ggcaccaggc attcctgaca    900
gcagaagctc tgaccagtat ttctcagact acgctgcaaa acttaagcaa tctggaaaaa    960
ggcgaaacct gcccgaacga actggtttaa                                    990
```

```
<210> SEQ ID NO 39
<211> LENGTH: 246
<212> TYPE: PRT
<213> ORGANISM: Escherichia coli (strain K12)

<400> SEQUENCE: 39

Met Ser Val Ile Gly Arg Ile His Ser Phe Glu Ser Cys Gly Thr Val
1               5                   10                  15

Asp Gly Pro Gly Ile Arg Phe Ile Thr Phe Phe Gln Gly Cys Leu Met
            20                  25                  30

Arg Cys Leu Tyr Cys His Asn Arg Asp Thr Trp Asp Thr His Gly Gly
        35                  40                  45

Lys Glu Val Thr Val Glu Asp Leu Met Lys Glu Val Val Thr Tyr Arg
    50                  55                  60

His Phe Met Asn Ala Ser Gly Gly Val Thr Ala Ser Gly Gly Glu
65                  70                  75                  80

Ala Ile Leu Gln Ala Glu Phe Val Arg Asp Trp Phe Arg Ala Cys Lys
                85                  90                  95

Lys Glu Gly Ile His Thr Cys Leu Asp Thr Asn Gly Phe Val Arg Arg
            100                 105                 110

Tyr Asp Pro Val Ile Asp Glu Leu Leu Glu Val Thr Asp Leu Val Met
        115                 120                 125

Leu Asp Leu Lys Gln Met Asn Asp Glu Ile His Gln Asn Leu Val Gly
    130                 135                 140

Val Ser Asn His Arg Thr Leu Glu Phe Ala Lys Tyr Leu Ala Asn Lys
145                 150                 155                 160

Asn Val Lys Val Trp Ile Arg Tyr Val Val Pro Gly Trp Ser Asp
                165                 170                 175

Asp Asp Asp Ser Ala His Arg Leu Gly Glu Phe Thr Arg Asp Met Gly
            180                 185                 190

Asn Val Glu Lys Ile Glu Leu Leu Pro Tyr His Glu Leu Gly Lys His
        195                 200                 205

Lys Trp Val Ala Met Gly Glu Glu Tyr Lys Leu Asp Gly Val Lys Pro
    210                 215                 220
```

Pro Lys Lys Glu Thr Met Glu Arg Val Lys Gly Ile Leu Glu Gln Tyr
225                 230                 235                 240

Gly His Lys Val Met Phe
            245

<210> SEQ ID NO 40
<211> LENGTH: 741
<212> TYPE: DNA
<213> ORGANISM: Escherichia coli (strain K12)

<400> SEQUENCE: 40
atgtcagtta ttggtcgcat tcactccttt gaatcctgtg gaaccgtaga cggcccaggt      60
attcgcttta tcaccttttt ccagggctgc ctgatgcgct gcctgtattg tcataaccgc     120
gacacctggg acacgcatgg cggtaaagaa gttaccgttg aagatttgat gaaggaagtg     180
gtgacctatc gccactttat gaacgcttcc ggcggcggcg ttaccgcatc cggcggtgaa     240
gcaatcctgc aagctgagtt tgttcgtgac tggttccgcg cctgcaaaaa agaaggcatt     300
catacctgtc tggacaccaa cggttttgtt cgtcgttacg atccggtgat tgatgaactg     360
ctggaagtaa ccgacctggt aatgctcgat ctcaaacaga tgaacgacga gatccaccaa     420
aatctggttg gagtttccaa ccaccgcacg ctggagttcg ctaaatatct ggcgaacaaa     480
aatgtgaagg tgtggatccg ctacgttgtt gtcccaggct ggtctgacga tgacgattca     540
gcgcatcgcc tcggtgaatt tacccgtgat atgggcaacg ttgagaaaat cgagcttctc     600
ccctaccacg agctgggcaa acacaaatgg gtggcaatgg gtgaagagta caaactcgac     660
ggtgttaaac caccgaagaa agagaccatg aacgcgtga aaggcattct tgagcagtac     720
ggtcataagg taatgttcta a                                              741

<210> SEQ ID NO 41
<211> LENGTH: 760
<212> TYPE: PRT
<213> ORGANISM: Escherichia coli (strain K12)

<400> SEQUENCE: 41

Met Ser Glu Leu Asn Glu Lys Leu Ala Thr Ala Trp Glu Gly Phe Thr
1               5                   10                  15

Lys Gly Asp Trp Gln Asn Glu Val Asn Val Arg Asp Phe Ile Gln Lys
            20                  25                  30

Asn Tyr Thr Pro Tyr Glu Gly Asp Glu Ser Phe Leu Ala Gly Ala Thr
        35                  40                  45

Glu Ala Thr Thr Thr Leu Trp Asp Lys Val Met Glu Gly Val Lys Leu
50                  55                  60

Glu Asn Arg Thr His Ala Pro Val Asp Phe Asp Thr Ala Val Ala Ser
65                  70                  75                  80

Thr Ile Thr Ser His Asp Ala Gly Tyr Ile Asn Lys Gln Leu Glu Lys
                85                  90                  95

Ile Val Gly Leu Gln Thr Glu Ala Pro Leu Lys Arg Ala Leu Ile Pro
            100                 105                 110

Phe Gly Gly Ile Lys Met Ile Glu Gly Ser Cys Lys Ala Tyr Asn Arg
        115                 120                 125

Glu Leu Asp Pro Met Ile Lys Lys Ile Phe Thr Glu Tyr Arg Lys Thr
    130                 135                 140

His Asn Gln Gly Val Phe Asp Val Tyr Thr Pro Asp Ile Leu Arg Cys
145                 150                 155                 160

Arg Lys Ser Gly Val Leu Thr Gly Leu Pro Asp Ala Tyr Gly Arg Gly

```
            165                 170                 175
Arg Ile Ile Gly Asp Tyr Arg Arg Val Ala Leu Tyr Gly Ile Asp Tyr
            180                 185                 190

Leu Met Lys Asp Lys Leu Ala Gln Phe Thr Ser Leu Gln Ala Asp Leu
            195                 200                 205

Glu Asn Gly Val Asn Leu Glu Gln Thr Ile Arg Leu Arg Glu Glu Ile
            210                 215                 220

Ala Glu Gln His Arg Ala Leu Gly Gln Met Lys Glu Met Ala Ala Lys
225                 230                 235                 240

Tyr Gly Tyr Asp Ile Ser Gly Pro Ala Thr Asn Ala Gln Glu Ala Ile
                245                 250                 255

Gln Trp Thr Tyr Phe Gly Tyr Leu Ala Ala Val Lys Ser Gln Asn Gly
                260                 265                 270

Ala Ala Met Ser Phe Gly Arg Thr Ser Thr Phe Leu Asp Val Tyr Ile
                275                 280                 285

Glu Arg Asp Leu Lys Ala Gly Lys Ile Thr Glu Gln Glu Ala Gln Glu
                290                 295                 300

Met Val Asp His Leu Val Met Lys Leu Arg Met Val Arg Phe Leu Arg
305                 310                 315                 320

Thr Pro Glu Tyr Asp Glu Leu Phe Ser Gly Asp Pro Ile Trp Ala Thr
                325                 330                 335

Glu Ser Ile Gly Gly Met Gly Leu Asp Gly Arg Thr Leu Val Thr Lys
                340                 345                 350

Asn Ser Phe Arg Phe Leu Asn Thr Leu Tyr Thr Met Gly Pro Ser Pro
                355                 360                 365

Glu Pro Asn Met Thr Ile Leu Trp Ser Glu Lys Leu Pro Leu Asn Phe
                370                 375                 380

Lys Lys Phe Ala Ala Lys Val Ser Ile Asp Thr Ser Ser Leu Gln Tyr
385                 390                 395                 400

Glu Asn Asp Asp Leu Met Arg Pro Asp Phe Asn Asn Asp Asp Tyr Ala
                405                 410                 415

Ile Ala Cys Cys Val Ser Pro Met Ile Val Gly Lys Gln Met Gln Phe
                420                 425                 430

Phe Gly Ala Arg Ala Asn Leu Ala Lys Thr Met Leu Tyr Ala Ile Asn
                435                 440                 445

Gly Gly Val Asp Glu Lys Leu Lys Met Gln Val Gly Pro Lys Ser Glu
                450                 455                 460

Pro Ile Lys Gly Asp Val Leu Asn Tyr Asp Glu Val Met Glu Arg Met
465                 470                 475                 480

Asp His Phe Met Asp Trp Leu Ala Lys Gln Tyr Ile Thr Ala Leu Asn
                485                 490                 495

Ile Ile His Tyr Met His Asp Lys Tyr Ser Tyr Glu Ala Ser Leu Met
                500                 505                 510

Ala Leu His Asp Arg Asp Val Ile Arg Thr Met Ala Cys Gly Ile Ala
                515                 520                 525

Gly Leu Ser Val Ala Ala Asp Ser Leu Ser Ala Ile Lys Tyr Ala Lys
                530                 535                 540

Val Lys Pro Ile Arg Asp Glu Asp Gly Leu Ala Ile Asp Phe Glu Ile
545                 550                 555                 560

Glu Gly Glu Tyr Pro Gln Phe Gly Asn Asn Asp Pro Arg Val Asp Asp
                565                 570                 575

Leu Ala Val Asp Leu Val Glu Arg Phe Met Lys Lys Ile Gln Lys Leu
                580                 585                 590
```

```
His Thr Tyr Arg Asp Ala Ile Pro Thr Gln Ser Val Leu Thr Ile Thr
            595                 600                 605

Ser Asn Val Val Tyr Gly Lys Lys Thr Gly Asn Thr Pro Asp Gly Arg
610                 615                 620

Arg Ala Gly Ala Pro Phe Gly Pro Gly Ala Asn Pro Met His Gly Arg
625                 630                 635                 640

Asp Gln Lys Gly Ala Val Ala Ser Leu Thr Ser Val Ala Lys Leu Pro
            645                 650                 655

Phe Ala Tyr Ala Lys Asp Gly Ile Ser Tyr Thr Phe Ser Ile Val Pro
            660                 665                 670

Asn Ala Leu Gly Lys Asp Asp Glu Val Arg Lys Thr Asn Leu Ala Gly
            675                 680                 685

Leu Met Asp Gly Tyr Phe His His Glu Ala Ser Ile Glu Gly Gly Gln
            690                 695                 700

His Leu Asn Val Asn Val Met Asn Arg Glu Met Leu Leu Asp Ala Met
705                 710                 715                 720

Glu Asn Pro Glu Lys Tyr Pro Gln Leu Thr Ile Arg Val Ser Gly Tyr
            725                 730                 735

Ala Val Arg Phe Asn Ser Leu Thr Lys Glu Gln Gln Gln Asp Val Ile
            740                 745                 750

Thr Arg Thr Phe Thr Gln Ser Met
            755                 760

<210> SEQ ID NO 42
<211> LENGTH: 2283
<212> TYPE: DNA
<213> ORGANISM: Escherichia coli (strain K12)

<400> SEQUENCE: 42
```

| | | | | |
|---|---|---|---|---|
| atgtccgagc ttaatgaaaa gttagccaca gcctgggaag ttttaccaa aggtgactgg | 60 |
| cagaatgaag taaacgtccg tgacttcatt cagaaaaact acactccgta cgagggtgac | 120 |
| gagtccttcc tggctggcgc tactgaagcg accaccaccc tgtgggacaa agtaatggaa | 180 |
| ggcgttaaac tggaaaaccg cactcacgcg ccagttgact ttgacaccgc tgttgcttcc | 240 |
| accatcacct ctcacgacgc tggctacatc aacaagcagc ttgagaaaat cgttggtctg | 300 |
| cagactgaag ctccgctgaa acgtgctctt atcccgttcg gtggtatcaa aatgatcgaa | 360 |
| ggttcctgca aagcgtacaa ccgcgaactg gatccgatga tcaaaaaaat cttcactgaa | 420 |
| taccgtaaaa ctcacaacca gggcgtgttc gacgtttaca ctccggacat cctgcgttgc | 480 |
| cgtaaatctg tgttctgac cggtctgcca gatgcatatg ccgtggccg tatcatcggt | 540 |
| gactaccgtc gcgttgcgct gtacggtatc gactacctga tgaaagacaa actggcacag | 600 |
| ttcacttctc tgcaggctga tctggaaaac ggcgtaaacc tggaacagac tatccgtctg | 660 |
| cgcgaagaaa tcgctgaaca gcaccgcgct ctgggtcaga tgaaagaaat ggctgcgaaa | 720 |
| tacggctacg acatctctgg tccggctacc aacgctcagg aagctatcca gtggacttac | 780 |
| ttcggctacc tggctgctgt taagtctcag aacggtgctg caatgtcctt cggtcgtacc | 840 |
| tccaccttcc tggatgtgta catcgaacgt gacctgaaag ctggcaagat caccgaacaa | 900 |
| gaagcgcagg aaatggttga ccacctggtc atgaaactgc gtatggttcg cttcctgcgt | 960 |
| actccggaat acgatgaact gttctctggc gacccgatct gggcaaccga atctatcggt | 1020 |
| ggtatgggcc tcgacggtcg tacccctggtt accaaaaaca gcttccgttt cctgaacacc | 1080 |
| ctgtacacca tgggtccgtc tccggaaccg aacatgacca ttctgtggtc tgaaaaactg | 1140 |

```
ccgctgaact tcaagaaatt cgccgctaaa gtgtccatcg acacctcttc tctgcagtat   1200
gagaacgatg acctgatgcg tccggacttc aacaacgatg actacgctat tgcttgctgc   1260
gtaagcccga tgatcgttgg taaacaaatg cagttcttcg gtgcgcgtgc aaacctggcg   1320
aaaaccatgc tgtacgcaat caacggcggc gttgacgaaa aactgaaaat gcaggttggt   1380
ccgaagtctg aaccgatcaa aggcgatgtc ctgaactatg atgaagtgat ggagcgcatg   1440
gatcacttca tggactggct ggctaaacag tacatcactg cactgaacat catccactac   1500
atgcacgaca gtacagcta cgaagcctct ctgatggcgc tgcacgaccg tgacgttatc   1560
cgcaccatgg cgtgtggtat cgctggtctg tccgttgctg ctgactccct gtctgcaatc   1620
aaatatgcga agttaaaacc gattcgtgac gaagacggtc tggctatcga cttcgaaatc   1680
gaaggcgaat acccgcagtt tggtaacaat gatccgcgtg tagatgacct ggctgttgac   1740
ctggtagaac gtttcatgaa gaaaattcag aaactgcaca cctaccgtga cgctatcccg   1800
actcagtctg ttctgaccat cacttctaac gttgtgtatg gtaagaaaac gggtaacacc   1860
ccagacggtc gtcgtgctgg cgcgccgttc ggaccgggtg ctaacccgat gcacggtcgt   1920
gaccagaaag gtgcagtagc ctctctgact tccgttgcta aactgccgtt tgcttacgct   1980
aaagatggta tctcctacac cttctctatc gttccgaacg cactgggtaa agacgacgaa   2040
gttcgtaaga ccaacctggc tggtctgatg gatggttact tccaccacga agcatccatc   2100
gaaggtggtc agcacctgaa cgttaacgtg atgaaccgtg aaatgctgct cgacgcgatg   2160 gaaaaccccgg aaaatatcc gcagctgacc atccgtgtat ctggctacgc agtacgtttc   2220
aactcgctga ctaaagaaca gcagcaggac gttattactc gtaccttcac tcaatctatg   2280
taa                                                                2283
```

<210> SEQ ID NO 43
<211> LENGTH: 891
<212> TYPE: PRT
<213> ORGANISM: Escherichia coli (strain K12)

<400> SEQUENCE: 43

```
Met Ala Val Thr Asn Val Ala Glu Leu Asn Ala Leu Val Glu Arg Val
1               5                   10                  15

Lys Lys Ala Gln Arg Glu Tyr Ala Ser Phe Thr Gln Glu Gln Val Asp
            20                  25                  30

Lys Ile Phe Arg Ala Ala Ala Leu Ala Ala Ala Asp Ala Arg Ile Pro
        35                  40                  45

Leu Ala Lys Met Ala Val Ala Glu Ser Gly Met Gly Ile Val Glu Asp
    50                  55                  60

Lys Val Ile Lys Asn His Phe Ala Ser Glu Tyr Ile Tyr Asn Ala Tyr
65                  70                  75                  80

Lys Asp Glu Lys Thr Cys Gly Val Leu Ser Glu Asp Asp Thr Phe Gly
                85                  90                  95

Thr Ile Thr Ile Ala Glu Pro Ile Gly Ile Ile Cys Gly Ile Val Pro
            100                 105                 110

Thr Thr Asn Pro Thr Ser Thr Ala Ile Phe Lys Ser Leu Ile Ser Leu
        115                 120                 125

Lys Thr Arg Asn Ala Ile Ile Phe Ser Pro His Pro Arg Ala Lys Asp
    130                 135                 140

Ala Thr Asn Lys Ala Ala Asp Ile Val Leu Gln Ala Ala Ile Ala Ala
145                 150                 155                 160
```

```
Gly Ala Pro Lys Asp Leu Ile Gly Trp Ile Asp Gln Pro Ser Val Glu
            165                 170                 175

Leu Ser Asn Ala Leu Met His His Pro Asp Ile Asn Leu Ile Leu Ala
        180                 185                 190

Thr Gly Gly Pro Gly Met Val Lys Ala Ala Tyr Ser Ser Gly Lys Pro
            195                 200                 205

Ala Ile Gly Val Gly Ala Gly Asn Thr Pro Val Val Ile Asp Glu Thr
        210                 215                 220

Ala Asp Ile Lys Arg Ala Val Ala Ser Val Leu Met Ser Lys Thr Phe
225                 230                 235                 240

Asp Asn Gly Val Ile Cys Ala Ser Glu Gln Ser Val Val Val Asp
                245                 250                 255

Ser Val Tyr Asp Ala Val Arg Glu Arg Phe Ala Thr His Gly Gly Tyr
            260                 265                 270

Leu Leu Gln Gly Lys Glu Leu Lys Ala Val Gln Asp Val Ile Leu Lys
        275                 280                 285

Asn Gly Ala Leu Asn Ala Ala Ile Val Gly Gln Pro Ala Tyr Lys Ile
        290                 295                 300

Ala Glu Leu Ala Gly Phe Ser Val Pro Glu Asn Thr Lys Ile Leu Ile
305                 310                 315                 320

Gly Glu Val Thr Val Val Asp Glu Ser Glu Pro Phe Ala His Glu Lys
            325                 330                 335

Leu Ser Pro Thr Leu Ala Met Tyr Arg Ala Lys Asp Phe Glu Asp Ala
            340                 345                 350

Val Glu Lys Ala Glu Lys Leu Val Ala Met Gly Gly Ile Gly His Thr
        355                 360                 365

Ser Cys Leu Tyr Thr Asp Gln Asp Asn Gln Pro Ala Arg Val Ser Tyr
        370                 375                 380

Phe Gly Gln Lys Met Lys Thr Ala Arg Ile Leu Ile Asn Thr Pro Ala
385                 390                 395                 400

Ser Gln Gly Gly Ile Gly Asp Leu Tyr Asn Phe Lys Leu Ala Pro Ser
            405                 410                 415

Leu Thr Leu Gly Cys Gly Ser Trp Gly Gly Asn Ser Ile Ser Glu Asn
            420                 425                 430

Val Gly Pro Lys His Leu Ile Asn Lys Lys Thr Val Ala Lys Arg Ala
        435                 440                 445

Glu Asn Met Leu Trp His Lys Leu Pro Lys Ser Ile Tyr Phe Arg Arg
        450                 455                 460

Gly Ser Leu Pro Ile Ala Leu Asp Glu Val Ile Thr Asp Gly His Lys
465                 470                 475                 480

Arg Ala Leu Ile Val Thr Asp Arg Phe Leu Phe Asn Asn Gly Tyr Ala
            485                 490                 495

Asp Gln Ile Thr Ser Val Leu Lys Ala Ala Gly Val Glu Thr Glu Val
            500                 505                 510

Phe Phe Glu Val Glu Ala Asp Pro Thr Leu Ser Ile Val Arg Lys Gly
        515                 520                 525

Ala Glu Leu Ala Asn Ser Phe Lys Pro Asp Val Ile Ile Ala Leu Gly
        530                 535                 540

Gly Gly Ser Pro Met Asp Ala Ala Lys Ile Met Trp Val Met Tyr Glu
545                 550                 555                 560

His Pro Glu Thr His Phe Glu Glu Leu Ala Leu Arg Phe Met Asp Ile
            565                 570                 575

Arg Lys Arg Ile Tyr Lys Phe Pro Lys Met Gly Val Lys Ala Lys Met
```

```
              580             585             590
Ile Ala Val Thr Thr Thr Ser Gly Thr Gly Ser Glu Val Thr Pro Phe
            595                 600                 605

Ala Val Val Thr Asp Asp Ala Thr Gly Gln Lys Tyr Pro Leu Ala Asp
            610                 615                 620

Tyr Ala Leu Thr Pro Asp Met Ala Ile Val Asp Ala Asn Leu Val Met
625                 630                 635                 640

Asp Met Pro Lys Ser Leu Cys Ala Phe Gly Gly Leu Asp Ala Val Thr
                    645                 650                 655

His Ala Met Glu Ala Tyr Val Ser Val Leu Ala Ser Glu Phe Ser Asp
                660                 665                 670

Gly Gln Ala Leu Gln Ala Leu Lys Leu Leu Lys Glu Tyr Leu Pro Ala
                675                 680                 685

Ser Tyr His Glu Gly Ser Lys Asn Pro Val Ala Arg Glu Arg Val His
            690                 695                 700

Ser Ala Ala Thr Ile Ala Gly Ile Ala Phe Ala Asn Ala Phe Leu Gly
705                 710                 715                 720

Val Cys His Ser Met Ala His Lys Leu Gly Ser Gln Phe His Ile Pro
                725                 730                 735

His Gly Leu Ala Asn Ala Leu Leu Ile Cys Asn Val Ile Arg Tyr Asn
                740                 745                 750

Ala Asn Asp Asn Pro Thr Lys Gln Thr Ala Phe Ser Gln Tyr Asp Arg
            755                 760                 765

Pro Gln Ala Arg Arg Arg Tyr Ala Glu Ile Ala Asp His Leu Gly Leu
            770                 775                 780

Ser Ala Pro Gly Asp Arg Thr Ala Ala Lys Ile Glu Lys Leu Leu Ala
785                 790                 795                 800

Trp Leu Glu Thr Leu Lys Ala Glu Leu Gly Ile Pro Lys Ser Ile Arg
                805                 810                 815

Glu Ala Gly Val Gln Glu Ala Asp Phe Leu Ala Asn Val Asp Lys Leu
                820                 825                 830

Ser Glu Asp Ala Phe Asp Asp Gln Cys Thr Gly Ala Asn Pro Arg Tyr
                835                 840                 845

Pro Leu Ile Ser Glu Leu Lys Gln Ile Leu Leu Asp Thr Tyr Tyr Gly
            850                 855                 860

Arg Asp Tyr Val Glu Gly Glu Thr Ala Ala Lys Lys Glu Ala Ala Pro
865                 870                 875                 880

Ala Lys Ala Glu Lys Lys Ala Lys Lys Ser Ala
                885                 890

<210> SEQ ID NO 44
<211> LENGTH: 2676
<212> TYPE: DNA
<213> ORGANISM: Escherichia coli (strain K12)

<400> SEQUENCE: 44
atggctgtta ctaatgtcgc tgaacttaac gcactcgtag agcgtgtaaa aaaagcccag    60
cgtgaatatg ccagtttcac tcaagagcaa gtagacaaaa tcttccgcgc cgccgctctg    120
gctgctgcaa atgctcgaat cccactcgcg aaaatggccg ttgccgaatc cggcatgggt    180
atcgtcgaag ataaagtgat caaaaaccac tttgcttctg aatatatcta caacgcctat    240
aaagatgaaa aacctgtggt gttctgtctg gaagacgaca cttttggtac catcactatc    300
gctgaaccaa tcggtattat ttgcggtatc gttccgacca ctaacccgac ttcaactgct    360
```

```
atcttcaaat cgctgatcag tctgaagacc cgtaacgcca ttatcttctc cccgcacccg    420
cgtgcaaaag atgccaccaa caaagcggct gatatcgttc tgcaggctgc tatcgctgcc    480
ggtgctccga aagatctgat cggctggatc gatcaacctt ctgttgaact gtctaacgca    540
ctgatgcacc acccagacat caacctgatc ctcgcgactg gtggtccggg catggttaaa    600
gccgcataca gctccggtaa accagctatc ggtgtaggcg cgggcaacac tccagttgtt    660
atcgatgaaa ctgctgatat caaacgtgca gttgcatctg tactgatgtc caaaaccttc    720
gacaacggcg taatctgtgc ttctgaacag tctgttgttg ttgttgactc tgtttatgac    780
gctgtacgtg aacgttttgc aacccacggc ggctatctgt tgcagggtaa agagctgaaa    840
gctgttcagg atgttatcct gaaaaacggt gcgctgaacg cggctatcgt tggtcagcca    900
gcctataaaa ttgctgaact ggcaggcttc tctgtaccag aaaacaccaa gattctgatc    960
ggtgaagtga ccgttgttga tgaaagcgaa ccgttcgcac atgaaaaact gtccccgact   1020
ctggcaatgt accgcgctaa agatttcgaa gacgcggtag aaaaagcaga gaaactggtt   1080
gctatgggcg gtatcggtca tacctcttgc ctgtacactg accaggataa ccaaccggct   1140 cgcgttttctt acttcggtca gaaaatgaaa acggcgcgta tcctgattaa cacccccagcg  1200 tctcagggtg gtatcggtga cctgtataac ttcaaactcg caccttccct gactctgggt   1260
tgtggttctt ggggtggtaa ctccatctct gaaaacgttg gtccgaaaca cctgatcaac   1320
aagaaaaccg ttgctaagcg agctgaaaac atgttgtggc acaaacttcc gaaatctatc   1380
tacttccgcc gtggctccct gccaatcgcg ctggatgaag tgattactga tggccacaaa   1440
cgtgcgctca tcgtgactga ccgcttcctg ttcaacaatg ttatgctga tcagatcact    1500 tccgtactga aagcagcagg cgttgaaact gaagtcttct tcgaagtaga agcggacccg   1560
accctgagca tcgttcgtaa aggtgcagaa ctggcaaact ccttcaaacc agacgtgatt   1620
atcgcgctgg gtggtggttc cccgatggac gccgcgaaga tcatgtgggt tatgtacgaa   1680
catccggaaa ctcacttcga agagctggcg ctgcgcttta tggatatccg taacgtatc   1740 tacaagttcc cgaaaatggg cgtgaaagcg aaaatgatcg ctgtcaccac cacttctggt   1800
acaggttctg aagtcactcc gtttgcggtt gtaactgacg acgctactgg tcagaaatat   1860
ccgctggcag actatgcgct gactccggat atggcgattg tcgacgccaa cctggttatg   1920
gacatgccga gtccctgtg tgctttcggt ggtctggacg cagtaactca cgccatggaa   1980
gcttatgttt ctgtactggc atctgagttc tctgatggtc aggctctgca ggcactgaaa   2040
ctgctgaaag aatatctgcc agcgtcctac cacgaagggt ctaaaaatcc ggtagcgcgt   2100
gaacgtgttc acagtgcagc gactatcgcg ggtatcgcgt ttgcgaacgc cttcctgggt   2160
gtatgtcact caatggcgca caaactgggt tcccagttcc atattccgca cggtctggca   2220
aacgccctgc tgatttgtaa cgttattcgc tacaatgcga acgacaaccc gaccaagcag   2280
actgcattca gccagtatga ccgtccgcag gctcgccgtc gttatgctga aattgccgac   2340
cacttgggtc tgagcgcacc gggcgaccgt actgctgcta agatcgagaa actgctggca   2400
tggctggaaa cgctgaaagc tgaactgggt attccgaaat ctatccgtga agctggcgtt   2460
caggaagcag acttcctggc gaacgtggat aaactgtctg aagatgcatt cgatgaccag   2520
tgcaccggcg ctaacccgcg ttacccgctg atctccgagc tgaaacagat tctgctggat   2580
acctactacg tcgtgatta tgtagaaggt gaaactgcag cgaagaaaga agctgctccg   2640
gctaaagctg agaaaaaagc gaaaaaatcc gcttaa                            2676
```

<210> SEQ ID NO 45
<211> LENGTH: 400
<212> TYPE: PRT
<213> ORGANISM: Escherichia coli (strain K12)

<400> SEQUENCE: 45

Met Ser Ser Lys Leu Val Leu Val Leu Asn Cys Gly Ser Ser Ser Leu
1               5                   10                  15

Lys Phe Ala Ile Ile Asp Ala Val Asn Gly Glu Glu Tyr Leu Ser Gly
            20                  25                  30

Leu Ala Glu Cys Phe His Leu Pro Glu Ala Arg Ile Lys Trp Lys Met
        35                  40                  45

Asp Gly Asn Lys Gln Glu Ala Ala Leu Gly Ala Gly Ala Ala His Ser
    50                  55                  60

Glu Ala Leu Asn Phe Ile Val Asn Thr Ile Leu Ala Gln Lys Pro Glu
65                  70                  75                  80

Leu Ser Ala Gln Leu Thr Ala Ile Gly His Arg Ile Val His Gly Gly
                85                  90                  95

Glu Lys Tyr Thr Ser Ser Val Val Ile Asp Glu Ser Val Ile Gln Gly
            100                 105                 110

Ile Lys Asp Ala Ala Ser Phe Ala Pro Leu His Asn Pro Ala His Leu
        115                 120                 125

Ile Gly Ile Glu Glu Ala Leu Lys Ser Phe Pro Gln Leu Lys Asp Lys
    130                 135                 140

Asn Val Ala Val Phe Asp Thr Ala Phe His Gln Thr Met Pro Glu Glu
145                 150                 155                 160

Ser Tyr Leu Tyr Ala Leu Pro Tyr Asn Leu Tyr Lys Glu His Gly Ile
                165                 170                 175

Arg Arg Tyr Gly Ala His Gly Thr Ser His Phe Tyr Val Thr Gln Glu
            180                 185                 190

Ala Ala Lys Met Leu Asn Lys Pro Val Glu Glu Leu Asn Ile Ile Thr
        195                 200                 205

Cys His Leu Gly Asn Gly Gly Ser Val Ser Ala Ile Arg Asn Gly Lys
    210                 215                 220

Cys Val Asp Thr Ser Met Gly Leu Thr Pro Leu Glu Gly Leu Val Met
225                 230                 235                 240

Gly Thr Arg Ser Gly Asp Ile Asp Pro Ala Ile Ile Phe His Leu His
                245                 250                 255

Asp Thr Leu Gly Met Ser Val Asp Ala Ile Asn Lys Leu Leu Thr Lys
            260                 265                 270

Glu Ser Gly Leu Leu Gly Leu Thr Glu Val Thr Ser Asp Cys Arg Tyr
        275                 280                 285

Val Glu Asp Asn Tyr Ala Thr Lys Glu Asp Ala Lys Arg Ala Met Asp
    290                 295                 300

Val Tyr Cys His Arg Leu Ala Lys Tyr Ile Gly Ala Tyr Thr Ala Leu
305                 310                 315                 320

Met Asp Gly Arg Leu Asp Ala Val Val Phe Thr Gly Gly Ile Gly Glu
                325                 330                 335

Asn Ala Ala Met Val Arg Glu Leu Ser Leu Gly Lys Leu Gly Val Leu
            340                 345                 350

Gly Phe Glu Val Asp His Glu Arg Asn Leu Ala Ala Arg Phe Gly Lys
        355                 360                 365

Ser Gly Phe Ile Asn Lys Glu Gly Thr Arg Pro Ala Val Val Ile Pro
    370                 375                 380

Thr Asn Glu Glu Leu Val Ile Ala Gln Asp Ala Ser Arg Leu Thr Ala
385                 390                 395                 400

<210> SEQ ID NO 46
<211> LENGTH: 1203
<212> TYPE: DNA
<213> ORGANISM: Escherichia coli (strain K12)

<400> SEQUENCE: 46

| | | |
|---|---|---|
| atgtcgagta agttagtact ggttctgaac tgcggtagtt cttcactgaa atttgccatc | 60 |
| atcgatgcag taaatggtga agagtacctt tctggtttag ccgaatgttt ccacctgccc | 120 |
| gaagcacgta tcaaatggaa aatggacggc aataaacagg aagcggcttt aggtgcaggc | 180 |
| gccgctcaca gcgaagcgct caactttatc gttaatacta ttctggcaca aaaaccagaa | 240 |
| ctgtctgcgc agctgactgc tatcggtcac cgtatcgtac acggcggcga aaagtatacc | 300 |
| agctccgtag tgatcgatga gtctgttatt cagggtatca agatgcagc ttcttttgca | 360 |
| ccgctgcaca acccggctca cctgatcggt atcgaagaag ctctgaaatc tttcccacag | 420 |
| ctgaaagaca aaacgttgc tgtatttgac accgcgttcc accagactat gccggaagag | 480 |
| tcttacctct acgccctgcc ttacaacctg tacaaagagc acggcatccg tcgttacggc | 540 |
| gcgcacggca ccagccactt ctatgtaacc caggaagcgg caaaaatgct gaacaaaccg | 600 |
| gtagaagaac tgaacatcat cacctgccac ctgggcaacg gtggttccgt ttctgctatc | 660 |
| cgcaacggta atgcgttga cacctctatg ggcctgaccc cgctggaagg tctggtcatg | 720 |
| ggtacccgtt ctggtgatat cgatccggcg atcatcttcc acctgcacga caccctgggc | 780 |
| atgagcgttg acgcaatcaa caaactgctg accaaagagt ctggcctgct gggtctgacc | 840 |
| gaagtgacca cgcgactgcc ctatgttgaa gacaactacg cgacgaaaga agacgcgaag | 900 |
| cgcgcaatgg acgtttactg ccaccgcctg gcgaaataca tcggtgccta cactgcgctg | 960 |
| atggatggtc gtctggacgc tgttgtattc actggtggta tcggtgaaaa tgccgcaatg | 1020 |
| gttcgtgaac tgtctctggg caaactgggc gtgctgggct ttgaagttga tcatgaacgc | 1080 |
| aacctggctg cacgtttcgg caaatctggt ttcatcaaca agaaggtac ccgtcctgcg | 1140 |
| gtggttatcc caaccaacga agaactggtt atcgcgcaag acgcgagccg cctgactgcc | 1200 |
| tga | 1203 |

<210> SEQ ID NO 47
<211> LENGTH: 714
<212> TYPE: PRT
<213> ORGANISM: Escherichia coli (strain K12)

<400> SEQUENCE: 47

Met Ser Arg Ile Ile Met Leu Ile Pro Thr Gly Thr Ser Val Gly Leu
1               5                   10                  15

Thr Ser Val Ser Leu Gly Val Ile Arg Ala Met Glu Arg Lys Gly Val
                20                  25                  30

Arg Leu Ser Val Phe Lys Pro Ile Ala Gln Pro Arg Thr Gly Gly Asp
            35                  40                  45

Ala Pro Asp Gln Thr Thr Thr Ile Val Arg Ala Asn Ser Ser Thr Thr
        50                  55                  60

Thr Ala Ala Glu Pro Leu Lys Met Ser Tyr Val Glu Gly Leu Leu Ser
65                  70                  75                  80

Ser Asn Gln Lys Asp Val Leu Met Glu Glu Ile Val Ala Asn Tyr His
                85                  90                  95

```
Ala Asn Thr Lys Asp Ala Glu Val Val Leu Val Glu Gly Leu Val Pro
                100                 105                 110

Thr Arg Lys His Gln Phe Ala Gln Ser Leu Asn Tyr Glu Ile Ala Lys
            115                 120                 125

Thr Leu Asn Ala Glu Ile Val Phe Val Met Ser Gln Gly Thr Asp Thr
        130                 135                 140

Pro Glu Gln Leu Lys Glu Arg Ile Glu Leu Thr Arg Asn Ser Phe Gly
145                 150                 155                 160

Gly Ala Lys Asn Thr Asn Ile Thr Gly Val Ile Val Asn Lys Leu Asn
                165                 170                 175

Ala Pro Val Asp Glu Gln Gly Arg Thr Arg Pro Asp Leu Ser Glu Ile
            180                 185                 190

Phe Asp Asp Ser Ser Lys Ala Lys Val Asn Asn Val Asp Pro Ala Lys
        195                 200                 205

Leu Gln Glu Ser Ser Pro Leu Pro Val Leu Gly Ala Val Pro Trp Ser
210                 215                 220

Phe Asp Leu Ile Ala Thr Arg Ala Ile Asp Met Ala Arg His Leu Asn
225                 230                 235                 240

Ala Thr Ile Ile Asn Glu Gly Asp Ile Asn Thr Arg Arg Val Lys Ser
                245                 250                 255

Val Thr Phe Cys Ala Arg Ser Ile Pro His Met Leu Glu His Phe Arg
            260                 265                 270

Ala Gly Ser Leu Leu Val Thr Ser Ala Asp Arg Pro Asp Val Leu Val
        275                 280                 285

Ala Ala Cys Leu Ala Ala Met Asn Gly Val Glu Ile Gly Ala Leu Leu
290                 295                 300

Leu Thr Gly Gly Tyr Glu Met Asp Ala Arg Ile Ser Lys Leu Cys Glu
305                 310                 315                 320

Arg Ala Phe Ala Thr Gly Leu Pro Val Phe Met Val Asn Thr Asn Thr
                325                 330                 335

Trp Gln Thr Ser Leu Ser Leu Gln Ser Phe Asn Leu Glu Val Pro Val
            340                 345                 350

Asp Asp His Glu Arg Ile Glu Lys Val Gln Glu Tyr Val Ala Asn Tyr
        355                 360                 365

Ile Asn Ala Asp Trp Ile Glu Ser Leu Thr Ala Thr Ser Glu Arg Ser
370                 375                 380

Arg Arg Leu Ser Pro Pro Ala Phe Arg Tyr Gln Leu Thr Glu Leu Ala
385                 390                 395                 400

Arg Lys Ala Gly Lys Arg Ile Val Leu Pro Glu Gly Asp Glu Pro Arg
                405                 410                 415

Thr Val Lys Ala Ala Ile Cys Ala Glu Arg Gly Ile Ala Thr Cys
            420                 425                 430

Val Leu Leu Gly Asn Pro Ala Glu Ile Asn Arg Val Ala Ala Ser Gln
        435                 440                 445

Gly Val Glu Leu Gly Ala Gly Ile Glu Ile Val Asp Pro Glu Val Val
450                 455                 460

Arg Glu Ser Tyr Val Gly Arg Leu Val Glu Leu Arg Lys Asn Lys Gly
465                 470                 475                 480

Met Thr Glu Thr Val Ala Arg Glu Gln Leu Glu Asp Asn Val Val Leu
                485                 490                 495

Gly Thr Leu Met Leu Glu Gln Asp Glu Val Asp Gly Leu Val Ser Gly
            500                 505                 510

Ala Val His Thr Thr Ala Asn Thr Ile Arg Pro Pro Leu Gln Leu Ile
```

```
                515                 520                 525
Lys Thr Ala Pro Gly Ser Ser Leu Val Ser Ser Val Phe Phe Met Leu
            530                 535                 540

Leu Pro Glu Gln Val Tyr Val Tyr Gly Asp Cys Ala Ile Asn Pro Asp
545                 550                 555                 560

Pro Thr Ala Glu Gln Leu Ala Glu Ile Ala Ile Gln Ser Ala Asp Ser
                565                 570                 575

Ala Ala Ala Phe Gly Ile Glu Pro Arg Val Ala Met Leu Ser Tyr Ser
            580                 585                 590

Thr Gly Thr Ser Gly Ala Gly Ser Asp Val Glu Lys Val Arg Glu Ala
                595                 600                 605

Thr Arg Leu Ala Gln Glu Lys Arg Pro Asp Leu Met Ile Asp Gly Pro
            610                 615                 620

Leu Gln Tyr Asp Ala Ala Val Met Ala Asp Val Ala Lys Ser Lys Ala
625                 630                 635                 640

Pro Asn Ser Pro Val Ala Gly Arg Ala Thr Val Phe Ile Phe Pro Asp
                645                 650                 655

Leu Asn Thr Gly Asn Thr Thr Tyr Lys Ala Val Gln Arg Ser Ala Asp
            660                 665                 670

Leu Ile Ser Ile Gly Pro Met Leu Gln Gly Met Arg Lys Pro Val Asn
            675                 680                 685

Asp Leu Ser Arg Gly Ala Leu Val Asp Asp Ile Val Tyr Thr Ile Ala
            690                 695                 700

Leu Thr Ala Ile Gln Ser Ala Gln Gln Gln
705                 710
```

<210> SEQ ID NO 48
<211> LENGTH: 2145
<212> TYPE: DNA
<213> ORGANISM: Escherichia coli (strain K12)

<400> SEQUENCE: 48

```
gtgtcccgta ttattatgct gatccctacc ggaaccagcg tcggtctgac cagcgtcagc    60
cttggcgtga tccgtgcaat ggaacgcaaa ggcgttcgtc tgagcgtttt caaacctatc   120
gctcagccgc gtaccggtgg cgatgcgccc gatcagacta cgactatcgt gcgtgcgaac   180
tcttccacca cgacggccgc tgaaccgctg aaaatgagct acgttgaagg tctgcttttcc  240
agcaatcaga aagatgtgct gatggaagag atcgtcgcaa actaccacgc taacaccaaa   300
gacgctgaag tcgttctggt tgaaggtctg gtcccgacac gtaagcacca gtttgcccag   360
tctctgaact acgaaatcgc taaaacgctg aatgcggaaa tcgtcttcgt tatgtctcag   420
ggcactgaca ccccggaaca gctgaaagag cgtatcgaac tgacccgcaa cagcttcggc   480
ggtgccaaaa acaccaacat caccggcgtt atcgttaaca aactgaacgc accggttgat   540
gaacagggtc gtactcgccc ggatctgtcc gagattttcg acgactcttc caaagctaaa   600
gtaaacaatg ttgatccggc gaagctgcaa gaatccagcc cgctgccggt tctcggcgct   660
gtgccgtgga gctttgacct gatcgcgact cgtgcgatcg atatggctcg ccacctgaat   720
gcgaccatca tcaacgaagg cgacatcaat actcgccgcg ttaaatccgt cacttttctgc  780
gcacgcagca ttccgcacat gctggagcac ttccgtgccg ttctctgct ggtgacttcc   840
gcagaccgtc ctgacgtgct ggtggccgct gcctggcag ccatgaacgg cgtagaaatc   900
ggtgccctgc tgctgactgg cggttacgaa atggacgcgc gcattctaa actgtgcgaa   960
cgtgctttcg ctaccggcct gccggtattt atggtgaaca ccaacacctg gcagacctct  1020
```

```
ctgagcctgc agagcttcaa cctggaagtt ccggttgacg atcacgaacg tatcgagaaa    1080
gttcaggaat acgttgctaa ctacatcaac gctgactgga tcgaatctct gactgccact    1140
tctgagcgca gccgtcgtct gtctccgcct gcgttccgtt atcagctgac tgaacttgcg    1200
cgcaaagcgg gcaaacgtat cgtactgccg gaaggtgacg aaccgcgtac cgttaaagca    1260
gccgctatct gtgctgaacg tggtatcgca acttgcgtac tgctgggtaa ccggcagag     1320 atcaaccgtg ttgcagcgtc tcagggtgta gaactgggtg cagggattga aatcgttgat    1380
ccagaagtgg ttcgcgaaag ctatgttggt cgtctggtcg aactgcgtaa gaacaaaggc    1440
atgaccgaaa ccgttgcccg cgaacagctg gaagacaacg tggtgctcgg tacgctgatg    1500
ctggaacagg atgaagttga tggtctggtt ccggtgctg ttcacactac cgcaaacacc     1560
atccgtccgc cgctgcagct gatcaaaact gcaccgggca gctccctggt atcttccgtg    1620
ttcttcatgc tgctgccgga acaggtttac gtttacggtg actgtgcgat caacccggat    1680
ccgaccgctg aacagctggc agaaatcgcg attcagtccg ctgattccgc tgcggccttc    1740
ggtatcgaac gcgcgttgc tatgctctcc tactccaccg gtacttctgg tgcaggtagc     1800
gacgtagaaa aagttcgcga agcaactcgt ctggcgcagg aaaaacgtcc tgacctgatg    1860
atcgacggtc cgctgcagta cgacgctgcg gtaatggctg acgttgcgaa atccaaagcg    1920
ccgaactctc cggttgcagg tcgcgctacc gtgttcatct cccggatct gaacaccggt     1980 aacaccacct acaaagcggt acagcgttct gccgacctga tctccatcgg gccgatgctg    2040
cagggtatgc gcaagccggt taacgacctg tcccgtggcg cactggttga cgatatcgtc    2100
tacaccatcg cgctgactgc gattcagtct gcacagcagc agtaa                    2145

<210> SEQ ID NO 49
<211> LENGTH: 572
<212> TYPE: PRT
<213> ORGANISM: Escherichia coli (strain K12)

<400> SEQUENCE: 49

Met Lys Gln Thr Val Ala Ala Tyr Ile Ala Lys Thr Leu Glu Ser Ala
1               5                   10                  15

Gly Val Lys Arg Ile Trp Gly Val Thr Gly Asp Ser Leu Asn Gly Leu
            20                  25                  30

Ser Asp Ser Leu Asn Arg Met Gly Thr Ile Glu Trp Met Ser Thr Arg
        35                  40                  45

His Glu Glu Val Ala Ala Phe Ala Ala Gly Ala Glu Ala Gln Leu Ser
    50                  55                  60

Gly Glu Leu Ala Val Cys Ala Gly Ser Cys Gly Pro Gly Asn Leu His
65                  70                  75                  80

Leu Ile Asn Gly Leu Phe Asp Cys His Arg Asn His Val Pro Val Leu
                85                  90                  95

Ala Ile Ala Ala His Ile Pro Ser Ser Glu Ile Gly Ser Gly Tyr Phe
            100                 105                 110

Gln Glu Thr His Pro Gln Glu Leu Phe Arg Glu Cys Ser His Tyr Cys
        115                 120                 125

Glu Leu Val Ser Ser Pro Glu Gln Ile Pro Gln Val Leu Ala Ile Ala
    130                 135                 140

Met Arg Lys Ala Val Leu Asn Arg Gly Val Ser Val Val Val Leu Pro
145                 150                 155                 160

Gly Asp Val Ala Leu Lys Pro Ala Pro Glu Gly Ala Thr Met His Trp
                165                 170                 175
```

-continued

Tyr His Ala Pro Gln Pro Val Val Thr Pro Glu Glu Glu Leu Arg
            180                 185                 190

Lys Leu Ala Gln Leu Leu Arg Tyr Ser Ser Asn Ile Ala Leu Met Cys
        195                 200                 205

Gly Ser Gly Cys Ala Gly Ala His Lys Glu Leu Val Glu Phe Ala Gly
    210                 215                 220

Lys Ile Lys Ala Pro Ile Val His Ala Leu Arg Gly Lys Glu His Val
225                 230                 235                 240

Glu Tyr Asp Asn Pro Tyr Asp Val Gly Met Thr Gly Leu Ile Gly Phe
                245                 250                 255

Ser Ser Gly Phe His Thr Met Met Asn Ala Asp Thr Leu Val Leu Leu
            260                 265                 270

Gly Thr Gln Phe Pro Tyr Arg Ala Phe Tyr Pro Thr Asp Ala Lys Ile
        275                 280                 285

Ile Gln Ile Asp Ile Asn Pro Ala Ser Ile Gly Ala His Ser Lys Val
    290                 295                 300

Asp Met Ala Leu Val Gly Asp Ile Lys Ser Thr Leu Arg Ala Leu Leu
305                 310                 315                 320

Pro Leu Val Glu Glu Lys Ala Asp Arg Lys Phe Leu Asp Lys Ala Leu
                325                 330                 335

Glu Asp Tyr Arg Asp Ala Arg Lys Gly Leu Asp Leu Ala Lys Pro
            340                 345                 350

Ser Glu Lys Ala Ile His Pro Gln Tyr Leu Ala Gln Gln Ile Ser His
        355                 360                 365

Phe Ala Asp Asp Ala Ile Phe Thr Cys Asp Val Gly Thr Pro Thr
    370                 375                 380

Val Trp Ala Ala Arg Tyr Leu Lys Met Asn Gly Lys Arg Arg Leu Leu
385                 390                 395                 400

Gly Ser Phe Asn His Gly Ser Met Ala Asn Ala Met Pro Gln Ala Leu
                405                 410                 415

Gly Ala Gln Ala Thr Glu Pro Glu Arg Gln Val Val Ala Met Cys Gly
            420                 425                 430

Asp Gly Gly Phe Ser Met Leu Met Gly Asp Phe Leu Ser Val Val Gln
        435                 440                 445

Met Lys Leu Pro Val Lys Ile Val Val Phe Asn Asn Ser Val Leu Gly
    450                 455                 460

Phe Val Ala Met Glu Met Lys Ala Gly Gly Tyr Leu Thr Asp Gly Thr
465                 470                 475                 480

Glu Leu His Asp Thr Asn Phe Ala Arg Ile Ala Glu Ala Cys Gly Ile
                485                 490                 495

Thr Gly Ile Arg Val Glu Lys Ala Ser Glu Val Asp Glu Ala Leu Gln
            500                 505                 510

Arg Ala Phe Ser Ile Asp Gly Pro Val Leu Val Asp Val Val Val Ala
        515                 520                 525

Lys Glu Glu Leu Ala Ile Pro Pro Gln Ile Lys Leu Glu Gln Ala Lys
    530                 535                 540

Gly Phe Ser Leu Tyr Met Leu Arg Ala Ile Ile Ser Gly Arg Gly Asp
545                 550                 555                 560

Glu Val Ile Glu Leu Ala Lys Thr Asn Trp Leu Arg
                565                 570

<210> SEQ ID NO 50
<211> LENGTH: 1719

<212> TYPE: DNA
<213> ORGANISM: Escherichia coli (strain K12)

<400> SEQUENCE: 50

```
atgaaacaaa cggttgcagc ttatatcgcc aaaacactcg aatcggcagg ggtgaaacgc    60
atctggggag tcacaggcga ctctctgaac ggtcttagtg acagtcttaa tcgcatgggc   120
accatcgagt ggatgtccac ccgccacgaa gaagtggcgg cctttgccgc tggcgctgaa   180
gcacaactta gcggagaact ggcggtctgc gccggatcgt gcggcccggg caacctgcac   240
ttaatcaacg gcctgttcga ttgccaccgc aatcacgttc cggtactggc gattgccgct   300
catattccct ccagcgaaat tggcagcggc tatttccagg aaacccaccc acaagagcta   360
ttccgcgaat gtagtcacta ttgcgagctg gtttccagcc cggagcagat cccacaagta   420
ctggcgattg ccatgcgcaa agcggtgctt aaccgtggcg tttcggttgt cgtgttacca   480
ggcgacgtgg cgttaaaacc tgcgccagaa ggggcaacca tgcactggta tcatgcgcca   540
caaccagtcg tgacgccgga agaagaagag ttacgcaaac tggcgcaact gctgcgttat   600
tccagcaata tcgccctgat gtgtggcagc ggctgcgcgg gggcgcataa agagttagtt   660
gagtttgccg ggaaaattaa agcgcctatt gttcatgccc tgcgcggtaa agaacatgtc   720
gaatacgata atccgtatga tgttggaatg accgggttaa tcggcttctc gtcaggtttc   780
cataccatga tgaacgccga cacgttagtg ctactcggca cgcaatttcc ctaccgcgcc   840
ttctacccga ccgatgccaa atcattcag attgatatca cccagccag catcggcgct   900
cacagcaagg tggatatggc actggtcggc gatatcaagt cgactctgcg tgcattgctt   960
ccattggtgg aagaaaaagc cgatcgcaag tttctggata agcgctgga agattaccgc  1020
gacgcccgca aagggctgga cgatttagct aaaccgagcg agaaagccat tcacccgcaa  1080
tatctggcgc agcaaattag tcattttgcc gccgatgacg ctattttcac ctgtgacgtt  1140
ggtacgccaa cggtgtgggc ggcacgttat ctaaaaatga acggcaagcg tcgcctgtta  1200
ggttcgttta accacggttc gatggctaac gccatgccgc aggcgctggg tgcgcaggcg  1260
acagagccag aacgtcaggt ggtcgccatg tgcggcgatg gcggttttag catgttgatg  1320
ggcgatttcc tctcagtagt gcagatgaaa ctgccagtga aaattgtcgt ctttaacaac  1380
agcgtgctgg gctttgtggc gatggagatg aaagctggtg gctatttgac tgacggcacc  1440
gaactacacg acacaaactt tgcccgcatt gccgaagcgt gcggcattac gggtatccgt  1500
gtagaaaaag cgtctgaagt tgatgaagcc ctgcaacgcg ccttctccat cgacggtccg  1560
gtgttggtgg atgtggtggt cgccaaagaa gagttagcca ttccaccgca gatcaaactc  1620
gaacaggcca aggtttcag cctgtatatg ctgcgcgcaa tcatcagcgg acgcggtgat  1680
gaagtgatcg aactggcgaa aacaaactgg ctaaggtaa                         1719
```

<210> SEQ ID NO 51
<211> LENGTH: 480
<212> TYPE: PRT
<213> ORGANISM: Escherichia coli (strain K12)

<400> SEQUENCE: 51

Met Ser Arg Arg Leu Arg Arg Thr Lys Ile Val Thr Thr Leu Gly Pro
1               5                   10                  15

Ala Thr Asp Arg Asp Asn Asn Leu Glu Lys Val Ile Ala Ala Gly Ala
                20                  25                  30

Asn Val Val Arg Met Asn Phe Ser His Gly Ser Pro Glu Asp His Lys
        35                  40                  45

-continued

```
Met Arg Ala Asp Lys Val Arg Glu Ile Ala Ala Lys Leu Gly Arg His
     50                  55                  60
Val Ala Ile Leu Gly Asp Leu Gln Gly Pro Lys Ile Arg Val Ser Thr
 65                  70                  75                  80
Phe Lys Glu Gly Lys Val Phe Leu Asn Ile Gly Asp Lys Phe Leu Leu
                 85                  90                  95
Asp Ala Asn Leu Gly Lys Gly Glu Gly Asp Lys Glu Lys Val Gly Ile
                100                 105                 110
Asp Tyr Lys Gly Leu Pro Ala Asp Val Val Pro Gly Asp Ile Leu Leu
            115                 120                 125
Leu Asp Asp Gly Arg Val Gln Leu Lys Val Leu Glu Val Gln Gly Met
    130                 135                 140
Lys Val Phe Thr Glu Val Thr Val Gly Gly Pro Leu Ser Asn Asn Lys
145                 150                 155                 160
Gly Ile Asn Lys Leu Gly Gly Leu Ser Ala Glu Ala Leu Thr Glu
                165                 170                 175
Lys Asp Lys Ala Asp Ile Lys Thr Ala Ala Leu Ile Gly Val Asp Tyr
            180                 185                 190
Leu Ala Val Ser Phe Pro Arg Cys Gly Glu Asp Leu Asn Tyr Ala Arg
            195                 200                 205
Arg Leu Ala Arg Asp Ala Gly Cys Asp Ala Lys Ile Val Ala Lys Val
    210                 215                 220
Glu Arg Ala Glu Ala Val Cys Ser Gln Asp Ala Met Asp Asp Ile Ile
225                 230                 235                 240
Leu Ala Ser Asp Val Val Met Val Ala Arg Gly Asp Leu Gly Val Glu
                245                 250                 255
Ile Gly Asp Pro Glu Leu Val Gly Ile Gln Lys Ala Leu Ile Arg Arg
            260                 265                 270
Ala Arg Gln Leu Asn Arg Ala Val Ile Thr Ala Thr Gln Met Met Glu
    275                 280                 285
Ser Met Ile Thr Asn Pro Met Pro Thr Arg Ala Glu Val Met Asp Val
290                 295                 300
Ala Asn Ala Val Leu Asp Gly Thr Asp Ala Val Met Leu Ser Ala Glu
305                 310                 315                 320
Thr Ala Ala Gly Gln Tyr Pro Ser Glu Thr Val Ala Ala Met Ala Arg
                325                 330                 335
Val Cys Leu Gly Ala Glu Lys Ile Pro Ser Ile Asn Val Ser Lys His
            340                 345                 350
Arg Leu Asp Val Gln Phe Asp Asn Val Glu Glu Ala Ile Ala Met Ser
    355                 360                 365
Ala Met Tyr Ala Ala Asn His Leu Lys Gly Val Thr Ala Ile Ile Thr
370                 375                 380
Met Thr Glu Ser Gly Arg Thr Ala Leu Met Thr Ser Arg Ile Ser Ser
385                 390                 395                 400
Gly Leu Pro Ile Phe Ala Met Ser Arg His Glu Arg Thr Leu Asn Leu
                405                 410                 415
Thr Ala Leu Tyr Arg Gly Val Thr Pro Val His Phe Asp Ser Ala Asn
            420                 425                 430
Asp Gly Val Ala Ala Ser Glu Ala Val Asn Leu Leu Arg Asp Lys
    435                 440                 445
Gly Tyr Leu Met Ser Gly Asp Leu Val Ile Val Thr Gln Gly Asp Val
450                 455                 460
```

Met Ser Thr Val Gly Ser Thr Asn Thr Thr Arg Ile Leu Thr Val Glu
465                 470                 475                 480

<210> SEQ ID NO 52
<211> LENGTH: 1443
<212> TYPE: DNA
<213> ORGANISM: Escherichia coli (strain K12)

<400> SEQUENCE: 52

| | |
|---|---|
| atgtccagaa ggcttcgcag aacaaaaatc gttaccacgt taggcccagc aacagatcgc | 60 |
| gataataatc ttgaaaaagt tatcgcggcg ggtgccaacg ttgtacgtat gaactttttct | 120 |
| cacggctcgc ctgaagatca caaaatgcgc gcggataaag ttcgtgagat tgccgcaaaa | 180 |
| ctggggcgtc atgtggctat tctgggtgac ctccaggggc ccaaaatccg tgtatccacc | 240 |
| tttaaagaag gcaaagttt cctcaatatt ggggataaat tcctgctcga cgccaacctg | 300 |
| ggtaaaggtg aaggcgacaa agaaaaagtc ggtatcgact acaaaggcct gcctgctgac | 360 |
| gtcgtgcctg gtgacatcct gctgctggac gatggtcgcg tccagttaaa agtactggaa | 420 |
| gttcagggca tgaaagtgtt caccgaagtc accgtcggtg gtcccctctc caacaataaa | 480 |
| ggtatcaaca aacttggcgg cggttttgtcg gctgaagcgc tgaccgaaaa agacaaagca | 540 |
| gacattaaga ctgcggcgtt gattggcgta gattacctgg ctgtctcctt cccacgctgt | 600 |
| ggcgaagatc tgaactatgc ccgtcgcctg cacgcgatg caggatgtga tgcgaaaatt | 660 |
| gttgccaagg ttgaacgtgc ggaagccgtt tgcagccagg atgcaatgga tgacatcatc | 720 |
| ctcgcctctg acgtggtaat ggttcacgt ggcgacctcg tgtgtgaaat tggcgacccg | 780 |
| gaactggtcg gcattcagaa agcgttgatc cgtcgtgcgc gtcagctaaa ccgagcggta | 840 |
| atcacggcga cccagatgat ggagtcaatg attactaacc gatgccgac gcgtgcagaa | 900 |
| gtcatggacg tagcaaacgc cgttctggat ggtactgacg ctgtgatgct gtctgcagaa | 960 |
| actgccgctg ggcagtatcc gtcagaaacc gttgcagcca tggcgcgcgt ttgcctgggt | 1020 |
| gcggaaaaaa tcccgagcat caacgtttct aaacaccgtc tggacgttca gttcgacaat | 1080 |
| gtggaagaag ctattgccat gtcagcaatg tacgcagcta accacctgaa aggcgttacg | 1140 |
| gcgatcatca ccatgaccga atcgggtcgt accgcgctga tgacctcccg tatcagctct | 1200 |
| ggtctgccaa ttttcgccat gtcgcgccat gaacgtacgc tgaacctgac tgctctctat | 1260 |
| cgtggcgtta cgccggtgca ctttgatagc gctaatgacg cgctagcagc tgccagcgaa | 1320 |
| gcggttaatc tgctgcgcga taaaggttac ttgatgtctg gtgacctggt gattgtcacc | 1380 |
| cagggcgacg tgatgagtac cgtgggttct actaatacca cgcgtatttt aacggtagag | 1440 |
| taa | 1443 |

<210> SEQ ID NO 53
<211> LENGTH: 470
<212> TYPE: PRT
<213> ORGANISM: Escherichia coli (strain K12)

<400> SEQUENCE: 53

Met Lys Lys Thr Lys Ile Val Cys Thr Ile Gly Pro Lys Thr Glu Ser
1               5                   10                  15

Glu Glu Met Leu Ala Lys Met Leu Asp Ala Gly Met Asn Val Met Arg
                20                  25                  30

Leu Asn Phe Ser His Gly Asp Tyr Ala Glu His Gly Gln Arg Ile Gln
                35                  40                  45

Asn Leu Arg Asn Val Met Ser Lys Thr Gly Lys Thr Ala Ala Ile Leu

```
            50                  55                  60
Leu Asp Thr Lys Gly Pro Glu Ile Arg Thr Met Lys Leu Glu Gly Gly
65                  70                  75                  80

Asn Asp Val Ser Leu Lys Ala Gly Gln Thr Phe Thr Phe Thr Thr Asp
                85                  90                  95

Lys Ser Val Ile Gly Asn Ser Glu Met Val Ala Val Thr Tyr Glu Gly
                100                 105                 110

Phe Thr Thr Asp Leu Ser Val Gly Asn Thr Val Leu Val Asp Asp Gly
                115                 120                 125

Leu Ile Gly Met Glu Val Thr Ala Ile Glu Gly Asn Lys Val Ile Cys
            130                 135                 140

Lys Val Leu Asn Asn Gly Asp Leu Gly Glu Asn Lys Gly Val Asn Leu
145                 150                 155                 160

Pro Gly Val Ser Ile Ala Leu Pro Ala Leu Ala Glu Lys Asp Lys Gln
                165                 170                 175

Asp Leu Ile Phe Gly Cys Glu Gln Gly Val Asp Phe Val Ala Ala Ser
                180                 185                 190

Phe Ile Arg Lys Arg Ser Asp Val Ile Glu Ile Arg Glu His Leu Lys
            195                 200                 205

Ala His Gly Gly Glu Asn Ile His Ile Ile Ser Lys Ile Glu Asn Gln
            210                 215                 220

Glu Gly Leu Asn Asn Phe Asp Glu Ile Leu Glu Ala Ser Asp Gly Ile
225                 230                 235                 240

Met Val Ala Arg Gly Asp Leu Gly Val Glu Ile Pro Val Glu Glu Val
                245                 250                 255

Ile Phe Ala Gln Lys Met Met Ile Glu Lys Cys Ile Arg Ala Arg Lys
                260                 265                 270

Val Val Ile Thr Ala Thr Gln Met Leu Asp Ser Met Ile Lys Asn Pro
            275                 280                 285

Arg Pro Thr Arg Ala Glu Ala Gly Asp Val Ala Asn Ala Ile Leu Asp
            290                 295                 300

Gly Thr Asp Ala Val Met Leu Ser Gly Glu Ser Ala Lys Gly Lys Tyr
305                 310                 315                 320

Pro Leu Glu Ala Val Ser Ile Met Ala Thr Ile Cys Glu Arg Thr Asp
                325                 330                 335

Arg Val Met Asn Ser Arg Leu Glu Phe Asn Asn Asp Asn Arg Lys Leu
            340                 345                 350

Arg Ile Thr Glu Ala Val Cys Arg Gly Ala Val Glu Thr Ala Glu Lys
            355                 360                 365

Leu Asp Ala Pro Leu Ile Val Val Ala Thr Gln Gly Gly Lys Ser Ala
370                 375                 380

Arg Ala Val Arg Lys Tyr Phe Pro Asp Ala Thr Ile Leu Ala Leu Thr
385                 390                 395                 400

Thr Asn Glu Lys Thr Ala His Gln Leu Val Leu Ser Lys Gly Val Val
                405                 410                 415

Pro Gln Leu Val Lys Glu Ile Thr Ser Thr Asp Asp Phe Tyr Arg Leu
                420                 425                 430

Gly Lys Glu Leu Ala Leu Gln Ser Gly Leu Ala His Lys Gly Asp Val
            435                 440                 445

Val Val Met Val Ser Gly Ala Leu Val Pro Ser Gly Thr Thr Asn Thr
            450                 455                 460

Ala Ser Val His Val Leu
465                 470
```

<210> SEQ ID NO 54
<211> LENGTH: 1413
<212> TYPE: DNA
<213> ORGANISM: Escherichia coli (strain K12)

<400> SEQUENCE: 54

```
atgaaaaaga ccaaaattgt ttgcaccatc ggaccgaaaa ccgaatctga agagatgtta      60
gctaaaatgc tggacgctgg catgaacgtt atgcgtctga acttctctca tggtgactat     120
gcagaacacg gtcagcgcat tcagaatctg cgcaacgtga tgagcaaaac tggtaaaacc     180
gccgctatcc tgcttgatac caaaggtccg gaaatccgca ccatgaaact ggaaggcggt     240
aacgacgttt ctctgaaagc tggtcagacc tttactttca ccactgataa atctgttatc     300
ggcaacagcg aaatggttgc ggtaacgtat gaaggtttca ctactgacct gtctgttggc     360
aacaccgtac tggttgacga tggtctgatc ggtatggaag ttaccgccat gaaggtaac      420
aaagttatct gtaaagtgct gaacaacggt gacctgggcg aaaacaaagg tgtgaacctg     480
cctggcgttt ccattgctct gccagcactg gctgaaaaag acaaacagga cctgatcttt     540
ggttgcgaac aaggcgtaga cttttgttgct gcttcctttta ttcgtaagcg ttctgacgtt     600
atcgaaatcc gtgagcacct gaaagcgcac ggcggcgaaa acatccacat catctccaaa     660
atcgaaaacc aggaaggcct caacaacttc gacgaaatcc tcgaagcctc tgacggcatc     720
atggttgcgc gtggcgacct gggtgtagaa atcccggtag aagaagttat cttcgcccag     780
aagatgatga tcgaaaaatg tatccgtgca cgtaaagtcg ttatcactgc gacccagatg     840
ctggattcca tgatcaaaaa cccacgcccg actcgcgcag aagccggtga cgttgcaaac     900
gccatcctcg acggtactga cgcagtgatg ctgtctggtg aatccgcaaa aggtaaatac     960
ccgctggaag cggtttctat catggcgacc atctgcgaac gtaccgaccg cgtgatgaac    1020
agccgtctcg agttcaacaa tgacaaccgt aaactgcgca ttaccgaagc ggtatgccgt    1080
ggtgccgttg aaactgctga aaaactggat gctccgctga tcgtggttgc tactcagggc    1140
ggtaaatctg ctcgcgcagt acgtaaatac ttcccggatg ccaccatcct ggcactgacc    1200
accaacgaaa aacggctca tcagttggta ctgagcaaag gcgttgtgcc gcagcttgtt    1260
aaagagatca cttctactga tgatttctac cgtctgggta agaactggc tctgcagagc    1320
ggtctggcac acaaaggtga cgttgtagtt atggtttctg gtgcactggt accgagcggc    1380
actactaaca ccgcatctgt tcacgtcctg taa                                 1413
```

<210> SEQ ID NO 55
<211> LENGTH: 792
<212> TYPE: PRT
<213> ORGANISM: Escherichia coli (strain K12)

<400> SEQUENCE: 55

```
Met Ser Asn Asn Gly Ser Ser Pro Leu Val Leu Trp Tyr Asn Gln Leu
1               5                   10                  15

Gly Met Asn Asp Val Asp Arg Val Gly Gly Lys Asn Ala Ser Leu Gly
            20                  25                  30

Glu Met Ile Thr Asn Leu Ser Gly Met Gly Val Ser Val Pro Asn Gly
        35                  40                  45

Phe Ala Thr Thr Ala Asp Ala Phe Asn Gln Phe Leu Asp Gln Ser Gly
    50                  55                  60

Val Asn Gln Arg Ile Tyr Glu Leu Leu Asp Lys Thr Asp Ile Asp Asp
65                  70                  75                  80
```

```
Val Thr Gln Leu Ala Lys Ala Gly Ala Gln Ile Arg Gln Trp Ile Ile
                85                  90                  95

Asp Thr Pro Phe Gln Pro Glu Leu Glu Asn Ala Ile Arg Glu Ala Tyr
            100                 105                 110

Ala Gln Leu Ser Ala Asp Asp Glu Asn Ala Ser Phe Ala Val Arg Ser
        115                 120                 125

Ser Ala Thr Ala Glu Asp Met Pro Asp Ala Ser Phe Ala Gly Gln Gln
    130                 135                 140

Glu Thr Phe Leu Asn Val Gln Gly Phe Asp Ala Val Leu Val Ala Val
145                 150                 155                 160

Lys His Val Phe Ala Ser Leu Phe Asn Asp Arg Ala Ile Ser Tyr Arg
                165                 170                 175

Val His Gln Gly Tyr Asp His Arg Gly Val Ala Leu Ser Ala Gly Val
            180                 185                 190

Gln Arg Met Val Arg Ser Asp Leu Ala Ser Ser Gly Val Met Phe Ser
        195                 200                 205

Ile Asp Thr Glu Ser Gly Phe Asp Gln Val Val Phe Ile Thr Ser Ala
    210                 215                 220

Trp Gly Leu Gly Glu Met Val Val Gln Gly Ala Val Asn Pro Asp Glu
225                 230                 235                 240

Phe Tyr Val His Lys Pro Thr Leu Ala Ala Asn Arg Pro Ala Ile Val
                245                 250                 255

Arg Arg Thr Met Gly Ser Lys Lys Ile Arg Met Val Tyr Ala Pro Thr
            260                 265                 270

Gln Glu His Gly Lys Gln Val Lys Ile Glu Asp Val Pro Gln Glu Gln
        275                 280                 285

Arg Asp Ile Phe Ser Leu Thr Asn Glu Glu Val Gln Glu Leu Ala Lys
    290                 295                 300

Gln Ala Val Gln Ile Glu Lys His Tyr Gly Arg Pro Met Asp Ile Glu
305                 310                 315                 320

Trp Ala Lys Asp Gly His Thr Gly Lys Leu Phe Ile Val Gln Ala Arg
                325                 330                 335

Pro Glu Thr Val Arg Ser Arg Gly Gln Val Met Glu Arg Tyr Thr Leu
            340                 345                 350

His Ser Gln Gly Lys Ile Ile Ala Glu Gly Arg Ala Ile Gly His Arg
        355                 360                 365

Ile Gly Ala Gly Pro Val Lys Val Ile His Asp Ile Ser Glu Met Asn
    370                 375                 380

Arg Ile Glu Pro Gly Asp Val Leu Val Thr Asp Met Thr Asp Pro Asp
385                 390                 395                 400

Trp Glu Pro Ile Met Lys Lys Ala Ser Ala Ile Val Thr Asn Arg Gly
                405                 410                 415

Gly Arg Thr Cys His Ala Ala Ile Ile Ala Arg Glu Leu Gly Ile Pro
            420                 425                 430

Ala Val Val Gly Cys Gly Asp Ala Thr Glu Arg Met Lys Asp Gly Glu
        435                 440                 445

Asn Val Thr Val Ser Cys Ala Glu Gly Asp Thr Gly Tyr Val Tyr Ala
    450                 455                 460

Glu Leu Leu Glu Phe Ser Val Lys Ser Ser Val Glu Thr Met Pro
465                 470                 475                 480

Asp Leu Pro Leu Lys Val Met Met Asn Val Gly Asn Pro Asp Arg Ala
                485                 490                 495
```

Phe Asp Phe Ala Cys Leu Pro Asn Glu Gly Val Gly Leu Ala Arg Leu
            500                 505                 510

Glu Phe Ile Ile Asn Arg Met Ile Gly Val His Pro Arg Ala Leu Leu
        515                 520                 525

Glu Phe Asp Asp Gln Glu Pro Gln Leu Gln Asn Glu Ile Arg Glu Met
    530                 535                 540

Met Lys Gly Phe Asp Ser Pro Arg Glu Phe Tyr Val Gly Arg Leu Thr
545                 550                 555                 560

Glu Gly Ile Ala Thr Leu Gly Ala Ala Phe Tyr Pro Lys Arg Val Ile
                565                 570                 575

Val Arg Leu Ser Asp Phe Lys Ser Asn Glu Tyr Ala Asn Leu Val Gly
            580                 585                 590

Gly Glu Arg Tyr Glu Pro Asp Glu Asn Pro Met Leu Gly Phe Arg
        595                 600                 605

Gly Ala Gly Arg Tyr Val Ser Asp Ser Phe Arg Asp Cys Phe Ala Leu
    610                 615                 620

Glu Cys Glu Ala Val Lys Arg Val Arg Asn Asp Met Gly Leu Thr Asn
625                 630                 635                 640

Val Glu Ile Met Ile Pro Phe Val Arg Thr Val Asp Gln Ala Lys Ala
                645                 650                 655

Val Val Glu Glu Leu Ala Arg Gln Gly Leu Lys Arg Gly Glu Asn Gly
            660                 665                 670

Leu Lys Ile Ile Met Met Cys Glu Ile Pro Ser Asn Ala Leu Leu Ala
        675                 680                 685

Glu Gln Phe Leu Glu Tyr Phe Asp Gly Phe Ser Ile Gly Ser Asn Asp
    690                 695                 700

Met Thr Gln Leu Ala Leu Gly Leu Asp Arg Asp Ser Gly Val Val Ser
705                 710                 715                 720

Glu Leu Phe Asp Glu Arg Asn Asp Ala Val Lys Ala Leu Leu Ser Met
                725                 730                 735

Ala Ile Arg Ala Ala Lys Lys Gln Gly Lys Tyr Val Gly Ile Cys Gly
            740                 745                 750

Gln Gly Pro Ser Asp His Glu Asp Phe Ala Ala Trp Leu Met Glu Glu
        755                 760                 765

Gly Ile Asp Ser Leu Ser Leu Asn Pro Asp Thr Val Val Gln Thr Trp
    770                 775                 780

Leu Ser Leu Ala Glu Leu Lys Lys
785                 790

<210> SEQ ID NO 56
<211> LENGTH: 2379
<212> TYPE: DNA
<213> ORGANISM: Escherichia coli (strain K12)

<400> SEQUENCE: 56
atgtccaaca atggctcgtc accgctggtg ctttggtata accaactcgg catgaatgat     60
gtagacaggg ttgggggcaa aaatgcctcc ctgggtgaaa tgattactaa tctttccgga    120
atgggtgttt ccgttccgaa tggtttcgcc acaaccgccg acgcgtttaa ccagtttctg    180
gaccaaagcg gcgtaaacca gcgcatttat gaactgctgg ataaaacgga tattgacgat    240
gttactcagc ttgcgaaagc gggcgcgcaa atccgccagt ggattatcga cactcccttc    300
cagcctgagc tggaaaacgc catccgcgaa gcctatgcac agcttccgc cgatgacgaa    360 aacgcctctt ttgcggtgcg ctcctccgcc accgcagaag atatgccgga cgcttctttt    420

```
gccggtcagc aggaaacctt cctcaacgtt cagggttttg acgccgttct cgtggcagtg     480
aaacatgtat tgcttctct gtttaacgat cgcgccatct cttatcgtgt gcaccagggt      540
tacgatcacc gtggtgtggc gctctccgcc ggtgttcaac ggatggtgcg ctctgacctc     600
gcatcatctg gcgtgatgtt ctccattgat accgaatccg gctttgacca ggtggtgttt     660
atcacttccg catggggcct tggtgagatg gtcgtgcagg gtgcggttaa cccggatgag     720
ttttacgtgc ataaaccgac actggcggcg aatcgcccgg ctatcgtgcg ccgcaccatg     780
gggtcgaaaa aaatccgcat ggtttacgcg ccgacccagg agcacggcaa gcaggttaaa     840
atcgaagacg taccgcagga acagcgtgac atcttctcgc tgaccaacga agaagtgcag     900
gaactggcaa acaggccgt acaaattgag aaacactacg gtcgcccgat ggatattgag      960
tgggcgaaag atggccacac cggtaaactg ttcattgtgc aggcgcgtcc ggaaaccgtg    1020
cgctcacgcg gtcaggtcat ggagcgttat acgctgcatt cacagggtaa gattatcgcc    1080
gaaggccgtg ctatcggtca tcgcatcggt gcgggtccgg tgaaagtcat ccatgacatc    1140
agcgaaatga accgcatcga acctggcgac gtgctggtta ctgacatgac cgacccggac    1200
tgggaaccga tcatgaagaa agcatctgcc atcgtcacca accgtggcgg tcgtacctgt    1260
cacgcggcga tcatcgctcg tgaactgggc attccggcgg tagtgggctg tggagatgca    1320
acagaacgga tgaaagacgg tgagaacgtc actgtttctt gtgccgaagg tgataccggt    1380
tacgtctatg cggagttgct ggaatttagc gtgaaaagct ccagcgtaga aacgatgccg    1440
gatctgccgt tgaaagtgat gatgaacgtc ggtaacccgg accgtgcttt cgacttcgcc    1500
tgcctaccga acgaaggcgt gggccttgcg cgtctggaat ttatcatcaa ccgtatgatt    1560
ggcgtccacc cacgcgcact gcttgagttt gacgatcagg aaccgcagtt gcaaaacgaa    1620
atccgcgaga tgatgaaagg ttttgattct ccgcgtgaat tttacgttgg tcgtctgact    1680
gaagggatcg cgacgctggg tgccgcgttt tatccgaagc gcgtcattgt ccgtctctct    1740 gatttttaaat cgaacgaata tgccaacctg gtcggtggtg agcgttacga gccagatgaa    1800
gagaacccga tgctcggctt ccgtggcgcg ggccgctatg tttccgacag cttccgcgac    1860
tgtttcgcgc tggagtgtga agcagtgaaa cgtgtgcgca acgacatggg actgaccaac    1920
gttgagatca tgatcccgtt cgtgcgtacc gtagatcagg cgaaagcggt ggttgaagaa    1980
ctggcgcgtc aggggctgaa acgtggcgag aacgggctga aaatcatcat gatgtgtgaa    2040
atcccgtcca acgccttgct ggccgagcag ttcctcgaat atttcgacgg cttctcaatt    2100
ggctcaaacg atatgacgca gctggcgctc ggtctggacc gtgactccgg cgtggtgtct    2160
gaattgttcg atgagcgcaa cgatgcggtg aaagcactgc tgtcgatggc tatccgtgcc    2220
gcgaagaaac agggcaaata tgtcgggatt tgccggtcagg gtccgtccga ccacgaagac    2280
tttgccgcat ggttgatgga agaggggatc gatagcctgt ctctgaaccc ggacaccgtg    2340
gtgcaaacct ggttaagcct ggctgaactg aagaaataa                            2379
```

<210> SEQ ID NO 57
<211> LENGTH: 474
<212> TYPE: PRT
<213> ORGANISM: Escherichia coli (strain K12)

<400> SEQUENCE: 57

```
Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30
```

-continued

Val Ile Val Glu Arg Tyr Asn Thr Leu Gly Gly Val Cys Leu Asn Val
             35                  40                  45

Gly Cys Ile Pro Ser Lys Ala Leu Leu His Val Ala Lys Val Ile Glu
 50                  55                  60

Glu Ala Lys Ala Leu Ala Glu His Gly Ile Val Phe Gly Glu Pro Lys
 65                  70                  75                  80

Thr Asp Ile Asp Lys Ile Arg Thr Trp Lys Glu Lys Val Ile Asn Gln
                 85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
                115                 120                 125

Gly Glu Asn Gly Lys Thr Val Ile Asn Phe Asp Asn Ala Ile Ile Ala
            130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
                180                 185                 190

Val Tyr His Ala Leu Gly Ser Gln Ile Asp Val Val Glu Met Phe Asp
            195                 200                 205

Gln Val Ile Pro Ala Ala Asp Lys Asp Ile Val Lys Val Phe Thr Lys
        210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
                260                 265                 270

Arg Val Pro Asn Gly Lys Asn Leu Asp Ala Gly Lys Ala Gly Val Glu
            275                 280                 285

Val Asp Asp Arg Gly Phe Ile Arg Val Asp Lys Gln Leu Arg Thr Asn
        290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
                340                 345                 350

Thr Glu Pro Glu Val Ala Trp Val Gly Leu Thr Glu Lys Glu Ala Lys
            355                 360                 365

Glu Lys Gly Ile Ser Tyr Glu Thr Ala Thr Phe Pro Trp Ala Ala Ser
        370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 58
<211> LENGTH: 1425
<212> TYPE: DNA
<213> ORGANISM: Escherichia coli (strain K12)

<400> SEQUENCE: 58

| | | | | | |
|---|---|---|---|---|---|
| atgagtactg | aaatcaaaac | tcaggtcgtg | gtacttgggg | caggccccgc | aggttactcc | 60 |
| gctgccttcc | gttgcgctga | tttaggtctg | gaaaccgtaa | tcgtagaacg | ttacaacacc | 120 |
| cttggcggtg | tttgcctgaa | cgtcggctgt | atcccttcta | aagcactgct | gcacgtagca | 180 |
| aaagttatcg | aagaagccaa | agcgctggct | gaacacggta | tcgtcttcgg | cgaaccgaaa | 240 |
| accgatatcg | acaagattcg | tacctggaaa | gagaaagtga | tcaatcagct | gaccggtggt | 300 |
| ctggctggta | tggcgaaagg | ccgcaaagtc | aaagtggtca | acggtctggg | taaattcacc | 360 |
| ggggctaaca | ccctggaagt | tgaaggtgag | aacggcaaaa | ccgtgatcaa | cttcgacaac | 420 |
| gcgatcattg | cagcgggttc | tcgcccgatc | caactgccgt | ttattccgca | tgaagatccg | 480 |
| cgtatctggg | actccactga | cgcgctggaa | ctgaaagaag | taccagaacg | cctgctggta | 540 |
| atgggtggcg | gtatcatcgg | tctggaaatg | ggcaccgttt | accacgcgct | gggttcacag | 600 |
| attgacgtgg | ttgaaatgtt | cgaccaggtt | atcccggcag | ctgacaaaga | catcgttaaa | 660 |
| gtcttcacca | agcgtatcag | caagaaattc | aacctgatgc | tggaaaccaa | agttaccgcc | 720 |
| gttgaagcga | agaagacgg | catttatgtg | acgatggaag | gcaaaaaagc | acccgctgaa | 780 |
| ccgcagcgtt | acgacgccgt | gctggtagcg | attggtcgtg | tgccgaacgg | taaaaacctc | 840 |
| gacgcaggca | aagcaggcgt | ggaagttgac | gaccgtggtt | tcatccgcgt | tgacaaacag | 900 |
| ctgcgtacca | acgtaccgca | catctttgct | atcggcgata | tcgtcggtca | accgatgctg | 960 |
| gcacacaaag | gtgttcacga | aggtcacgtt | gccgctgaag | ttatcgccgg | taagaaacac | 1020 |
| tacttcgatc | cgaaagttat | cccgtccatc | gcctataccg | aaccagaagt | tgcatgggtg | 1080 |
| ggtctgactg | agaaagaagc | gaaagagaaa | ggcatcagct | atgaaaccgc | caccttcccg | 1140 |
| tgggctgctt | ctggtcgtgc | tatcgcttcc | gactgcgcag | acggtatgac | caagctgatt | 1200 |
| ttcgacaaag | aatctcaccg | tgtgatcggt | ggtgcgattg | tcggtactaa | cggcggcgag | 1260 |
| ctgctgggtg | aaatcggcct | ggcaatcgaa | atgggttgtg | atgctgaaga | catcgcactg | 1320 |
| accatccacg | cgcacccgac | tctgcacgag | tctgtgggcc | tggcggcaga | agtgttcgaa | 1380 |
| ggtagcatta | ccgacctgcc | gaacccgaaa | gcgaagaaga | agtaa | | 1425 |

<210> SEQ ID NO 59
<211> LENGTH: 238
<212> TYPE: PRT
<213> ORGANISM: Escherichia coli (strain K12)

<400> SEQUENCE: 59

Met Gln Thr Pro His Ile Leu Ile Val Glu Asp Glu Leu Val Thr Arg
1               5                   10                  15

Asn Thr Leu Lys Ser Ile Phe Glu Ala Glu Gly Tyr Asp Val Phe Glu
                20                  25                  30

Ala Thr Asp Gly Ala Glu Met His Gln Ile Leu Ser Glu Tyr Asp Ile
            35                  40                  45

Asn Leu Val Ile Met Asp Ile Asn Leu Pro Gly Lys Asn Gly Leu Leu
    50                  55                  60

Leu Ala Arg Glu Leu Arg Glu Gln Ala Asn Val Ala Leu Met Phe Leu
65                  70                  75                  80

Thr Gly Arg Asp Asn Glu Val Asp Lys Ile Leu Gly Leu Glu Ile Gly
                85                  90                  95

Ala Asp Asp Tyr Ile Thr Lys Pro Phe Asn Pro Arg Glu Leu Thr Ile
            100                 105                 110

Arg Ala Arg Asn Leu Leu Ser Arg Thr Met Asn Leu Gly Thr Val Ser
            115                 120                 125

Glu Glu Arg Arg Ser Val Glu Ser Tyr Lys Phe Asn Gly Trp Glu Leu
    130                 135                 140

Asp Ile Asn Ser Arg Ser Leu Ile Gly Pro Asp Gly Glu Gln Tyr Lys
145                 150                 155                 160

Leu Pro Arg Ser Glu Phe Arg Ala Met Leu His Phe Cys Glu Asn Pro
                165                 170                 175

Gly Lys Ile Gln Ser Arg Ala Glu Leu Leu Lys Lys Met Thr Gly Arg
            180                 185                 190

Glu Leu Lys Pro His Asp Arg Thr Val Asp Val Thr Ile Arg Arg Ile
            195                 200                 205

Arg Lys His Phe Glu Ser Thr Pro Asp Thr Pro Glu Ile Ile Ala Thr
    210                 215                 220

Ile His Gly Glu Gly Tyr Arg Phe Cys Gly Asp Leu Glu Asp
225                 230                 235

<210> SEQ ID NO 60
<211> LENGTH: 717
<212> TYPE: DNA
<213> ORGANISM: Escherichia coli (strain K12)

<400> SEQUENCE: 60
atgcagaccc cgcacattct tatcgttgaa gacgagttgg taacacgcaa cacgttgaaa      60
agtattttcg aagcggaagg ctatgatgtt ttcgaagcga cagatggcgc ggaaatgcat     120
cagatcctct ctgaatatga catcaacctg gtgatcatgg atatcaatct gccgggtaag     180
aacggtcttc tgttagcgcg tgaactgcgc gagcaggcga atgttgcgtt gatgttcctg     240
actggccgtg acaacgaagt cgataaaatt ctcggcctcg aaatcggtgc agatgactac     300
atcaccaaac cgttcaaccc gcgtgaactg acgattcgtg cacgcaacct actgtcccgt     360
accatgaatc tgggtactgt cagcgaagaa cgtcgtagcg ttgaaagcta caagttcaat     420
ggttgggaac tggacatcaa cagccgttcg ttgatcggcc ctgatggcga gcagtacaag     480
ctgccgcgca gcgagttccg cgccatgctt cacttctgtg aaaacccagg caaaattcag     540
tcccgtgctg aactgctgaa gaaaatgacc ggccgtgagc tgaaaccgca cgaccgtact     600
gtagacgtga cgatccgccg tattcgtaaa catttcgaat ctacgccgga tacgccggaa     660
atcatcgcca ccattcacgg tgaaggttat cgcttctgcg gtgatctgga agattaa       717

<210> SEQ ID NO 61
<211> LENGTH: 434
<212> TYPE: PRT
<213> ORGANISM: Escherichia coli (strain K12)

<400> SEQUENCE: 61

Met Thr Thr Pro Leu Lys Lys Ile Val Ile Val Gly Gly Gly Ala Gly
1               5                   10                  15

```
Gly Leu Glu Met Ala Thr Gln Leu Gly His Lys Leu Gly Arg Lys Lys
             20                  25                  30

Lys Ala Lys Ile Thr Leu Val Asp Arg Asn His Ser His Leu Trp Lys
         35                  40                  45

Pro Leu Leu His Glu Val Ala Thr Gly Ser Leu Asp Glu Gly Val Asp
 50                  55                  60

Ala Leu Ser Tyr Leu Ala His Ala Arg Asn His Gly Phe Gln Phe Gln
 65                  70                  75                  80

Leu Gly Ser Val Ile Asp Ile Asp Arg Glu Ala Lys Thr Ile Thr Ile
                 85                  90                  95

Ala Glu Leu Arg Asp Glu Lys Gly Glu Leu Leu Val Pro Glu Arg Lys
            100                 105                 110

Ile Ala Tyr Asp Thr Leu Val Met Ala Leu Gly Ser Thr Ser Asn Asp
            115                 120                 125

Phe Asn Thr Pro Gly Val Lys Glu Asn Cys Ile Phe Leu Asp Asn Pro
130                 135                 140

His Gln Ala Arg Arg Phe His Gln Glu Met Leu Asn Leu Phe Leu Lys
145                 150                 155                 160

Tyr Ser Ala Asn Leu Gly Ala Asn Gly Lys Val Asn Ile Ala Ile Val
                165                 170                 175

Gly Gly Gly Ala Thr Gly Val Glu Leu Ser Ala Glu Leu His Asn Ala
            180                 185                 190

Val Lys Gln Leu His Ser Tyr Gly Tyr Lys Gly Leu Thr Asn Glu Ala
            195                 200                 205

Leu Asn Val Thr Leu Val Glu Ala Gly Glu Arg Ile Leu Pro Ala Leu
            210                 215                 220

Pro Pro Arg Ile Ser Ala Ala His Asn Glu Leu Thr Lys Leu Gly
225                 230                 235                 240

Val Arg Val Leu Thr Gln Thr Met Val Thr Ser Ala Asp Glu Gly Gly
                245                 250                 255

Leu His Thr Lys Asp Gly Glu Tyr Ile Glu Ala Asp Leu Met Val Trp
            260                 265                 270

Ala Ala Gly Ile Lys Ala Pro Asp Phe Leu Lys Asp Ile Gly Gly Leu
            275                 280                 285

Glu Thr Asn Arg Ile Asn Gln Leu Val Val Glu Pro Thr Leu Gln Thr
290                 295                 300

Thr Arg Asp Pro Asp Ile Tyr Ala Ile Gly Asp Cys Ala Ser Cys Pro
305                 310                 315                 320

Arg Pro Glu Gly Gly Phe Val Pro Pro Arg Ala Gln Ala Ala His Gln
                325                 330                 335

Met Ala Thr Cys Ala Met Asn Asn Ile Leu Ala Gln Met Asn Gly Lys
            340                 345                 350

Pro Leu Lys Asn Tyr Gln Tyr Lys Asp His Gly Ser Leu Val Ser Leu
            355                 360                 365

Ser Asn Phe Ser Thr Val Gly Ser Leu Met Gly Asn Leu Thr Arg Gly
370                 375                 380

Ser Met Met Ile Glu Gly Arg Ile Ala Arg Phe Val Tyr Ile Ser Leu
385                 390                 395                 400

Tyr Arg Met His Gln Ile Ala Leu His Gly Tyr Phe Lys Thr Gly Leu
                405                 410                 415

Met Met Leu Val Gly Ser Ile Asn Arg Val Ile Arg Pro Arg Leu Lys
            420                 425                 430

Leu His
```

<210> SEQ ID NO 62
<211> LENGTH: 1305
<212> TYPE: DNA
<213> ORGANISM: Escherichia coli (strain K12)

<400> SEQUENCE: 62

```
ttgactacgc cattgaaaaa gattgtgatt gtcggcggcg gtgctggtgg gctggaaatg      60
gcaacacagc tggggcataa gctgggacgc aagaaaaaag ccaaaattac gctggtcgat     120
cgtaaccaca gccacctgtg gaaaccgctg ctgcacgaag tggcgactgg ctcgcttgat     180
gaaggcgtcg atgcgttgag ctatctggcc catgcgcgca atcatggttt ccagttccag     240
ctgggttccg tcattgatat tgatcgtgaa gcgaaaacaa tcactattgc agaactgcgc     300
gacgagaaag gtgaactgct ggttccggaa cgtaaaatcg cctatgacac cctggtaatg     360
gcgctgggta gcacctctaa cgatttcaat acgccaggtg tcaaagagaa ctgcattttc     420
ctcgataacc cgcaccaggc gcgtcgcttc caccaggaga tgctgaattt gttcctgaaa     480
tactccgcca acctgggcgc gaatggcaaa gtgaacattg cgattgtcgg cggcggcgcg     540
acgggtgtag aactctccgc tgaattgcac aacgcggtca gcaactgca cagctacggt     600
tacaaaggcc tgaccaacga agccctgaac gtaacgctgg tagaagcggg agaacgtatt     660
ttgcctgcgt taccgccacg tatctctgct gcggcccaca acgagctaac gaaacttggc     720
gttcgcgtgc tgacgcaaac catggtcacc agtgctgatg aaggcggcct gcacactaaa     780
gatggcgaat atattgaggc tgatctgatg gtatgggcag ccgggatcaa agcgccagac     840
ttcctgaaag atatcggtgg tcttgaaact aaccgtatca accagctggt ggtggaaccg     900
acgctgcaaa ccacccgcga tccagacatt tacgctattg cgactgcgc gtcatgcccg     960
cgtccggaag ggggctttgt tccgccgcgt gctcaggctg cacaccagat ggcgacttgc    1020
gcaatgaaca acattctggc gcagatgaac ggtaagccgc tgaaaaatta tcagtataaa    1080
gatcatggtt cgctggtatc gctgtcgaac ttctccaccg tcggtagcct gatgggtaac    1140
ctgacgcgcg gctcaatgat gattgaagga cgaattgcgc gctttgtata tatctcgcta    1200
taccgaatgc atcagattgc gctgcatggt tactttaaaa ccggattaat gatgctggtg    1260
gggagtatta accgcgttat ccgtccgcgt ttgaagttgc attaa                    1305
```

<210> SEQ ID NO 63
<211> LENGTH: 331
<212> TYPE: PRT
<213> ORGANISM: Escherichia coli (strain K12)

<400> SEQUENCE: 63

```
Met Thr Ile Lys Val Gly Ile Asn Gly Phe Gly Arg Ile Gly Arg Ile
1               5                   10                  15

Val Phe Arg Ala Ala Gln Lys Arg Ser Asp Ile Glu Ile Val Ala Ile
            20                  25                  30

Asn Asp Leu Leu Asp Ala Asp Tyr Met Ala Tyr Met Leu Lys Tyr Asp
        35                  40                  45

Ser Thr His Gly Arg Phe Asp Gly Thr Val Glu Val Lys Asp Gly His
    50                  55                  60

Leu Ile Val Asn Gly Lys Lys Ile Arg Val Thr Ala Glu Arg Asp Pro
65                  70                  75                  80

Ala Asn Leu Lys Trp Asp Glu Val Gly Val Asp Val Val Ala Glu Ala
                85                  90                  95
```

```
Thr Gly Leu Phe Leu Thr Asp Glu Thr Ala Arg Lys His Ile Thr Ala
            100                 105                 110
Gly Ala Lys Lys Val Val Met Thr Gly Pro Ser Lys Asp Asn Thr Pro
        115                 120                 125
Met Phe Val Lys Gly Ala Asn Phe Asp Lys Tyr Ala Gly Gln Asp Ile
    130                 135                 140
Val Ser Asn Ala Ser Cys Thr Thr Asn Cys Leu Ala Pro Leu Ala Lys
145                 150                 155                 160
Val Ile Asn Asp Asn Phe Gly Ile Ile Glu Gly Leu Met Thr Thr Val
                165                 170                 175
His Ala Thr Thr Ala Thr Gln Lys Thr Val Asp Gly Pro Ser His Lys
            180                 185                 190
Asp Trp Arg Gly Gly Arg Gly Ala Ser Gln Asn Ile Ile Pro Ser Ser
        195                 200                 205
Thr Gly Ala Ala Lys Ala Val Gly Lys Val Leu Pro Glu Leu Asn Gly
    210                 215                 220
Lys Leu Thr Gly Met Ala Phe Arg Val Pro Thr Pro Asn Val Ser Val
225                 230                 235                 240
Val Asp Leu Thr Val Arg Leu Glu Lys Ala Ala Thr Tyr Glu Gln Ile
                245                 250                 255
Lys Ala Ala Val Lys Ala Ala Ala Glu Gly Glu Met Lys Gly Val Leu
            260                 265                 270
Gly Tyr Thr Glu Asp Asp Val Val Ser Thr Asp Phe Asn Gly Glu Val
        275                 280                 285
Cys Thr Ser Val Phe Asp Ala Lys Ala Gly Ile Ala Leu Asn Asp Asn
    290                 295                 300
Phe Val Lys Leu Val Ser Trp Tyr Asp Asn Glu Thr Gly Tyr Ser Asn
305                 310                 315                 320
Lys Val Leu Asp Leu Ile Ala His Ile Ser Lys
                325                 330

<210> SEQ ID NO 64
<211> LENGTH: 996
<212> TYPE: DNA
<213> ORGANISM: Escherichia coli (strain K12)

<400> SEQUENCE: 64
atgactatca aagtaggtat caacggtttt ggccgtatcg gtcgcattgt tttccgtgct      60
gctcagaaac gttctgacat cgagatcgtt gcaatcaacg acctgttaga cgctgattac     120
atggcataca tgctgaaata tgactccact cacggccgtt cgacggtac cgttgaagtg      180 aaagacggtc atctgatcgt taacggtaaa aaaatccgtg ttaccgctga acgtgatccg     240
gctaacctga aatgggacga agttggtgtt gacgttgtcg ctgaagcaac tggtctgttc     300
ctgactgacg aaactgctcg taaacacatc accgctggtg cgaagaaagt ggttatgact     360
ggtccgtcta agacaacac tccgatgttc gttaaaggcg ctaacttcga caaatatgct     420
ggccaggaca tcgtttccaa cgcttcctgc accaccaact gcctggctcc gctggctaaa     480
gttatcaacg ataacttcgg catcatcgaa ggtctgatga ccaccgttca cgctactacc     540
gctactcaga aaccgttga tggcccgtct cacaaagact ggcgcggcgg ccgcggcgct     600
tcccagaaca tcatcccgtc ctctaccggt gctgctaaag ctgtaggtaa agtactgcca     660
gaactgaatg gcaaactgac tggtatggcg ttccgcgttc cgaccccgaa cgtatctgta     720
gttgacctga ccgttcgtct ggaaaaagct gcaacttacg agcagatcaa agctgccgtt     780
```

```
aaagctgctg ctgaaggcga atgaaaggc gttctgggct acaccgaaga tgacgtagta    840
tctaccgatt tcaacggcga agtttgcact tccgtgttcg atgctaaagc tggtatcgct    900
ctgaacgaca acttcgtgaa actggtatcc tggtacgaca acgaaaccgg ttactccaac    960
aaagttctgg acctgatcgc tcacatctcc aaataa                              996
```

```
<210> SEQ ID NO 65
<211> LENGTH: 415
<212> TYPE: PRT
<213> ORGANISM: Escherichia coli (strain W)

<400> SEQUENCE: 65
```

```
Met Ala Leu Asn Ile Pro Phe Arg Asn Ala Tyr Tyr Arg Phe Ala Ser
1               5                   10                  15

Ser Tyr Ser Phe Leu Phe Phe Ile Ser Trp Ser Leu Trp Trp Ser Leu
            20                  25                  30

Tyr Ala Ile Trp Leu Lys Gly His Leu Gly Leu Thr Gly Thr Glu Leu
        35                  40                  45

Gly Thr Leu Tyr Ser Val Asn Gln Phe Thr Ser Ile Leu Phe Met Met
    50                  55                  60

Phe Tyr Gly Ile Val Gln Asp Lys Leu Gly Leu Lys Lys Pro Leu Ile
65                  70                  75                  80

Trp Cys Met Ser Phe Ile Leu Val Leu Thr Gly Pro Phe Met Ile Tyr
                85                  90                  95

Val Tyr Glu Pro Leu Leu Gln Ser Asn Phe Ser Val Gly Leu Ile Leu
            100                 105                 110

Gly Ala Leu Phe Phe Gly Leu Gly Tyr Leu Ala Gly Cys Gly Leu Leu
        115                 120                 125

Asp Ser Phe Thr Glu Lys Met Ala Arg Asn Phe His Phe Glu Tyr Gly
    130                 135                 140

Thr Ala Arg Ala Trp Gly Ser Phe Gly Tyr Ala Ile Gly Ala Phe Phe
145                 150                 155                 160

Ala Gly Ile Phe Phe Ser Ile Ser Pro His Ile Asn Phe Trp Leu Val
                165                 170                 175

Ser Leu Phe Gly Ala Val Phe Met Met Ile Asn Met Arg Phe Lys Asp
            180                 185                 190

Lys Asp His Gln Cys Ile Ala Ala Asp Ala Gly Gly Val Lys Lys Glu
        195                 200                 205

Asp Phe Ile Ala Val Phe Lys Asp Arg Asn Phe Trp Val Phe Val Ile
    210                 215                 220

Phe Ile Val Gly Thr Trp Ser Phe Tyr Asn Ile Phe Asp Gln Gln Leu
225                 230                 235                 240

Phe Pro Val Phe Tyr Ala Gly Leu Phe Glu Ser His Asp Val Gly Thr
                245                 250                 255

Arg Leu Tyr Gly Tyr Leu Asn Ser Phe Gln Val Val Leu Glu Ala Leu
            260                 265                 270

Cys Met Ala Ile Ile Pro Phe Phe Val Asn Arg Val Gly Pro Lys Asn
        275                 280                 285

Ala Leu Leu Ile Gly Val Val Ile Met Ala Leu Arg Ile Leu Ser Cys
    290                 295                 300

Ala Leu Phe Val Asn Pro Trp Ile Ile Ser Leu Val Lys Leu Leu His
305                 310                 315                 320

Ala Ile Glu Val Pro Leu Cys Val Ile Ser Val Phe Lys Tyr Ser Val
                325                 330                 335
```

Ala Asn Phe Asp Lys Arg Leu Ser Ser Thr Ile Phe Leu Ile Gly Phe
                340                 345                 350

Gln Ile Ala Ser Ser Leu Gly Ile Val Leu Leu Ser Thr Pro Thr Gly
        355                 360                 365

Ile Leu Phe Asp His Ala Gly Tyr Gln Thr Val Phe Phe Ala Ile Ser
370                 375                 380

Gly Ile Val Cys Leu Met Leu Leu Phe Gly Ile Phe Phe Leu Ser Lys
385                 390                 395                 400

Lys Arg Glu Gln Ile Val Met Glu Thr Pro Val Pro Ser Ala Ile
                405                 410                 415

<210> SEQ ID NO 66
<211> LENGTH: 1248
<212> TYPE: DNA
<213> ORGANISM: Escherichia coli (strain W)

<400> SEQUENCE: 66
atggcactga atattccatt cagaaatgcg tactatcgtt ttgcatccag ttactcattt      60 ctcttttta tttcctggtc gctgtggtgg tcgttatacg ctatttggct gaaaggacat     120
ctaggattaa cagggacgga attaggtaca ctttattcgg tcaaccagtt taccagcatt     180
ctatttatga tgttctacgg catcgttcag gataaactcg gtctgaagaa accgctcatc     240
tggtgtatga gtttcattct ggtcttgacc ggaccgttta tgatttacgt ttatgaaccg     300
ttactgcaaa gcaattttc tgtaggtcta attctggggg cgctcttttt tggcctgggg     360
tatctggcgg gatgcggttt gcttgacagc ttcaccgaaa aaatggcgcg aaattttcat     420
ttcgaatatg aacagcgcg cgcctgggga tcttttggct atgctattgg cgcgttcttt     480
gccggtatat tttttagtat cagtccccat atcaacttct ggttggtctc gctatttggc     540
gctgtattta tgatgatcaa catgcgtttt aaagataagg atcaccagtg catagcggcg     600
gatgcgggag gggtaaaaaa agaggatttt atcgcagttt tcaaggatcg aaacttctgg     660
gttttcgtca tatttattgt ggggacgtgg tctttctata acattttga tcaacaactc     720 tttcctgtct tttatgcagg tttattcgaa tcacacgatg taggaacgcg cctgtatggt     780
tatctcaact cattccaggt ggtactcgaa gcgctgtgca tggcgattat tccttctctt     840
gtgaatcggg tagggccaaa aaatgcatta cttatcggtg ttgtgattat ggcgttgcgt     900
atcctttcct gcgcgttgtt cgttaacccc tggattattt cattagtgaa gctgttacat     960
gccattgagg ttccactttg tgtcatatcc gtcttcaaat acagcgtggc aaactttgat    1020
aagcgcctgt cgtcgacgat ctttctgatt ggttttcaaa ttgccagttc gcttgggatt    1080
gtgctgcttt caacgccgac tgggatactc tttgaccacg caggctacca gacagttttc    1140
ttcgcaattt cgggtattgt ctgcctgatg ttgctatttg gcattttctt cctgagtaaa    1200
aaacgcgagc aaatagttat ggaaacgcct gtaccttcag caatatag                  1248

<210> SEQ ID NO 67
<211> LENGTH: 477
<212> TYPE: PRT
<213> ORGANISM: Escherichia coli (strain W)

<400> SEQUENCE: 67

Met Thr Gln Ser Arg Leu His Ala Ala Gln Asn Ala Leu Ala Lys Leu
1               5                   10                  15

His Glu Arg Arg Gly Asn Thr Phe Tyr Pro His Phe His Leu Ala Pro
                20                  25                  30

```
Pro Ala Gly Trp Met Asn Asp Pro Asn Gly Leu Ile Trp Phe Asn Asp
             35                  40                  45

Arg Tyr His Ala Phe Tyr Gln His His Pro Met Ser Glu His Trp Gly
 50                  55                  60

Pro Met His Trp Gly His Ala Thr Ser Asp Asp Met Ile His Trp Gln
65                   70                  75                  80

His Glu Pro Ile Ala Leu Ala Pro Gly Asp Glu Asn Asp Lys Asp Gly
                 85                  90                  95

Cys Phe Ser Gly Ser Ala Val Asp Asp Asn Gly Val Leu Ser Leu Ile
                100                 105                 110

Tyr Thr Gly His Val Trp Leu Asp Gly Ala Gly Asn Asp Asp Ala Ile
            115                 120                 125

Arg Glu Val Gln Cys Leu Ala Thr Ser Arg Asp Gly Ile His Phe Glu
            130                 135                 140

Lys Gln Gly Val Ile Leu Thr Pro Pro Glu Gly Ile Met His Phe Arg
145                 150                 155                 160

Asp Pro Lys Val Trp Arg Glu Ala Asp Thr Trp Trp Met Val Val Gly
                165                 170                 175

Ala Lys Asp Pro Gly Asn Thr Gly Gln Ile Leu Leu Tyr Arg Gly Ser
            180                 185                 190

Ser Leu Arg Glu Trp Thr Phe Asp Arg Val Leu Ala His Ala Asp Ala
        195                 200                 205

Gly Glu Ser Tyr Met Trp Glu Cys Pro Asp Phe Phe Ser Leu Gly Asp
        210                 215                 220

Gln His Tyr Leu Met Phe Ser Pro Gln Gly Met Asn Ala Glu Gly Tyr
225                 230                 235                 240

Ser Tyr Arg Asn Arg Phe Gln Ser Gly Val Ile Pro Gly Met Trp Ser
                245                 250                 255

Pro Gly Arg Leu Phe Ala Gln Ser Gly His Phe Thr Glu Leu Asp Asn
            260                 265                 270

Gly His Asp Phe Tyr Ala Pro Gln Ser Phe Val Ala Lys Asp Gly Arg
        275                 280                 285

Arg Ile Val Ile Gly Trp Met Asp Met Trp Glu Ser Pro Met Pro Ser
        290                 295                 300

Lys Arg Glu Gly Trp Ala Gly Cys Met Thr Leu Ala Arg Glu Leu Ser
305                 310                 315                 320

Glu Ser Asn Gly Lys Leu Leu Gln Arg Pro Val His Glu Ala Glu Ser
                325                 330                 335

Leu Arg Gln Gln His Gln Ser Ile Ser Pro Arg Thr Ile Ser Asn Lys
            340                 345                 350

Tyr Val Leu Gln Glu Asn Ala Gln Ala Val Glu Ile Gln Leu Gln Trp
        355                 360                 365

Ala Leu Lys Asn Ser Asp Ala Glu His Tyr Gly Leu Gln Leu Gly Ala
        370                 375                 380

Gly Met Arg Leu Tyr Ile Asp Asn Gln Ser Glu Arg Leu Val Leu Trp
385                 390                 395                 400

Arg Tyr Tyr Pro His Glu Asn Leu Asp Gly Tyr Arg Ser Ile Pro Leu
                405                 410                 415

Pro Gln Gly Asp Met Leu Ala Leu Arg Ile Phe Ile Asp Thr Ser Ser
            420                 425                 430

Val Glu Val Phe Ile Asn Asp Gly Glu Ala Val Met Ser Ser Arg Ile
        435                 440                 445

Tyr Pro Gln Pro Glu Glu Arg Glu Leu Ser Leu Tyr Ala Ser His Gly
```

```
                450               455               460
Val Ala Val Leu Gln His Gly Ala Leu Trp Gln Leu Gly
465                 470               475
```

<210> SEQ ID NO 68
<211> LENGTH: 1434
<212> TYPE: DNA
<213> ORGANISM: Escherichia coli (strain W)

<400> SEQUENCE: 68

```
atgacgcaat ctcgattgca tgcggcgcaa aacgcactag caaaacttca cgagcgccga    60
ggtaacactt tctatcccca ttttcacctc gcgcctcctg ccgggtggat gaacgatcca   120
aacggcctga tctggtttaa cgatcgttat cacgcgtttt atcaacatca cccgatgagc   180
gaacactggg ggccaatgca ctggggacat gccaccagcg acgatatgat ccactggcag   240
catgagccta ttgcgctagc gccaggagac gagaatgaca agacggggtg ttttttcaggt   300
agtgctgtcg atgacaatgg tgtcctctca cttatctaca ccggacacgt ctggctcgat   360
ggtgcaggta atgacgatgc aattcgcgaa gtacaatgtc tggctaccag tcgggatggt   420
attcatttcg agaaacaggg tgtgatcctc actccaccag aaggcatcat gcacttccgc   480
gatcctaaag tgtggcgtga agccgacaca tggtggatgg tagtcggggc gaaagaccca   540
ggcaacacgg ggcagatcct gctttatcgc ggcagttcat tgcgtgaatg actttcgat   600
cgcgtactgg cccacgctga tgcgggtgaa agctatatgt gggaatgtcc ggacttttc   660
agccttggcg atcagcatta tctgatgttt tccccgcagg gaatgaatgc cgagggatac   720
agttatcgaa atcgctttca aagtggcgta ataccggaa tgtggtcgcc aggacgactt   780
tttgcacaat ccgggcattt tactgaactt gataacgggc atgacttta tgcaccacaa   840
agctttgtag cgaaggatgg tcggcgtatt gttatcggct ggatggatat gtgggaatcg   900
ccaatgccct caaaacgtga aggctgggca ggctgcatga cgctggcgcg cgagctatca   960
gagagcaatg gcaaactcct acaacgcccg gtacacgaag ctgagtcgtt acgccagcag  1020
catcaatcta tctctccccg cacaatcagc aataaatatg ttttgcagga aaacgcgcaa  1080
gcagttgaga ttcagttgca gtgggcgctg aagaacagta tgccgaaca ttacggatta  1140
cagctcggcg ctggaatgcg gctgtatatt gataaccaat ctgagcgact tgttttgtgg  1200
cggtattacc cacacgagaa tttagatggc taccgtagta ttccccctccc gcagggtgac  1260
atgctcgccc taaggatatt tatcgataca tcatccgtgg aagtatttat taacgacggg  1320
gaggcggtga tgagtagccg aatatatccg cagccagaag aacgggaact gtcgctctat  1380
gcctcccacg gagtggctgt gctgcaacat ggagcactct ggcaactggg ttaa        1434
```

<210> SEQ ID NO 69
<211> LENGTH: 307
<212> TYPE: PRT
<213> ORGANISM: Escherichia coli (strain W)

<400> SEQUENCE: 69

```
Met Ser Ala Lys Val Trp Val Leu Gly Asp Ala Val Val Asp Leu Leu
1               5                   10                  15

Pro Glu Ser Asp Gly Arg Leu Leu Pro Cys Pro Gly Gly Ala Pro Ala
            20                  25                  30

Asn Val Ala Val Gly Ile Ala Arg Leu Gly Gly Thr Ser Gly Phe Ile
        35                  40                  45

Gly Arg Val Gly Asp Asp Pro Phe Gly Ala Leu Met Gln Arg Thr Leu
```

| | | | | | | | | | | | |
|---|---|---|---|---|---|---|---|---|---|---|---|
| | | 50 | | | 55 | | | 60 | | | |
| Leu | Thr | Glu | Gly | Val | Asp | Ile | Thr | Tyr | Leu | Lys | Gln | Asp | Glu | Trp | His |
| 65 | | | | 70 | | | | 75 | | | | | | | 80 |

Leu Thr Glu Gly Val Asp Ile Thr Tyr Leu Lys Gln Asp Glu Trp His
65                  70                  75                  80

Arg Thr Ser Thr Val Leu Val Asp Leu Asn Asp Gln Gly Glu Arg Ser
                85                  90                  95

Phe Thr Phe Met Val Arg Pro Ser Ala Asp Leu Phe Leu Glu Thr Thr
            100                 105                 110

Asp Leu Pro Cys Trp Arg His Gly Glu Trp Leu His Leu Cys Ser Ile
        115                 120                 125

Ala Leu Ser Ala Glu Pro Ser Arg Thr Ser Ala Phe Thr Ala Met Thr
    130                 135                 140

Ala Ile Arg His Ala Gly Gly Phe Val Ser Phe Asp Pro Asn Ile Arg
145                 150                 155                 160

Glu Asp Leu Trp Gln Asp Glu His Leu Leu Arg Leu Cys Leu Arg Gln
                165                 170                 175

Ala Leu Gln Leu Ala Asp Val Val Lys Leu Ser Glu Glu Trp Arg
            180                 185                 190

Leu Ile Ser Gly Lys Thr Gln Asn Asp Arg Asp Ile Cys Ala Leu Ala
        195                 200                 205

Lys Glu Tyr Glu Ile Ala Met Leu Leu Val Thr Lys Gly Ala Glu Gly
    210                 215                 220

Val Val Cys Tyr Arg Gly Gln Val His His Phe Ala Gly Met Ser
225                 230                 235                 240

Val Asn Cys Val Asp Ser Thr Gly Ala Gly Asp Ala Phe Val Ala Gly
                245                 250                 255

Leu Leu Thr Gly Leu Ser Ser Thr Gly Leu Ser Thr Asp Glu Arg Glu
            260                 265                 270

Met Arg Arg Ile Ile Asp Leu Ala Gln Arg Cys Gly Ala Leu Ala Val
        275                 280                 285

Thr Ala Lys Gly Ala Met Thr Ala Leu Pro Cys Arg Gln Glu Leu Glu
    290                 295                 300

Ser Glu Lys
305

<210> SEQ ID NO 70
<211> LENGTH: 924
<212> TYPE: DNA
<213> ORGANISM: Escherichia coli (strain W)

<400> SEQUENCE: 70

| | | |
|---|---|---|
| atgtcagcca aagtatgggt tttaggggat gcggtcgtag atctcttgcc agaatcagac | 60 |
| gggcggctac tgccttgtcc tggcggcgcg ccagctaacg ttgcggtggg aatcgcaga | 120 |
| ttaggcggaa caagtgggtt tataggtcgg gtcggtgatg atccttttgg tgcgttaatg | 180 |
| caaagaacgc tgctaactga gggtgtcgat atcacgtatc tgaagcaaga tgaatggcac | 240 |
| cggacatcca cggtgcttgt cgatctgaac gatcaaggag aacgttcatt tacgtttatg | 300 |
| gtccgcccca gtgccgatct ttttttagag acgacagact tgccctgctg gcgacatggc | 360 |
| gaatggttac atctctgttc aattgcgttg tctgccgagc cttcgcgtac cagcgcattt | 420 |
| actgcgatga cggcgatccg gcatgccgga ggttttgtca gcttcgatcc caatattcgt | 480 |
| gaagatctat ggcaagacga gcatttgctc cgcttgtgtt tgcggcaggc gctacaactg | 540 |
| gcggatgtcg tcaagctctc ggaagaagaa tggcgactta tcagtggaaa aacacagaac | 600 |
| gatcgggata tatgcgccct ggcaaaagag tatgagatcg ccatgctgtt ggtgactaaa | 660 |

```
ggtgcagaag gggtggtggt ctgttatcga ggacaagtcc accatttgc tggaatgtct      720 gtgaattgtg tcgatagcac tggggcggga gatgcgttcg ttgccgggtt actcacaggt      780
ctgtcctcta cgggattatc tacagatgag agagaaatgc gacgaattat cgatctcgct      840
caacgttgcg gagcgcttgc agtaacagcg aaagggggcaa tgacagcgct gccatgtcga     900
caagaactgg aaagtgagaa gtaa                                              924
```

<210> SEQ ID NO 71
<211> LENGTH: 456
<212> TYPE: PRT
<213> ORGANISM: Salmonella enterica subsp. enterica serovar Typhimurium

<400> SEQUENCE: 71

```
Met Asp Phe Glu Gln Ile Ser Cys Ser Leu Leu Pro Leu Leu Gly Gly
1               5                   10                  15

Lys Glu Asn Ile Ala Ser Ala Ala His Cys Ala Thr Arg Leu Arg Leu
            20                  25                  30

Val Leu Val Asp Asp Ser Leu Ala Asp Gln Gln Ala Ile Gly Lys Val
        35                  40                  45

Glu Gly Val Lys Gly Cys Phe Arg Asn Ala Gly Gln Met Gln Ile Ile
    50                  55                  60

Phe Gly Thr Gly Val Val Asn Lys Val Tyr Ala Ala Phe Thr Gln Ala
65                  70                  75                  80

Ala Gly Ile Ser Glu Ser Ser Lys Ser Glu Ala Ala Asp Ile Ala Ala
                85                  90                  95

Lys Lys Leu Asn Pro Phe Gln Arg Ile Ala Arg Leu Leu Ser Asn Ile
            100                 105                 110

Phe Val Pro Ile Ile Pro Ala Ile Val Ala Ser Gly Leu Leu Met Gly
        115                 120                 125

Leu Leu Gly Met Val Lys Thr Tyr Gly Trp Val Asp Pro Gly Asn Ala
130                 135                 140

Ile Tyr Ile Met Leu Asp Met Cys Ser Ser Ala Ala Phe Ile Ile Leu
145                 150                 155                 160

Pro Ile Leu Ile Gly Phe Thr Ala Ala Arg Glu Phe Gly Gly Asn Pro
                165                 170                 175

Tyr Leu Gly Ala Thr Leu Gly Gly Ile Leu Thr His Pro Ala Leu Thr
            180                 185                 190

Asn Ala Trp Gly Val Ala Ala Gly Phe His Thr Met Asn Phe Phe Gly
        195                 200                 205

Phe Glu Ile Ala Met Ile Gly Tyr Gln Gly Thr Val Phe Pro Val Leu
    210                 215                 220

Leu Ala Val Trp Phe Met Ser Ile Val Glu Lys Gln Leu Arg Arg Ala
225                 230                 235                 240

Ile Pro Asp Ala Leu Asp Leu Ile Leu Thr Pro Phe Leu Thr Val Ile
                245                 250                 255

Ile Ser Gly Phe Ile Ala Leu Leu Ile Gly Pro Ala Gly Arg Ala
            260                 265                 270

Leu Gly Asp Gly Ile Ser Phe Val Leu Ser Thr Leu Ile Ser His Ala
        275                 280                 285

Gly Trp Leu Ala Gly Leu Leu Phe Gly Gly Leu Tyr Ser Val Ile Val
    290                 295                 300

Ile Thr Gly Ile His His Ser Phe His Ala Val Glu Ala Gly Leu Leu
305                 310                 315                 320
```

```
Gly Asn Pro Ser Ile Gly Val Asn Phe Leu Leu Pro Ile Trp Ala Met
            325                 330                 335

Ala Asn Val Ala Gln Gly Gly Ala Cys Leu Ala Val Trp Phe Lys Thr
        340                 345                 350

Lys Asp Ala Lys Ile Lys Ala Ile Thr Leu Pro Ser Ala Phe Ser Ala
        355                 360                 365

Met Leu Gly Ile Thr Glu Ala Ala Ile Phe Gly Ile Asn Leu Arg Phe
    370                 375                 380

Val Lys Pro Phe Ile Ala Ala Leu Ile Gly Ala Ala Gly Gly Ala
385                 390                 395                 400

Trp Val Val Ser Val His Val Tyr Met Thr Ala Val Gly Leu Thr Ala
                405                 410                 415

Ile Pro Gly Met Ala Ile Val Gln Ala Ser Ser Leu Leu Asn Tyr Ile
                420                 425                 430

Ile Gly Met Val Ile Ala Phe Gly Val Ala Phe Thr Val Ser Leu Val
            435                 440                 445

Leu Lys Tyr Lys Thr Asp Ala Glu
        450                 455
```

<210> SEQ ID NO 72
<211> LENGTH: 1371
<212> TYPE: DNA
<213> ORGANISM: Salmonella enterica subsp. enterica serovar Typhimurium

<400> SEQUENCE: 72

```
atggattttg aacagatttc ctgctcgctg cttccgcttc ttggaggcaa agaaaatatc      60
gccagcgccg cgcactgcgc cacgcgcctg cgcctggtgc tggtcgatga ttcgctggcc     120
gaccagcagg ccatcggcaa agttgaaggg gtgaagggct gttttcgtaa tgccggacag     180
atgcagatta ttttcggcac cggggtggta ataaggtctc acgctgcctt tactcaggcg     240
gcgggtatta gcgaatccag caaatcggaa ccgccgacaa tcgcggcaaa aaagctcaat     300
ccgttccagc gcatcgcccg cctgctatca acatcttcg tgccgataat ccctgccatc     360
gtcgcctctg gtctgctgat gggcctgctg gaatggtca aaacatacgg ctgggttgac     420
ccgggcaacg ccatctacat catgctggat atgtgcagct cggcggcatt tatcattctg     480
ccgattctga ttggctttac cgccgcccgc gaattcggcg gtaatcctta tctcggcgcg     540
acgcttggcg gcattctgac tcatccagcg ctgactaacg cctggggcgt ggccgcgggt     600
ttccacacca tgaacttttt cggcttcgaa attgccatga tcggctatca gggtacggtg     660
ttcccggtac tgctggcagt atggtttatg agcatcgttg agaagcagtt gcgtcgcgca     720
atccccgatg ccctggattt gatcctgacg ccgttcctga cggtgattat atccggtttt     780
atcgccctgt tgattatcgg cccggccggt cgcgcactgg cgacggtat ctcgtttgtc     840 ctcagcaccc tgattagcca cgccggctgg ctcgccgggt tactgtttgg cggtctctat     900
tcagttatcg tcattaccgg tattcatcac agcttccatg cggttgaagc cgggttgctg     960
ggcaatccct ccatcggcgt caacttcctg ctgccgattt gggcgatggc caacgtcgct    1020
cagggcggag cctgtctggc ggtgtggttc aaaaccaaag atgcaaaaat taaagccatt    1080 actctgcct cggcgttttc cgccatgctg gcatcaccg aggcggcgat ttttggtatt    1140
aacctgcgct ttgtgaagcc atttattgcg gcgctgattg gtggtgcggc gggcggcgca    1200
tgggtggtat ctgtacacgt ctacatgacc gcggtcggct tgacagcgat ccccggcatg    1260
gccatcgtgc aggccagttc gctgttgaac tacattatcg ggatggttat cgcctttggc    1320
```

```
gtcgccttta cggtctccct ggttttgaaa tacaaaacgg acgctgaata a            1371
```

<210> SEQ ID NO 73
<211> LENGTH: 307
<212> TYPE: PRT
<213> ORGANISM: Salmonella enterica subsp. enterica serovar Typhimurium

<400> SEQUENCE: 73

```
Met Asn Ala Lys Val Trp Val Leu Gly Asp Ala Val Val Asp Leu Leu
1               5                   10                  15

Pro Glu Ser Glu Gly Arg Leu Leu Gln Cys Pro Gly Gly Ala Pro Ala
            20                  25                  30

Asn Val Ala Val Gly Val Ala Arg Leu Gly Gly Asn Ser Gly Phe Ile
        35                  40                  45

Gly Ala Val Gly Gly Asp Pro Phe Gly Arg Tyr Met Arg His Thr Leu
    50                  55                  60

Gln Gln Glu Gln Val Asp Val Ser His Met Tyr Leu Asp Asp Gln His
65                  70                  75                  80

Arg Thr Ser Thr Val Val Asp Leu Asp Asp Gln Gly Glu Arg Thr
                85                  90                  95

Phe Thr Phe Met Val Arg Pro Ser Ala Asp Leu Phe Leu Val Glu Glu
            100                 105                 110

Asp Leu Pro Gln Phe Ala Ala Gly Gln Trp Leu His Val Cys Ser Ile
        115                 120                 125

Ala Leu Ser Ala Glu Pro Ser Arg Ser Thr Thr Phe Ala Ala Met Glu
    130                 135                 140

Ser Ile Arg Ser Ala Gly Gly Arg Val Ser Phe Asp Pro Asn Ile Arg
145                 150                 155                 160

Pro Asp Leu Trp Gln Asp Gln Ala Leu Leu Leu Ala Cys Leu Asp Arg
                165                 170                 175

Ala Leu His Met Ala Asn Val Val Lys Leu Ser Glu Glu Glu Leu Val
            180                 185                 190

Phe Ile Ser Ser Ser Asn Asp Leu Ala Tyr Gly Ile Ala Ser Val Thr
        195                 200                 205

Glu Arg Tyr Gln Pro Glu Leu Leu Leu Val Thr Arg Gly Lys Ala Gly
    210                 215                 220

Val Leu Ala Ala Phe Gln Gln Lys Phe Thr His Phe Asn Ala Arg Pro
225                 230                 235                 240

Val Ala Ser Val Asp Thr Thr Gly Ala Gly Asp Ala Phe Val Ala Gly
                245                 250                 255

Leu Leu Ala Ser Leu Ala Ala Asn Gly Met Pro Thr Asp Met Thr Ala
            260                 265                 270

Leu Glu Pro Thr Leu Thr Leu Ala Gln Thr Cys Gly Ala Leu Ala Thr
        275                 280                 285

Thr Ala Lys Gly Ala Met Thr Ala Leu Pro Tyr Gln Arg Asp Leu Asn
    290                 295                 300

Arg Gln Phe
305
```

<210> SEQ ID NO 74
<211> LENGTH: 924
<212> TYPE: DNA
<213> ORGANISM: Salmonella enterica subsp. enterica serovar Typhimurium

<400> SEQUENCE: 74

```
atgaatgcaa aagtttgggt tctgggcgac gcggtggtgg acctgctgcc ggagagcgaa    60
```

-continued

```
gggcgcctgc tgcagtgccc tggaggcgcg ccggctaacg tggcggtagg ggttgcccgc    120
cttggcggca acagcggatt tatcggcgcc gtcggcggtg acccgtttgg ccgctacatg    180
cgtcataccc tgcaacagga gcaggtcgac gtcagccata tgtatctcga cgatcagcac    240
cgcacgtcca ctgtggtcgt cgaccttgac gaccaggggg aacgcacctt tacctttatg    300
gtacgcccca gcgcggacct gttcctggtt gaagaagacc tgccacagtt tgccgccgga    360
cagtggttgc acgtctgctc catcgcgctc agcgccgagc ccagccgtag cactaccttc    420
gcggcgatgg agagcatcag gtctgccggc ggtcgggtca gctttgaccc taatattcgt    480
cccgatctct ggcaggatca ggcttttgctg ctagcctgcc tcgatcgcgc tttgcacatg    540
gccaacgtgg taaagctatc ggaagaggag ctggtcttca tcagcagcag taatgattta    600
gcatacggaa tcgccagcgt aacggagcgc tatcagccag aattgctact ggtgacccgg    660
ggcaaagcgg gggtgcttgc cgcgtttcag cagaagttta cccatttcaa cgcccggcct    720
gtggccagcg tggacaccac cggcgcggga gacgcatttg tcgccggact gctcgccagc    780
cttgcggcta acgggatgcc aacggacatg accgcactgg aaccgacact cacgcttgca    840
cagacctgcg gcgccctggc caccacagcc aaaggtgcga tgaccgcctt gccttatcag    900
cgcgatctca accgtcagtt ttaa                                            924
```

<210> SEQ ID NO 75
<211> LENGTH: 466
<212> TYPE: PRT
<213> ORGANISM: Salmonella enterica subsp. enterica serovar Typhimurium

<400> SEQUENCE: 75

```
Met Ser Leu Pro Ser Arg Leu Pro Ala Ile Leu Gln Ala Val Met Gln
1               5                   10                  15

Gly Gln Pro Arg Ala Leu Ala Asp Ser His Tyr Pro Arg Trp His His
            20                  25                  30

Ala Pro Val Thr Gly Leu Met Asn Asp Pro Asn Gly Phe Ile Glu Phe
        35                  40                  45

Ala Gly Arg Tyr His Leu Phe Tyr Gln Trp Asn Pro Leu Ala Cys Asp
    50                  55                  60

His Thr Phe Lys Cys Trp Ala His Trp Ser Ser Ile Asp Leu Leu His
65                  70                  75                  80

Trp Gln His Glu Pro Ile Ala Leu Met Pro Asp Glu Glu Tyr Asp Arg
                85                  90                  95

Asn Gly Cys Tyr Ser Gly Ser Ala Val Asp Asn Asn Gly Thr Leu Thr
            100                 105                 110

Leu Cys Tyr Thr Gly Asn Val Lys Phe Ala Glu Gly Gly Arg Thr Ala
        115                 120                 125

Trp Gln Cys Leu Ala Thr Glu Asn Ala Asp Gly Thr Phe Arg Lys Ile
    130                 135                 140

Gly Pro Val Leu Pro Leu Pro Glu Gly Tyr Thr Gly His Val Arg Asp
145                 150                 155                 160

Pro Lys Val Trp Arg His Glu Asp Leu Trp Tyr Met Val Leu Gly Ala
                165                 170                 175

Gln Asp Arg Gln Lys Arg Gly Lys Val Leu Leu Phe Ser Ser Ala Asp
            180                 185                 190

Leu His Gln Trp Thr Ser Met Gly Glu Ile Ala Gly His Gly Ile Asn
        195                 200                 205

Gly Leu Asp Asp Val Gly Tyr Met Trp Glu Cys Pro Asp Leu Phe Pro
```

```
      210                 215                 220
Leu Gly Asp Gln His Ile Leu Ile Cys Cys Pro Gln Gly Ile Ala Arg
225                 230                 235                 240

Glu Glu Glu Cys Tyr Leu Asn Thr Tyr Pro Ala Val Trp Met Ala Gly
                245                 250                 255

Glu Phe Asp Tyr Ala Ala Gly Ala Phe Arg His Gly Glu Leu His Glu
                260                 265                 270

Leu Asp Ala Gly Phe Glu Phe Tyr Ala Pro Gln Thr Met Leu Thr Ser
            275                 280                 285

Asp Gly Arg Arg Leu Leu Val Gly Trp Met Gly Val Pro Glu Gly Glu
            290                 295                 300

Glu Met Leu Gln Pro Thr Leu Asn Asn Gly Trp Ile His Gln Met Thr
305                 310                 315                 320

Cys Leu Arg Glu Leu Glu Phe Ile Asn Gly Gln Leu Tyr Gln Arg Pro
                325                 330                 335

Leu Arg Glu Leu Ser Ala Leu Arg Gly Glu Ala Asn Gly Trp Ser Gly
                340                 345                 350

Asn Ala Leu Pro Leu Ala Pro Met Glu Ile Asp Leu Gln Thr Arg Gly
            355                 360                 365

Gly Asp Met Leu Ser Leu Asp Phe Gly Gly Val Leu Thr Leu Glu Cys
        370                 375                 380

Asp Ala Ser Gly Leu Arg Leu Ala Arg Arg Ser Leu Ala Ser Asp Glu
385                 390                 395                 400

Met His Tyr Arg Tyr Trp Arg Gly Asn Val Arg Ser Leu Arg Val Phe
                405                 410                 415

Ile Asp Gln Ser Ser Val Glu Ile Phe Ile Asn Gly Gly Glu Gly Val
                420                 425                 430

Met Ser Ser Arg Tyr Phe Pro Ala Cys Ser Gly Gln Leu Thr Phe Ser
            435                 440                 445

Gly Ile Thr Pro Asp Ala Phe Cys Tyr Trp Pro Leu Arg Thr Cys Met
        450                 455                 460

Val Glu
465
```

<210> SEQ ID NO 76
<211> LENGTH: 1401
<212> TYPE: DNA
<213> ORGANISM: Salmonella enterica subsp. enterica serovar Typhimurium

<400> SEQUENCE: 76

```
atgtctcttc catcacgact gcctgcgatt ttgcaggccg taatgcaggg ccagccgcgc      60
gcgctggccg atagccacta tccgcgctgg caccatgcgc cggtcaccgg gctgatgaac     120
gaccccaacg gctttatcga atttgccgga cgctatcatc tgttttatca gtggaacccg     180
ctcgcctgcg atcatacgtt taagtgctgg gcgcactgga gttccatcga tctgctgcac     240
tggcagcatg agcccattgc gctgatgccg acgaagagt atgaccgtaa cggctgctac     300
tccggcagcg cggtggataa caacggtacg cttaccctgt gctataccgg caacgtgaag     360
tttgccgagg agggcgaac cgcctggcaa tgcctggcaa cggaaaacgc tgacggcacc     420
ttccgcaaaa tcggtccggt cctgccgctg ccggagggct acaccggcca cgtgcgcgac     480
ccaaaagtct ggcgacacga agacctgtgg tacatggtgc tgggcgcgca ggatcggcaa     540
aagcgcggca aggtgctgct gttcagctct gcggatctcc atcagtggac gagtatgggt     600
gaaatcgccg ccacggcat caatggcctc gacgacgtcg gctatatgtg ggagtgcccg     660
```

```
gatcttttc cactcggcga ccagcatatt ctaatctgct gtccgcaggg gattgcccgt      720
gaggaagagt gctacctgaa cacctacccg gcagtatgga tggcgggcga gtttgattac      780
gctgctggcg ctttcagaca cggcgaactg cacgaactgg acgccgggtt tgagttctac      840
gccccgcaaa ccatgcttac cagtgatggc cgtcgtctgc tggtcggctg gatgggcgtg      900
ccggagggcg aagagatgct tcagccgacc ctgaacaacg gctggatcca tcagatgacc      960
tgcctgcgtg agctggagtt tatcaacggt cagctctatc agcgtccgct acgggaactg     1020
agcgccctgc gcggtgaagc gaacggctgg tcggggaacg ccctgccgct ggcaccgatg     1080
gaaatcgatt tgcaaacccg cggggcgat atgttgagcc tcgattttgg cggcgtatta      1140
acccttgagt gcgatgccag cggactccgc ctggcccgac gcagtctcgc cagtgacgag     1200
atgcattatc gttactggcg cggaaacgtc cgctcgctgc gtgttttcat cgaccagtcg     1260
agcgtggaga tttcataaa cggcggtgaa ggggtgatga gcagccgcta cttcccggcc      1320
tgctccggtc agctaacatt ctccggcatc acgccggacg cattctgcta ctggccgctg     1380
cgaacttgca tggtagaata a                                                1401
```

<210> SEQ ID NO 77
<211> LENGTH: 505
<212> TYPE: PRT
<213> ORGANISM: Salmonella enterica subsp. enterica serovar Typhimurium

<400> SEQUENCE: 77

```
Met Tyr Arg Lys Ser Thr Leu Ala Met Leu Ile Ala Leu Leu Thr Ser
1               5                   10                  15

Ala Ala Ser Ala His Ala Gln Thr Asp Ile Ser Thr Ile Glu Ala Arg
            20                  25                  30

Leu Asn Ala Leu Glu Lys Arg Leu Gln Glu Ala Glu Asn Arg Ala Gln
        35                  40                  45

Thr Ala Glu Asn Arg Ala Gly Ala Ala Glu Lys Lys Val Gln Gln Leu
    50                  55                  60

Thr Ala Gln Gln Gln Lys Asn Gln Asn Ser Thr Gln Glu Val Ala Gln
65                  70                  75                  80

Arg Thr Ala Arg Leu Glu Lys Lys Ala Asp Asp Lys Ser Gly Phe Glu
                85                  90                  95

Phe His Gly Tyr Ala Arg Ser Gly Val Ile Met Asn Asp Ser Gly Ala
            100                 105                 110

Ser Thr Lys Ser Gly Ala Tyr Ile Thr Pro Ala Gly Glu Thr Gly Gly
        115                 120                 125

Ala Ile Gly Arg Leu Gly Asn Gln Ala Asp Thr Tyr Val Glu Met Asn
    130                 135                 140

Leu Glu His Lys Gln Thr Leu Asp Asn Gly Ala Thr Thr Arg Phe Lys
145                 150                 155                 160

Val Met Val Ala Asp Gly Gln Thr Ser Tyr Asn Asp Trp Thr Ala Ser
                165                 170                 175

Thr Ser Asp Leu Asn Val Arg Gln Ala Phe Val Glu Leu Gly Asn Leu
            180                 185                 190

Pro Thr Phe Ala Gly Pro Phe Lys Gly Ser Thr Leu Trp Ala Gly Lys
        195                 200                 205

Arg Phe Asp Arg Asp Asn Phe Asp Ile His Trp Ile Asp Ser Asp Val
    210                 215                 220

Val Phe Leu Ala Gly Thr Gly Gly Gly Ile Tyr Asp Val Lys Trp Asn
225                 230                 235                 240
```

```
Asp Gly Leu Arg Ser Asn Phe Ser Leu Tyr Gly Arg Asn Phe Gly Asp
            245                 250                 255

Ile Asp Asp Ser Ser Asn Ser Val Gln Asn Tyr Ile Leu Thr Met Asn
        260                 265                 270

His Phe Ala Gly Pro Leu Gln Met Met Val Ser Gly Leu Arg Ala Lys
    275                 280                 285

Asp Asn Asp Glu Arg Lys Asp Ser Asn Gly Asn Leu Ala Lys Gly Asp
290                 295                 300

Ala Ala Asn Thr Gly Val His Ala Leu Leu Gly Leu His Asn Asp Ser
305                 310                 315                 320

Phe Tyr Gly Leu Arg Asp Gly Ser Ser Lys Thr Ala Leu Leu Tyr Gly
            325                 330                 335

His Gly Leu Gly Ala Glu Val Lys Gly Ile Gly Ser Asp Gly Ala Leu
        340                 345                 350

Arg Pro Gly Ala Asp Thr Trp Arg Ile Ala Ser Tyr Gly Thr Thr Pro
    355                 360                 365

Leu Ser Glu Asn Trp Ser Val Ala Pro Ala Met Leu Ala Gln Arg Ser
370                 375                 380

Lys Asp Arg Tyr Ala Asp Gly Asp Ser Tyr Gln Trp Ala Thr Phe Asn
385                 390                 395                 400

Leu Arg Leu Ile Gln Ala Ile Asn Gln Asn Phe Ala Leu Ala Tyr Glu
            405                 410                 415

Gly Ser Tyr Gln Tyr Met Asp Leu Lys Pro Glu Gly Tyr Asn Asp Arg
        420                 425                 430

Gln Ala Val Asn Gly Ser Phe Tyr Lys Leu Thr Phe Ala Pro Thr Phe
    435                 440                 445

Lys Val Gly Ser Ile Gly Asp Phe Phe Ser Arg Pro Glu Ile Arg Phe
450                 455                 460

Tyr Thr Ser Trp Met Asp Trp Ser Lys Lys Leu Asn Asn Tyr Ala Ser
465                 470                 475                 480

Asp Asp Ala Leu Gly Ser Asp Gly Phe Asn Ser Gly Gly Glu Trp Ser
            485                 490                 495

Phe Gly Val Gln Met Glu Thr Trp Phe
        500                 505

<210> SEQ ID NO 78
<211> LENGTH: 1518
<212> TYPE: DNA
<213> ORGANISM: Salmonella enterica subsp. enterica serovar Typhimurium

<400> SEQUENCE: 78
atgtacagaa aaagcacact tgcgatgctt atcgctttgc taaccagcgc tgcctcagcc      60
catgcgcaaa cggatataag caccattgaa gcccgactca acgcgctgga aaaacgcctg     120
caggaggcag aaaacagggc gcaaacggcg gaaaaccgcg ccggggcggc ggagaaaaaa     180
gttcagcaac tcaccgcgca gcagcaaaaa accagaactc gactcaggaa gtggctcag      240 cgtaccgcca gacttgagaa aaaagccgat gacaaaagcg gatttgagtt tcacggttac     300
gcccgctccg gcgtgataat gaatgattcc ggcgccagca ccaaatccgg agcctacata     360
acgccggcag gtgaaaccgg cggagctatc ggccgtctgg aaaccaggc cgatacctat     420 gttgaaatga atcttgaaca taagcagacc ctggataatg gggccacgac ccgctttaag     480
gtgatggtcg ccgacgggca aacctcttat aacgactgga ctgcaagcac cagcgatctg     540
aacgttcgtc aggccttttgt cgaattgggt aacctgccga cgttcgctgg gccatttaag     600
```

```
ggctccaccc tgtgggccgg gaaacgtttc gaccgcgaca atttcgatat tcactggatt    660
gactctgatg tcgtgttcct cgccggtacc ggtggtggta tctatgacgt gaagtggaac    720
gacggcctgc ggagtaattt ctccctgtac gggcgtaact tcggcgacat tgatgattcc    780
agcaacagcg tgcagaacta tatcctcacc atgaatcact tcgcaggtcc gctgcagatg    840
atggtcagcg gtctgcgggc gaaggataac gacgagcgta agatagcaa cggcaatctg     900 gcaaaaggcg atgcggcaaa caccggcgtg catgcgctgc tcggcctgca taacgacagt    960
ttctacggcc tgcgcgacgg tagcagtaaa accgctctgc tttatggtca tggtctgggc   1020
gcagaggtta aaggtatcgg atctgatggc gcacttcgtc cgggagccga cacatggcgc   1080
attgccagtt acggcaccac gccgctcagc gaaaactggt ctgttgcccc ggcaatgctg   1140
gcgcaacgca gtaaagaccg ctatgccgat ggcgacagct atcagtgggc aacattcaac   1200
ctgcgtctga ttcaggcaat caatcagaat ttcgctctcg cctacgaagg cagctaccag   1260
tacatggatc ttaaacccga aggttataac gatcgtcagg cggtgaacgg tagcttctac   1320
aagctcacct tcgccccgac atttaaggtc ggcagtatcg gtgatttctt cagtcgcccg   1380
gagattcgtt tctataccct ctggatggac tggagcaaaa aactgaataa ttacgccagc   1440
gacgacgccc tgggcagtga cggttttaac tcgggcggcg aatggtcttt cggtgtgcag   1500
atggaaacct ggttctga                                                  1518
```

<210> SEQ ID NO 79
<211> LENGTH: 351
<212> TYPE: PRT
<213> ORGANISM: Clostridium beijerinckii (Clostridium MP)

<400> SEQUENCE: 79

```
Met Lys Gly Phe Ala Met Leu Gly Ile Asn Lys Leu Gly Trp Ile Glu
1               5                   10                  15

Lys Glu Arg Pro Val Ala Gly Ser Tyr Asp Ala Ile Val Arg Pro Leu
            20                  25                  30

Ala Val Ser Pro Cys Thr Ser Asp Ile His Thr Val Phe Glu Gly Ala
        35                  40                  45

Leu Gly Asp Arg Lys Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Gly Glu Tyr Phe His Val Asn Asp
        115                 120                 125

Ala Asp Met Asn Leu Ala Ile Leu Pro Lys Asp Met Pro Leu Glu Asn
    130                 135                 140

Ala Val Met Ile Thr Asp Met Met Thr Thr Gly Phe His Gly Ala Glu
145                 150                 155                 160

Leu Ala Asp Ile Gln Met Gly Ser Ser Val Val Ile Gly Ile Gly
            165                 170                 175

Ala Val Gly Leu Met Gly Ile Ala Gly Ala Lys Leu Arg Gly Ala Gly
        180                 185                 190

Arg Ile Ile Gly Val Gly Ser Arg Pro Ile Cys Val Glu Ala Ala Lys
    195                 200                 205
```

```
Phe Tyr Gly Ala Thr Asp Ile Leu Asn Tyr Lys Asn Gly His Ile Val
    210                 215                 220

Asp Gln Val Met Lys Leu Thr Asn Gly Lys Gly Val Asp Arg Val Ile
225                 230                 235                 240

Met Ala Gly Gly Gly Ser Glu Thr Leu Ser Gln Ala Val Ser Met Val
                245                 250                 255

Lys Pro Gly Gly Ile Ile Ser Asn Ile Asn Tyr His Gly Ser Gly Asp
                260                 265                 270

Ala Leu Leu Ile Pro Arg Val Glu Trp Gly Cys Gly Met Ala His Lys
            275                 280                 285

Thr Ile Lys Gly Gly Leu Cys Pro Gly Gly Arg Leu Arg Ala Glu Met
        290                 295                 300

Leu Arg Asp Met Val Val Tyr Asn Arg Val Asp Leu Ser Lys Leu Val
305                 310                 315                 320

Thr His Val Tyr His Gly Phe Asp His Ile Glu Glu Ala Leu Leu Leu
                325                 330                 335

Met Lys Asp Lys Pro Lys Asp Leu Ile Lys Ala Val Val Ile Leu
                340                 345                 350
```

<210> SEQ ID NO 80
<211> LENGTH: 1056
<212> TYPE: DNA
<213> ORGANISM: Clostridium beijerinckii (Clostridium MP)

<400> SEQUENCE: 80

```
atgaaaggtt ttgcaatgct aggtattaat aagttaggat ggatcgaaaa agaaaggcca      60
gttgcgggtt catatgatgc tattgtacgc ccattagcag tatctccgtg tacatcagat     120
atacatactg tttttgaggg agctcttgga gataggaaga atatgatttt agggcatgaa     180
gctgtaggtg aagttgttga agtaggaagt gaagtgaagg attttaaacc tggtgacaga     240
gttatagttc cttgtacaac tccagattgg agatctttgg aagttcaagc tggttttcaa     300
cagcactcaa acggtatgct cgcaggatgg aaattttcaa atttcaagga tggagttttt     360
ggtgaatatt ttcatgtaaa tgatgcggat atgaatcttg cgattctacc taaagacatg     420
ccattagaaa atgctgttat gataacagat atgatgacta ctggatttca tggagcagaa     480
cttgcagata ttcaaatggg ttcaagtgtt gtggtaattg gcattggagc tgttggctta     540
atgggaatag caggtgctaa attacgtgga gcaggtagaa taattggagt ggggagcagg     600
ccgatttgtg ttgaggctgc aaaattttat ggagcaacag atattctaaa ttataaaaat     660
ggtcatatag ttgatcaagt tatgaaatta acgaatggaa aaggcgttga ccgcgtaatt     720
atggcaggcg gtggttctga aacattatcc caagcagtat ctatggttaa accaggagga     780
ataatttcta atataaatta tcatggaagt ggagatgctt tactaatacc acgtgtagaa     840
tggggatgtg gaatggctca caagactata aaaggaggtc tttgtcctgg gggacgtttg     900
agagcagaaa tgttaagaga tatggtagta tataatcgtg ttgatctaag taaattagtt     960
acacatgtat atcatggatt tgatcacata gaagaagcac tgttattaat gaaagacaag    1020
ccaaaagact taattaaagc agtagttata ttataa                             1056
```

<210> SEQ ID NO 81
<211> LENGTH: 352
<212> TYPE: PRT
<213> ORGANISM: Thermoanaerobacter brockii (Thermoanaerobium brockii)

<400> SEQUENCE: 81

```
Met Lys Gly Phe Ala Met Leu Ser Ile Gly Lys Val Gly Trp Ile Glu
1               5                   10                  15

Lys Glu Lys Pro Ala Pro Gly Pro Phe Asp Ala Ile Val Arg Pro Leu
            20                  25                  30

Ala Val Ala Pro Cys Thr Ser Asp Ile His Thr Val Phe Glu Gly Ala
        35                  40                  45

Ile Gly Glu Arg His Asn Met Ile Leu Gly His Glu Ala Val Gly Glu
    50                  55                  60

Val Val Glu Val Gly Ser Glu Val Lys Asp Phe Lys Pro Gly Asp Arg
65                  70                  75                  80

Val Val Val Pro Ala Ile Thr Pro Asp Trp Arg Thr Ser Glu Val Gln
                85                  90                  95

Arg Gly Tyr His Gln His Ser Gly Gly Met Leu Ala Gly Trp Lys Phe
                100                 105                 110

Ser Asn Val Lys Asp Gly Val Phe Gly Glu Phe Phe His Val Asn Asp
            115                 120                 125

Ala Asp Met Asn Leu Ala His Leu Pro Lys Glu Ile Pro Leu Glu Ala
        130                 135                 140

Ala Val Met Ile Pro Asp Met Met Thr Thr Gly Phe His Gly Ala Glu
145                 150                 155                 160

Leu Ala Asp Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
                180                 185                 190

Arg Ile Ile Ala Val Gly Ser Arg Pro Val Cys Val Asp Ala Ala Lys
            195                 200                 205

Tyr Tyr Gly Ala Thr Asp Ile Val Asn Tyr Lys Asp Gly Pro Ile Glu
        210                 215                 220

Ser Gln Ile Met Asn Leu Thr Glu Gly Lys Gly Val Asp Ala Ala Ile
225                 230                 235                 240

Ile Ala Gly Gly Asn Ala Asp Ile Met Ala Thr Ala Val Lys Ile Val
                245                 250                 255

Lys Pro Gly Gly Thr Ile Ala Asn Val Asn Tyr Phe Gly Glu Gly Glu
            260                 265                 270

Val Leu Pro Val Pro Arg Leu Glu Trp Gly Cys Gly Met Ala His Lys
        275                 280                 285

Thr Ile Lys Gly Gly Leu Cys Pro Gly Gly Arg Leu Arg Met Glu Arg
        290                 295                 300

Leu Ile Asp Leu Val Phe Tyr Lys Arg Val Asp Pro Ser Lys Leu Val
305                 310                 315                 320

Thr His Val Phe Arg Gly Phe Asp Asn Ile Glu Lys Ala Phe Met Leu
        325                 330                 335

Met Lys Asp Lys Pro Lys Asp Leu Ile Lys Pro Val Val Ile Leu Ala
            340                 345                 350

<210> SEQ ID NO 82
<211> LENGTH: 1059
<212> TYPE: DNA
<213> ORGANISM: Thermoanaerobacter brockii (Thermoanaerobium brockii)

<400> SEQUENCE: 82
atgaaaggtt ttgcaatgct cagtatcggt aaagttggct ggattgagaa ggaaaagcct      60
gctcctggcc catttgatgc tattgtaaga cctctagctg tggccccttg cacttcggac     120
```

```
attcataccg ttttgaagg cgccattggc gaaagacata acatgatact cggtcacgaa       180
gctgtaggtg aagtagttga agtaggtagt gaggtaaaag attttaaacc tggtgatcgc       240
gttgttgtgc cagctattac ccctgattgg cggacctctg aagtacaaag aggatatcac       300
cagcactccg gtggaatgct ggcaggctgg aaattttcga atgtaaaaga tggtgttttt       360
ggtgaatttt ttcatgtgaa tgatgctgat atgaatttag cacatctgcc taagaaaatt       420
ccattggaag ctgcagttat gattcccgat atgatgacca ctggttttca cggagctgaa       480
ctggcagata tagaattagg tgcgacggta gcagttttgg gtattggccc agtaggtctt       540
atggcagtcg ctggtgccaa attgcgtgga gccggaagaa ttattgccgt aggcagtaga       600
ccagtttgtg tagatgctgc aaaatactat ggagctactg atattgtaaa ctataaagat       660
ggtcctatcg aaagtcagat tatgaatcta actgaaggca aggtgtcga tgctgccatc       720
atcgctggag gaaatgctga cattatggct acagcagtta agattgttaa acctggtggc       780
accatcgcta atgtaaatta ttttggcgaa ggagaggttt tgcctgttcc tcgtcttgaa       840
tgggggttgcg gcatggctca taaaactata aaggcgggc tatgccccgg tggacgtcta       900
agaatggaaa gactgattga ccttgttttt tataagcgtg tcgatccttc taagctcgtc       960
actcacgttt tccggggatt tgacaatatt gaaaaagcct ttatgttgat gaaagacaaa      1020
ccaaaagacc taatcaaacc tgttgtaata ttagcataa                            1059

<210> SEQ ID NO 83
<211> LENGTH: 360
<212> TYPE: PRT
<213> ORGANISM: Entamoeba histolytica

<400> SEQUENCE: 83

Met Lys Gly Leu Ala Met Leu Gly Ile Gly Arg Ile Gly Trp Ile Glu
1               5                   10                  15

Lys Lys Ile Pro Glu Cys Gly Pro Leu Asp Ala Leu Val Arg Pro Leu
                20                  25                  30

Ala Leu Ala Pro Cys Thr Ser Asp Thr His Thr Val Trp Ala Gly Ala
            35                  40                  45

Ile Gly Asp Arg His Asp Met Ile Leu Gly His Glu Ala Val Gly Gln
        50                  55                  60

Ile Val Lys Val Gly Ser Leu Val Lys Arg Leu Lys Val Gly Asp Lys
65                  70                  75                  80

Val Ile Val Pro Ala Ile Thr Pro Asp Trp Gly Glu Glu Ser Gln
                85                  90                  95

Arg Gly Tyr Pro Met His Ser Gly Gly Met Leu Gly Gly Trp Lys Phe
                100                 105                 110

Ser Asn Phe Lys Asp Gly Val Phe Ser Glu Val Phe His Val Asn Glu
            115                 120                 125

Ala Asp Ala Asn Leu Ala Leu Leu Pro Arg Asp Ile Lys Pro Glu Asp
        130                 135                 140

Ala Val Met Leu Ser Asp Met Val Thr Thr Gly Phe His Gly Ala Glu
145                 150                 155                 160

Leu Ala Asn Ile Lys Leu Gly Asp Thr Val Cys Val Ile Gly Ile Gly
                165                 170                 175

Pro Val Gly Leu Met Ser Val Ala Gly Ala Asn His Leu Gly Ala Gly
                180                 185                 190

Arg Ile Phe Ala Val Gly Ser Arg Lys His Cys Cys Asp Ile Ala Leu
            195                 200                 205
```

```
Glu Tyr Gly Ala Thr Asp Ile Ile Asn Tyr Lys Asn Gly Asp Ile Val
            210                 215                 220

Glu Gln Ile Leu Lys Ala Thr Asp Gly Lys Gly Val Asp Lys Val Val
225                 230                 235                 240

Ile Ala Gly Gly Asp Val His Thr Phe Ala Gln Ala Val Lys Met Ile
                245                 250                 255

Lys Pro Gly Ser Asp Ile Gly Asn Val Asn Tyr Leu Gly Glu Gly Asp
            260                 265                 270

Asn Ile Asp Ile Pro Arg Ser Glu Trp Gly Val Gly Met Gly His Lys
        275                 280                 285

His Ile His Gly Gly Leu Thr Pro Gly Gly Arg Val Arg Met Glu Lys
    290                 295                 300

Leu Ala Ser Leu Ile Ser Thr Gly Lys Leu Asp Thr Ser Lys Leu Ile
305                 310                 315                 320

Thr His Arg Phe Glu Gly Leu Glu Lys Val Glu Asp Ala Leu Met Leu
                325                 330                 335

Met Lys Asn Lys Pro Ala Asp Leu Ile Lys Pro Val Val Arg Ile His
            340                 345                 350

Tyr Asp Asp Glu Asp Thr Leu His
        355                 360

<210> SEQ ID NO 84
<211> LENGTH: 1083
<212> TYPE: DNA
<213> ORGANISM: Entamoeba histolytica

<400> SEQUENCE: 84
atgaaaggac ttgctatgct tggaattgga agaattggat ggattgaaaa gaaaatccca      60
gaatgtggac cacttgatgc attagttaga ccattagcac ttgcaccatg tacatcagat     120
acacataccg tttgggcagg agctattgga gatagacatg atatgattct ggacatgaa     180 gcggttggac aaaattgttaa agttggatca ttagttaaga gattaaaagt tggagataaa     240
gttattgtac cagctattac accagattgg ggagaagaag aatcgcaaag aggatatcca     300
atgcattcag gaggaatgct tggaggatgg aaattctcaa atttcaagga tggagttttt     360
tcagaagttt tccatgttaa tgaagcagat gccaatcttg cacttcttcc aagagatatt     420
aaaccagaag atgcagttat gttatcagat atggtaacta ctggattcca tggagcagaa     480
ttagctaata ttaaacttgg agatactgtt tgtgttattg gtattggacc agttggatta     540
atgtcagttg caggagcaaa ccatcttgga gcaggaagaa tctttgcagt aggatcaaga     600
aaacattgtt gtgatattgc attggaatat ggagcaacag atattattaa ttataaaaat     660
ggagatattg taaacaaat tcttaaagct acagacggca aaggagttga taagtcgtt     720 attgcaggag gtgatgttca tacatttgca caagcagtca aaatgattaa accaggatca     780
gatattggaa atgttaatta tcttggagaa ggagataata ttgatattcc aagaagtgaa     840
tggggagttg gaatgggtca taaacacatt catggaggtt taaccccagg tggaagagtc     900
agaatggaaa aattagcatc acttatttca actggtaaat tagatacttc taaacttatt     960
acacatagat ttgaaggatt agaaaaagtt gaagatgcat taatgttaat gaagaataaa    1020
ccagcagacc ttatcaaacc agttgtcaga attcattatg atgatgaaga tactcttcat    1080
taa                                                                  1083

<210> SEQ ID NO 85
<211> LENGTH: 318
```

<212> TYPE: PRT
<213> ORGANISM: Hypocrea jecorina (Trichoderma reesei)

<400> SEQUENCE: 85

Met Ala Ser Lys Thr Tyr Thr Leu Asn Thr Gly Ala Lys Ile Pro Ala
1               5                   10                  15

Val Gly Phe Gly Thr Phe Ala Asn Glu Gly Ala Lys Gly Glu Thr Tyr
            20                  25                  30

Ala Ala Val Thr Lys Ala Leu Asp Val Gly Tyr Arg His Leu Asp Cys
        35                  40                  45

Ala Trp Phe Tyr His Asn Glu Asp Glu Val Gly Asp Ala Val Arg Asp
    50                  55                  60

Phe Leu Ala Arg Arg Pro Asp Val Lys Arg Glu Asp Leu Phe Ile Cys
65                  70                  75                  80

Thr Lys Val Trp Asn His Leu His Glu Pro Gly Asp Val Lys Trp Ser
                85                  90                  95

Ala Lys Asn Ser Cys Glu Asn Leu Lys Val Asp Tyr Ile Asp Leu Phe
            100                 105                 110

Leu Val His Trp Pro Ile Ala Ala Glu Lys Asn Ser Asp Arg Ser Val
        115                 120                 125

Lys Leu Gly Pro Asp Gly Lys Tyr Val Ile Asn Gln Ala Leu Thr Glu
    130                 135                 140

Asn Pro Glu Pro Thr Trp Arg Ala Met Glu Glu Leu Val Glu Ser Gly
145                 150                 155                 160

Leu Val Lys Ala Ile Gly Val Ser Asn Trp Thr Ile Pro Gly Leu Lys
                165                 170                 175

Lys Leu Leu Gln Ile Ala Lys Ile Lys Pro Ala Val Asn Gln Ile Glu
            180                 185                 190

Ile His Pro Phe Leu Pro Asn Glu Glu Leu Val Ala Phe Cys Phe Glu
        195                 200                 205

Asn Gly Ile Leu Pro Glu Ala Tyr Ser Pro Leu Gly Ser Gln Asn Gln
    210                 215                 220

Val Pro Ser Thr Gly Glu Arg Val Arg Asp Asn Pro Thr Leu Lys Ala
225                 230                 235                 240

Val Ala Glu Arg Ser Gly Tyr Ser Leu Ala Gln Ile Leu Leu Ala Trp
                245                 250                 255

Gly Leu Lys Arg Gly Tyr Val Val Leu Pro Lys Ser Ser Thr Pro Ser
            260                 265                 270

Arg Ile Glu Ser Asn Phe Asn Ile Pro Glu Leu Ser Asp Glu Asp Phe
        275                 280                 285

Glu Ala Ile Gln Gln Val Ala Lys Gly Arg His Thr Arg Phe Val Asn
    290                 295                 300

Met Lys Asp Thr Phe Gly Tyr Asn Val Trp Pro Glu Glu Glu
305                 310                 315

<210> SEQ ID NO 86
<211> LENGTH: 957
<212> TYPE: DNA
<213> ORGANISM: Hypocrea jecorina (Trichoderma reesei)

<400> SEQUENCE: 86
atggcctcca agacgtacac tctgaacacc ggtgccaaga tacccgcggt cgggttcggc      60
acattcgcca atgagggtgc caagggcgag acatacgcag ctgttacaaa ggcactggac     120
gttggatacc gccaccttga ttgcgcgtgg ttttaccaca cgaagatgga ggttggtgac     180

```
gcggtacgcg attttctcgc ccgccgaccc gacgtgaaac gcgaggatct cttcatttgc    240
accaaagttt ggaaccacct gcatgagcca gaggacgtca agtggagcgc caagaactcg    300
tgcgaaaacc tcaaggtcga ttacattgac ctgttcctcg tccactggcc aatcgcggcc    360
gagaagaaca gcgacaggag cgtcaagctg ggccccgatg caagtatgt catcaaccaa     420
gccctgacgg aaaacccaga gccaacatgg cgagccatgg aagagcttgt tgaaagcggc    480
ctcgtcaagg caattggagt atccaactgg acgattccgg ggttgaagaa gctccttcag    540
atcgccaaga tcaagccggc agtgaaccag attgagattc acccattcct accaaacgaa    600
gagcttgtgg cgttctgctt tgagaacggg atcctgcccg aagcctactc gccgctgggc    660
tcgcagaacc aggtcccaag caccggcgag cgagtgcgcg acaacccgac actcaaagcg    720
gttgccgagc gaagcggcta cagccttgcc cagatcctat ggcatgggg cctgaagcga     780
ggatatgtgg tcctcccaaa gagctcaact ccaagccgta ttgaaagcaa cttcaacatt    840
ccggagctga gtgatgaaga ctttgaggcg attcaacagg ttgctaaggg gagacatact    900
agatttgtca acatgaagga cacgtttgga tacaacgttt ggccagagga ggaataa       957

<210> SEQ ID NO 87
<211> LENGTH: 367
<212> TYPE: PRT
<213> ORGANISM: artificial
<220> FEATURE:
<223> OTHER INFORMATION: GldA* (D37G, P161S, L164A )

<400> SEQUENCE: 87

Met Asp Arg Ile Ile Gln Ser Pro Gly Lys Tyr Ile Gln Gly Ala Asp
1               5                   10                  15

Val Ile Asn Arg Leu Gly Glu Tyr Leu Lys Pro Leu Ala Glu Arg Trp
                20                  25                  30

Leu Val Val Gly Gly Lys Phe Val Leu Gly Phe Ala Gln Ser Thr Val
            35                  40                  45

Glu Lys Ser Phe Lys Asp Ala Gly Leu Val Val Glu Ile Ala Pro Phe
        50                  55                  60

Gly Gly Glu Cys Ser Gln Asn Glu Ile Asp Arg Leu Arg Gly Ile Ala
65                  70                  75                  80

Glu Thr Ala Gln Cys Gly Ala Ile Leu Gly Ile Gly Gly Gly Lys Thr
                85                  90                  95

Leu Asp Thr Ala Lys Ala Leu Ala His Phe Met Gly Val Pro Val Ala
                100                 105                 110

Ile Ala Pro Thr Ile Ala Ser Thr Asp Ala Pro Cys Ser Ala Leu Ser
            115                 120                 125

Val Ile Tyr Thr Asp Glu Gly Glu Phe Asp Arg Tyr Leu Leu Leu Pro
        130                 135                 140

Asn Asn Pro Asn Met Val Ile Val Asp Thr Lys Ile Val Ala Gly Ala
145                 150                 155                 160

Ser Ala Arg Ala Leu Ala Ala Gly Ile Gly Asp Ala Leu Ala Thr Trp
                165                 170                 175

Phe Glu Ala Arg Ala Cys Ser Arg Ser Gly Ala Thr Thr Met Ala Gly
            180                 185                 190

Gly Lys Cys Thr Gln Ala Ala Leu Ala Leu Ala Glu Leu Cys Tyr Asn
        195                 200                 205

Thr Leu Leu Glu Glu Gly Glu Lys Ala Met Leu Ala Ala Glu Gln His
    210                 215                 220

Val Val Thr Pro Ala Leu Glu Arg Val Ile Glu Ala Asn Thr Tyr Leu
```

```
            225                 230                 235                 240

Ser Gly Val Gly Phe Glu Ser Gly Gly Leu Ala Ala His Ala Val
                245                 250                 255

His Asn Gly Leu Thr Ala Ile Pro Asp Ala His His Tyr Tyr His Gly
                260                 265                 270

Glu Lys Val Ala Phe Gly Thr Leu Thr Gln Leu Val Leu Glu Asn Ala
                275                 280                 285

Pro Val Glu Glu Ile Glu Thr Val Ala Ala Leu Ser His Ala Val Gly
            290                 295                 300

Leu Pro Ile Thr Leu Ala Gln Leu Asp Ile Lys Glu Asp Val Pro Ala
305                 310                 315                 320

Lys Met Arg Ile Val Ala Glu Ala Ala Cys Ala Glu Gly Glu Thr Ile
                325                 330                 335

His Asn Met Pro Gly Gly Ala Thr Pro Asp Gln Val Tyr Ala Ala Leu
                340                 345                 350

Leu Val Ala Asp Gln Tyr Gly Gln Arg Phe Leu Gln Glu Trp Glu
                355                 360                 365

<210> SEQ ID NO 88
<211> LENGTH: 1104
<212> TYPE: DNA
<213> ORGANISM: artificial
<220> FEATURE:
<223> OTHER INFORMATION: GldA* (D37G, P161S, L164A )

<400> SEQUENCE: 88
atggaccgca ttattcaatc accgggtaaa tacatccagg gcgctgatgt gattaatcgt      60
ctgggcgaat acctgaagcc gctggcagaa cgctggttag tggtgggtgg caaatttgtt     120
ttaggttttg ctcaatccac tgtcgagaaa agctttaaag atgctggact ggtagtagaa     180
attgcgccgt ttggcggtga atgttcgcaa atgagatcg accgtctgcg tggcatcgcg     240
gagactgcgc agtgtggcgc aattctcggt atcggtggcg aaaaaccct cgatactgcc     300 aaagcactgg cacatttcat gggtgttccg gtagcgatcg caccgactat cgcctctacc     360
gatgcaccgt gcagcgcatt gtctgttatc tacaccgatg agggtgagtt tgaccgctat     420
ctgctgttgc aaataaccc gaatatggtc attgtcgaca ccaaaatcgt cgctggcgca     480
tctgcacgtg cgttagcggc gggtatcggc gatgcgctgg caacctggtt tgaagcgcgt     540
gcctgctctc gtagcggcgc gaccaccatg gcgggcggca agtgcaccca ggctgcgctg     600
gcactggctg aactgtgcta caacaccctg ctggaagaag cgaaaaagc gatgcttgct     660 gccgaacagc atgtagtgac tccggcgctg agcgcgtga ttgaagcgaa cacctattg     720 agcggtgttg gttttgaaag tggtggtctg gctgcggcgc acgcagtgca taacggcctg     780
accgctatcc cggacgcgca tcactattat cacggtgaaa aagtggcatt cggtacgctg     840
acgcagctgg ttctgaaaa tgcgccggtg gaggaaatcg aaaccgtagc tgcccttagc     900
catgcggtag gtttgccaat aactctcgct caactggata ttaaagaaga tgtcccggcg     960
aaaatgcgaa ttgtggcaga agcggcatgt gcagaaggtg aaaccattca caacatgcct    1020
ggcggcgcga cgccagatca ggtttacgcc gctctgctgg tagccgacca gtacggtcag    1080
cgtttcctgc aagagtggga ataa                                           1104

<210> SEQ ID NO 89
<211> LENGTH: 510
<212> TYPE: PRT
<213> ORGANISM: Escherichia coli (strain K12)
```

<400> SEQUENCE: 89

```
Met Arg Ile Gly Ile Pro Arg Glu Arg Leu Thr Asn Glu Thr Arg Val
1               5                   10                  15

Ala Ala Thr Pro Lys Thr Val Glu Gln Leu Leu Lys Leu Gly Phe Thr
            20                  25                  30

Val Ala Val Glu Ser Gly Ala Gly Gln Leu Ala Ser Phe Asp Asp Lys
        35                  40                  45

Ala Phe Val Gln Ala Gly Ala Glu Ile Val Glu Gly Asn Ser Val Trp
    50                  55                  60

Gln Ser Glu Ile Ile Leu Lys Val Asn Ala Pro Leu Asp Asp Glu Ile
65                  70                  75                  80

Ala Leu Leu Asn Pro Gly Thr Thr Leu Val Ser Phe Ile Trp Pro Ala
                85                  90                  95

Gln Asn Pro Glu Leu Met Gln Lys Leu Ala Glu Arg Asn Val Thr Val
            100                 105                 110

Met Ala Met Asp Ser Val Pro Arg Ile Ser Arg Ala Gln Ser Leu Asp
        115                 120                 125

Ala Leu Ser Ser Met Ala Asn Ile Ala Gly Tyr Arg Ala Ile Val Glu
    130                 135                 140

Ala Ala His Glu Phe Gly Arg Phe Phe Thr Gly Gln Ile Thr Ala Ala
145                 150                 155                 160

Gly Lys Val Pro Pro Ala Lys Val Met Val Ile Gly Ala Gly Val Ala
                165                 170                 175

Gly Leu Ala Ala Ile Gly Ala Ala Asn Ser Leu Gly Ala Ile Val Arg
            180                 185                 190

Ala Phe Asp Thr Arg Pro Glu Val Lys Glu Gln Val Gln Ser Met Gly
        195                 200                 205

Ala Glu Phe Leu Glu Leu Asp Phe Lys Glu Glu Ala Gly Ser Gly Asp
    210                 215                 220

Gly Tyr Ala Lys Val Met Ser Asp Ala Phe Ile Lys Ala Glu Met Glu
225                 230                 235                 240

Leu Phe Ala Ala Gln Ala Lys Glu Val Asp Ile Ile Val Thr Thr Ala
                245                 250                 255

Leu Ile Pro Gly Lys Pro Ala Pro Lys Leu Ile Thr Arg Glu Met Val
            260                 265                 270

Asp Ser Met Lys Ala Gly Ser Val Ile Val Asp Leu Ala Ala Gln Asn
        275                 280                 285

Gly Gly Asn Cys Glu Tyr Thr Val Pro Gly Glu Ile Phe Thr Thr Glu
    290                 295                 300

Asn Gly Val Lys Val Ile Gly Tyr Thr Asp Leu Pro Gly Arg Leu Pro
305                 310                 315                 320

Thr Gln Ser Ser Gln Leu Tyr Gly Thr Asn Leu Val Asn Leu Leu Lys
                325                 330                 335

Leu Leu Cys Lys Glu Lys Asp Gly Asn Ile Thr Val Asp Phe Asp Asp
            340                 345                 350

Val Val Ile Arg Gly Val Thr Val Ile Arg Ala Gly Glu Ile Thr Trp
        355                 360                 365

Pro Ala Pro Pro Ile Gln Val Ser Ala Gln Pro Gln Ala Ala Gln Lys
    370                 375                 380

Ala Ala Pro Glu Val Lys Thr Glu Glu Lys Cys Thr Cys Ser Pro Trp
385                 390                 395                 400

Arg Lys Tyr Ala Leu Met Ala Leu Ala Ile Ile Leu Phe Gly Trp Met
```

```
              405                 410                 415
Ala Ser Val Ala Pro Lys Glu Phe Leu Gly His Phe Thr Val Phe Ala
            420                 425                 430

Leu Ala Cys Val Val Gly Tyr Tyr Val Val Trp Asn Val Ser His Ala
            435                 440                 445

Leu His Thr Pro Leu Met Ser Val Thr Asn Ala Ile Ser Gly Ile Ile
            450                 455                 460

Val Val Gly Ala Leu Leu Gln Ile Gly Gln Gly Gly Trp Val Ser Phe
465                 470                 475                 480

Leu Ser Phe Ile Ala Val Leu Ile Ala Ser Ile Asn Ile Phe Gly Gly
                485                 490                 495

Phe Thr Val Thr Gln Arg Met Leu Lys Met Phe Arg Lys Asn
            500                 505                 510
```

<210> SEQ ID NO 90
<211> LENGTH: 1533
<212> TYPE: DNA
<213> ORGANISM: Escherichia coli (strain K12)

<400> SEQUENCE: 90

| | | | | | |
|---|---|---|---|---|---|
| atgcgaattg | gcataccaag | agaacggtta | accaatgaaa | cccgtgttgc | agcaacgcca | 60 |
| aaaacagtgg | aacagctgct | gaaactgggt | tttaccgtcg | cggtagagag | cggcgcgggt | 120 |
| caactggcaa | gttttgacga | taaagcgttt | gtgcaagcgg | gcgctgaaat | tgtagaaggg | 180 |
| aatagcgtct | ggcagtcaga | gatcattctg | aaggtcaatg | cgccgttaga | tgatgaaatt | 240 |
| gcgttactga | tcctgggac | aacgctggtg | agttttatct | ggcctgcgca | gaatccggaa | 300 |
| ttaatgcaaa | aacttgcgga | acgtaacgtg | accgtgatgg | cgatggactc | tgtgccgcgt | 360 |
| atctcacgcg | cacaatcgct | ggacgcacta | agctcgatgg | cgaacatcgc | cggttatcgc | 420 |
| gccattgttg | aagcggcaca | tgaatttggg | cgcttcttta | ccgggcaaat | tactgcggcc | 480 |
| gggaaagtgc | caccggcaaa | agtgatggtg | attggtgcgg | gtgttgcagg | tctggccgcc | 540 |
| attggcgcag | caaacagtct | cggcgcgatt | gtgcgtgcat | tcgacacccg | cccggaagtg | 600 |
| aaagaacaag | ttcaaagtat | gggcgcggaa | ttcctcgagc | tggattttaa | agaggaagct | 660 |
| ggcagcggcg | atggctatgc | caaagtgatg | tcggacgcgt | tcatcaaagc | ggaaatggaa | 720 |
| ctctttgccg | cccaggcaaa | agaggtcgat | atcattgtca | ccaccgcgct | tattccaggc | 780 |
| aaaccagcgc | gaagctaat | acccgtgaaa | tggttgact | ccatgaaggc | gggcagtgtg | 840 |
| attgtcgacc | tggcagccca | aaacggcggc | aactgtgaat | acaccgtgcc | gggtgaaatc | 900 |
| ttcactacgg | aaaatggtgt | caaagtgatt | ggttataccg | atcttccggg | ccgtctgccg | 960 |
| acgcaatcct | cacagcttta | cggcacaaac | ctcgttaatc | tgctgaaact | gttgtgcaaa | 1020 |
| gagaaagacg | gcaatatcac | tgttgatttt | gatgatgtgg | tgattcgcgg | cgtgaccgtg | 1080 |
| atccgtgcgg | gcgaaattac | ctggccggca | ccgccgattc | aggtatcagc | tcagccgcag | 1140 |
| gcggcacaaa | aagcggcacc | ggaagtgaaa | actgaggaaa | atgtacctg | ctcaccgtgg | 1200 |
| cgtaaatacg | cgttgatggc | gctggcaatc | attcttttg | gctggatggc | aagcgttgcg | 1260 |
| ccgaaagaat | tccttgggca | cttcaccgtt | ttcgcgctgg | cctgcgttgt | cggttattac | 1320 |
| gtggtgtgga | atgtatcgca | cgcgctgcat | acaccgttga | tgtcggtcac | caacgcgatt | 1380 |
| tcagggatta | ttgttgtcgg | agcactgttg | cagattggcc | agggcggctg | ggttagcttc | 1440 |
| cttagtttta | tcgcggtgct | tatagccagc | attaatattt | tcggtggctt | caccgtgact | 1500 |
| cagcgcatgc | tgaaaatgtt | ccgcaaaaat | taa | | | 1533 |

```
<210> SEQ ID NO 91
<211> LENGTH: 462
<212> TYPE: PRT
<213> ORGANISM: Escherichia coli (strain K12)

<400> SEQUENCE: 91
```

Met Ser Gly Gly Leu Val Thr Ala Ala Tyr Ile Val Ala Ala Ile Leu
1               5                   10                  15

Phe Ile Phe Ser Leu Ala Gly Leu Ser Lys His Glu Thr Ser Arg Gln
            20                  25                  30

Gly Asn Asn Phe Gly Ile Ala Gly Met Ala Ile Ala Leu Ile Ala Thr
        35                  40                  45

Ile Phe Gly Pro Asp Thr Gly Asn Val Gly Trp Ile Leu Leu Ala Met
    50                  55                  60

Val Ile Gly Gly Ala Ile Gly Ile Arg Leu Ala Lys Lys Val Glu Met
65                  70                  75                  80

Thr Glu Met Pro Glu Leu Val Ala Ile Leu His Ser Phe Val Gly Leu
                85                  90                  95

Ala Ala Val Leu Val Gly Phe Asn Ser Tyr Leu His His Asp Ala Gly
            100                 105                 110

Met Ala Pro Ile Leu Val Asn Ile His Leu Thr Glu Val Phe Leu Gly
        115                 120                 125

Ile Phe Ile Gly Ala Val Thr Phe Thr Gly Ser Val Val Ala Phe Gly
    130                 135                 140

Lys Leu Cys Gly Lys Ile Ser Ser Lys Pro Leu Met Leu Pro Asn Arg
145                 150                 155                 160

His Lys Met Asn Leu Ala Ala Leu Val Val Ser Phe Leu Leu Leu Ile
                165                 170                 175

Val Phe Val Arg Thr Asp Ser Val Gly Leu Gln Val Leu Ala Leu Leu
            180                 185                 190

Ile Met Thr Ala Ile Ala Leu Val Phe Gly Trp His Leu Val Ala Ser
        195                 200                 205

Ile Gly Gly Ala Asp Met Pro Val Val Val Ser Met Leu Asn Ser Tyr
    210                 215                 220

Ser Gly Trp Ala Ala Ala Ala Gly Phe Met Leu Ser Asn Asp Leu
225                 230                 235                 240

Leu Ile Val Thr Gly Ala Leu Val Gly Ser Ser Gly Ala Ile Leu Ser
                245                 250                 255

Tyr Ile Met Cys Lys Ala Met Asn Arg Ser Phe Ile Ser Val Ile Ala
            260                 265                 270

Gly Gly Phe Gly Thr Asp Gly Ser Ser Thr Gly Asp Asp Gln Glu Val
        275                 280                 285

Gly Glu His Arg Glu Ile Thr Ala Glu Glu Thr Ala Glu Leu Leu Lys
    290                 295                 300

Asn Ser His Ser Val Ile Ile Thr Pro Gly Tyr Gly Met Ala Val Ala
305                 310                 315                 320

Gln Ala Gln Tyr Pro Val Ala Glu Ile Thr Glu Lys Leu Arg Ala Arg
                325                 330                 335

Gly Ile Asn Val Arg Phe Gly Ile His Pro Val Ala Gly Arg Leu Pro
            340                 345                 350

Gly His Met Asn Val Leu Leu Ala Glu Ala Lys Val Pro Tyr Asp Ile
        355                 360                 365

Val Leu Glu Met Asp Glu Ile Asn Asp Asp Phe Ala Asp Thr Asp Thr

Val Leu Val Ile Gly Ala Asn Asp Thr Val Asn Pro Ala Ala Gln Asp
385                 390                 395                 400

Asp Pro Lys Ser Pro Ile Ala Gly Met Pro Val Leu Glu Val Trp Lys
            405                 410                 415

Ala Gln Asn Val Ile Val Phe Lys Arg Ser Met Asn Thr Gly Tyr Ala
            420                 425                 430

Gly Val Gln Asn Pro Leu Phe Phe Lys Glu Asn Thr His Met Leu Phe
            435                 440                 445

Gly Asp Ala Lys Ala Ser Val Asp Ala Ile Leu Lys Ala Leu
            450                 455                 460

<210> SEQ ID NO 92
<211> LENGTH: 1389
<212> TYPE: DNA
<213> ORGANISM: Escherichia coli (strain K12)

<400> SEQUENCE: 92

```
atgtctggag gattagttac agctgcatac attgttgccg cgatcctgtt tatcttcagt      60
ctggccggtc tttcgaaaca tgaaacgtct cgccagggta acaacttcgg tatcgccggg     120
atggcgattg cgttaatcgc aaccattttt ggaccggata cgggtaatgt tggctggatc     180
ttgctggcga tggtcattgg tggggcaatt ggtatccgtc tggcgaagaa agttgaaatg     240
accgaaatgc cagaactggt ggcgatcctg catagcttcg tgggtctggc ggcagtgctg     300
gttggcttta acagctatct gcatcatgac gcgggaatgg caccgattct ggtcaatatt     360
cacctgacgg aagtgttcct cggtatcttc atcggggcgg taacgttcac gggttcggtg     420
gtggcgttcg gcaaactgtg tggcaagatt cgtctaaaac cattgatgct gccaaaccgt     480
cacaaaatga acctggcggc tctggtcgtt ccttcctgc tgctgattgt atttgttcgc     540
acggacagcg tcggcctgca agtgctggca ttgctgataa tgaccgcaat tgcgctggta     600
ttcggctggc atttagtcgc ctccatcggt ggtgcagata tgccagtggt ggtgtcgatg     660
ctgaactcgt actccggctg gcgggctgcg gctgcgggct ttatgctcag caacgacctg     720
ctgattgtga ccggtgcgct ggtcggttct tcggggcta tcctttctta cattatgtgt     780
aaggcgatga accgttcctt tatcagcgtt attgcgggtg gtttcggcac cgacggctct     840
tctactggcg atgatcagga agtgggtgag caccgcgaaa tcaccgcaga agagacagcg     900
gaactgctga aaaactccca ttcagtgatc attactccgg ggtacggcat ggcagtcgcg     960
caggcgcaat atcctgtcgc tgaaattact gagaaattgc gcgctcgtgg tattaatgtg    1020
cgtttcggta tccacccggt cgcggggcgt ttgcctggac atatgaacgt attgctggct    1080
gaagcaaaag taccgtatga catcgtgctg gaaatggacg agatcaatga tgactttgct    1140
gataccgata ccgtactggt gattggtgct aacgatacgg ttaacccggc ggcgcaggat    1200
gatccgaaga gtccgattgc tggtatgcct gtgctggaag tgtggaaagc gcagaacgtg    1260
attgtcttta acgttcgat gaacactggc tatgctggtg tgcaaaaccc gctgttcttc    1320
aaggaaaaca cccacatgct gtttggtgac gccaaagcca gcgtggatgc aatcctgaaa    1380
gctctgtaa                                                           1389
```

<210> SEQ ID NO 93
<211> LENGTH: 549
<212> TYPE: PRT
<213> ORGANISM: Escherichia coli (strain K12)

```
<400> SEQUENCE: 93

Met Lys Asn Ile Asn Pro Thr Gln Thr Ala Ala Trp Gln Ala Leu Gln
1               5                   10                  15

Lys His Phe Asp Glu Met Lys Asp Val Thr Ile Ala Asp Leu Phe Ala
            20                  25                  30

Lys Asp Gly Asp Arg Phe Ser Lys Phe Ser Ala Thr Phe Asp Asp Gln
        35                  40                  45

Met Leu Val Asp Tyr Ser Lys Asn Arg Ile Thr Glu Glu Thr Leu Ala
    50                  55                  60

Lys Leu Gln Asp Leu Ala Lys Glu Cys Asp Leu Ala Gly Ala Ile Lys
65                  70                  75                  80

Ser Met Phe Ser Gly Glu Lys Ile Asn Arg Thr Glu Asn Arg Ala Val
                85                  90                  95

Leu His Val Ala Leu Arg Asn Arg Ser Asn Thr Pro Ile Leu Val Asp
            100                 105                 110

Gly Lys Asp Val Met Pro Glu Val Asn Ala Val Leu Glu Lys Met Lys
        115                 120                 125

Thr Phe Ser Glu Ala Ile Ile Ser Gly Glu Trp Lys Gly Tyr Thr Gly
    130                 135                 140

Lys Ala Ile Thr Asp Val Val Asn Ile Gly Ile Gly Gly Ser Asp Leu
145                 150                 155                 160

Gly Pro Tyr Met Val Thr Glu Ala Leu Arg Pro Tyr Lys Asn His Leu
                165                 170                 175

Asn Met His Phe Val Ser Asn Val Asp Gly Thr His Ile Ala Glu Val
            180                 185                 190

Leu Lys Lys Val Asn Pro Glu Thr Thr Leu Phe Leu Val Ala Ser Lys
        195                 200                 205

Thr Phe Thr Thr Gln Glu Thr Met Thr Asn Ala His Ser Ala Arg Asp
    210                 215                 220

Trp Phe Leu Lys Ala Ala Gly Asp Glu Lys His Val Ala Lys His Phe
225                 230                 235                 240

Ala Ala Leu Ser Thr Asn Ala Lys Ala Val Gly Glu Phe Gly Ile Asp
                245                 250                 255

Thr Ala Asn Met Phe Glu Phe Trp Asp Trp Val Gly Gly Arg Tyr Ser
            260                 265                 270

Leu Trp Ser Ala Ile Gly Leu Ser Ile Val Leu Ser Ile Gly Phe Asp
        275                 280                 285

Asn Phe Val Glu Leu Leu Ser Gly Ala His Ala Met Asp Lys His Phe
    290                 295                 300

Ser Thr Thr Pro Ala Glu Lys Asn Leu Pro Val Leu Leu Ala Leu Ile
305                 310                 315                 320

Gly Ile Trp Tyr Asn Asn Phe Phe Gly Ala Glu Thr Glu Ala Ile Leu
                325                 330                 335

Pro Tyr Asp Gln Tyr Met His Arg Phe Ala Ala Tyr Phe Gln Gln Gly
            340                 345                 350

Asn Met Glu Ser Asn Gly Lys Tyr Val Asp Arg Asn Gly Asn Val Val
        355                 360                 365

Asp Tyr Gln Thr Gly Pro Ile Ile Trp Gly Glu Pro Gly Thr Asn Gly
    370                 375                 380

Gln His Ala Phe Tyr Gln Leu Ile His Gln Gly Thr Lys Met Val Pro
385                 390                 395                 400

Cys Asp Phe Ile Ala Pro Ala Ile Thr His Asn Pro Leu Ser Asp His
                405                 410                 415
```

His Gln Lys Leu Leu Ser Asn Phe Phe Ala Gln Thr Glu Ala Leu Ala
              420                 425                 430

Phe Gly Lys Ser Arg Glu Val Val Glu Gln Glu Tyr Arg Asp Gln Gly
          435                 440                 445

Lys Asp Pro Ala Thr Leu Asp Tyr Val Val Pro Phe Lys Val Phe Glu
      450                 455                 460

Gly Asn Arg Pro Thr Asn Ser Ile Leu Leu Arg Glu Ile Thr Pro Phe
465                 470                 475                 480

Ser Leu Gly Ala Leu Ile Ala Leu Tyr Glu His Lys Ile Phe Thr Gln
              485                 490                 495

Gly Val Ile Leu Asn Ile Phe Thr Phe Asp Gln Trp Gly Val Glu Leu
          500                 505                 510

Gly Lys Gln Leu Ala Asn Arg Ile Leu Pro Glu Leu Lys Asp Asp Lys
      515                 520                 525

Glu Ile Ser Ser His Asp Ser Ser Thr Asn Gly Leu Ile Asn Arg Tyr
      530                 535                 540

Lys Ala Trp Arg Gly
545

<210> SEQ ID NO 94
<211> LENGTH: 1650
<212> TYPE: DNA
<213> ORGANISM: Escherichia coli (strain K12)

<400> SEQUENCE: 94
atgaaaaaca tcaatccaac gcagaccgct gcctggcagg cactacagaa acacttcgat      60
gaaatgaaag acgttacgat cgccgatctt tttgctaaag acggcgatcg tttttctaag     120
ttctccgcaa ccttcgacga tcagatgctg gtggattact ccaaaaaccg catcactgaa     180
gagacgctgg cgaaattaca ggatctggcg aaagagtgcg atctggcggg cgcgattaag     240
tcgatgttct ctggcgagaa gatcaaccgc actgaaaacc gcgccgtgct gcacgtagcg     300
ctgcgtaacc gtagcaatac cccgattttg gttgatggca agacgtaat gccggaagtc      360 aacgcggtgc tggagaagat gaaaaccttc tcagaagcga ttatttccgg tgagtggaaa     420
ggttataccg gcaaagcaat cactgacgta gtgaacatcg ggatcggcgg ttctgacctc     480
ggcccataca tggtgaccga agctctgcgt ccgtacaaaa accacctgaa catgcacttt     540
gtttctaacg tcgatgggac tcacatcgcg gaagtgctga aaaagtaaa cccggaaacc      600 acgctgttct ggtagcatc taaaaccttc accactcagg aaactatgac caacgcccat     660
agcgcgcgtg actggttcct gaaagcggca ggtgatgaaa acacgttgc aaaacacttt      720 gcggcgcttt ccaccaatgc caaagccgtt ggcgagtttg gtattgatac tgccaacatg     780
ttcgagttct gggactgggt tggcggccgt tactcttttgt ggtcagcgat tggcctgtcg     840
attgttctct ccatcggctt tgataacttc gttgaactgc tttccggcgc acacgcgatg     900
gacaagcatt tctccaccac gcctgccgag aaaaacctgc tgtactgct ggcgctgatt      960 ggcatctggt acaacaattt ctttggtgcg aaactgaag cgattctgcc gtatgaccag     1020
tatatgcacc gttcgcggc gtacttccag cagggcaata tggagtccaa cggtaagtat     1080
gttgaccgta acggtaacgt tgtggattac cagactggcc cgattatctg gggtgaacca     1140
ggcactaacg tcagcacgc gttctaccag ctgatccacc agggaaccaa aatggtaccg     1200
tgcgatttca tcgctccggc tatcacccat aaccgctct ctgatcatca ccagaaactg      1260
ctgtctaact tcttcgccca gaccgaagcg ctggcgtttg gtaaatcccg cgaagtggtt     1320

-continued

```
gagcaggaat atcgtgatca gggtaaagat ccggcaacgc ttgactacgt ggtgccgttc   1380
aaagtattcg aaggtaaccg cccgaccaac tccatcctgc tgcgtgaaat cactccgttc   1440
agcctgggtg cgttgattgc gctgtatgag cacaaaatct ttactcaggg cgtgatcctg   1500
aacatcttca ccttcgacca gtggggcgtg gaactgggta acagctggc gaaccgtatt    1560 ctgccagagc tgaaagatga taaagaaatc agcagccacg atagctcgac caatggtctg   1620
attaaccgct ataaagcgtg gcgcggttaa                                     1650
```

<210> SEQ ID NO 95
<211> LENGTH: 320
<212> TYPE: PRT
<213> ORGANISM: Escherichia coli (strain K12)

<400> SEQUENCE: 95

```
Met Ile Lys Lys Ile Gly Val Leu Thr Ser Gly Gly Asp Ala Pro Gly
1               5                   10                  15

Met Asn Ala Ala Ile Arg Gly Val Val Arg Ser Ala Leu Thr Glu Gly
                20                  25                  30

Leu Glu Val Met Gly Ile Tyr Asp Gly Tyr Leu Gly Leu Tyr Glu Asp
            35                  40                  45

Arg Met Val Gln Leu Asp Arg Tyr Ser Val Ser Asp Met Ile Asn Arg
        50                  55                  60

Gly Gly Thr Phe Leu Gly Ser Ala Arg Phe Pro Glu Phe Arg Asp Glu
65                  70                  75                  80

Asn Ile Arg Ala Val Ala Ile Glu Asn Leu Lys Lys Arg Gly Ile Asp
                85                  90                  95

Ala Leu Val Val Ile Gly Gly Asp Gly Ser Tyr Met Gly Ala Met Arg
            100                 105                 110

Leu Thr Glu Met Gly Phe Pro Cys Ile Gly Leu Pro Gly Thr Ile Asp
        115                 120                 125

Asn Asp Ile Lys Gly Thr Asp Tyr Thr Ile Gly Phe Phe Thr Ala Leu
    130                 135                 140

Ser Thr Val Val Glu Ala Ile Asp Arg Leu Arg Asp Thr Ser Ser Ser
145                 150                 155                 160

His Gln Arg Ile Ser Val Val Glu Val Met Gly Arg Tyr Cys Gly Asp
                165                 170                 175

Leu Thr Leu Ala Ala Ala Ile Ala Gly Gly Cys Glu Phe Val Val Val
            180                 185                 190

Pro Glu Val Glu Phe Ser Arg Glu Asp Leu Val Asn Glu Ile Lys Ala
        195                 200                 205

Gly Ile Ala Lys Gly Lys Lys His Ala Ile Val Ala Ile Thr Glu His
    210                 215                 220

Met Cys Asp Val Asp Glu Leu Ala His Phe Ile Glu Lys Glu Thr Gly
225                 230                 235                 240

Arg Glu Thr Arg Ala Thr Val Leu Gly His Ile Gln Arg Gly Gly Ser
                245                 250                 255

Pro Val Pro Tyr Asp Arg Ile Leu Ala Ser Arg Met Gly Ala Tyr Ala
            260                 265                 270

Ile Asp Leu Leu Leu Ala Gly Tyr Gly Gly Arg Cys Val Gly Ile Gln
        275                 280                 285

Asn Glu Gln Leu Val His His Asp Ile Ile Asp Ala Ile Glu Asn Met
    290                 295                 300

Lys Arg Pro Phe Lys Gly Asp Trp Leu Asp Cys Ala Lys Lys Leu Tyr
```

<210> SEQ ID NO 96
<211> LENGTH: 963
<212> TYPE: DNA
<213> ORGANISM: Escherichia coli (strain K12)

<400> SEQUENCE: 96

```
atgattaaga aaatcggtgt gttgacaagc ggcggtgatg cgccaggcat gaacgccgca      60
attcgcgggg ttgttcgttc tgcgctgaca gaaggtctgg aagtaatggg tatttatgac     120
ggctatctgg gtctgtatga agaccgtatg gtacagctag accgttacag cgtgtctgac     180
atgatcaacc gtggcggtac gttcctcggt tctgcgcgtt tcccggaatt ccgcgacgag     240
aacatccgcg ccgtggctat cgaaaacctg aaaaaacgtg gtatcgacgc gctggtggtt     300
atcggcggtg acggttccta catgggtgca atgcgtctga ccgaaatggg cttcccgtgc     360
atcggtctgc cgggcactat cgacaacgac atcaaaggca ctgactacac tatcggtttc     420
ttcactgcgc tgagcaccgt tgtagaagcg atcgaccgtc tgcgtgacac ctcttcttct     480
caccagcgta tttccgtggt ggaagtgatg ggccgttatt gtggagatct gacgttggct     540
gcggccattg ccggtggctg tgaattcgtt gtggttccgg aagttgaatt cagccgtgaa     600
gacctggtaa acgaaatcaa agcgggtatc gcgaaaggta aaaacacgc gatcgtggcg      660
attaccgaac atatgtgtga tgttgacgaa ctggcgcatt tcatcgagaa agaaaccggt     720
cgtgaaaccc gcgcaactgt gctgggccac atccagcgcg tggttctcc ggtgccttac      780
gaccgtattc tggcttcccg tatgggcgct tacgctatcg atctgctgct ggcaggttac     840
ggcggtcgtt gtgtaggtat ccagaacgaa cagctggttc accacgacat catcgacgct     900
atcgaaaaca tgaagcgtcc gttcaaaggt gactggctgg actgcgcgaa aaaactgtat     960
taa                                                                   963
```

<210> SEQ ID NO 97
<211> LENGTH: 491
<212> TYPE: PRT
<213> ORGANISM: Escherichia coli (strain K12)

<400> SEQUENCE: 97

Met Ala Val Thr Gln Thr Ala Gln Ala Cys Asp Leu Val Ile Phe Gly
1               5                   10                  15

Ala Lys Gly Asp Leu Ala Arg Arg Lys Leu Leu Pro Ser Leu Tyr Gln
            20                  25                  30

Leu Glu Lys Ala Gly Gln Leu Asn Pro Asp Thr Arg Ile Ile Gly Val
        35                  40                  45

Gly Arg Ala Asp Trp Asp Lys Ala Ala Tyr Thr Lys Val Val Arg Glu
    50                  55                  60

Ala Leu Glu Thr Phe Met Lys Glu Thr Ile Asp Glu Gly Leu Trp Asp
65                  70                  75                  80

Thr Leu Ser Ala Arg Leu Asp Phe Cys Asn Leu Asp Val Asn Asp Thr
                85                  90                  95

Ala Ala Phe Ser Arg Leu Gly Ala Met Leu Asp Gln Lys Asn Arg Ile
            100                 105                 110

Thr Ile Asn Tyr Phe Ala Met Pro Pro Ser Thr Phe Gly Ala Ile Cys
        115                 120                 125

Lys Gly Leu Gly Glu Ala Lys Leu Asn Ala Lys Pro Ala Arg Val Val
    130                 135                 140

Met Glu Lys Pro Leu Gly Thr Ser Leu Ala Thr Ser Gln Glu Ile Asn
145                 150                 155                 160

Asp Gln Val Gly Glu Tyr Phe Glu Glu Cys Gln Val Tyr Arg Ile Asp
                165                 170                 175

His Tyr Leu Gly Lys Glu Thr Val Leu Asn Leu Leu Ala Leu Arg Phe
            180                 185                 190

Ala Asn Ser Leu Phe Val Asn Asn Trp Asp Asn Arg Thr Ile Asp His
        195                 200                 205

Val Glu Ile Thr Val Ala Glu Val Gly Ile Glu Gly Arg Trp Gly
    210                 215                 220

Tyr Phe Asp Lys Ala Gly Gln Met Arg Asp Met Ile Gln Asn His Leu
225                 230                 235                 240

Leu Gln Ile Leu Cys Met Ile Ala Met Ser Pro Pro Ser Asp Leu Ser
                245                 250                 255

Ala Asp Ser Ile Arg Asp Glu Lys Val Lys Val Leu Lys Ser Leu Arg
                260                 265                 270

Arg Ile Asp Arg Ser Asn Val Arg Glu Lys Thr Val Arg Gly Gln Tyr
            275                 280                 285

Thr Ala Gly Phe Ala Gln Gly Lys Lys Val Pro Gly Tyr Leu Glu Glu
        290                 295                 300

Glu Gly Ala Asn Lys Ser Ser Asn Thr Glu Thr Phe Val Ala Ile Arg
305                 310                 315                 320

Val Asp Ile Asp Asn Trp Arg Trp Ala Gly Val Pro Phe Tyr Leu Arg
                325                 330                 335

Thr Gly Lys Arg Leu Pro Thr Lys Cys Ser Glu Val Val Tyr Phe
            340                 345                 350

Lys Thr Pro Glu Leu Asn Leu Phe Lys Glu Ser Trp Gln Asp Leu Pro
        355                 360                 365

Gln Asn Lys Leu Thr Ile Arg Leu Gln Pro Asp Glu Gly Val Asp Ile
370                 375                 380

Gln Val Leu Asn Lys Val Pro Gly Leu Asp His Lys His Asn Leu Gln
385                 390                 395                 400

Ile Thr Lys Leu Asp Leu Ser Tyr Ser Glu Thr Phe Asn Gln Thr His
                405                 410                 415

Leu Ala Asp Ala Tyr Glu Arg Leu Leu Leu Glu Thr Met Arg Gly Ile
            420                 425                 430

Gln Ala Leu Phe Val Arg Arg Asp Glu Val Glu Glu Ala Trp Lys Trp
        435                 440                 445

Val Asp Ser Ile Thr Glu Ala Trp Ala Met Asp Asn Asp Ala Pro Lys
450                 455                 460

Pro Tyr Gln Ala Gly Thr Trp Gly Pro Val Ala Ser Val Ala Met Ile
465                 470                 475                 480

Thr Arg Asp Gly Arg Ser Trp Asn Glu Phe Glu
                485                 490

<210> SEQ ID NO 98
<211> LENGTH: 1476
<212> TYPE: DNA
<213> ORGANISM: Escherichia coli (strain K12)

<400> SEQUENCE: 98
atggcggtaa cgcaaacagc ccaggcctgt gacctggtca ttttcggcgc gaaaggcgac        60
cttgcgcgtc gtaaattgct gccttccctg tatcaactgg aaaaagccgg tcagctcaac       120
ccggacaccc ggattatcgg cgtagggcgt gctgactggg ataaagcggc atataccaaa       180

```
gttgtccgcg aggcgctcga aactttcatg aaagaaacca ttgatgaagg tttatgggac    240
accctgagtg cacgtctgga tttttgtaat ctcgatgtca atgacactgc tgcattcagc    300
cgtctcggcg cgatgctgga tcaaaaaaat cgtatcacca ttaactactt tgccatgccg    360
cccagcactt ttggcgcaat ttgcaaaggg cttggcgagg caaaactgaa tgctaaaccg    420
gcacgcgtag tcatggagaa accgctgggg acgtcgctgg cgacctcgca ggaaatcaat    480
gatcaggttg gcgaatactt cgaggagtgc caggtttacc gtatcgacca ctatcttggt    540
aaagaaacgg tgctgaacct gttggcgctg cgttttgcta actccctgtt tgtgaataac    600
tgggacaatc gcaccattga tcatgttgag attaccgtgg cagaagaagt ggggatcgaa    660
gggcgctggg gctattttga taaagccggt cagatgcgcg acatgatcca gaaccacctg    720
ctgcaaattc tttgcatgat tgcgatgtct ccgccgtctg acctgagcgc agacagcatc    780
cgcgatgaaa aagtgaaagt actgaagtct ctgcgccgca tcgaccgctc caacgtacgc    840 gaaaaaccg tacgcgggca atatactgcg ggcttcgccc agggcaaaaa agtgccggga    900
tatctggaag aagagggcgc gaacaagagc agcaatacag aaactttcgt ggcgatccgc    960
gtcgacattg taactggcg ctgggccggt gtgccattct acctgcgtac tggtaaacgt   1020
ctgccgacca atgttctga agtcgtggtc tatttcaaaa cacctgaact gaatctgttt   1080
aaagaatcgt ggcaggatct gccgcagaat aaactgacta ccgtctgca acctgatgaa   1140 ggcgtggata tccaggtact gaataaagtt cctggccttg accacaaaca taacctgcaa   1200
atcaccaagc tggatctgag ctattcagaa acctttaatc agacgcatct ggcggatgcc   1260
tatgaacgtt tgctgctgga aaccatgcgt ggtattcagg cactgtttgt acgtcgcgac   1320
gaagtggaag aagcctggaa atgggtagac tccattactg aggcgtgggc gatggacaat   1380
gatgcgccga accgtatca ggccggaacc tggggacccg ttgcctcggt ggcgatgatt   1440
acccgtgatg gtcgttcctg aatgagttt gagtaa                            1476
```

<210> SEQ ID NO 99
<211> LENGTH: 515
<212> TYPE: PRT
<213> ORGANISM: Escherichia coli (strain K12)

<400> SEQUENCE: 99

```
Met Thr Asp His Thr Met Lys Lys Asn Pro Val Ser Ile Pro His Thr
1               5                  10                  15

Val Trp Tyr Ala Asp Asp Ile Arg Arg Gly Glu Arg Glu Ala Ala Asp
            20                  25                  30

Val Leu Gly Leu Thr Leu Tyr Glu Leu Met Leu Arg Ala Gly Glu Ala
        35                  40                  45

Ala Phe Gln Val Cys Arg Ser Ala Tyr Pro Asp Ala Arg His Trp Leu
    50                  55                  60

Val Leu Cys Gly His Gly Asn Asn Gly Gly Asp Gly Tyr Val Val Ala
65                  70                  75                  80

Arg Leu Ala Lys Ala Val Gly Ile Glu Val Thr Leu Ala Gln Glu
                85                  90                  95

Ser Asp Lys Pro Leu Pro Glu Glu Ala Ala Leu Ala Arg Glu Ala Trp
            100                 105                 110

Leu Asn Ala Gly Gly Glu Ile His Ala Ser Asn Ile Val Trp Pro Glu
        115                 120                 125

Ser Val Asp Leu Ile Val Asp Ala Leu Leu Gly Thr Gly Leu Arg Gln
    130                 135                 140
```

Ala Pro Arg Glu Ser Ile Ser Gln Leu Ile Asp His Ala Asn Ser His
145                 150                 155                 160

Pro Ala Pro Ile Val Ala Val Asp Ile Pro Ser Gly Leu Leu Ala Glu
            165                 170                 175

Thr Gly Ala Thr Pro Gly Ala Val Ile Asn Ala Asp His Thr Ile Thr
            180                 185                 190

Phe Ile Ala Leu Lys Pro Gly Leu Leu Thr Gly Lys Ala Arg Asp Val
        195                 200                 205

Thr Gly Gln Leu His Phe Asp Ser Leu Gly Leu Asp Ser Trp Leu Ala
        210                 215                 220

Gly Gln Glu Thr Lys Ile Gln Arg Phe Ser Ala Glu Gln Leu Ser His
225                 230                 235                 240

Trp Leu Lys Pro Arg Arg Pro Thr Ser His Lys Gly Asp His Gly Arg
                245                 250                 255

Leu Val Ile Ile Gly Gly Asp His Gly Thr Ala Gly Ala Ile Arg Met
            260                 265                 270

Thr Gly Glu Ala Ala Leu Arg Ala Gly Ala Gly Leu Val Arg Val Leu
        275                 280                 285

Thr Arg Ser Glu Asn Ile Ala Pro Leu Leu Thr Ala Arg Pro Glu Leu
290                 295                 300

Met Val His Glu Leu Thr Met Asp Ser Leu Thr Glu Ser Leu Glu Trp
305                 310                 315                 320

Ala Asp Val Val Val Ile Gly Pro Gly Leu Gly Gln Gln Glu Trp Gly
                325                 330                 335

Lys Lys Ala Leu Gln Lys Val Glu Asn Phe Arg Lys Pro Met Leu Trp
            340                 345                 350

Asp Ala Asp Ala Leu Asn Leu Leu Ala Ile Asn Pro Asp Lys Arg His
        355                 360                 365

Asn Arg Val Ile Thr Pro His Pro Gly Glu Ala Ala Arg Leu Leu Gly
    370                 375                 380

Cys Ser Val Ala Glu Ile Glu Ser Asp Arg Leu His Cys Ala Lys Arg
385                 390                 395                 400

Leu Val Gln Arg Tyr Gly Gly Val Ala Val Leu Lys Gly Ala Gly Thr
                405                 410                 415

Val Val Ala Ala His Pro Asp Ala Leu Gly Ile Ile Asp Ala Gly Asn
                420                 425                 430

Ala Gly Met Ala Ser Gly Gly Met Gly Asp Val Leu Ser Gly Ile Ile
            435                 440                 445

Gly Ala Leu Leu Gly Gln Lys Leu Ser Pro Tyr Asp Ala Ala Cys Ala
        450                 455                 460

Gly Cys Val Ala His Gly Ala Ala Asp Val Leu Ala Ala Arg Phe
465                 470                 475                 480

Gly Thr Arg Gly Met Leu Ala Thr Asp Leu Phe Ser Thr Leu Gln Arg
                485                 490                 495

Ile Val Asn Pro Glu Val Thr Asp Lys Asn His Asp Glu Ser Ser Asn
            500                 505                 510

Ser Ala Pro
        515

<210> SEQ ID NO 100
<211> LENGTH: 1548
<212> TYPE: DNA
<213> ORGANISM: Escherichia coli (strain K12)

<400> SEQUENCE: 100

```
atgacggacc atacaatgaa gaaaaacccc gtaagtatac cacacaccgt ctggtacgcc      60
gacgatatcc gccgcggaga acgcgaggcg gcagatgtgc tggggctcac actctatgag     120
ctgatgcttc gcgctggcga ggccgcattc caggtgtgtc gttcggcgta tcctgacgcc     180
cgccactggc tggtgctgtg cggtcatggt aataacggcg gcgatggcta cgtggtcgcg     240
cgactggcca aagcggtcgg cattgaggtc acgttgttgg cccaggagag cgacaaaccg     300
ttgccggaag aggccgcgct ggcacgcgaa gcatggttaa acgcgggtgg cgagatccat     360
gcttcgaata ttgtctggcc cgaatcggta gatctgattg ttgatgcgct gctcggtacc     420
ggtttgcggc aagcgccccg cgaatccatt agccagttaa tcgaccacgc taattcccat     480
cctgcgccga ttgtggcggt tgatatccct tccggcctgc tggctgaaac tggcgctacg     540
ccaggcgcgg tgatcaacgc cgatcacacc atcactttta ttgcgctgaa accaggcttg     600
ctcactggaa aagcgcggga tgttaccgga caactgcatt ttgactcact ggggctggat     660
agttggctgg caggtcagga gacgaaaatt cagcggtttt cagcagaaca actttctcac     720
tggctaaaac gcgtcgccc gacttcgcat aaaggcgatc acgggcggct ggtaattatc     780
ggtggcgatc acggcacggc gggggctatt cgtatgacgg gggaagcggc gctgcgtgct     840
ggtgctggtt tagtccgagt actgacccgc agtgaaaaca ttgcgccgct gctgactgca     900
cgaccggaat tgatggtgca tgaactgacg atggactctc ttaccgaaag cctgaatgg     960
gccgatgtgg tggtgattgg tcccggtctg gccagcaag agtgggggaa aaaagcactg    1020
caaaaagttg agaattttcg caaaccgatg ttgtgggatg ccgatgcatt gaacctgctg    1080
gcaatcaatc ccgataagcg tcacaatcgc gtgatcacgc cgcatcctgg cgaggccgca    1140
cggttgttag gctgttccgt cgctgaaatt gaaagtgacc gcttacattg cgccaaacgt    1200
ctggtacaac gttatggcgg cgtagcggtg ctgaaaggtg ccggaaccgt ggtcgccgcc    1260
catcctgacg ctttaggcat tattgatgcc ggaaatgcag gcatggcgag cggcggcatg    1320
ggcgatgtgc tctctggtat tattggcgca ttgcttgggc aaaaactgtc gccgtatgat    1380
gcagcctgtg caggctgtgt cgcgcacggt cggcagctg acgtactggc ggcgcgtttt    1440
ggaacgcgcg ggatgctggc aaccgatctc ttttccacgc tacagcgtat tgttaacccg    1500
gaagtgactg ataaaaacca tgatgaatcg agtaattccg ctccctga                1548
```

<210> SEQ ID NO 101
<211> LENGTH: 475
<212> TYPE: PRT
<213> ORGANISM: Streptococcus mutans

<400> SEQUENCE: 101

```
Met Thr Lys Gln Tyr Lys Asn Tyr Val Asn Gly Glu Trp Lys Leu Ser
1               5                   10                  15

Glu Asn Glu Ile Lys Ile Tyr Glu Pro Ala Ser Gly Ala Glu Leu Gly
            20                  25                  30

Ser Val Pro Ala Met Ser Thr Glu Glu Val Asp Tyr Val Tyr Ala Ser
        35                  40                  45

Ala Lys Lys Ala Gln Pro Ala Trp Arg Ala Leu Ser Tyr Ile Glu Arg
    50                  55                  60

Ala Ala Tyr Leu His Lys Val Ala Asp Ile Leu Met Arg Asp Lys Glu
65                  70                  75                  80

Lys Ile Gly Ala Ile Leu Ser Lys Glu Val Ala Lys Gly Tyr Lys Ser
                85                  90                  95
```

Ala Val Ser Glu Val Val Arg Thr Ala Glu Ile Ile Asn Tyr Ala Ala
            100                 105                 110

Glu Glu Gly Leu Arg Met Gly Glu Val Leu Glu Gly Gly Ser Phe
        115                 120                 125

Glu Ala Ala Ser Lys Lys Ile Ala Val Val Arg Arg Glu Pro Val
130                 135                 140

Gly Leu Val Leu Ala Ile Ser Pro Phe Asn Tyr Pro Val Asn Leu Ala
145                 150                 155                 160

Gly Ser Lys Ile Ala Pro Ala Leu Ile Ala Gly Asn Val Ile Ala Phe
                165                 170                 175

Lys Pro Pro Thr Gln Gly Ser Ile Ser Gly Leu Leu Ala Glu Ala
            180                 185                 190

Phe Ala Glu Ala Gly Leu Pro Ala Gly Val Phe Asn Thr Ile Thr Gly
        195                 200                 205

Arg Gly Ser Glu Ile Gly Asp Tyr Ile Val Glu His Gln Ala Val Asn
210                 215                 220

Phe Ile Asn Phe Thr Gly Ser Thr Gly Ile Gly Glu Arg Ile Gly Lys
225                 230                 235                 240

Met Ala Gly Met Arg Pro Ile Met Leu Glu Leu Gly Gly Lys Asp Ser
                245                 250                 255

Ala Ile Val Leu Glu Asp Ala Asp Leu Glu Leu Thr Ala Lys Asn Ile
            260                 265                 270

Ile Ala Gly Ala Phe Gly Tyr Ser Gly Gln Arg Cys Thr Ala Val Lys
        275                 280                 285

Arg Val Leu Val Met Glu Ser Val Ala Asp Glu Leu Val Glu Lys Ile
290                 295                 300

Arg Glu Lys Val Leu Ala Leu Thr Ile Gly Asn Pro Glu Asp Asp Ala
305                 310                 315                 320

Asp Ile Thr Pro Leu Ile Asp Thr Lys Ser Ala Asp Tyr Val Glu Gly
                325                 330                 335

Leu Ile Asn Asp Ala Asn Asp Lys Gly Ala Thr Ala Leu Thr Glu Ile
            340                 345                 350

Lys Arg Glu Gly Asn Leu Ile Cys Pro Ile Leu Phe Asp Lys Val Thr
        355                 360                 365

Thr Asp Met Arg Leu Ala Trp Glu Glu Pro Phe Gly Pro Val Leu Pro
370                 375                 380

Ile Ile Arg Val Thr Ser Val Glu Glu Ala Ile Glu Ile Ser Asn Lys
385                 390                 395                 400

Ser Glu Tyr Gly Leu Gln Ala Ser Ile Phe Thr Asn Asp Phe Pro Arg
                405                 410                 415

Ala Phe Gly Ile Ala Glu Gln Leu Glu Val Gly Thr Val His Ile Asn
            420                 425                 430

Asn Lys Thr Gln Arg Gly Thr Asp Asn Phe Pro Phe Leu Gly Ala Lys
        435                 440                 445

Lys Ser Gly Ala Gly Ile Gln Gly Val Lys Tyr Ser Ile Glu Ala Met
450                 455                 460

Thr Thr Val Lys Ser Val Val Phe Asp Ile Lys
465                 470                 475

<210> SEQ ID NO 102
<211> LENGTH: 1428
<212> TYPE: DNA
<213> ORGANISM: Streptococcus mutans

<400> SEQUENCE: 102

```
atgacaaaac aatataaaaa ttatgtcaat ggcgagtgga agctttcaga aaatgaaatt      60
aaaatctacg aaccagccag tggagctgaa ttgggttcag ttccagcaat gagtactgaa     120
gaagtagatt atgtttatgc ttcagccaag aaagctcaac cagcttggcg agcactttca     180
tacatagaac gtgctgccta ccttcataag gtagcagata ttttgatgcg tgataaagaa     240
aaaataggtg ctattctttc caaagaggtt gctaaaggtt ataaatcagc agtcagcgaa     300
gttgttcgta ctgcagaaat cattaattat gcagctgaag aaggtcttcg tatggaaggt     360
gaagtccttg aaggcggcag ttttgaagca gccagcaaga aaaaaattgc cgttgttcgt     420
cgtgaaccag taggtcttgt attagctatt tcaccattta actaccctgt taacttggca     480
ggttcgaaaa ttgcaccggc tcttattgcg ggaaatgtta ttgcttttaa accaccgacg     540
caaggatcaa tctcagggct cttacttgct gaagcatttg ctgaagctgg acttcctgca     600
ggtgtcttta taccattac aggtcgtggt tctgaaattg gagactatat tgtagaacat     660
caagccgtta actttatcaa tttcactggt tcaacaggaa ttggcgaacg tattggcaaa     720
atggctggta tgcgtccgat tatgcttgaa ctcggtggaa agattcagc catcgttctt     780
gaagatgcgg accttgaatt gactgctaaa aatattattg caggtgcttt tggttattca     840
ggtcaacgct gtacagcagt taaacgtgtt cttgtgatgg aaagtgttgc tgatgaactg     900
gtcgaaaaaa tccgtgaaaa agttcttgca ttaacaattg gtaatccaga agacgatgca     960
gatattacac cgttgattga tacaaaatca gctgattatg tagaaggtct tattaatgat    1020
gccaatgata aaggagccac tgcccttact gaaatcaaac gtgaaggtaa tcttatctgt    1080
ccaatcctct ttgataaggt aacgacagat atgcgtcttg cttgggaaga accatttggt    1140
cctgttcttc cgatcattcg tgtgacatct gtagaagaag ccattgaaat ttctaacaaa    1200
tcggaatatg gacttcaggc ttctatcttt acaaatgatt tcccacgcgc ttttggtatt    1260
gctgagcagc ttgaagttgg tacagttcat atcaataata agacacagcg cggcacggac    1320
aacttcccat tcttaggggc taaaaaatca ggtgcaggta ttcaaggggt aaaatattct    1380
attgaagcta tgacaactgt taaatccgtc gtatttgata tcaaataa               1428
```

<210> SEQ ID NO 103
<211> LENGTH: 474
<212> TYPE: PRT
<213> ORGANISM: artificial
<220> FEATURE:
<223> OTHER INFORMATION: Lpd* (A55V/G185A/G189A/E203V/M204R/F205K/
D206H/P210R)

<400> SEQUENCE: 103

```
Met Ser Thr Glu Ile Lys Thr Gln Val Val Val Leu Gly Ala Gly Pro
  1               5                  10                  15

Ala Gly Tyr Ser Ala Ala Phe Arg Cys Ala Asp Leu Gly Leu Glu Thr
                 20                  25                  30

Val Ile Val Glu Arg Tyr Asn Thr Leu Gly Gly Val Cys Leu Asn Val
             35                  40                  45

Gly Cys Ile Pro Ser Lys Val Leu Leu His Val Ala Lys Val Ile Glu
         50                  55                  60

Glu Ala Lys Ala Leu Ala Glu His Gly Ile Val Phe Gly Glu Pro Lys
     65                  70                  75                  80

Thr Asp Ile Asp Lys Ile Arg Thr Trp Lys Glu Lys Val Ile Asn Gln
                 85                  90                  95
```

```
Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Ala Leu Glu Met Ala Thr
            180                 185                 190

Val Tyr His Ala Leu Gly Ser Gln Ile Asp Val Val Arg Lys His
        195                 200                 205

Gln Val Ile Arg Ala Ala Asp Lys Asp Ile Val Lys Val Phe Thr Lys
    210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Pro Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Ala Trp Val Gly Leu Thr Glu Lys Glu Ala Lys
        355                 360                 365

Glu Lys Gly Ile Ser Tyr Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470
```

<210> SEQ ID NO 104
<211> LENGTH: 1425
<212> TYPE: DNA
<213> ORGANISM: artificial
<220> FEATURE:
<223> OTHER INFORMATION: Lpd* (A55V/G185A/G189A/E203V/M204R/F205K/

D206H/P210R)

<400> SEQUENCE: 104

| | |
|---|---:|
| atgagtactg aaatcaaaac tcaggtcgtg gtacttgggg caggccccgc aggttactcc | 60 |
| gctgccttcc gttgcgctga tttaggtctg gaaaccgtaa tcgtagaacg ttacaacacc | 120 |
| cttggcggtg tttgcctgaa cgtcggctgt atcccttcta aagtactgct gcacgtagca | 180 |
| aaagttatcg aagaagccaa agcgctggct gaacacggta tcgtcttcgg cgaaccgaaa | 240 |
| accgatatcg acaagattcg tacctggaaa gagaaagtga tcaatcagct gaccggtggt | 300 |
| ctggctggta tggcgaaagg ccgcaaagtc aaagtggtca acggtctggg taaattcacc | 360 |
| ggggctaaca ccctggaagt tgaaggtgag aacggcaaaa ccgtgatcaa cttcgacaac | 420 |
| gcgatcattg cagcgggttc tcgcccgatc caactgccgt ttattccgca tgaagatccg | 480 |
| cgtatctggg actccactga cgcgctggaa ctgaagaag taccagaacg cctgctggta | 540 |
| atgggtggcg gtatcatcgc cctggaaatg gcgaccgttt accacgcgct gggttcacag | 600 |
| attgacgtgg ttgtgcgcaa gcaccaggtt atccgcgcag ctgacaaaga catcgttaaa | 660 |
| gtcttcacca gcgtatcag caagaaattc aacctgatgc tggaaaccaa agttaccgcc | 720 |
| gttgaagcga agaagacgg catttatgtg acgatggaag gcaaaaaagc acccgctgaa | 780 |
| ccgcagcgtt acgacgccgt gctggtagcg attggtcgtg tgccgaacgg taaaaacctc | 840 |
| gacgcaggca agcaggcgt ggaagttgac gaccgtggt catccgcgt tgacaaacag | 900 |
| ctgcgtacca acgtaccgca catctttgct atcggcgata tcgtcggtca accgatgctg | 960 |
| gcacacaaag gtgttcacga aggtcacgtt gccgctgaag ttatcgccgg taagaaacac | 1020 |
| tacttcgatc cgaaagttat cccgtccatc gcctataccg aaccagaagt tgcatgggtg | 1080 |
| ggtctgactg agaagaagc gaaagagaaa ggcatcagct atgaaaccgc cacctttccg | 1140 |
| tgggctgctt ctggtcgtgc tatcgcttcc gactgcgcag acggtatgac caagctgatt | 1200 |
| ttcgacaaag aatctcaccg tgtgatcggt ggtgcgattg tcggtactaa cggcggcgag | 1260 |
| ctgctgggtg aaatcggcct ggcaatcgaa atgggttgtg atgctgaaga catcgcactg | 1320 |
| accatccacg cgcaccccga ctctgcacga gtctgtgggcc tggcggcaga agtgttcgaa | 1380 |
| ggtagcatta ccgacctgcc gaacccgaaa gcgaagaaga agtaa | 1425 |

<210> SEQ ID NO 105
<211> LENGTH: 326
<212> TYPE: PRT
<213> ORGANISM: artificial
<220> FEATURE:
<223> OTHER INFORMATION: YdjG*(D232E)

<400> SEQUENCE: 105

Met Lys Lys Ile Pro Leu Gly Thr Thr Asp Ile Thr Leu Ser Arg Met
1               5                   10                  15

Gly Leu Gly Thr Trp Ala Ile Gly Gly Gly Pro Ala Trp Asn Gly Asp
            20                  25                  30

Leu Asp Arg Gln Ile Cys Ile Asp Thr Ile Leu Glu Ala His Arg Cys
        35                  40                  45

Gly Ile Asn Leu Ile Asp Thr Ala Pro Gly Tyr Asn Phe Gly Asn Ser
    50                  55                  60

Glu Val Ile Val Gly Gln Ala Leu Lys Lys Leu Pro Arg Glu Gln Val
65                  70                  75                  80

Val Val Glu Thr Lys Cys Gly Ile Val Trp Glu Arg Lys Gly Ser Leu
                85                  90                  95

Phe Asn Lys Val Gly Asp Arg Gln Leu Tyr Lys Asn Leu Ser Pro Glu
            100                 105                 110

Ser Ile Arg Glu Glu Val Ala Ala Ser Leu Gln Arg Leu Gly Ile Asp
        115                 120                 125

Tyr Ile Asp Ile Tyr Met Thr His Trp Gln Ser Val Pro Pro Phe Phe
    130                 135                 140

Thr Pro Ile Ala Glu Thr Val Ala Val Leu Asn Glu Leu Lys Ser Glu
145                 150                 155                 160

Gly Lys Ile Arg Ala Ile Gly Ala Ala Asn Val Asp Ala Asp His Ile
                165                 170                 175

Arg Glu Tyr Leu Gln Tyr Gly Glu Leu Asp Ile Ile Gln Ala Lys Tyr
            180                 185                 190

Ser Ile Leu Asp Arg Ala Met Glu Asn Glu Leu Leu Pro Leu Cys Arg
        195                 200                 205

Asp Asn Gly Ile Val Val Gln Val Tyr Ser Pro Leu Glu Gln Gly Leu
    210                 215                 220

Leu Thr Gly Thr Ile Thr Arg Glu Tyr Val Pro Gly Gly Ala Arg Ala
225                 230                 235                 240

Asn Lys Val Trp Phe Gln Arg Glu Asn Met Leu Lys Val Ile Asp Met
                245                 250                 255

Leu Glu Gln Trp Gln Pro Leu Cys Ala Arg Tyr Gln Cys Thr Ile Pro
            260                 265                 270

Thr Leu Ala Leu Ala Trp Ile Leu Lys Gln Ser Asp Leu Ile Ser Ile
        275                 280                 285

Leu Ser Gly Ala Thr Ala Pro Glu Gln Val Arg Glu Asn Val Ala Ala
    290                 295                 300

Leu Asn Ile Asn Leu Ser Asp Ala Asp Ala Thr Leu Met Arg Glu Met
305                 310                 315                 320

Ala Glu Ala Leu Glu Arg
                325

<210> SEQ ID NO 106
<211> LENGTH: 981
<212> TYPE: DNA
<213> ORGANISM: artificial
<220> FEATURE:
<223> OTHER INFORMATION: YdjG*(D232E)

<400> SEQUENCE: 106
atgaaaaaga tacctttagg cacaacggat attacgcttt cgcgaatggg gttggggaca      60
tgggccattg gcggcggtcc tgcatggaat ggcgatctcg atcggcaaat atgtattgat     120
acgattcttg aagcccatcg ttgtggcatt aatctgattg atactgcgcc aggatataac     180
tttggcaata gtgaagttat cgtcggtcag gcgttaaaaa aactgccccg tgaacaggtt     240
gtagtagaaa ccaaatgcgg cattgtctgg aacgaaaag gaagtttatt caacaaagtt     300
ggcgatcggc agttgtataa aaacctttcc ccggaatcta tccgcgaaga ggtagcagcg     360
agcttgcaac gtctgggtat tgattacatc gatatctaca tgacgcactg gcagtcggtg     420
ccgccatttt ttacgccgat cgctgaaact gtcgcagtgc ttaatgagtt aaagtctgaa     480
gggaaaattc gcgctatagg cgctgctaac gtcgatgctg accatatccg cgagtatctg     540
caatatggtg aactggatat tattcaggcg aaatacagta tcctcgaccg ggcaatggaa     600
aacgaactgc tgccactatg tcgtgataat ggcattgtgg ttcaggttta ttccccgcta     660
gagcagggat tgttgaccgg caccatcact cgtgaatacg ttccgggcgg cgctcgggca     720

```
aataaagtct ggttccagcg tgaaaacatg ctgaaagtga ttgatatgct tgaacagtgg    780
cagccacttt gtgctcgtta tcagtgcaca attcccactc tggcactggc gtggatatta    840
aaacagagtg atttaatctc cattcttagt ggggctactg caccggaaca ggtacgcgaa    900
aatgtcgcgg cactgaatat caacttatcg gatgcagacg caacattgat gagggaaatg    960
gcagaggccc tggagcgtta a                                              981
```

<210> SEQ ID NO 107
<211> LENGTH: 387
<212> TYPE: PRT
<213> ORGANISM: Dickeya zeae

<400> SEQUENCE: 107

```
Met Gln Asn Phe Thr Leu His Thr Pro Thr Lys Ile Leu Phe Gly Glu
1               5                   10                  15

Gly Gln Ile Ala Ala Leu Ala Asp Gln Ile Pro Ala Asp Ala Arg Ile
            20                  25                  30

Leu Ile Thr Tyr Gly Gly Gly Ser Ile Lys Lys Asn Gly Val Phe Asp
        35                  40                  45

Gln Val Ile Asn Ala Leu Lys Gly Arg Asn Val Glu Phe Ser Gly
    50                  55                  60

Ile Glu Pro Asn Pro Thr Tyr Glu Thr Leu Met Lys Ala Val Glu Ile
65                  70                  75                  80

Val Arg Lys Glu Asn Ile Asp Phe Leu Leu Ala Val Gly Gly Gly Ser
                85                  90                  95

Val Ala Asp Gly Thr Lys Phe Ile Ala Ala Val Asn Tyr Lys Ala
            100                 105                 110

Ala Glu Asp Pro Trp His Ile Leu Gln Thr Trp Gly Ala His Val Glu
        115                 120                 125

Ser Ala Ile Pro Leu Gly Val Val Leu Thr Leu Pro Ala Thr Gly Ser
    130                 135                 140

Glu Ser Asn Ser Gly Ala Val Ile Thr Arg Lys Ser Thr Gly Asp Lys
145                 150                 155                 160

Gln Ala Phe Met Asn Pro Leu Val Cys Pro Arg Phe Ala Val Leu Asp
                165                 170                 175

Pro Val Thr Tyr Thr Leu Pro Glu Arg Gln Ile Ala Asn Gly Val
            180                 185                 190

Val Asp Ala Phe Val His Thr Val Glu Gln Tyr Leu Thr Tyr Pro Val
        195                 200                 205

Asp Ala Lys Val Gln Asp Arg Phe Ala Glu Gly Leu Leu Leu Thr Leu
    210                 215                 220

Ile Glu Glu Gly Pro Arg Ala Leu Lys Glu Gln His Asn Tyr Asn Val
225                 230                 235                 240

Arg Ala Asn Val Met Trp Ser Ala Thr Met Ala Leu Asn Gly Leu Ile
                245                 250                 255

Gly Ala Gly Val Pro Gln Asp Trp Ser Thr His Met Leu Gly His Glu
            260                 265                 270

Ile Thr Ala Met His Gly Leu Asp His Ala Gln Thr Leu Ala Ile Val
        275                 280                 285

Leu Pro Ala Met Leu Asn Glu Arg Arg Val Gln Lys Arg Glu Lys Leu
    290                 295                 300

Leu Gln Tyr Ala Glu Arg Val Trp Asn Leu Arg Asp Gly Ser Asp Asp
305                 310                 315                 320
```

```
Gln Arg Ile Asp Gly Ala Ile Ala Ala Thr Arg Ala Phe Phe Glu Gln
                325                 330                 335

Met Gly Val Pro Thr Arg Leu Ser Asp Tyr Gln Leu Asp Gly Ser Ser
            340                 345                 350

Ile Pro Ala Leu Val Ala Lys Leu Glu Glu His Gly Met Thr Ala Leu
        355                 360                 365

Gly Glu Asn Lys Asp Ile Thr Leu Asp Ile Ser Lys Arg Val Tyr Glu
    370                 375                 380

Ala Ala Arg
385

<210> SEQ ID NO 108
<211> LENGTH: 1164
<212> TYPE: DNA
<213> ORGANISM: Dickeya zeae

<400> SEQUENCE: 108
atgcagaact ttacgcttca taccccgact aaaatcctgt tcggcgaagg gcaaatcgct      60
gctctggccg accagatccc ggctgacgcc cgcattctta tcacttacgg cggcggcagc     120
atcaagaaaa acggcgtatt cgaccaggtc atcaacgcgc tgaaaggccg caacgttgtg     180
gagttctcgg gcattgagcc taaccccacc tacgaaacgc tcatgaaagc ggttgagatc     240
gtacgcaagg aaaacatcga ctttctgctg gcggtcggcg gtggttcggt tgccgatggc     300
accaaattca tcgcggcagc ggtgaactac aaggcagccg aagaccgtg gcatattctg      360 caaacctggg gagcacacgt agaaagcgcc atcccgctgg gtgtggtgct gacgctgcca     420
gcgaccggtt ccgaatccaa cagcggcgca gtgattaccc gcaagagcac cggcgacaaa     480
caggcgttca tgaacccatt ggtatgcccg cgttttgccg tgcttgaccc ggtcgtaacc     540
tatacgctgc ctgaacgtca gattgccaac ggcgtggtcg atgccttcgt ccataccgtc     600
gagcagtatc tgacctaccc ggttgacgcc aaagtgcagg accgcttcgc gaagggctg      660 ttactgacgt tgatcgaaga aggcccgcgc gccctcaaag agcagcataa ctacaatgtt     720
cgtgccaacg tgatgtggag tgccaccatg gcgctcaatg gcctgattgg cgcaggggtg     780
ccgcaagact ggtcaaccca tatgctgggc acgaaaatca cggcaatgca cggactggac     840
catgcgcaga cactggctat cgtactcccg gcgatgctca acgaacgtcg tgttcagaaa     900
cgtgagaaac tgctgcaata cgccgaacgc gtctggaatc tgcgtgacgg ttcagacgac     960
caacgcattg atggtgcgat cgccgccacc cgcgctttct tcgaacaaat gggcgtaccg    1020
acccgcctgt cagactacca gttggacggc agttctattc cggcgctggt cgcgaagctc    1080
gaagagcacg gtatgacagc gttgggcgaa acaaagaca tcacgctgga catcagcaaa     1140
cgcgtgtacg aagccgcccg ctaa                                           1164

<210> SEQ ID NO 109
<211> LENGTH: 298
<212> TYPE: PRT
<213> ORGANISM: Escherichia coli (strain K12)

<400> SEQUENCE: 109

Met Val Gln Arg Ile Thr Ile Ala Pro Gln Gly Pro Glu Phe Ser Arg
1               5                   10                  15

Phe Val Met Gly Tyr Trp Arg Leu Met Asp Trp Asn Met Ser Ala Arg
            20                  25                  30

Gln Leu Val Ser Phe Ile Glu Glu His Leu Asp Leu Gly Val Thr Thr
        35                  40                  45
```

Val Asp His Ala Asp Ile Tyr Gly Gly Tyr Gln Cys Glu Ala Ala Phe
 50                  55                  60

Gly Glu Ala Leu Lys Leu Ala Pro His Leu Arg Glu Arg Met Glu Ile
 65                  70                  75                  80

Val Ser Lys Cys Gly Ile Ala Thr Thr Ala Arg Glu Glu Asn Val Ile
                 85                  90                  95

Gly His Tyr Ile Thr Asp Arg Asp His Ile Ile Lys Ser Ala Glu Gln
                100                 105                 110

Ser Leu Ile Asn Leu Ala Thr Asp His Leu Asp Leu Leu Ile His
            115                 120                 125

Arg Pro Asp Pro Leu Met Asp Ala Asp Glu Val Ala Asp Ala Phe Lys
130                 135                 140

His Leu His Gln Ser Gly Lys Val Arg His Phe Gly Val Ser Asn Phe
145                 150                 155                 160

Thr Pro Ala Gln Phe Ala Leu Leu Gln Ser Arg Leu Pro Phe Thr Leu
                165                 170                 175

Ala Thr Asn Gln Val Glu Ile Ser Pro Val His Gln Pro Leu Leu Leu
                180                 185                 190

Asp Gly Thr Leu Asp Gln Leu Gln Gln Leu Arg Val Arg Pro Met Ala
            195                 200                 205

Trp Ser Cys Leu Gly Gly Gly Arg Leu Phe Asn Asp Asp Tyr Phe Gln
210                 215                 220

Pro Leu Arg Asp Glu Leu Ala Val Val Ala Glu Leu Asn Ala Gly
225                 230                 235                 240

Ser Ile Glu Gln Val Val Tyr Ala Trp Val Leu Arg Leu Pro Ser Gln
                245                 250                 255

Pro Leu Pro Ile Ile Gly Ser Gly Lys Ile Glu Arg Val Arg Ala Ala
            260                 265                 270

Val Glu Ala Glu Thr Leu Lys Met Thr Arg Gln Gln Trp Phe Arg Ile
275                 280                 285

Arg Lys Ala Ala Leu Gly Tyr Asp Val Pro
290                 295

<210> SEQ ID NO 110
<211> LENGTH: 897
<212> TYPE: DNA
<213> ORGANISM: Escherichia coli (strain K12)

<400> SEQUENCE: 110

| | |
|---|---|
| atggttcagc gtattactat tgcgccgcaa ggcccggagt tttcccgttt tgtgatgggc | 60 |
| tactggcgat tgatggactg gaatatgtcc gcccgccagc tggtcagttt tattgaagag | 120 |
| catctggatc tcggcgtgac caccgtggac catgctgata tttatggtgg ctatcagtgc | 180 |
| gaagcggcgt ttggcgaggc actgaaactg gcacctcacc tgcgtgaacg gatggaaatc | 240 |
| gtcagtaaat gcggtatcgc gacgaccgcg cgtgaagaaa acgtcattgg tcattacatc | 300 |
| actgaccgcg atcacatcat taagagcgcc gaacagtcgc taattaatct cgcgaccgat | 360 |
| catctggatt gctgttaat ccaccgacca gaccgttaa tggatgccga tgaagtggcg | 420 |
| gacgcgttca acatctgca tcagagcggc aaagtgcgtc attttggcgt atcgaacttt | 480 |
| acgcctgcgc aatttgccct gttgcaatca cgtctgccgt ttacccttgc cactaatcag | 540 |
| gtggaaatat ccccggtgca tcagccgtta ctgctggatg gcacgctcga ccaactacaa | 600 |
| caactgcgtg ttcgtccgat ggcgtggtcc tgccttggtg gtggtcgtct gtttaatgat | 660 |

```
gattatttcc agccgctgcg tgatgaactg gctgtggtgg cagaggagtt aaacgcgggc    720
tcgattgaac aggtggttta cgcctgggta ttacgtttac catcgcagcc gctgccaatt    780
atcggttcag gtaaaattga gcgcgtacgg gcagctgtcg aagcagaaac actgaaaatg    840
acccgtcaac aatggtttcg tatccgtaaa gcggcactgg ggtacgacgt accgtaa      897
```

<210> SEQ ID NO 111
<211> LENGTH: 284
<212> TYPE: PRT
<213> ORGANISM: Escherichia coli (strain K12)

<400> SEQUENCE: 111

```
Met Gln Gln Lys Met Ile Gln Phe Ser Gly Asp Val Ser Leu Pro Ala
1               5                   10                  15

Val Gly Gln Gly Thr Trp Tyr Met Gly Glu Asp Ala Ser Gln Arg Lys
            20                  25                  30

Thr Glu Val Ala Ala Leu Arg Ala Gly Ile Glu Leu Gly Leu Thr Leu
        35                  40                  45

Ile Asp Thr Ala Glu Met Tyr Ala Asp Gly Gly Ala Glu Lys Val Val
    50                  55                  60

Gly Glu Ala Leu Thr Gly Leu Arg Glu Lys Val Phe Leu Val Ser Lys
65                  70                  75                  80

Val Tyr Pro Trp Asn Ala Gly Gly Gln Lys Ala Ile Asn Ala Cys Glu
                85                  90                  95

Ala Ser Leu Arg Arg Leu Asn Thr Asp Tyr Leu Asp Leu Tyr Leu Leu
            100                 105                 110

His Trp Ser Gly Ser Phe Ala Phe Glu Glu Thr Val Ala Ala Met Glu
        115                 120                 125

Lys Leu Ile Ala Gln Gly Lys Ile Arg Arg Trp Gly Val Ser Asn Leu
    130                 135                 140

Asp Tyr Ala Asp Met Gln Glu Leu Trp Gln Leu Pro Gly Gly Asn Gln
145                 150                 155                 160

Cys Ala Thr Asn Gln Val Leu Tyr His Leu Gly Ser Arg Gly Ile Glu
                165                 170                 175

Tyr Asp Leu Leu Pro Trp Cys Gln Gln Gln Met Pro Val Met Ala
            180                 185                 190

Tyr Ser Pro Leu Ala Gln Ala Gly Arg Leu Arg Asn Gly Leu Leu Lys
        195                 200                 205

Asn Ala Val Val Asn Glu Ile Ala His Ala His Asn Ile Ser Ala Ala
    210                 215                 220

Gln Val Leu Leu Ala Trp Val Ile Ser His Gln Gly Val Met Ala Ile
225                 230                 235                 240

Pro Lys Ala Ala Thr Ile Ala His Val Gln Gln Asn Ala Ala Val Leu
                245                 250                 255

Glu Val Glu Leu Ser Ser Ala Glu Leu Ala Met Leu Asp Lys Ala Tyr
            260                 265                 270

Pro Ala Pro Lys Gly Lys Thr Ala Leu Asp Met Val
        275                 280
```

<210> SEQ ID NO 112
<211> LENGTH: 855
<212> TYPE: DNA
<213> ORGANISM: Escherichia coli (strain K12)

<400> SEQUENCE: 112

```
atgcaacaaa aaatgattca atttagtggc gatgtctcac tgccagccgt agggcaggga    60
```

```
acatggtata tgggcgaaga tgccagtcag cgcaaaacag aagttgctgc actacgcgcg    120
ggcattgaac tcggtttaac cctcattgat accgccgaaa tgtatgccga tggcggtgcc    180
gaaaaggtgg ttggggaagc attaaccggt ctgcgagaga aggtctttct cgtctctaaa    240
gtctatccgt ggaatgctgg cgggcaaaaa gcgataaatg catgcgaagc cagtttacgc    300
cgtctcaata ctgattatct cgatctttac ttattacact ggtctggcag tttcgctttt    360
gaagagactg tcgcagcgat ggaaaaattg atcgcccagg gaaaaatccg ccgctggggc    420
gtttctaacc ttgattatgc tgatatgcag gaactctggc agctgccggg gggaaatcag    480
tgtgccacta atcaggtgct ttaccatctc ggttcacgag gaattgagta cgatctactc    540
ccctggtgcc agcaacagca gatgccggtg atggcttaca gtccgttagc ccaggccggg    600
cggttgcgca atggactgtt aaaaaacgcg gtagtcaacg aaattgcaca tgctcacaat    660
atcagcgcgg cacaagtatt gttggcgtgg gtgatcagtc atcagggtgt gatggcgatt    720
ccaaaagcgg ccacgattgc ccatgtccaa caaaatgcgg ctgtgcttga ggtcgaactt    780
tcttcagcgg aattagctat gctggataag gcatatccgg caccaaaagg aaaaactgcg    840
ctggatatgg tgtga                                                     855
```

<210> SEQ ID NO 113
<211> LENGTH: 318
<212> TYPE: PRT
<213> ORGANISM: Hypocrea jecorina

<400> SEQUENCE: 113

```
Met Ala Ser Lys Thr Tyr Thr Leu Asn Thr Gly Ala Lys Ile Pro Ala
1               5                   10                  15

Val Gly Phe Gly Thr Phe Ala Asn Glu Gly Ala Lys Gly Glu Thr Tyr
            20                  25                  30

Ala Ala Val Thr Lys Ala Leu Asp Val Gly Tyr Arg His Leu Asp Cys
        35                  40                  45

Ala Trp Phe Tyr His Asn Glu Asp Glu Val Gly Asp Ala Val Arg Asp
    50                  55                  60

Phe Leu Ala Arg Arg Pro Asp Val Lys Arg Glu Asp Leu Phe Ile Cys
65                  70                  75                  80

Thr Lys Val Trp Asn His Leu His Glu Pro Glu Asp Val Lys Trp Ser
                85                  90                  95

Ala Lys Asn Ser Cys Glu Asn Leu Lys Val Asp Tyr Ile Asp Leu Phe
            100                 105                 110

Leu Val His Trp Pro Ile Ala Ala Glu Lys Asn Ser Asp Arg Ser Val
        115                 120                 125

Lys Leu Gly Pro Asp Gly Lys Tyr Val Ile Asn Gln Ala Leu Thr Glu
    130                 135                 140

Asn Pro Glu Pro Thr Trp Arg Ala Met Glu Glu Leu Val Glu Ser Gly
145                 150                 155                 160

Leu Val Lys Ala Ile Gly Val Ser Asn Trp Thr Ile Pro Gly Leu Lys
                165                 170                 175

Lys Leu Leu Gln Ile Ala Lys Ile Lys Pro Ala Val Asn Gln Ile Glu
            180                 185                 190

Ile His Pro Phe Leu Pro Asn Glu Glu Leu Val Ala Phe Cys Phe Glu
        195                 200                 205

Asn Gly Ile Leu Pro Glu Ala Tyr Ser Pro Leu Gly Ser Gln Asn Gln
    210                 215                 220
```

Val Pro Ser Thr Gly Glu Arg Val Arg Asp Asn Pro Thr Leu Lys Ala
225                 230                 235                 240

Val Ala Glu Arg Ser Gly Tyr Ser Leu Ala Gln Ile Leu Leu Ala Trp
            245                 250                 255

Gly Leu Lys Arg Gly Tyr Val Val Leu Pro Lys Ser Ser Thr Pro Ser
        260                 265                 270

Arg Ile Glu Ser Asn Phe Asn Ile Pro Glu Leu Ser Asp Glu Asp Phe
    275                 280                 285

Glu Ala Ile Gln Gln Val Ala Lys Gly Arg His Thr Arg Phe Val Asn
290                 295                 300

Met Lys Asp Thr Phe Gly Tyr Asn Val Trp Pro Glu Glu Glu
305                 310                 315

<210> SEQ ID NO 114
<211> LENGTH: 957
<212> TYPE: DNA
<213> ORGANISM: artificial
<220> FEATURE:
<223> OTHER INFORMATION: codon optimized gene gld2

<400> SEQUENCE: 114
atggcaagca aaacctatac cctgaataca ggtgcaaaaa ttccggcagt tggttttggc        60
acctttgcaa tgaaggtgc gaaaggtgaa acctatgcag cagttaccaa agcactggat       120
gttggttatc gtcatctgga ttgtgcatgg ttttatcaca tgaagatga gttggtgat        180 gccgttcgtg atttctggc acgtcgtccg gatgttaaac gtgaggacct gtttatttgt       240
accaaagtgt ggaatcatct gcacgaaccg gaagatgtta atggtcagc aaaaaatagc       300 tgcgagaacc tgaaagtgga ttatattgac ctgtttctgg ttcattggcc gattgcagca     360
gaaaaaaaca gcgatcgtag cgttaaactg ggtccggatg caaatatgt tattaatcag     420 gcactgaccg aaaatccgga accgacctgg cgtgcaatgg aagaactggt tgaaagcggt     480
ctggttaaag caattggtgt tagcaattgg accattccgg gtctgaaaaa actgctgcag     540
attgcaaaaa tcaaaccggc agttaaccag attgaaatcc atccgtttct gccgaatgag     600
gaactggtgg cattttgttt tgaaaatggt attctgccgg aagcatatag tccgctgggt     660
agccagaatc aggttccgag cacaggtgaa cgtgttcgtg ataatccgac cctgaaagca     720
gttgcagaaa cgtagcggtta tagcctggca cagattctgc tggcatgggg actgaaacgt     780
ggttatgttg tgctgccgaa aagcagcacc ccgagccgta ttgaaagcaa tttcaatatt     840
ccggaactga gcgacgaaga ttttgaagca attcagcagg ttgcaaaagg tcgtcatacc     900
cgttttgtga atatgaaaga taccttcggc tataacgttt ggcctgaaga agaataa        957

<210> SEQ ID NO 115
<211> LENGTH: 383
<212> TYPE: PRT
<213> ORGANISM: Escherichia coli (strain K12)

<400> SEQUENCE: 115

Met Ala Ala Ser Thr Phe Phe Ile Pro Ser Val Asn Val Ile Gly Ala
1               5                   10                  15

Asp Ser Leu Thr Asp Ala Met Asn Met Ala Asp Tyr Gly Phe Thr
            20                  25                  30

Arg Thr Leu Ile Val Thr Asp Asn Met Leu Thr Lys Leu Gly Met Ala
        35                  40                  45

Gly Asp Val Gln Lys Ala Leu Glu Glu Arg Asn Ile Phe Ser Val Ile
    50                  55                  60

Tyr Asp Gly Thr Gln Pro Asn Pro Thr Thr Glu Asn Val Ala Ala Gly
65                  70                  75                  80

Leu Lys Leu Leu Lys Glu Asn Asn Cys Asp Ser Val Ile Ser Leu Gly
            85                  90                  95

Gly Gly Ser Pro His Asp Cys Ala Lys Gly Ile Ala Leu Val Ala Ala
        100                 105                 110

Asn Gly Gly Asp Ile Arg Asp Tyr Glu Gly Val Asp Arg Ser Ala Lys
    115                 120                 125

Pro Gln Leu Pro Met Ile Ala Ile Asn Thr Thr Ala Gly Thr Ala Ser
130                 135                 140

Glu Met Thr Arg Phe Cys Ile Ile Thr Asp Glu Ala Arg His Ile Lys
145                 150                 155                 160

Met Ala Ile Val Asp Lys His Val Thr Pro Leu Leu Ser Val Asn Asp
                165                 170                 175

Ser Ser Leu Met Ile Gly Met Pro Lys Ser Leu Thr Ala Ala Thr Gly
            180                 185                 190

Met Asp Ala Leu Thr His Ala Ile Glu Ala Tyr Val Ser Ile Ala Ala
        195                 200                 205

Thr Pro Ile Thr Asp Ala Cys Ala Leu Lys Ala Val Thr Met Ile Ala
    210                 215                 220

Glu Asn Leu Pro Leu Ala Val Glu Asp Gly Ser Asn Ala Lys Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Phe
            260                 265                 270

Tyr Asn Leu Pro His Gly Val Cys Asn Ala Val Leu Leu Pro His Val
        275                 280                 285

Gln Val Phe Asn Ser Lys Val Ala Ala Ala Arg Leu Arg Asp Cys Ala
    290                 295                 300

Ala Ala Met Gly Val Asn Val Thr Gly Lys Asn Asp Ala Glu Gly Ala
305                 310                 315                 320

Glu Ala Cys Ile Asn Ala Ile Arg Glu Leu Ala Lys Lys Val Asp Ile
                325                 330                 335

Pro Ala Gly Leu Arg Asp Leu Asn Val Lys Glu Glu Asp Phe Ala Val
            340                 345                 350

Leu Ala Thr Asn Ala Leu Lys Asp Ala Cys Gly Phe Thr Asn Pro Ile
        355                 360                 365

Gln Ala Thr His Glu Glu Ile Val Ala Ile Tyr Arg Ala Ala Met
    370                 375                 380

<210> SEQ ID NO 116
<211> LENGTH: 1152
<212> TYPE: DNA
<213> ORGANISM: Escherichia coli (strain K12)

<400> SEQUENCE: 116
atggcagctt caacgttctt tattccttct gtgaatgtca tcggcgctga ttcattgact      60
gatgcaatga atatgatggc agattatgga tttacccgta ccttaattgt cactgacaat     120
atgttaacga aattaggtat ggcgggcgat gtgcaaaaag cactggaaga acgcaatatt     180
tttagcgtta tttatgatgg cacccaacct aaccccacca cggaaaacgt cgccgcaggt     240
ttgaaattac ttaaagagaa taattgcgat agcgtgatct ccttaggcgg tggttctcca     300

```
cacgactgcg caaaaggtat tgcgctggtg gcagccaatg gcggcgatat tcgcgattac    360
gaaggcgttg accgctctgc aaaaccgcag ctgccgatga tcgccatcaa taccacggcg    420
ggtacggcct ctgaaatgac ccgtttctgc atcatcactg acgaagcgcg tcatatcaaa    480
atggcgattg ttgataaaca tgtcactccg ctgctttctg tcaatgactc ctctctgatg    540
attggtatgc cgaagtcact gaccgccgca acgggtatgg atgccttaac gcacgctatc    600
gaagcatatg tttctattgc cgccacgccg atcactgacg cttgtgcact gaaagccgtg    660
accatgattg ccgaaaacct gccgttagcc gttgaagatg gcagtaatgc gaaagcgcgt    720
gaagcaatgg cttatgccca gttcctcgcc ggtatggcgt tcaataatgc ttctctgggt    780
tatgttcatg cgatggcgca ccagctgggc ggtttctaca acctgccaca cggtgtatgt    840
aacgccgttt tgctgccgca cgttcaggta ttcaacagca agtcgccgc tgcacgtctg    900
cgtgactgtg ccgctgcaat gggcgtgaac gtgacaggta aaaacgacgc ggaaggtgct    960
gaagcctgca ttaacgccat ccgtgaactg gcgaagaaag tggatatccc ggcaggccta   1020
cgcgacctga acgtgaaaga agaagatttc gcggtattgg cgactaatgc cctgaaagat   1080
gcctgtggct ttactaaccc gatccaggca actcacgaag aaattgtggc gatttatcgc   1140
gcagcgatgt aa                                                       1152

<210> SEQ ID NO 117
<211> LENGTH: 256
<212> TYPE: PRT
<213> ORGANISM: Klebsiella pneumoniae

<400> SEQUENCE: 117

Met Lys Lys Val Ala Leu Val Thr Gly Ala Gly Gln Gly Ile Gly Lys
1               5                   10                  15

Ala Ile Ala Leu Arg Leu Val Lys Asp Gly Phe Ala Val Ala Ile Ala
            20                  25                  30

Asp Tyr Asn Asp Ala Thr Ala Lys Ala Val Ala Ser Glu Ile Asn Gln
        35                  40                  45

Ala Gly Gly Arg Ala Met Ala Val Lys Val Asp Val Ser Asp Arg Asp
    50                  55                  60

Gln Val Phe Ala Ala Val Glu Gln Ala Arg Lys Thr Leu Gly Gly Phe
65                  70                  75                  80

Asp Val Ile Val Asn Asn Ala Gly Val Ala Pro Ser Thr Pro Ile Glu
                85                  90                  95

Ser Ile Thr Pro Glu Ile Val Asp Lys Val Tyr Asn Ile Asn Val Lys
            100                 105                 110

Gly Val Ile Trp Gly Ile Gln Ala Ala Val Glu Ala Phe Lys Lys Glu
        115                 120                 125

Gly His Gly Gly Lys Ile Ile Asn Ala Cys Ser Gln Ala Gly His Val
    130                 135                 140

Gly Asn Pro Glu Leu Ala Val Tyr Ser Ser Ser Lys Phe Ala Val Arg
145                 150                 155                 160

Gly Leu Thr Gln Thr Ala Ala Arg Asp Leu Ala Pro Leu Gly Ile Thr
                165                 170                 175

Val Asn Gly Tyr Cys Pro Gly Ile Val Lys Thr Pro Met Trp Ala Glu
            180                 185                 190

Ile Asp Arg Gln Val Ser Glu Ala Ala Gly Lys Pro Leu Gly Tyr Gly
        195                 200                 205

Thr Ala Glu Phe Ala Lys Arg Ile Thr Leu Gly Arg Leu Ser Glu Pro
    210                 215                 220
```

```
Glu Asp Val Ala Ala Cys Val Ser Tyr Leu Ala Ser Pro Asp Ser Asp
225                 230                 235                 240

Tyr Met Thr Gly Gln Ser Leu Leu Ile Asp Gly Gly Met Val Phe Asn
                245                 250                 255
```

<210> SEQ ID NO 118
<211> LENGTH: 771
<212> TYPE: DNA
<213> ORGANISM: Klebsiella pneumoniae

<400> SEQUENCE: 118

```
atgaaaaaag tcgcacttgt taccggcgcc ggccagggga ttggtaaagc tatcgccctt      60
cgtctggtga aggatggatt tgccgtggcc attgccgatt ataacgacac caccgccaaa    120
gcggtcgcct ccgaaatcaa ccaggccggc ggccgcgcca tggcggtgaa agtggatgtc    180
tccgaccgcg atcaggtgtt tgccgccgtc gaacaggcgc gcaaaacgct gggcggcttc    240
gacgtcatcg tcaacaacgc cggcgtggcg ccgtccacgc cgatcgagtc cattaccccg    300
gagattgtcg ataaagtcta caacatcaac gttaaggggg tgatctgggg cattcaggcg    360
gcggtcgagg cctttaagaa agagggtcac ggcgggaaaa tcatcaacgc ctgttcccag    420
gccggccacg tcggcaaccc ggagctggcg gtatatagct cgagtaaatt cgccgtacgc    480
ggcttaaccc cagaccgccg ctcgcgacct cgcgccgctgg catcacagt caacggctac    540
tgcccgggga ttgtcaaaac gccaatgtgg gccgaaattg accgccaggt gtccgaagcc    600
gccggtaaac cgctgggtta cggtaccgcc gagttcgcca aacgcatcac cctcggccgc    660
ctgtccgagc cggaagatgt cgccgcctgc gtctcctatc ttgccagccc ggattctgat    720
tatatgaccg gtcagtcatt gctgatcgac ggcgggatgg tgtttaacta a             771
```

<210> SEQ ID NO 119
<211> LENGTH: 101
<212> TYPE: DNA
<213> ORGANISM: artificial
<220> FEATURE:
<223> OTHER INFORMATION: Oligonucleotide for deletion yqhD

<400> SEQUENCE: 119

```
atgaacaact ttaatctgca caccccaacc cgcattctgt ttggtaaagg cgcaatcgct      60
ggtttacgcg aacaaattcc gtgtaggctg gagctgcttc g                         101
```

<210> SEQ ID NO 120
<211> LENGTH: 101
<212> TYPE: DNA
<213> ORGANISM: artificial
<220> FEATURE:
<223> OTHER INFORMATION: Oligonucleotide for deletion yqhD

<400> SEQUENCE: 120

```
ttagcgggcg gcttcgtata tacggcggct gacatccaac gtaatgtcat gattttcgcc      60
cagttgggtc atgccgtgct ccatatgaat atcctcctta g                         101
```

<210> SEQ ID NO 121
<211> LENGTH: 101
<212> TYPE: DNA
<213> ORGANISM: artificial
<220> FEATURE:
<223> OTHER INFORMATION: Oligonucleotide for deletion ydjG

<400> SEQUENCE: 121
```

```
ttaacgctcc agggcctctg ccatttccct catcaatgtt gcgtctgcat ccgataagtt    60
gatattcagt gccgcgacat gtgtaggctg gagctgcttc g                      101
```

<210> SEQ ID NO 122
<211> LENGTH: 100
<212> TYPE: DNA
<213> ORGANISM: artificial
<220> FEATURE:
<223> OTHER INFORMATION: Oligonucleotide for deletion ydjG

<400> SEQUENCE: 122

```
atgaaaaaga tacctttagg cacaacggat attacgcttt cgcgaatggg gttggggaca    60
tgggccattg gcggcggtcc catatgaata tcctccttag                         100
```

<210> SEQ ID NO 123
<211> LENGTH: 100
<212> TYPE: DNA
<213> ORGANISM: artificial
<220> FEATURE:
<223> OTHER INFORMATION: Oligonucleotide for deletion ptsG

<400> SEQUENCE: 123

```
gtacacggcg aggctctccc cccttgccac gcgtgagaac gtaaaaaaag cacccatact    60
caggagcact ctcaattatg tgtaggctgg agctgcttcg                         100
```

<210> SEQ ID NO 124
<211> LENGTH: 100
<212> TYPE: DNA
<213> ORGANISM: artificial
<220> FEATURE:
<223> OTHER INFORMATION: Oligonucleotide for deletion ptsG

<400> SEQUENCE: 124

```
ataacacctg taaaaaaggc agccatctgg ctgccttagt ctccccaacg tcttacggat    60
tagtggttac ggatgtactc catatgaata tcctccttag                         100
```

<210> SEQ ID NO 125
<211> LENGTH: 339
<212> TYPE: PRT
<213> ORGANISM: artificial
<220> FEATURE:
<223> OTHER INFORMATION: YjgB*(I165V)

<400> SEQUENCE: 125

Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Gln Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
    50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

```
Arg Ala Asp Trp Gln Trp Val Ile Pro Leu Pro Glu Asn Ile Asp Ile
        130                 135                 140
Glu Ser Ala Gly Pro Leu Leu Cys Gly Gly Val Thr Val Phe Lys Pro
145                 150                 155                 160
Leu Leu Met His His Ile Thr Ala Thr Ser Arg Val Gly Val Ile Gly
                165                 170                 175
Ile Gly Gly Leu Gly His Ile Ala Ile Lys Leu Leu His Ala Met Gly
            180                 185                 190
Cys Glu Val Thr Ala Phe Ser Ser Asn Pro Ala Lys Glu Gln Glu Val
        195                 200                 205
Leu Ala Met Gly Ala Asp Lys Val Val Asn Ser Arg Asp Pro Gln Ala
210                 215                 220
Leu Lys Ala Leu Ala Gly Gln Phe Asp Leu Ile Ile Asn Thr Val Asn
225                 230                 235                 240
Val Ser Leu Asp Trp Gln Pro Tyr Phe Glu Ala Leu Thr Tyr Gly Gly
                245                 250                 255
Asn Phe His Thr Val Gly Ala Val Leu Thr Pro Leu Ser Val Pro Ala
            260                 265                 270
Phe Thr Leu Ile Ala Gly Asp Arg Ser Val Ser Gly Ser Ala Thr Gly
        275                 280                 285
Thr Pro Tyr Glu Leu Arg Lys Leu Met Arg Phe Ala Ala Arg Ser Lys
290                 295                 300
Val Ala Pro Thr Thr Glu Leu Phe Pro Met Ser Lys Ile Asn Asp Ala
305                 310                 315                 320
Ile Gln His Val Arg Asp Gly Lys Ala Arg Tyr Arg Val Val Leu Lys
                325                 330                 335
Ala Asp Phe

<210> SEQ ID NO 126
<211> LENGTH: 1020
<212> TYPE: DNA
<213> ORGANISM: artificial
<220> FEATURE:
<223> OTHER INFORMATION: yjgB*(I165V)

<400> SEQUENCE: 126
atgtcaatga ttaaatcgta tgcggcgaaa gaagcgggtg cgaactggaa agtgtatgaa      60
tacgacccag gcgaactgcg tccgcaggat gtggaagtcc aggtggatta ttgcggtatt     120
tgccatagcg acctgtctat gattgacaac gaatggggct ttagccagta tccgctggtg     180
gcgggtcacg aagtgattgg tcgtgtggtt gccctgggca gtgccgccca ggataaaggc     240
ttacaggtgg gtcagcgtgt gggcattggc tggacggcac gcagttgcgg tcattgcgat     300
gcgtgtatca gcggcaacca aatcaactgc gaacagggtg ccgttccgac gattatgaac     360
cgtggcggct tgccgagaaa actgcgtgcc gattggcagt gggtgattcc gctgcccgaa     420
aacattgata ttgaatctgc gggtccgctg ttatgtggcg tgttaccgt  gttcaaaccg     480 ctgttgatgc accacattac cgccaccagc cgtgttggcg tgattggcat cggcggtctg     540
ggtcacattg ccatcaaact gttacacgca atgggctgcg aagtgacggc gtttagcagt     600
aacccagcga agaacagga  agtgctggcg atgggtgcgg ataaagtggt gaacagccgt     660
gacccgcagg cactgaaagc cctggcgggt cagtttgacc tgattatcaa caccgtgaat     720
gtcagcctgg attggcagcc gtattttgaa gccctgacct atggcggtaa cttccatacc     780
gtgggtgccg tgctgacccc gctgagcgtg cctgcgttta ccctgattgc gggtgaccgc     840
```
agcgtgagcg gcagtgcgac gggcacccccg tatgaactgc gtaaactgat gcgttttgcc    900
gctcgcagca aagtggcacc gaccaccgaa ctgtttccga tgagcaaaat caacgatgcg    960
attcagcatg tgcgtgacgg caaagcccgc tatcgtgtgg tgctgaaagc ggattttaa    1020

<210> SEQ ID NO 127
<211> LENGTH: 339
<212> TYPE: PRT
<213> ORGANISM: artificial
<220> FEATURE:
<223> OTHER INFORMATION: YjgB*(Q39R/I165V/A296V)

<400> SEQUENCE: 127

```
Met Ser Met Ile Lys Ser Tyr Ala Ala Lys Glu Ala Gly Gly Glu Leu
1               5                   10                  15

Glu Val Tyr Glu Tyr Asp Pro Gly Glu Leu Arg Pro Arg Asp Val Glu
            20                  25                  30

Val Gln Val Asp Tyr Cys Gly Ile Cys His Ser Asp Leu Ser Met Ile
        35                  40                  45

Asp Asn Glu Trp Gly Phe Ser Gln Tyr Pro Leu Val Ala Gly His Glu
50                  55                  60

Val Ile Gly Arg Val Val Ala Leu Gly Ser Ala Ala Gln Asp Lys Gly
65                  70                  75                  80

Leu Gln Val Gly Gln Arg Val Gly Ile Gly Trp Thr Ala Arg Ser Cys
                85                  90                  95

Gly His Cys Asp Ala Cys Ile Ser Gly Asn Gln Ile Asn Cys Glu Gln
            100                 105                 110

Gly Ala Val Pro Thr Ile Met Asn Arg Gly Gly Phe Ala Glu Lys Leu
        115                 120                 125

Arg Ala Asp Trp Gln Trp Val Ile Pro Leu Pro Glu Asn Ile Asp Ile
130                 135                 140

Glu Ser Ala Gly Pro Leu Leu Cys Gly Gly Val Thr Val Phe Lys Pro
145                 150                 155                 160

Leu Leu Met His His Ile Thr Ala Thr Ser Arg Val Gly Val Ile Gly
                165                 170                 175

Ile Gly Gly Leu Gly His Ile Ala Ile Lys Leu Leu His Ala Met Gly
            180                 185                 190

Cys Glu Val Thr Ala Phe Ser Ser Asn Pro Ala Lys Glu Gln Glu Val
        195                 200                 205

Leu Ala Met Gly Ala Asp Lys Val Val Asn Ser Arg Asp Pro Gln Ala
210                 215                 220

Leu Lys Ala Leu Ala Gly Gln Phe Asp Leu Ile Ile Asn Thr Val Asn
225                 230                 235                 240

Val Ser Leu Asp Trp Gln Pro Tyr Phe Glu Ala Leu Thr Tyr Gly Gly
                245                 250                 255

Asn Phe His Thr Val Gly Ala Val Leu Thr Pro Leu Ser Val Pro Ala
            260                 265                 270

Phe Thr Leu Ile Ala Gly Asp Arg Ser Val Ser Gly Ser Val Thr Gly
        275                 280                 285

Thr Pro Tyr Glu Leu Arg Lys Leu Met Arg Phe Ala Ala Arg Ser Lys
    290                 295                 300

Val Ala Pro Thr Thr Glu Leu Phe Pro Met Ser Lys Ile Asn Asp Ala
305                 310                 315                 320
```

Ile Gln His Val Arg Asp Gly Lys Ala Arg Tyr Arg Val Val Leu Lys
                325                 330                 335
Ala Asp Phe

<210> SEQ ID NO 128
<211> LENGTH: 1020
<212> TYPE: DNA
<213> ORGANISM: artificial
<220> FEATURE:
<223> OTHER INFORMATION: yjgB*(Q39R/I165V/A296V)

<400> SEQUENCE: 128

```
atgtcaatga ttaaatcgta tgcggcgaaa gaagcgggtg gcgaactgga agtgtatgaa     60
tacgacccag gcgaactgcg tccgcgggat gtggaagtcc aggtggatta ttgcggtatt    120
tgccatagcg acctgtctat gattgacaac gaatggggct ttagccagta tccgctggtg    180
gcgggtcacg aagtgattgg tcgtgtggtt gccctgggca gtgccgccca ggataaaggc    240
ttacaggtgg gtcagcgtgt gggcattggc tggacggcac gcagttgcgg tcattgcgat    300
gcgtgtatca gcggcaacca aatcaactgc gaacagggtg ccgttccgac gattatgaac    360
cgtggcggct ttgccgagaa actgcgtgcc gattggcagt gggtgattcc gctgcccgaa    420
aacattgata ttgaatctgc gggtccgctg ttatgtggcg gtgttaccgt gttcaaaccg    480
ctgttgatgc accacattac cgccaccagc cgtgttggcg tgattggcat cggcggtctg    540
ggtcacattg ccatcaaact gttacacgca atgggctgcg aagtgacggc gtttagcagt    600
aacccagcga agaacagga agtgctggcg atgggtgcgg ataaagtggt gaacagccgt    660
gacccgcagg cactgaaagc cctggcgggt cagtttgacc tgattatcaa caccgtgaat    720
gtcagcctgg attggcagcc gtattttgaa gccctgacct atggcggtaa cttccatacc    780
gtgggtgccg tgctgacccc gctgagcgtg cctgcgttta ccctgattgc gggtgaccgc    840
agcgtgagcg gcagtgtgac gggcaccccg tatgaactgc gtaaactgat gcgttttgcc    900
gctcgcagca aagtggcacc gaccaccgaa ctgtttccga tgagcaaaat caacgatgcg    960
attcagcatg tgcgtgacgg caaagcccgc tatcgtgtgg tgctgaaagc ggattttaa    1020
```